United States Patent
Goldberg et al.

(10) Patent No.: US 11,034,658 B2
(45) Date of Patent: Jun. 15, 2021

(54) PYRIDINYL PYRAZOLES AS MODULATORS OF RORγT

(71) Applicant: Janssen Pharmaceutica NV, Beerse (BE)

(72) Inventors: Steven Goldberg, Carlsbad, CA (US); Connor L. Martin, San Diego, CA (US); Elizabeth G. Fennema, La Mesa, CA (US); Ronald L. Wolin, San Diego, CA (US); Anne M. Fourie, San Diego, CA (US); Xiaohua Xue, San Diego, CA (US)

(73) Assignee: Janssen Pharmaceutica NV, Beerse (BE)

(*) Notice: Subject to any disclaimer, the term of this patent is extended or adjusted under 35 U.S.C. 154(b) by 0 days.

(21) Appl. No.: 16/442,976

(22) Filed: Jun. 17, 2019

(65) Prior Publication Data
US 2019/0382350 A1 Dec. 19, 2019

Related U.S. Application Data

(60) Provisional application No. 62/686,349, filed on Jun. 18, 2018.

(51) Int. Cl.
| | | |
|---|---|---|
| C07D 231/14 | (2006.01) | |
| A61P 17/06 | (2006.01) | |
| A61P 37/06 | (2006.01) | |
| A61P 25/24 | (2006.01) | |
| C07D 401/04 | (2006.01) | |

(52) U.S. Cl.
CPC ............ C07D 231/14 (2013.01); A61P 17/06 (2018.01); A61P 25/24 (2018.01); A61P 37/06 (2018.01); C07D 401/04 (2013.01)

(58) Field of Classification Search
CPC ..... C07D 231/14; C07D 401/04; A61P 17/06; A61P 37/06; A61P 25/24
USPC .................................................. 546/297
See application file for complete search history.

(56) References Cited

U.S. PATENT DOCUMENTS

| | | | |
|---|---|---|---|
| 5,342,835 A | 8/1994 | Pepin et al. | |
| 8,809,547 B2 | 8/2014 | Bretschneider et al. | |
| 10,369,146 B2 | 8/2019 | Leonard et al. | |
| 2005/0014805 A1 | 1/2005 | Zhang et al. | |
| 2012/0245137 A1* | 9/2012 | Pajouhesh | A61K 31/095 |
| | | | 514/210.17 |
| 2014/0163001 A1* | 6/2014 | Yamamoto | C07D 417/04 |
| | | | 514/210.18 |
| 2015/0038350 A1 | 2/2015 | Nishinaga et al. | |
| 2015/0072890 A1 | 3/2015 | James | |
| 2015/0111870 A1* | 4/2015 | Leonard | C07D 413/14 |
| | | | 514/210.18 |
| 2015/0266824 A1* | 9/2015 | Beck | C07D 231/14 |
| | | | 514/210.18 |
| 2016/0120850 A1 | 5/2016 | Goldberg et al. | |
| 2016/0122326 A1 | 5/2016 | Goldberg et al. | |
| 2016/0122335 A1 | 5/2016 | Goldberg et al. | |
| 2016/0122336 A1 | 5/2016 | Goldberg et al. | |
| 2016/0304476 A1* | 10/2016 | Aicher | C07D 265/36 |
| 2016/0304505 A1* | 10/2016 | Aicher | C07D 471/04 |
| 2017/0253591 A1* | 9/2017 | Yamamoto | C07D 403/12 |
| 2017/0313691 A1* | 11/2017 | Goldberg | C07D 487/08 |
| 2019/0269134 A1 | 9/2019 | Fublein et al. | |
| 2019/0382349 A1 | 12/2019 | Goldberg et al. | |
| 2019/0382354 A1* | 12/2019 | Goldberg | A61P 29/00 |
| 2019/0382373 A1* | 12/2019 | Goldberg | C07D 401/14 |

FOREIGN PATENT DOCUMENTS

| | | |
|---|---|---|
| CL | 201102650 | 10/2011 |
| CL | 201200534 | 2/2012 |
| CL | 201803050 | 10/2018 |
| CL | 201901343 | 5/2019 |
| CN | 103333168 | 10/2013 |

(Continued)

OTHER PUBLICATIONS

Eastman; Oncotarget. 2017, 8, 8854-8866. DOI: 10.18632/oncotarget. 12673 (Year: 2017).*

Guendisch; PLoS ONE 2017, 12, e0188391. DOI: 10.1371/journal. pone.0188391 (Year: 2017).*

Huh; Eur. J. Immunol. 2012. 42, 2232-2237. DOI: 10.1002/eji. 201242740 (Year: 2012).*

(Continued)

*Primary Examiner* — Daniel R Carcanague
(74) *Attorney, Agent, or Firm* — Yuriy P. Stercho

(57) ABSTRACT

The present invention comprises compounds of Formula I.

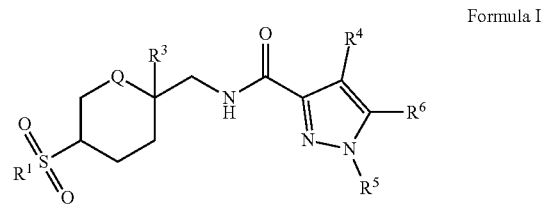

Formula I wherein:

$R^1$, $R^3$, $R^4$, $R^5$, $R^6$, and Q are defined in the specification.

The invention also comprises a method of treating or ameliorating a ROR-γ-t mediated syndrome, disorder or disease, including wherein the syndrome, disorder or disease is selected from the group consisting of rheumatoid arthritis, psoriatic arthritis, and psoriasis. The invention also comprises a method of modulating RORγt activity in a mammal by administration of a therapeutically effective amount of at least one compound of Formula I.

27 Claims, No Drawings

Specification includes a Sequence Listing.

(56) References Cited

FOREIGN PATENT DOCUMENTS

| | | |
|---|---|---|
| CN | 103833672 | 6/2014 |
| EP | 360701 A1 | 3/1990 |
| EP | 2433938 | 3/2012 |
| EP | 2474543 | 7/2012 |
| EP | 2738170 | 6/2014 |
| JP | 2005507932 | 3/2005 |
| WO | WO 1996003392 A1 | 2/1996 |
| WO | WO 2002083111 A2 | 10/2002 |
| WO | WO 2003015776 A1 | 2/2003 |
| WO | WO 2006087355 | 8/2006 |
| WO | WO 2006124687 A1 | 11/2006 |
| WO | WO 2007087427 A2 | 8/2007 |
| WO | WO 2008064317 A1 | 5/2008 |
| WO | WO 2008064318 A2 | 5/2008 |
| WO | WO 2009011850 | 1/2009 |
| WO | WO 2010006713 | 1/2010 |
| WO | WO 2011053948 A1 | 5/2011 |
| WO | WO 2011112263 A1 | 9/2011 |
| WO | WO 2011112264 A1 | 9/2011 |
| WO | WO 2011115892 A1 | 9/2011 |
| WO | WO 2012027965 | 3/2012 |
| WO | WO 2012074547 A2 | 6/2012 |
| WO | WO 2012129491 | 9/2012 |
| WO | WO 2012158784 A2 | 11/2012 |
| WO | WO 2012174362 | 12/2012 |
| WO | WO-2013029338 A1 * | 3/2013 ........... C07D 213/71 |
| WO | WO 2013036912 A2 | 3/2013 |
| WO | WO 2013079223 A | 6/2013 |
| WO | WO 2013092939 A1 | 6/2013 |
| WO | WO-2013171729 A2 * | 11/2013 |
| WO | WO 2013178362 A1 | 12/2013 |
| WO | WO 2014023367 | 2/2014 |
| WO | WO 2014093191 | 6/2014 |
| WO | WO 2015035278 A1 | 3/2015 |
| WO | WO 2015042212 A1 | 3/2015 |
| WO | WO 2015082533 A1 | 6/2015 |
| WO | WO 2015103507 A1 | 7/2015 |
| WO | WO 2015103508 A1 | 7/2015 |
| WO | WO 2015103509 A1 | 7/2015 |
| WO | WO 2015103510 A1 | 7/2015 |
| WO | WO 2015145371 A1 | 10/2015 |
| WO | WO 2016069974 | 5/2016 |
| WO | WO 2017/189823 | 11/2017 |
| WO | WO 2017/189829 | 11/2017 |
| WO | WO 2018123918 | 7/2018 |
| WO | WO-2018185236 A1 * | 10/2018 ........... C07D 405/12 |

OTHER PUBLICATIONS

Isono; Drug Discovery Today, 2014, 19, 1205-1211. DOI: 10.1016/j.drudis.2014.04.012 (Year: 2014).*

Xue; Scientific Reports 2016, 6, Article No. 37977. DOI: 10.1038/srep37977 (Year: 2016).*

Kiaei; Basic Clin Neurosci. 2013, 4, 3-4. URL: http://bcn.iums.ac.ir/article-1-307-en.html (Year: 2013).*

Angew. Chem. Int. Ed. Engl. 1982, 21, 567-583.

Barczyk, A., W. Pierzchala, et al. (2003). "Interleukin-17 in sputum correlates with airway hyperresponsiveness to methacholine." Respir Med 97(6): 726-33.

Beurel, E., Harrington, L. E., Jope, R. S. (2013) "Inflammatory T helper 17 cells promote depression-like behavior in mice." Biol Psychiatry 73(7): 622-30.

Bimekizumab demonstrates impressive joint and skin responses for psoriatic arthritis patients. Dec. 20, 2017. https//www.ucb.com/stories-media/Press-Releases/article/Bimekizumab-demonstrates-impressive-joint-and-skin-responses-for-psoriatic-arthritis-patients.nbsp.

Bowes, J. and A. Barton "The genetics of psoriatic arthritis: lessons from genome-wide association studies." Discov Med 10(52): 177-83 (2010).

Chang M, "Pharmacologic Repression of Retinoic Acid Receptor—Related Orphan Nuclear Receptor ☐ Is Therapeutic in the Collagen-Induced Arthritis Experimental Model", Arthritis & Rheumatology (2014), 66(3), 579-588.

Chang, M. R. et al. (2015) "Antiobesity Effect of a Small Molecule Repressor of RORγ." Mol Pharmacol. 88(1): 48-56.

Chen, Y., et al. (2011). "Emerging tendency towards autoimmune process in major depressive patients: A novel insight from Th17 cells." Psychiatry Research 188(2): 224-230.

Cheng, Chia-Chung et al., The Friedlander synthesis of quinolines, Organic Reactions, 1982, 28, pp. 37-201.

Cua, D. J., J. Sherlock, et al. (2003). "Interleukin-23 rather than interleukin-12 is the critical cytokine for autoimmune inflammation of the brain." Nature 421(6924): 744-8.

De Wit et al., ,RORγt inhibitors suppress TH17 responses in inflammatory arthritis and inflammatory bowel disease. Journal of Allergy and Clinical Immunology, vol. 137, Issue 3, (2016), 960-963.

Dolff S et al., Disturbed Th1, Th2, Th17 and T-reg balance in patients with systemic lupus erythematosus, Clinical Immunology 141(2):197-204 •Aug. 2011.

Dong, C. (2006). "Diversification of T-helper-cell lineages: finding the family root of IL-17-producing cells." Nat Rev Immunol 6(4): 329-33.

Fauber et al., J. Med. Chem. 2014, 57, 5871-5892.

Feagan BG, et al. Ustekinumab as induction and maintenance therapy for Crohn's disease. N Engl J Med. 2016;375(20):1946-60.

Fitzpatrick, Leo Robert. Ror-gamma T inhibition as a Pharmacological Approach for Inflammatory Bowel Disease. Medical Research Archives, [S.I.], v. 2, n. 2, Aug. 2015.

Fujino, S., A. Andoh, et al. (2003). "Increased expression of interleukin 17 in inflammatory bowel disease." Gut 52(1): 65-70.

Garber K. (2011). "Psoriasis: from bed to bench and back" Nat Biotech 29, 563-566.

Gazouli, M., I. Pachoula, et al. "NOD2/CARD15, ATG16L1 and IL23R gene polymorphisms and childhood-onset of Crohn's disease." World J Gastroenterol 16(14): 1753-8 (2010).

Hodgson et al., Ustekinumab for Treating Moderately to Severely Active Crohn's Disease after Prior Therapy: An Evidence Review Group Perspective of a NICE Single Technology Appraisal. PharmacoEconomics (2018) 36:4, 387-398.

Hueber, W., Patel, D.D., Dryja, T., Wright, A.M., Koroleva, I., Bruin, G., Antoni, C., Draelos, Z., Gold, M.H., Durez, P., Tak, P.P., Gomez-Reino, J.J., Foster, C.S., Kim, R.Y., Samson, C.M., Falk, N.S., Chu, D.S., Callanan, D., Nguyen, Q.D., Rose, K., Haider, A., Di Padova, F. (2010) Effects of AIN457, a fully human antibody to interleukin-17A, on psoriasis, rheumatoid arthritis, and uveitis. Sci Transl Med 2, 5272.

Innovimmune: ROR Gamma Inhibitor (INV-17) Tested in Lupus Model. 2015 EULAR Congress News. https://static1.squarespace.com/static/577aff0015d5db17f97d2d57/t/584f44f9725e254d6b032644/1481590043630/150611_INV-17+Lupus+Thursday_EULAR_2015+small+size.pdf.

Ivanov, II, B. S. McKenzie, et al. (2006). "The orphan nuclear receptor RORgammat directs the differentiation program of proinflammatory IL-17+ T helper cells." Cell 126(6): 1121-33.

Jethwa H at al., The interleukin (IL)-23/IL-17 axis in ankylosing spondylitis: new advances and potentials for treatment, Clinical and Experimental Immunology, 2015, 183: 30-36.

Kochi, Y., Y. Okada, et al. (2010) "A regulatory variant in CCR6 is associated with rheumatoid arthritis susceptibility." Nat Genet 42(6): 515-9.

Kolls, J. K. and A. Linden (2004). "Interleukin-17 family members and inflammation." Immunity 21(4): 467-76.

Korn, T., E. Bettelli, et al. (2009). "IL-17 and Th17 Cells." Annu Rev Immunol 27: 485-517.

Krueger, J. G., S. Fretzin, et al. "IL-17A is essential for cell activation and inflammatory gene circuits in subjects with psoriasis." J Allergy Clin Immunol 130(1): 145-154 e9 (2012).

Kumar N, "The Benzenesulfoamide T0901317 [N-(2,2,2-Trifluoroethyl)-N-[4-[2,2,2-trifluoro-1-hydroxy-1-(trifluoromethyl)ethyl]phenyl]-benzenesulfonamide] Is a Novel Retinoic Acid Receptor-Related Orphan Receptor-☐/☐ Inverse Agonist", Molecular Pharmacology (2010), 77(2), 228-236.

(56) References Cited

OTHER PUBLICATIONS

Langrish, C. L., Y. Chen, et al. (2005). "IL-23 drives a pathogenic T cell population that induces autoimmune inflammation." J Exp Med 201(2): 233-40.
Leonardi, C., R. Matheson, et al. "Anti-interleukin-17 monoclonal antibody ixekizumab in chronic plaque psoriasis." N Engl J Med 366(13): 1190-9 (2012).
Liegault, et al., "Establishment of Broadly Applicable reaction condisions for the Palladium-Catalyzed Direct Arylation of Heteroatom-Containing Aromatic Compounds", The Journal of Organic Chemistry, (2009), vol. 74, No. 5, 6, pp. 1826-1834.
Lock, C., G. Hermans, et al. (2002). "Gene-microarray analysis of multiple sclerosis lesions yields new targets validated in autoimmune encephalomyelitis." Nat Med 8(5): 500-8.
Matulis, D., Kranz, J. K., Salemme, F. R., and Todd, M. J. (2005) Thermodynamic stability of carbonic anhydrase: measurements of binding affinity and stoichiometry using ThermoFluor. *Biochemistry* 44, 5258-66.
McGinley et al., (2018) Th17 cells, γδ T cells and their interplay in EAE and multiple sclerosis. *Journal of Autoimmunity* 87, 97-108.
McKenzie, B. S., R. A. Kastelein, et al. (2006). "Understanding the IL-23-IL-17 immune pathway." Trends Immunol 27(1): 17-23.
Mease, P. J. et al. Brodalumab, an anti-IL17RA monoclonal antibody, in psoriatic arthritis, The New England Journal of Medicine 370, 2295-2306 (2014).
Meissburger, B. et al. (2011) "Adipogenesis and insulin sensitivity in obesity are regulated by retinoid-related orphan receptor gamma." EMBO Mol Med. 3(11): 637-651.
Nunez, C., B. Dema, et al. (2008). "IL23R: a susceptibility locus for celiac disease and multiple sclerosis?" Genes Immun 9(4): 289-93.
Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovery. *J Biomol Screen* 6, 429-40.
Papp, K. A., "Brodalumab, an anti-interleukin-17-receptor antibody for psoriasis." N Engl J Med 2012 366(13): 1181-9.
Poddhubnyy et al., Ann Rheum Dis 2014;0:1-7.
Pure & Appl. Chem. 45, 1976, 11-30.
Qian et al., Clin. Invest. (2012) 2(4), 417-421.
Registry(STN)[online], [Search Date: May 13, 2019]CAS Registration No. 791058-42-9,263386-02-3.
Sandborn WJ et al. Ustekinumab Induction and Maintenance Therapy in Refractory Crohn's Disease N Engl J Med 2012; 367:1519-1528.
Silva MJ et al, Glucocorticoid Resistant Asthma: The Potential Contribution of IL-17. Biomark J. 2016, 1:6.
Stamp, L. K., M. J. James, et al. (2004). "Interleukin-17: The missing link between T-cell accumulation and effector cell actions in rheumatoid arthritis" Immunol Cell Biol 82(1): 1-9.

Tonel, G., C. Conrad, et al. "Cutting edge: A critical functional role for IL-23 in psoriasis." J Immunol 185(10): 5688-91 (2010).
Wang X, Wei Y, Xiao H, et al. A novel IL-23p19/Ebi3 (IL-39) cytokine mediates inflammation in Lupus-like mice. Eur J Immunol. 2016;46(6):1343-1350.
Weitz JE et al., Ustekinumab: Targeting the IL-17 Pathway to Improve Outcomes in Psoriatic Arthritis. Expert Opin Biol Ther 2104 14, 515-526.
Withers DR, et al. Transient inhibition of ROR-γt therapeutically limits intestinal inflammation by reducing TH17 cells and preserving group 3 innate lymphoid cells Nature Medicine 2016, 22, 319.
Yang et al., Trends in Pharmacological Sciences, Oct. 2014, vol. 35, No. 10, 493-500.
Yang X et al. Does IL-17 Respond to the Disordered Lung Microbiome and Contribute to the Neutrophilic Phenotype in Asthma? Mediators of Inflammation. vol. 2016 (2016), Article ID 6470364, pp. 1-7.
Yao, et al, "Preparation Method of N-butyl-5-phenylthiazole-4-Formamide Derivative Via Coupling Reaction Under Catalysis of Copper Catalyst", Database accession No. 2014:924023.
Yen, D., J. Cheung, et al. (2006). "IL-23 is essential for T cell-mediated colitis and promotes inflammation via IL-17 and IL-6." J Clin Invest 116(5): 1310-6.
Zhang, et al., "Decarboxylative Cross-Coupling of Azoyl Carboxylic Acids with Aryl Halides", Organic Letters, (2010) vol. 12, No. 21, pp. 4745-47457.
PCT/US2015/058193, Written Opinion dated Jan. 26, 2016.
PCT/US2015/058198, Written Opinion dated Jan. 21, 2016.
PCT/US2015/058200, Written Opinion dated Jan. 27, 2016.
PCT/US2015/058193, International Search Report, dated Jan. 26, 2016.
PCT/US2015/058198, International Search Report, dated Jan. 21, 2016.
PCT/US2015/058200, International Search Report, dated Jan. 27, 2016.
PCT/US2017/029531, International Search Report, dated Sep. 15, 2017.
PCT/US2017/029531, International Preliminary Report on Patentability, dated Oct. 30, 2018.
PCT/IB2019/055043, International Search Report, dated Sep. 30, 2019.
PCT/IB2019/055045, International Search Report, dated Sep. 30, 2019.
PCT/IB2019/055046, International Search Report, dated Oct. 4, 2019.
PCT/IB2019/055048, International Search Report, dated Sep. 27, 2019.
Yao Chongzheng et al., Hydrolysis of carboxylate, Principles of Fine Chemical Product Synthesis, published on Dec. 31, 2000 (see English translation as provided).

* cited by examiner

SEQUENCE LISTING

```
<160> NUMBER OF SEQ ID NOS: 4

<210> SEQ ID NO 1
<211> LENGTH: 3054
<212> TYPE: DNA
<213> ORGANISM: Homo sapiens

<400> SEQUENCE: 1
agagagctag gtgcagagct tcaggctgag gcgctgctga gagggcctcg ccccgcctct      60
gccgccagct gcaccccact cctggaccac cccctgctga gaaggacagg gagccaaggc     120
cggcagagcc aaggctcagt catgagaaca caaattgaag tgatcccttg caaaatctgt     180
ggggacaagt cgtctgggat ccactacggg gttatcacct gtgaggggtg caagggcttc     240
ttccgccgga gccagcgctg taacgcggcc tactcctgca cccgtcagca gaactgcccc     300
atcgaccgca ccagccgaaa ccgatgccag cactgccgcc tgcagaaatg cctggcgctg     360
ggcatgtccc gagatgctgt caagttcggc cgcatgtcca agaagcagag ggacagcctg     420
catgcagaag tgcagaaaca gctgcagcag cggcaacagc agcaacagga accagtggtc     480
aagacccctc cagcaggggc caaggagca gataccctca cctacacctt ggggctccca     540
gacgggcagc tgcccctggg ctcctcgcct gacctgcctg aggcttctgc ctgtccccct     600
ggcctcctga aagcctcagg ctctgggccc tcatattcca caacttggc caaggcaggg     660 ctcaatgggg cctcatgcca ccttgaatac agccctgagc ggggcaaggc tgagggcaga     720
gagagcttct atagcacagg cagccagctg accctgaccc gatgtggact tcgttttgag     780
gaacacaggc atcctgggct tggggaactg ggacagggcc cagacagcta cggcagcccc     840
agtttccgca gcacaccgga ggcaccctat gcctccctga cagagataga gcacctggtg     900
cagagcgtct gcaagtccta cagggagaca tgccagctgc ggctggagga cctgctgcgg     960
cagcgctcca acatcttctc ccgggaggaa gtgactggct accagaggaa gtccatgtgg    1020
gagatgtggg aacggtgtgc ccaccacctc accgaggcca ttcagtacgt ggtggagttc    1080
gccaagaggc tctcaggctt tatggagctc tgccagaatg accagattgt gcttctcaaa    1140
gcaggagcaa tggaagtggt gctggttagg atgtgccggg cctacaatgc tgacaaccgc    1200
acggtctttt ttgaaggcaa atacggtggc atggagctgt tccgagcctt gggctgcagc    1260
gagctcatca gctccatctt tgacttctcc cactccctaa gtgccttgca cttttccgag    1320
gatgagattg ccctctacac agcccttgtt ctcatcaatg cccatcggcc agggctccaa    1380
gagaaaagga aagtagaaca gctgcagtac aatctggagc tggcctttca tcatcatctc    1440
tgcaagactc atcgccaaag catcctggca aagctgccac caagggaa gcttcggagc    1500 ctgtgtagcc agcatgtgga aaggctgcag atcttccagc acctccaccc catcgtggtc    1560
caagccgctt tccctccact ctacaaggag ctcttcagca ctgaaaccga gtcacctgtg    1620
gggctgtcca agtgacctgg aagagggact ccttgcctct ccctatggcc tgctggccca    1680
cctccctgga ccccgttcca ccctcaccct tttccttccc catgaaccct ggagggtggt    1740
ccccaccagc tctttggaag tgagcagatg ctgcggctgg ctttctgtca gcaggccggc    1800
ctggcagtgg gacaatcgcc agagggtggg gctggcagaa caccatctcc agcctcagct    1860
ttgacctgtc tcatttccca tattccttca cacccagctt ctggaaggca tggggtggct    1920
```

```
gggatttaag gacttctggg ggaccaagac atcctcaaga aaacaggggc atccagggct   1980
ccctggatga atagaatgca attcattcag aagctcagaa gctaagaata agcctttgaa   2040
atacctcatt gcatttccct ttgggcttcg gcttggggag atggatcaag ctcagagact   2100
ggcagtgaga gcccagaagg acctgtataa aatgaatctg gagctttaca ttttctgcct   2160
ctgccttcct cccagctcag caaggaagta tttgggcacc ctacccttta cctggggtct   2220
aaccaaaaat ggatgggatg aggatgagag gctggagata attgttttat ggatttggg    2280 tgtgggacta gggtacaatg aaggccaaga gcatctcaga catagagtta aaactcaaac   2340
ctcttatgtg cactttaaag atagacttta ggggctggca caaatctgat cagagacaca   2400
tatccataca caggtgaaac acatacagac tcaacagcaa tcatgcagtt ccagagacac   2460
atgaacctga cacaatctct cttatccttg aggccacagc ttggaggagc ctagaggcct   2520
caggggaaag tcccaatcct gagggaccct cccaaacatt tccatggtgc tccagtccac   2580
tgatcttggg tctggggtga tccaaatacc accccagctc cagctgtctt ctaccactag   2640
aagacccaag agaagcagaa gtcgctcgca ctggtcagtc ggaaggcaag atcagatcct   2700
ggaggacttt cctggcctgc cgccagccc tgctcttgtt gtggagaagg aagcagatgt    2760
gatcacatca ccccgtcatt gggcaccgct gactccagca tggaggacac cagggagcag   2820
ggcctgggcc tgtttcccca gctgtgatct tgcccagaac ctctcttggc ttcataaaca   2880
gctgtgaacc ctcccctgag ggattaacag caatgatggg cagtcgtgga gttgggggg    2940 ttggggtgg gattgtgtcc tctaaggga cgggttcatc tgagtaaaca taaacccccaa    3000 cttgtgccat tctttataaa atgattttaa aggcaaaaaa aaaaaaaaaa aaaa          3054

<210> SEQ ID NO 2
<211> LENGTH: 786
<212> TYPE: DNA
<213> ORGANISM: Homo sapiens

<400> SEQUENCE: 2
agcacaccgg aggcaccta tgcctccctg acagagatag agcacctggt gcagagcgtc      60
tgcaagtcct acagggagac atgccagctg cggctggagg acctgctgcg gcagcgctcc    120
aacatcttct cccgggagga agtgactggc taccagagga agtccatgtg ggagatgtgg    180
gaacggtgtg cccaccacct caccgaggcc attcagtacg tggtggagtt cgccaagagg    240
ctctcaggct ttatggagct ctgccagaat gaccagattg tgcttctcaa agcaggagca    300
atggaagtgg tgctggttag gatgtgccgg gcctacaatg ctgacaaccg cacggtcttt    360
tttgaaggca aatacggtgg catggagctg ttccgagcct tgggctgcag cgagctcatc    420
agctccatct ttgacttctc ccactcccta agtgccttgc acttttccga ggatgagatt    480
gccctctaca cagcccttgt tctcatcaat gcccatcggc cagggctcca agagaaaagg    540
aaagtagaac agctgcagta caatctggag ctggcctttc atcatcatct ctgcaagact    600
catcgccaaa gcatcctggc aaagctgcca cccaagggga agcttcggag cctgtgtagc    660
cagcatgtgg aaaggctgca gatcttccag cacctccacc ccatcgtggt ccaagccgct   720
ttccctccac tctacaagga gctcttcagc actgaaaccg agtcacctgt ggggctgtcc    780
aagtga                                                              786

<210> SEQ ID NO 3
<211> LENGTH: 7
<212> TYPE: PRT
```

```
<213> ORGANISM: Artificial Sequence
<220> FEATURE:
<223> OTHER INFORMATION: TurboTEV protease cleavage site

<400> SEQUENCE: 3

Glu Asn Leu Tyr Phe Gln Gly
1               5

<210> SEQ ID NO 4
<211> LENGTH: 283
<212> TYPE: PRT
<213> ORGANISM: Artificial Sequence
<220> FEATURE:
<223> OTHER INFORMATION: Construct used in the Thermofluor assay

<400> SEQUENCE: 4

Met Ala His His His His His His Ala Gly Gly Ala Glu Asn Leu Tyr
1               5                   10                  15

Phe Gln Gly Ala Met Asp Ser Thr Pro Glu Ala Pro Tyr Ala Ser Leu
                20                  25                  30

Thr Glu Ile Glu His Leu Val Gln Ser Val Cys Lys Ser Tyr Arg Glu
            35                  40                  45

Thr Cys Gln Leu Arg Leu Glu Asp Leu Leu Arg Gln Arg Ser Asn Ile
    50                  55                  60

Phe Ser Arg Glu Glu Val Thr Gly Tyr Gln Arg Lys Ser Met Trp Glu
65                  70                  75                  80

Met Trp Glu Arg Cys Ala His His Leu Thr Glu Ala Ile Gln Tyr Val
                85                  90                  95

Val Glu Phe Ala Lys Arg Leu Ser Gly Phe Met Glu Leu Cys Gln Asn
                100                 105                 110

Asp Gln Ile Val Leu Leu Lys Ala Gly Ala Met Glu Val Val Leu Val
            115                 120                 125

Arg Met Cys Arg Ala Tyr Asn Ala Asp Asn Arg Thr Val Phe Phe Glu
    130                 135                 140

Gly Lys Tyr Gly Gly Met Glu Leu Phe Arg Ala Leu Gly Cys Ser Glu
145                 150                 155                 160

Leu Ile Ser Ser Ile Phe Asp Phe Ser His Ser Leu Ser Ala Leu His
                165                 170                 175

Phe Ser Glu Asp Glu Ile Ala Leu Tyr Thr Ala Leu Val Leu Ile Asn
                180                 185                 190

Ala His Arg Pro Gly Leu Gln Glu Lys Arg Lys Val Glu Gln Leu Gln
        195                 200                 205

Tyr Asn Leu Glu Leu Ala Phe His His Leu Cys Lys Thr His Arg
    210                 215                 220

Gln Ser Ile Leu Ala Lys Leu Pro Pro Lys Gly Lys Leu Arg Ser Leu
225                 230                 235                 240

Cys Ser Gln His Val Glu Arg Leu Gln Ile Phe Gln His Leu His Pro
                245                 250                 255

Ile Val Val Gln Ala Ala Phe Pro Pro Leu Tyr Lys Glu Leu Phe Ser
                260                 265                 270

Thr Glu Thr Glu Ser Pro Val Gly Leu Ser Lys
            275                 280
```

PYRIDINYL PYRAZOLES AS MODULATORS OF RORγT

CROSS REFERENCE TO RELATED APPLICATIONS

This application claims priority from U.S. Provisional Application 62/686,349, filed on Jun. 18, 2018, which is incorporated by reference herein in its entirety.

SEQUENCE LISTING

The instant application contains a Sequence Listing which has been filed electronically in ASCII format and is hereby incorporated by reference in its entirety. Said ASCII copy, created on Jun. 11, 2019, is named PRD3480USNP.txt and is 8,199 bytes in size.

FIELD OF THE INVENTION

The invention is directed to substituted pyrazole compounds, which are modulators of the nuclear receptor RORγt, pharmaceutical compositions, and methods for use thereof. More particularly, the RORγt modulators are useful for preventing, treating or ameliorating an RORγt mediated inflammatory syndrome, disorder or disease.

BACKGROUND OF THE INVENTION

Retinoic acid-related nuclear receptor gamma t (RORγt) is a nuclear receptor, exclusively expressed in cells of the immune system, and a key transcription factor driving Th17 cell differentiation. Th17 cells are a subset of CD4+ T cells, expressing CCR6 on their surface to mediate their migration to sites of inflammation, and dependent on IL-23 stimulation, through the IL-23 receptor, for their maintenance and expansion. Th17 cells produce several proinflammatory cytokines including IL-17A, IL-17F, IL-21, and IL-22 (Korn, T., E. Bettelli, et al. (2009). "IL-17 and Th17 Cells." Annu Rev Immunol 27: 485-517.), which stimulate tissue cells to produce a panel of inflammatory chemokines, cytokines and metalloproteases, and promote recruitment of granulocytes (Kolls, J. K. and A. Linden (2004). "Interleukin-17 family members and inflammation." Immunity 21(4): 467-76; Stamp, L. K., M. J. James, et al. (2004). "Interleukin-17: the missing link between T-cell accumulation and effector cell actions in rheumatoid arthritis" Immunol Cell Biol 82(1): 1-9). Th17 cells have been shown to be the major pathogenic population in several models of autoimmune inflammation, including collagen-induced arthritis (CIA) and experimental autoimmune encephalomyelitis (EAE) (Dong, C. (2006). "Diversification of T-helper-cell lineages: finding the family root of IL-17-producing cells." Nat Rev Immunol 6(4): 329-33; McKenzie, B. S., R. A. Kastelein, et al. (2006). "Understanding the IL-23-IL-17 immune pathway." Trends Immunol 27(1): 17-23.). RORγt-deficient mice are healthy and reproduce normally, but have shown impaired Th17 cell differentiation in vitro, a significantly reduced Th17 cell population in vivo, and decreased susceptibility to EAE (Ivanov, II, B. S. McKenzie, et al. (2006). "The orphan nuclear receptor RORgammat directs the differentiation program of proinflammatory IL-17+T helper cells." Cell 126(6): 1121-33.). Mice deficient for IL-23, a cytokine required for Th17 cell survival, fail to produce Th17 cells and are resistant to EAE, CIA, and inflammatory bowel disease (IBD) (Cua, D. J., J. Sherlock, et al. (2003). "Interleukin-23 rather than interleukin-12 is the critical cytokine for autoimmune inflammation of the brain." Nature 421(6924): 744-8.; Langrish, C. L., Y. Chen, et al. (2005). "IL-23 drives a pathogenic T cell population that induces autoimmune inflammation." J Exp Med 201(2): 233-40; Yen, D., J. Cheung, et al. (2006). "IL-23 is essential for T cell-mediated colitis and promotes inflammation via IL-17 and IL-6." J Clin Invest 116(5): 1310-6.). Consistent with these findings, an anti-IL23-specific monoclonal antibody blocks development of psoriasis-like inflammation in a murine disease model (Tonel, G., C. Conrad, et al. "Cutting edge: A critical functional role for IL-23 in psoriasis." J Immunol 185(10): 5688-91).

RORγT deficient mice exhibited resistance to learned helplessness. Treatment with the RORγT inhibitor SR1001, or anti-interleukin-17A antibodies reduced Th17-dependent learned helplessness (Beurel, E., Harrington, L. E., Jope, R. S. (2013) "Inflammatory T helper 17 cells promote depression-like behavior in mice." Biol Psychiatry 73(7): 622-30). In human patients with major depressive disorder, both peripheral blood lymphocyte RORγT mRNA expression and peripheral Th17 cells were found to be elevated relative to the control group (Chen, Y., et al. (2011). "Emerging tendency towards autoimmune process in major depressive patients: A novel insight from Th17 cells." Psychiatry Research 188(2): 224-230).

Administration of RORγ inverse agonist SR1555 to obese diabetic mice resulted in a modest reduction in food intake accompanied with significant reduction in fat mass, resulting in reduced body weight and improved insulin sensitivity (Chang, M. R. et al. (2015) "Antiobesity Effect of a Small Molecule Repressor of RORγ." Mol Pharmacol. 88(1): 48-56). In addition, Rorγ−/− mice are protected from hyperglycemia and insulin resistance in the state of obesity (Meissburger, B. et al. (2011) "Adipogenesis and insulin sensitivity in obesity are regulated by retinoid-related orphan receptor gamma." EMBO Mol Med. 3(11): 637-651).

In humans, a number of observations support the role of the IL-23/Th17 pathway in the pathogenesis of inflammatory diseases. IL-17, the key cytokine produced by Th17 cells, is expressed at elevated levels in a variety of allergic and autoimmune diseases (Barczyk, A., W. Pierzchala, et al. (2003). "Interleukin-17 in sputum correlates with airway hyperresponsiveness to methacholine." Respir Med 97(6): 726-33.; Fujino, S., A. Andoh, et al. (2003). "Increased expression of interleukin 17 in inflammatory bowel disease." Gut 52(1): 65-70.; Lock, C., G. Hermans, et al. (2002). "Gene-microarray analysis of multiple sclerosis lesions yields new targets validated in autoimmune encephalomyelitis." Nat Med 8(5): 500-8.; Krueger, J. G., S. Fretzin, et al. "IL-17A is essential for cell activation and inflammatory gene circuits in subjects with psoriasis." J Allergy Clin Immunol 130(1): 145-154 e9.). Furthermore, human genetic studies have shown association of polymorphisms in the genes for Th17 cell-surface receptors, IL-23R and CCR6, with susceptibility to IBD, multiple sclerosis (MS), rheumatoid arthritis (RA) and psoriasis (Gazouli, M., I. Pachoula, et al. "NOD2/CARD15, ATG16L1 and IL23R gene polymorphisms and childhood-onset of Crohn's disease." World J Gastroenterol 16(14): 1753-8., Nunez, C., B. Dema, et al. (2008). "IL23R: a susceptibility locus for celiac disease and multiple sclerosis?" Genes Immun 9(4): 289-93.; Bowes, J. and A. Barton "The genetics of psoriatic arthritis: lessons from genome-wide association studies." Discov Med 10(52): 177-83; Kochi, Y., Y. Okada, et al. "A regulatory variant in CCR6 is associated with rheumatoid arthritis susceptibility." Nat Genet 42(6): 515-9.).

Ustekinumab (Stelara®), an anti-p40 monoclonal antibody blocking both IL-12 and IL-23, is approved for the treatment of adult patients (18 years or older), with moderate to severe plaque psoriasis, who are candidates for phototherapy or systemic therapy. Currently, monoclonal antibodies specifically targeting only IL-23, to more selectively inhibit the Th17 subset, are also in clinical development for psoriasis (Garber K. (2011). "Psoriasis: from bed to bench and back" Nat Biotech 29, 563-566), further implicating the important role of the IL-23- and RORγt-driven Th17 pathway in this disease. Results from recent phase II clinical studies strongly support this hypothesis, as anti-IL-17 receptor and anti-IL-17 therapeutic antibodies both demonstrated high levels of efficacy in patients with chronic psoriasis (Papp, K. A., "Brodalumab, an anti-interleukin-17-receptor antibody for psoriasis." N Engl J Med 2012 366(13): 1181-9.; Leonardi, C., R. Matheson, et al. "Anti-interleukin-17 monoclonal antibody ixekizumab in chronic plaque psoriasis." N Engl J Med 366(13): 1190-9.). Anti-IL-17 antibodies have also demonstrated clinically relevant responses in early trials in RA and uveitis (Hueber, W., Patel, D. D., Dryja, T., Wright, A. M., Koroleva, I., Bruin, G., Antoni, C., Draelos, Z., Gold, M. H., Durez, P., Tak, P. P., Gomez-Reino, J. J., Foster, C. S., Kim, R. Y., Samson, C. M., Falk, N. S., Chu, D. S., Callanan, D., Nguyen, Q. D., Rose, K., Haider, A., Di Padova, F. (2010) Effects of AIN457, a fully human antibody to interleukin-17A, on psoriasis, rheumatoid arthritis, and uveitis. Sci Transl Med 2, 5272.).

All the above evidence supports inhibition of the Th17 pathway by modulating RORγt activity as an effective strategy for the treatment of immune-mediated inflammatory diseases.

SUMMARY OF THE INVENTION

The present invention comprises a compound of Formula I:

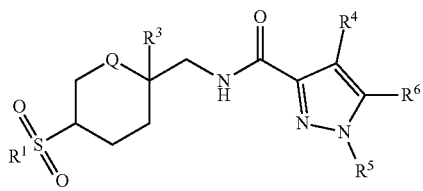

Formula I wherein
$R^1$ is $C_{(1-4)}$alkyl, —NH$_2$, —NHC(O)NH$_2$, —NHC(O)C$_{(1-4)}$alkyl, —NHC(O)NHC$_{(1-4)}$alkyl, —NHC$_{(1-4)}$alkyl, —NHC(O)H, or N(C$_{(1-4)}$alkyl)$_2$;
Q is CHR$^2$, NC(O)CH$_3$, NCH$_2$C(O)NH$_2$, NH, or O;
$R^2$ is H, —OH, or —NH$_2$;
$R^3$ is —H, —OH, —CN, —NH$_2$, —CONH$_2$, —CO$_2$H, —CO$_2$C$_{(1-4)}$alkyl, —CH$_2$OH, —CH$_2$NH$_2$, —CH$_2$CN, —NHC$_{(1-4)}$alkyl, or —CONHC$_{(1-4)}$alkyl;
$R^4$ is —Cl, —C$_{(1-4)}$alkyl, —F, —CN, —C(O)NH$_2$,

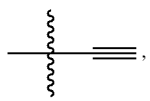

or —H; wherein said —C$_{(1-4)}$alkyl is optionally substituted with up to six fluorine atoms;

$R^5$ is —C$_{(1-4)}$alkyl, wherein said —C$_{(1-4)}$alkyl is optionally substituted with —CN, —OH, —OCH$_3$, —OCF$_3$, or up to six fluorine atoms;
$R^6$ is

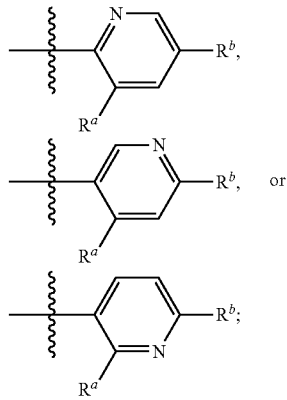

$R^a$ is —H, —F, —Cl, —OCD$_3$, —CN, —C$_{(1-3)}$alkyl, or —OC$_{(1-3)}$alkyl, wherein said —C$_{(1-3)}$alkyl and said OC$_{(1-3)}$alkyl are optionally substituted with up to three fluorine atoms;
$R^b$ is

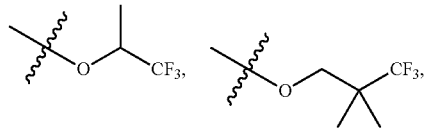

or —C$_{(4-6)}$alkyl, wherein said alkyl is optionally substituted with up to six fluorine atoms and pharmaceutically acceptable salts thereof.

DETAILED DESCRIPTION OF THE INVENTION

The present invention comprises a compound of Formula I:

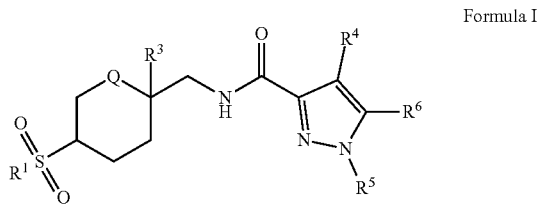

Formula I wherein
$R^1$ is $C_{(1-4)}$alkyl, —NH$_2$, —NHC(O)NH$_2$, —NHC(O)C$_{(1-4)}$alkyl, —NHC(O)NHC$_{(1-4)}$alkyl, —NHC$_{(1-4)}$alkyl, —NHC(O)H, or N(C$_{(1-4)}$alkyl)$_2$;
Q is CHR$^2$, NC(O)CH$_3$, NCH$_2$C(O)NH$_2$, NH, or O;
$R^2$ is H, —OH, or —NH$_2$;
$R^3$ is —H, —OH, —CN, —NH$_2$, —CONH$_2$, —CO$_2$H, —CO$_2$C$_{(1-4)}$alkyl, —CH$_2$OH, —CH$_2$NH$_2$, —CH$_2$CN, —NHC$_{(1-4)}$alkyl, or —CONHC$_{(1-4)}$alkyl;

R⁴ is —Cl, —C₍₁₋₄₎alkyl, —F, —CN, —C(O)NH₂,

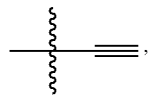 [SMILES: *C#C]

or —H; wherein said —C₍₁₋₄₎alkyl is optionally substituted with up to six fluorine atoms;
R⁵ is —C₍₁₋₄₎alkyl, wherein said —C₍₁₋₄₎alkyl is optionally substituted with —CN, —OH, —OCH₃, —OCF₃, or up to six fluorine atoms;
R⁶ is

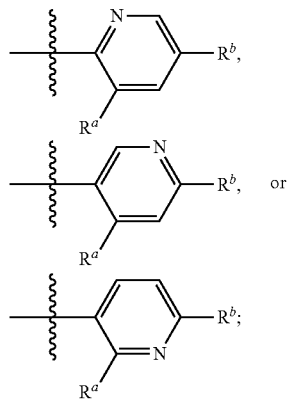

Rᵃ is —H, —F, —Cl, —OCD₃, —CN, —C₍₁₋₃₎alkyl, or —OC₍₁₋₃₎alkyl, wherein said —C₍₁₋₃₎alkyl and said OC₍₁₋₃₎alkyl are optionally substituted with up to three fluorine atoms;
Rᵇ is

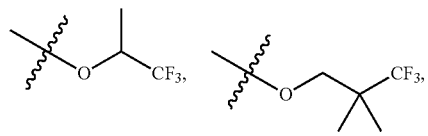

or —C₍₄₋₆₎alkyl, wherein said alkyl is optionally substituted with up to six fluorine atoms
and pharmaceutically acceptable salts thereof.
In another embodiment of the invention:
R¹ is —C₍₁₋₂₎alkyl, —NH₂, —NHC(O)NH₂, —NHC(O)C₍₁₋₂₎alkyl, —NHC(O)NHCH₃, —NHCH₃, —NHC(O)H, or —N(CH₃)₂;
Q is CHR², NC(O)CH₃, NCH₂C(O)NH₂, NH, or O;
R² is —H, —OH, or —NH₂;
R³ is —H, —OH, —CN, —NH₂, —CONH₂, —CO₂H, —CO₂CH₂CH₃, or —CH₂OH;
R⁴ is —Cl, —C₍₁₋₄₎alkyl, —F, —CN, —CF₃, —C(O)NH₂,

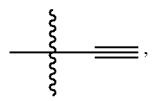

or —H;
R⁵ is C₍₁₋₄₎alkyl, wherein said C₍₁₋₄₎alkyl is optionally substituted with —CN, —OH, or —OCH₃;

R⁶ is

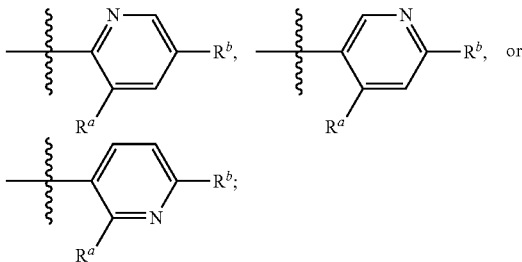

Rᵃ is —H, —F, —Cl, —OCD₃, —CN, —C₍₁₋₃₎alkyl, or —OC₍₁₋₃₎alkyl, wherein said —C₍₁₋₃₎alkyl and said OC₍₁₋₃₎alkyl are optionally substituted with up to three fluorine atoms;
Rᵇ is

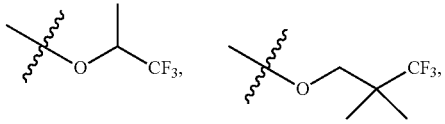

or —C₍₄₋₆₎alkyl, wherein said alkyl is optionally substituted with up to six fluorine atoms;
and pharmaceutically acceptable salts thereof.
In another embodiment of the invention:
R¹ is C₍₁₋₂₎alkyl, —NH₂, —NHC(O)NH₂, —NHC(O)C₍₁₋₂₎alkyl, —NHC(O)NHCH₃, —NHCH₃, —NHC(O)H, or —N(CH₃)₂;
Q is CHR²;
R² is —H or —OH;
R³ is —H, —OH, —CN, or —NH₂;
R⁴ is —Cl, —C₍₁₋₄₎alkyl, —F, or —CN;
R⁵ is —C₍₁₋₄₎alkyl;
R⁶ is

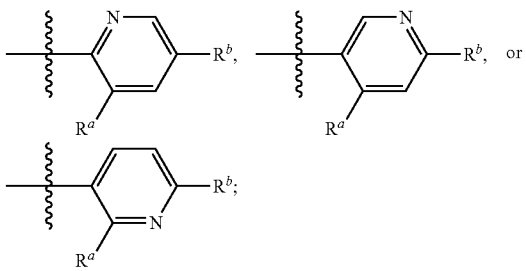

Rᵃ is —H, —F, —C₍₁₋₃₎alkyl, or —OC₍₁₋₃₎alkyl, wherein said —C₍₁₋₃₎alkyl and said OC₍₁₋₃₎alkyl are optionally substituted with up to three fluorine atoms;
Rᵇ is

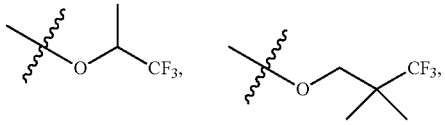

or —C$_{(4-6)}$alkyl, wherein said alkyl is optionally substituted with up to six fluorine atoms;
and pharmaceutically acceptable salts thereof.

In another embodiment of the invention:
R$^1$ is C$_{(1-2)}$alkyl, —NH$_2$, —NHC(O)NH$_2$, —NHC(O)C$_{(1-2)}$alkyl, or —NHC(O)NHCH$_3$;
Q is CHR$^2$;
R$^2$ is —H or —OH;
R$^3$ is —H or —OH;
R$^4$ is —Cl or —C$_{(1-4)}$alkyl;
R$^5$ is —C$_{(1-4)}$alkyl;
R$^6$ is

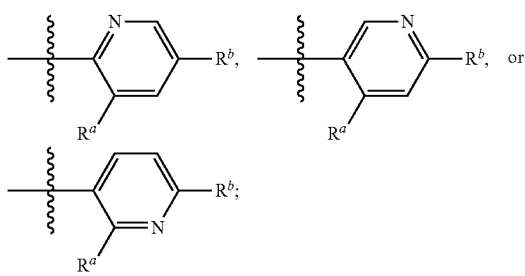

R$^a$ is —C$_{(1-3)}$alkyl, or —OC$_{(1-3)}$alkyl, wherein said —C$_{(1-3)}$alkyl and said OC$_{(1-3)}$alkyl are optionally substituted with up to three fluorine atoms;
R$^b$ is

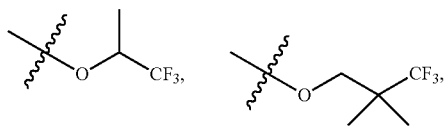

or —C$_{(4-6)}$alkyl, wherein said alkyl is optionally substituted with up to six fluorine atoms;
and pharmaceutically acceptable salts thereof.

In another embodiment of the invention:
R$^1$ is —CH$_3$, —NH$_2$, —NHC(O)NH$_2$, —NHC(O)CH$_3$, or —NHC(O)NHCH$_3$;
Q is CHR$^2$;
R$^2$ is —H or —OH;
R$^3$ is —H or —OH;
R$^4$ is —Cl or —CH$_3$;
R$^5$ is CH$_3$ or CH$_2$CH$_3$;
R$^6$ is

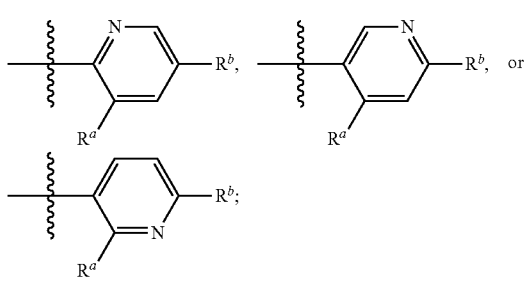

R$^a$ is —OCHF$_2$, —CF$_2$CH$_3$, —CH(CH$_3$)$_2$, —CHF$_2$, —CH$_2$CH$_3$, or —OCH$_3$;

R$^b$ is

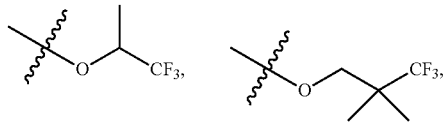

or —C$_{(4-6)}$alkyl, wherein said alkyl is optionally substituted with up to six fluorine atoms;
and pharmaceutically acceptable salts thereof.

Another embodiment of the invention is a compound selected from the group consisting of:

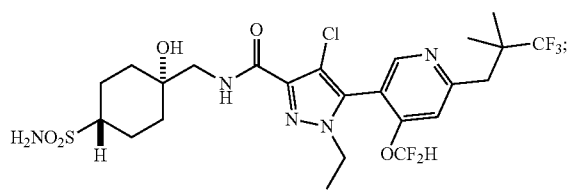

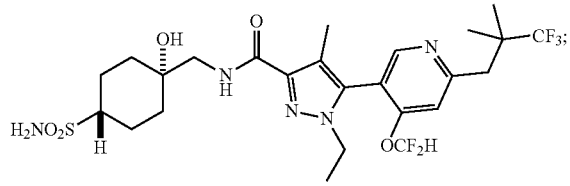

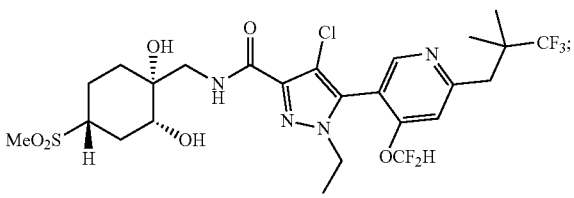

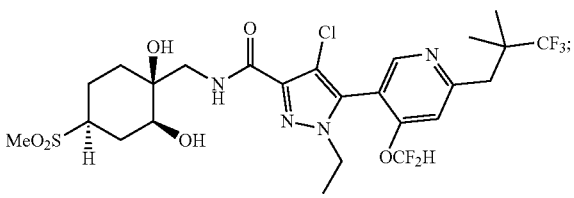

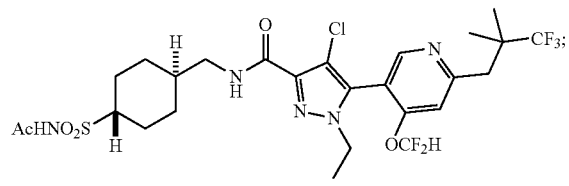

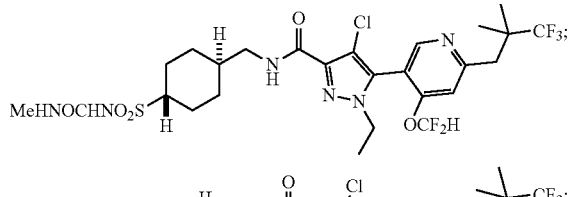

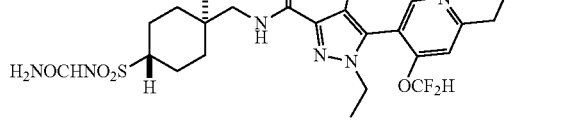

-continued

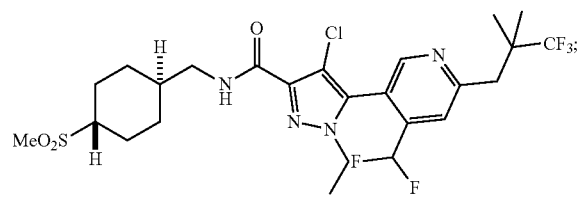
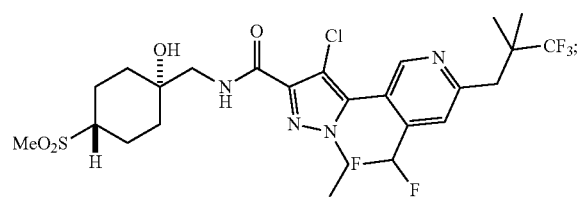
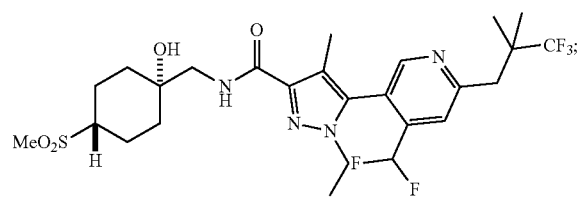
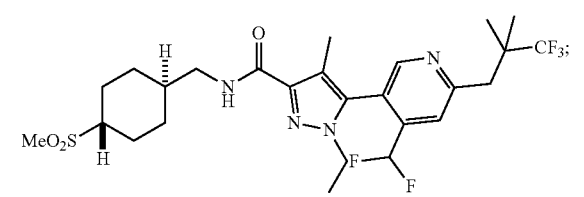
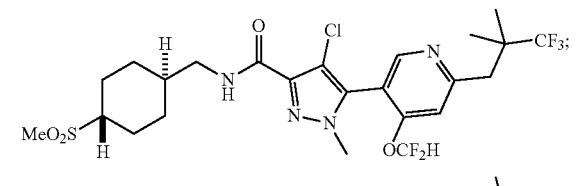
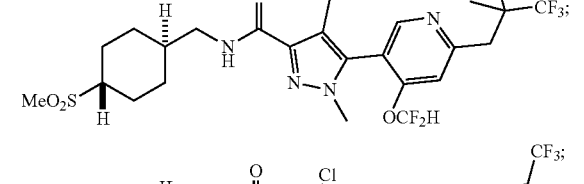
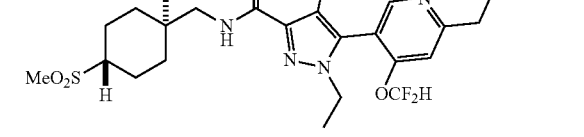
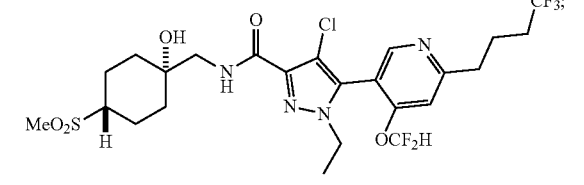
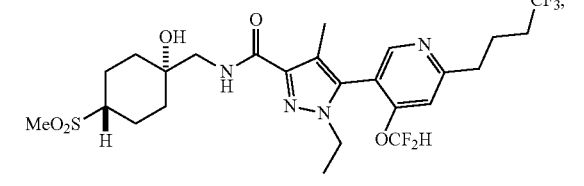
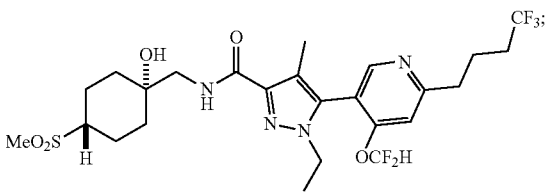
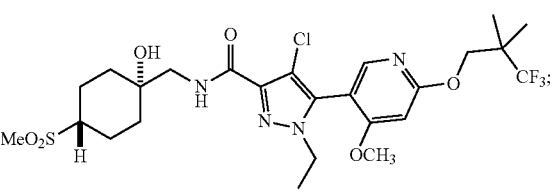
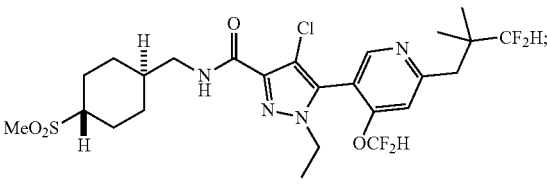
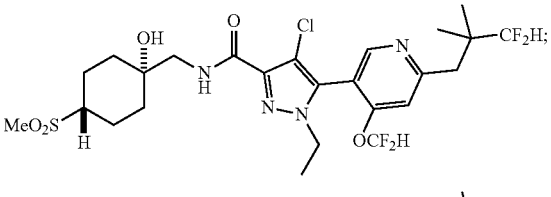
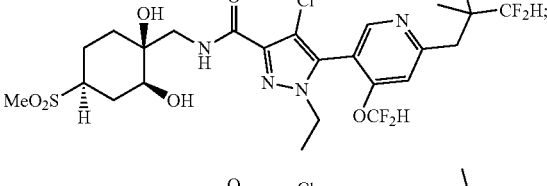
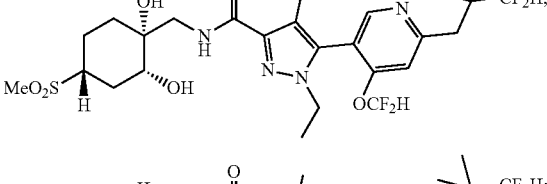
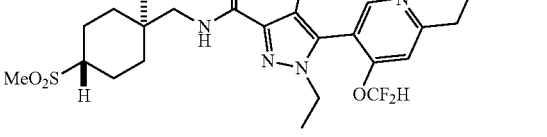
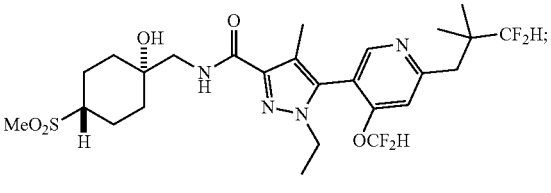
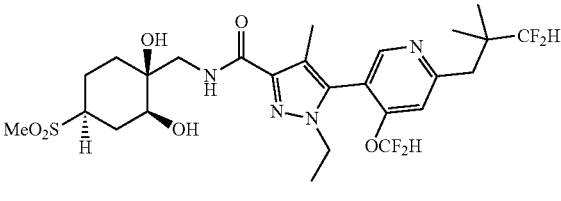

13
-continued
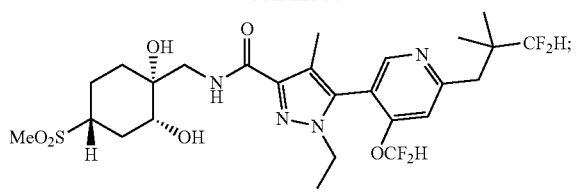
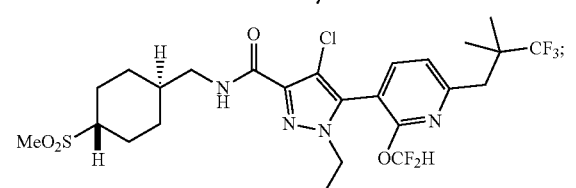
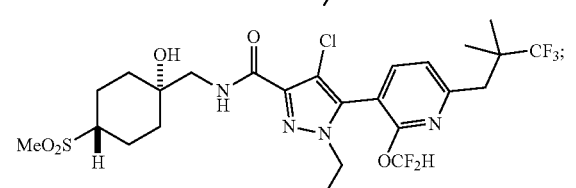
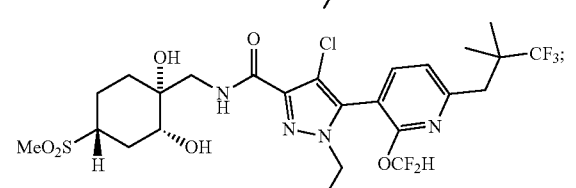
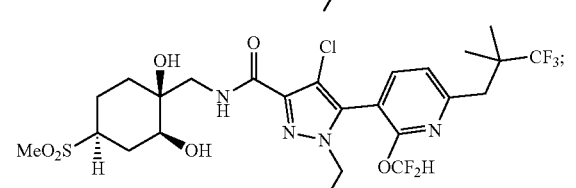
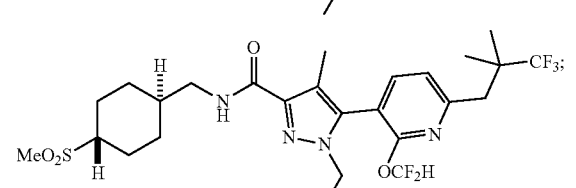
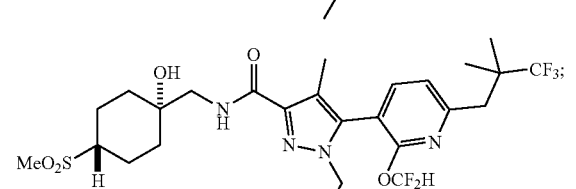
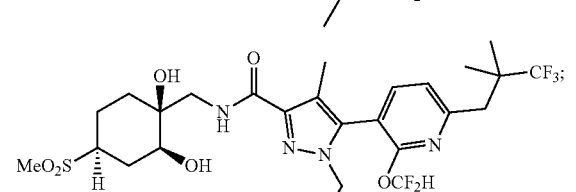
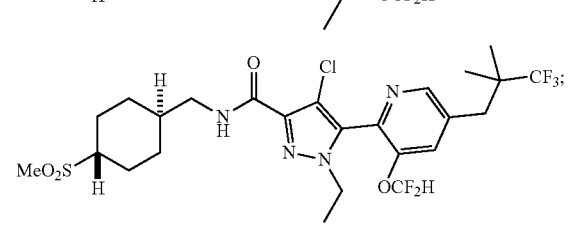
14
-continued
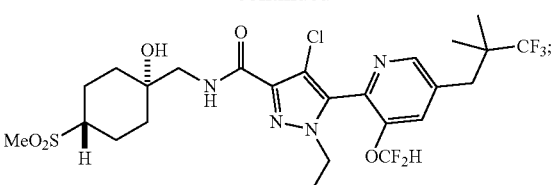
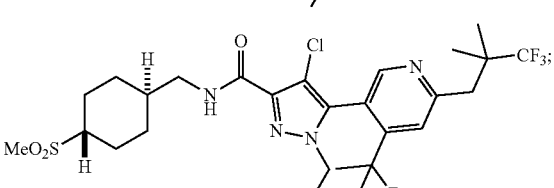
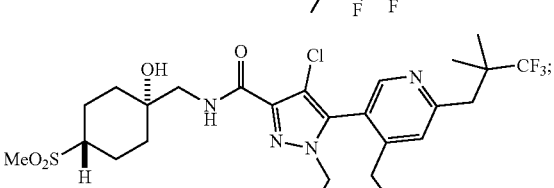
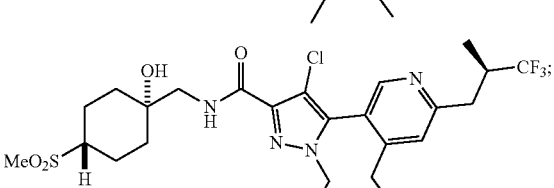
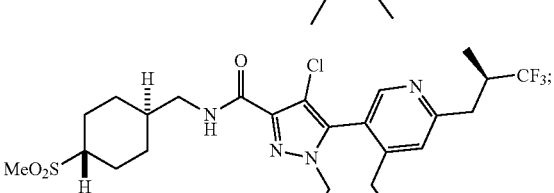
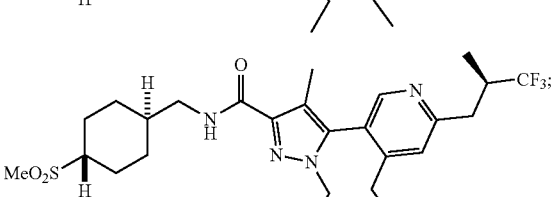
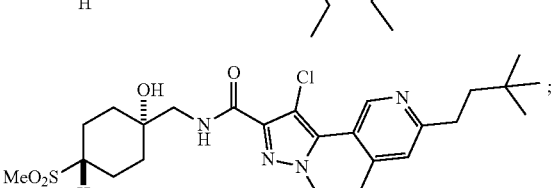
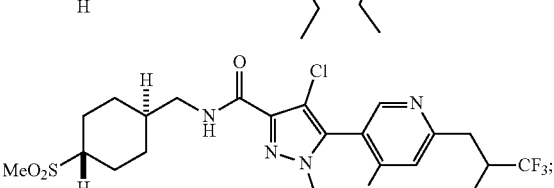
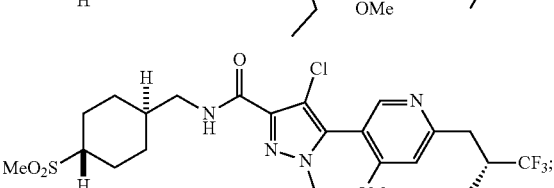

-continued

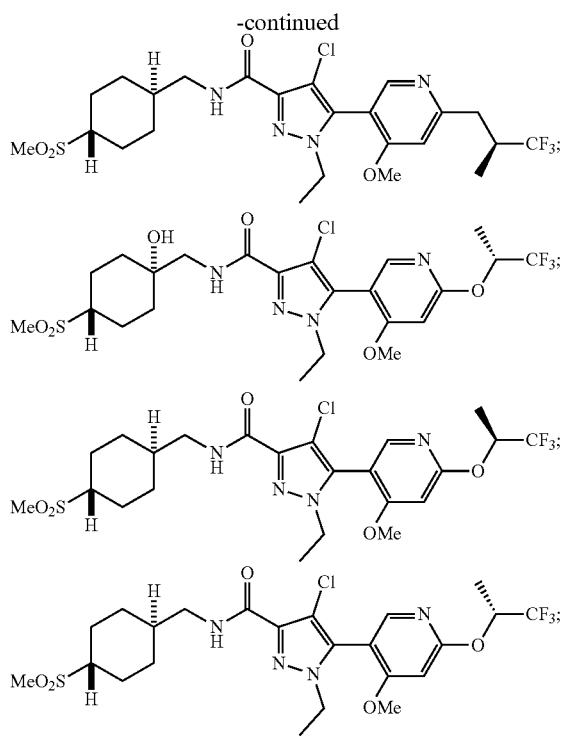

and pharmaceutically acceptable salts thereof.

Another embodiment of the invention comprises a compound of Formula I and a pharmaceutically acceptable carrier.

The present invention also provides a method for preventing, treating or ameliorating an RORγt mediated inflammatory syndrome, disorder or disease comprising administering to a subject in need thereof an effective amount of a compound of Formula I or a form, composition or medicament thereof.

The present invention provides a method of preventing, treating or ameliorating a syndrome, disorder or disease, wherein said syndrome, disorder or disease is selected from the group consisting of: ophthalmic disorders, uveitis, atherosclerosis, rheumatoid arthritis, psoriasis, psoriatic arthritis, atopic dermatitis, multiple sclerosis, Crohn's Disease, ulcerative colitis, ankylosing spondylitis, nephritis, organ allograft rejection, fibroid lung, systic fibrosis, renal insufficiency, diabetes and diabetic complications, diabetic nephropathy, diabetic retinopathy, diabetic retinitis, diabetic microangiopathy, tuberculosis, chronic obstructive pulmonary disease, sarcoidosis, invasive staphylococcia, inflammation after cataract surgery, allergic rhinitis, allergic conjunctivitis, chronic urticaria, systemic lupus erythematosus, asthma, allergic asthma, steroid resistant asthma, neutrophilic asthma, periodontal diseases, periodontitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, carcinomas of the bladder, breast, cervix, colon, lung, prostate, or stomach, depression and metabolic syndrome comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis.

The present invention provides a method of treating or ameliorating a syndrome, disorder or disease, wherein said syndrome, disorder or disease is selected from the group consisting of: depression and metabolic syndrome.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, systemic lupus erythematosus, depression and metabolic syndrome comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, and psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: psoriatic arthritis and psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: depression and metabolic syndrome comprising administering to a subject in need thereof an effective amount of a compound of Formula I or a form, composition or medicament thereof.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: rheumatoid arthritis, and psoriasis.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: psoriatic arthritis and psoriasis.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: depression and metabolic syndrome.

The present invention provides a method of treating or ameliorating a syndrome, disorder or disease, wherein said syndrome, disorder or disease is rheumatoid arthritis, comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is chronic obstructive pulmonary disorder comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriatic arthritis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is ankylosing spondylitis comprising administering to a subject in need thereof an effective amount of a compound of Formula I or a form, composition or medicament thereof.

The present invention provides a method of treating or ameliorating an inflammatory bowel disease, wherein said inflammatory bowel disease is Crohn's disease comprising administering to a subject in need thereof an effective amount of a compound of Formula I or a form, composition or medicament thereof.

The present invention provides a method of treating or ameliorating an inflammatory bowel disease, wherein said inflammatory bowel disease is ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is neutrophilic asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is steroid resistant asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is multiple sclerosis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is systemic lupus erythematosus comprising administering to a subject in need thereof an effective amount of a compound of Formula I or a form, composition or medicament thereof.

The present invention provides a method of treating or ameliorating a syndrome, disorder or disease, wherein said syndrome, disorder or disease is depression comprising administering to a subject in need thereof an effective amount of a compound of Formula I or a form, composition or medicament thereof.

The present invention provides a method of treating or ameliorating a syndrome, disorder or disease, wherein said syndrome, disorder or disease is metabolic syndrome comprising administering to a subject in need thereof an effective amount of a compound of Formula I or a form, composition or medicament thereof.

The invention also relates to methods of modulating RORγt activity in a mammal by administration of an effective amount of at least one compound of Formula I.

Another embodiment of the invention is a method of inhibiting production of interleukin-17, comprising administering to a subject in need thereof an effective amount of a compound of Formula I.

Definitions

The term "administering" with respect to the methods of the invention, means a method for therapeutically or prophylactically preventing, treating or ameliorating a syndrome, disorder or disease as described herein by using a compound of Formula I or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be an animal, typically a mammal, typically a human, which has been the object of treatment, observation or experiment and is at risk of (or susceptible to) developing a syndrome, disorder or disease that is associated with aberrant RORγt expression or RORγt overexpression, or a patient with an inflammatory condition that accompanies syndromes, disorders or diseases associated with aberrant RORγt expression or RORγt overexpression.

The term "effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

As used herein, the term "composition" is intended to encompass a product comprising the specified ingredients in the specified amounts, as well as any product which results, directly or indirectly, from combinations of the specified ingredients in the specified amounts.

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl. Any alkyl group may be optionally substituted with one $OCH_3$, one OH, or up to two fluorine atoms.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

Pharmaceutically Acceptable Salts

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate, sodium hydroxide, triethanolamine, or zinc.

Methods of Use

The present invention is directed to a method for preventing, treating or ameliorating a RORγt mediated inflammatory syndrome, disorder or disease comprising administering to a subject in need thereof an effective amount of a compound of Formula I or a form, composition or medicament thereof.

Since RORγt is an N-terminal isoform of RORγ, it is recognized that compounds of the present invention which are modulators of RORγt are likely to be modulators of RORγ as well. Therefore the mechanistic description "RORγt modulators" is intended to encompass RORγ modulators as well.

When employed as RORγt modulators, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in Formula I for use as a medicament.

In another embodiment, the invention relates to the use of a compound as described in Formula I for the preparation of a medicament for the treatment of a disease associated with an elevated or aberrant RORγt activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Furthermore, it is intended that within the scope of the present invention, any element, in particular when mentioned in relation to a compound of Formula I, shall comprise all isotopes and isotopic mixtures of said element, either naturally occurring or synthetically produced, either with natural abundance or in an isotopically enriched form. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O. The isotopes may be radioactive or non-radioactive. Radiolabelled compounds of Formula I may comprise a radioactive isotope selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

Some compounds of the present invention may exist as atropisomers. Atropisomers are stereoisomers resulting from hindered rotation about single bonds where the steric strain barrier to rotation is high enough to allow for the isolation of the conformers. It is to be understood that all such conformers and mixtures thereof are encompassed within the scope of the present invention.

Where the compounds according to this invention have at least one stereo center, they may accordingly exist as enantiomers or diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral column vial HPLC or SFC. In some instances rotamers of compounds may exist which are observable by 1H NMR leading to complex multiplets and peak integration in the 1H NMR spectrum.

Chiral centers, of which the absolute configurations are known, are labelled by prefixes R and S, assigned by the standard sequence-rule procedure, and preceded when necessary by the appropriate locants. Chiral centers, of which the relative but not the absolute configurations are known, are labelled arbitrarily by prefixes R* and S*, preceded when necessary by the appropriate locants. These prefixes are assigned by the standard sequence-rule procedure on the arbitrary assumption that the center of chirality with the lowest locant has chirality R. When a compound contains chiral centers with known absolute configurations and a sterically unrelated set of chiral centers with known relative configurations but unknown absolute configurations, then R* and S* are used to designate the latter. (*Pure & Appl. Chem.* 45, 1976, 11-30). Racemates containing a single chiral center are labelled RS or are not labelled. For racemates with more than one chiral center, the chiral center with the lowest locant is labelled RS and the others are labelled RS or SR according to whether they are R or S when the chiral center with the lowest locant is R. Pseudoasymmetric stereogenic centers are treated in the same way as chiral centers, but are given lower-case symbols, r or s (*Angew. Chem. Int. Ed. Engl.* 1982, 21, 567-583).

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Abbreviations

Herein and throughout the application, the following abbreviations may be used.

Ac acetyl
9-BBN 9-borabicyclo[3.3.1]nonane
Boc tert-butyloxycarbonyl
br broad
Bu butyl Cbz carboxybenzyl
δ NMR chemical shift in parts per million downfield from a standard
d doublet
DABSO 1,4-diazabicyclo[2.2.2]octane bis(sulfur dioxide) adduct
DAST (diethylamino)sulfur trifluoride
DCE dichloroethane
DCM dichloromethane
Deoxo-Fluor® bis(2-methoxyethyl)aminosulfur trifluoride
DIPEA N,N-diisopropylethylamine (Hünig's base)
DMA N,N-dimethylacetamide
DMAP 4-(dimethylamino)pyridine
DME 1,2-dimethoxyethane
DMEN N,N-dimethylethylenediamine
DMF N,N-dimethylformamide
DMSO dimethyl sulfoxide
DMI 1,3-dimethyl-2-imidazolidinone
dppf 1,1'-bis(diphenylphosphino)ferrocene
dtbpf 1,1'-bis(di-tert-butylphosphino)ferrocene
EDCI 1-ethyl-3-(3-dimethylaminopropyl) carbodiimide hydrochloride
ESI electrospray ionization
Et ethyl
g grams(s)
h hour(s)
HATU 0-(7-azabenzotriazol-1-yl)-N,N,N',N'-tetramethyluronium hexafluorophosphate
HMDS hexamethyldisilazane
HOBt 1-hydroxybenzotriazole
HPLC high-performance liquid chromatography
Hz Hertz
i iso
IPA isopropanol
J coupling constant (NMR spectroscopy)
L liter(s)
LAH lithium aluminum hydride
LDA lithium diisopropylamide
m milli or multiplet
m/z mass-to-charge ratio
M+ parent molecular ion
M molar (moles/liter) or mega
mCPBA 3-chloroperbenzoic acid
Me methyl
MeCN acetonitrile
min minute(s)
µ micro
MS mass spectrometry
MTBE tert-butyl methyl ether
n normal (chemical nomenclature prefix)
n nano
N normal (equivalent concentration)
NBS N-bromosuccinimide
NCS N-chlorosuccinimide
NFSI N-fluorobenzenesulfonimide
NMO 4-methylmorpholine N-oxide
NMP 1-methyl-2-pyrrolidone
NMR nuclear magnetic resonance
Pd/C palladium on carbon
PEPPSI-IPr [1,3-bis(2,6-diisopropylphenyl)imidazol-2-ylidene](3-chloropyridyl)palladium(II) dichloride
Ph phenyl
Pr propyl
q quartet
rt room temperature
RuPhos 2-Dicyclohexylphosphino-2',6'-diisopropoxybiphenyl
RuPhos G1 chloro-(2-dicyclohexylphosphino-2',6'-diisopropoxy-1,1'-biphenyl)[2-(2-aminoethyl)phenyl]palladium(II)
RuPhos G2 chloro(2-dicyclohexylphosphino-2',6'-diisopropoxy-1,1'-biphenyl)[2-(2'-amino-1,1'-biphenyl)]palladium(II)
s singlet
SFC supercritical fluid chromatography
t tert
t triplet
TEA triethylamine
TFA trifluoroacetic acid
THF tetrahydrofuran
TMS trimethylsilyl
TosMIC p-toluenesulfonylmethyl isocyanide
Ts p-toluenesulfonyl
T3P propanephosphonic acid anhydride
v/v volume-to-volume ratio
wt % weight percent
w/w weight-to-weigh ratio General Schemes:

Compounds of Formula I in the present invention can be synthesized in accordance with the general synthetic methods known to those who are skilled in the art. The following reaction schemes are only meant to represent examples of the invention and are in no way meant to be a limit of the invention.

Compounds of Formula I can be prepared according to Scheme 1. Pyrazole esters A-I can undergo hydrolysis using aqueous hydroxide solution in a cosolvent such as 1,4-dioxane or THF to give carboxylic acids A-II. Amides of Formula I can be formed by reaction of A-II with amines or amine salts promoted by a reagent such as HATU, T3P, or EDCI and a base such as DIPEA in a solvent such as DMF or MeCN. Amides of Formula I ($R^4$=Cl) can undergo Suzuki cross-coupling reaction with an organoboron reagent such as trimethylboroxine using a palladium precatalyst and ligand combination such as RuPhos G1/RuPhos and a carbonate base such as $K_2CO_3$ in a solvent such as 1,4-dioxane to give amides of Formula I ($R^4$=Me). Amides of Formula I ($R^1$=$NH_2$) can undergo reactions with electrophiles such as carboxylic acid anhydrides or isocyanates promoted by reagents such as Lewis acids or carbonate bases to give amides of Formula I ($R^1$=$NHCOR^7$). Chloropyridine pyrazole esters A-III can undergo palladium-catalyzed cross-coupling reaction with C-nucleophiles such as organoboron or organozinc reagents to give amides of Formula I.

Scheme 1

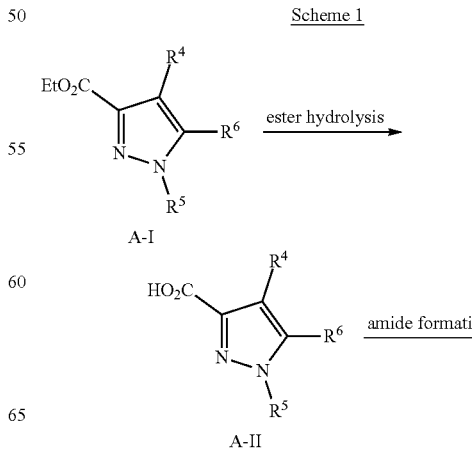

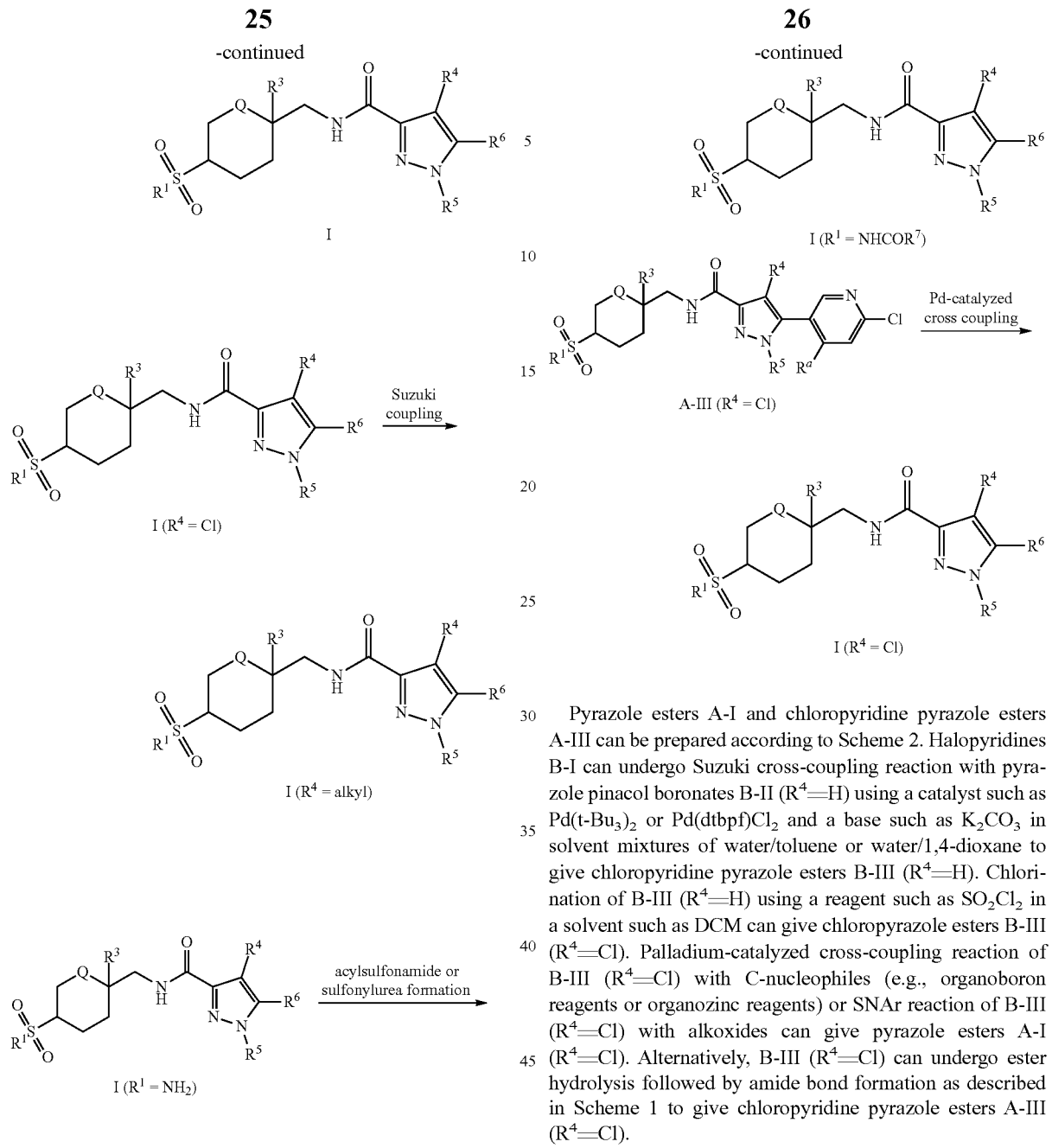

Pyrazole esters A-I and chloropyridine pyrazole esters A-III can be prepared according to Scheme 2. Halopyridines B-I can undergo Suzuki cross-coupling reaction with pyrazole pinacol boronates B-II ($R^4$=H) using a catalyst such as Pd(t-Bu$_3$)$_2$ or Pd(dtbpf)Cl$_2$ and a base such as K$_2$CO$_3$ in solvent mixtures of water/toluene or water/1,4-dioxane to give chloropyridine pyrazole esters B-III ($R^4$=H). Chlorination of B-III ($R^4$=H) using a reagent such as SO$_2$Cl$_2$ in a solvent such as DCM can give chloropyrazole esters B-III ($R^4$=Cl). Palladium-catalyzed cross-coupling reaction of B-III ($R^4$=Cl) with C-nucleophiles (e.g., organoboron reagents or organozinc reagents) or SNAr reaction of B-III ($R^4$=Cl) with alkoxides can give pyrazole esters A-I ($R^4$=Cl). Alternatively, B-III ($R^4$=Cl) can undergo ester hydrolysis followed by amide bond formation as described in Scheme 1 to give chloropyridine pyrazole esters A-III ($R^4$=Cl).

Scheme 2

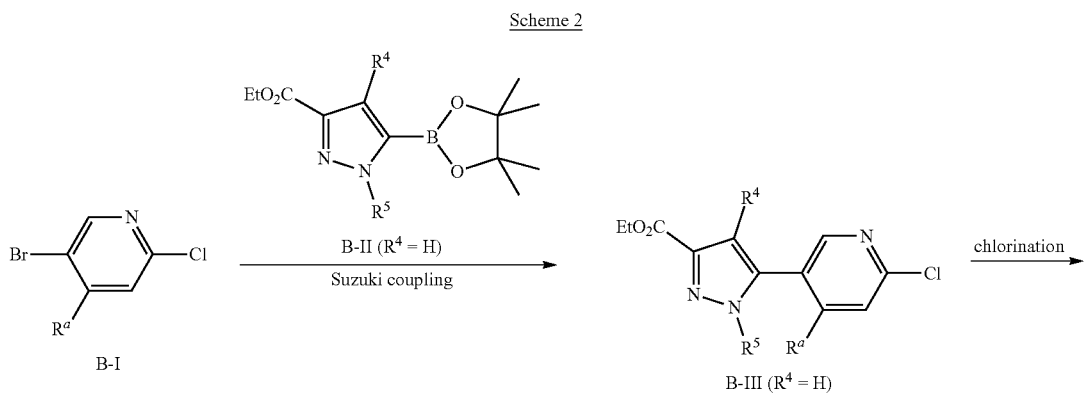

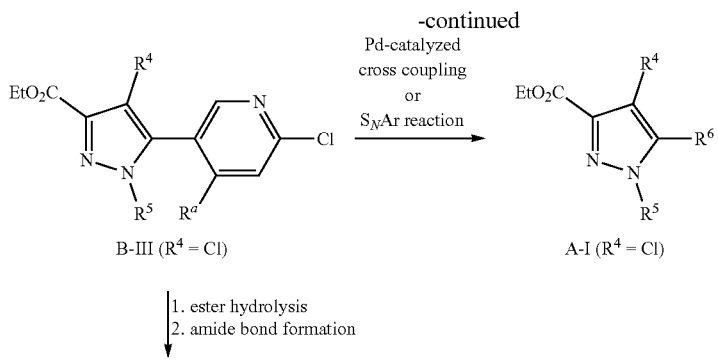

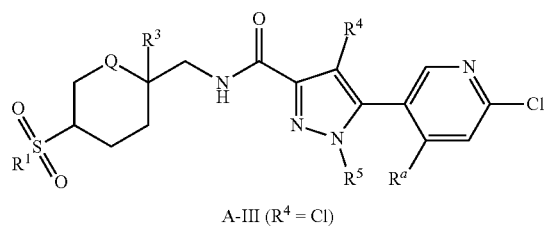

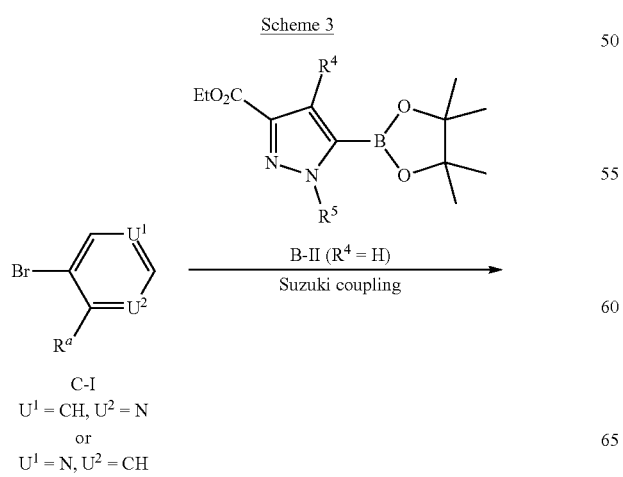

An alternative preparation of pyrazole esters A-I is described in Scheme 3. Bromopyridines C-I can undergo Suzuki cross-coupling reaction with pyrazole pinacol boronates B-II ($R^4$=H) using a catalyst such as Pd(t-Bu$_3$)$_2$ and a base such as K$_2$CO$_3$ in a solvent mixture such as 1,4-dioxane/water to give pyridine pyrazole esters C-II ($R^4$=H). Chlorination of C-II ($R^4$=H) using a reagent such as SO$_2$Cl$_2$ in a solvent such as DCM can give chloropyrazole esters C-II ($R^4$=Cl). Oxidation of C-II ($R^4$=Cl) using a reagent such as mCPBA in a solvent such as DCM can give the corresponding pyridine N-oxides, which can be converted to chloropyridines C-III ($R^4$=Cl) by heating in neat POCl$_3$. Palladium-catalyzed cross-coupling reaction of C-III ($R^4$=Cl) with C-nucleophiles such as organoboron reagents or organozinc reagents can give pyrazole esters A-I ($R^4$=Cl).

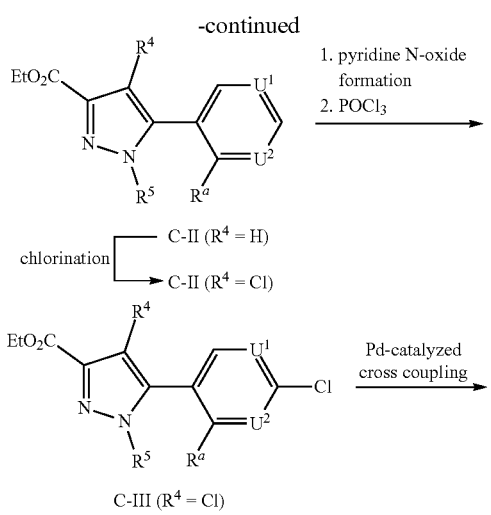

An additional preparation of pyrazole esters A-I is described in Scheme 4. Crossed-Claisen condensation reaction between 1-(5-bromo-3-methoxypyridin-2-yl)ethan-1-one (D-I) and diethyl oxalate, followed by condensation of the resulting ethyl dioxobutanoate with alkylhydrazines can give D-II ($R^4$=H). Methyl ether dealkylation of D-II ($R^4$=H) using TMSI in a solvent such as MeCN, followed by difluoromethylation using a reagent such as sodium 2-chloro-2,2-difluoroacetate and a base such as K$_2$CO$_3$ in a solvent such as DMF can give bromopyridine pyrazole esters D-III (R⁴=H). Chlorination of D-III (R⁴=H) using a reagent such as SO₂Cl₂ in a solvent such as DCM can give D-III (R⁴=Cl). Palladium-catalyzed cross-coupling reaction of D-III (R⁴=Cl) with C-nucleophiles such as organoboron reagents or organozinc reagents can give pyrazole esters A-I.

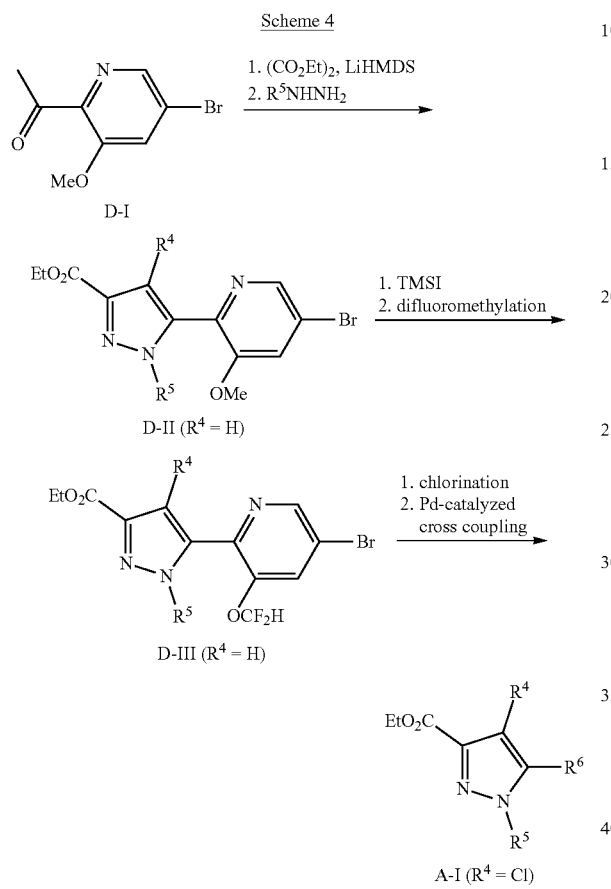

Pyrazole esters A-I can be transformed as described in Scheme 5. Chlorination of pyrazole esters A-I (R⁴=H) using a reagent such as SO₂Cl₂ in a solvent such as DCM can give A-I (R⁴=Cl). Pyrazole esters A-I (R⁴=Cl) can undergo Suzuki cross-coupling reaction with an organoboron reagent such as trimethylboroxine using a palladium precatalyst and ligand combination such as RuPhos G1/RuPhos and a carbonate base such as K₂CO₃ in a solvent such as 1,4-dioxane to give A-I (R⁴=Me).

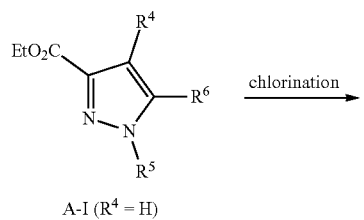

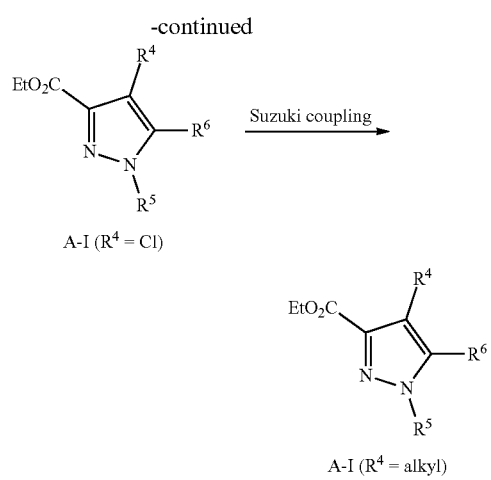

An alternative preparation of chloropyridine pyrazole esters B-III (R⁴=H) is described in Scheme 6. Crossed-Claisen condensation reaction between pyridinyl ketones E-I and diethyl oxalate, followed by condensation of the resulting ethyl dioxobutanoates with alkylhydrazines can give B-III (R⁴=H).

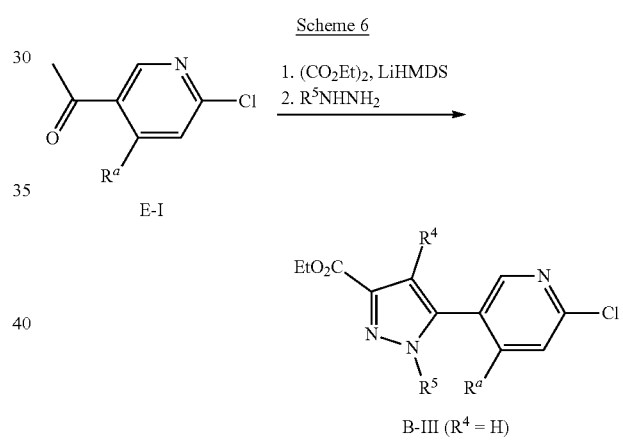

Pyrazole pinacol boronates B-II (R⁴=H) can be prepared as described in Scheme 7. Alkylation of pyrazole ester F-1 (R⁴=H) with an iodoalkane using a base such as K₂CO₃ in a solvent such as THF can give N-alkylpyrazole esters F-II (R⁴=H). Iridium catalyzed CH borylation of F-II (R⁴=H) using pinacolborane, a catalyst such as (1,5-cyclooctadiene)(methoxy)iridium(I) dimer and a ligand such as 1,10-phenanthroline in a solvent mixture such as pentane/THF can give pyrazole pinacol boronates B-II (R⁴=H).

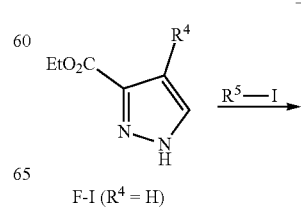

-continued

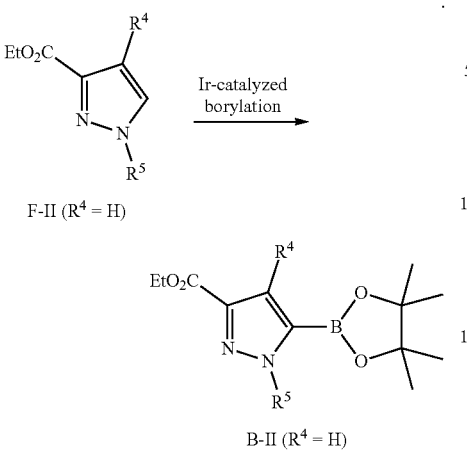

F-II (R⁴ = H)

Ir-catalyzed borylation

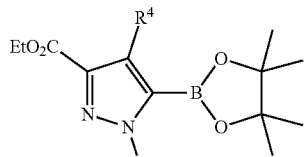

B-II (R⁴ = H)

Ketones D-I and E-I can be prepared as described in Scheme 8. Reaction of 5-bromo-3-nitropicolinonitrile (G-I) with NaOMe in a solvent such as MeOH can give 5-bromo-3-methoxypicolinonitrile (G-II). Grignard addition reaction between MeMgBr and G-II in a solvent such as THF can give 1-(5-bromo-3-methoxypyridin-2-yl)ethan-1-one (D-I). Hydrolysis of nicotinate ester G-III using aqueous NaOH in a cosolvent such as 1,4-dioxane, followed by conversion of the resulting carboxylic acid to the corresponding Weinreb amide using a combination of reagents such as EDCI, HOBt, and TEA in a solvent such as MeCN can give G-IV. Grignard addition reaction between MeMgBr and Weinreb amide G-IV in a solvent such as THF can give pyridinyl ketones E-I.

-continued

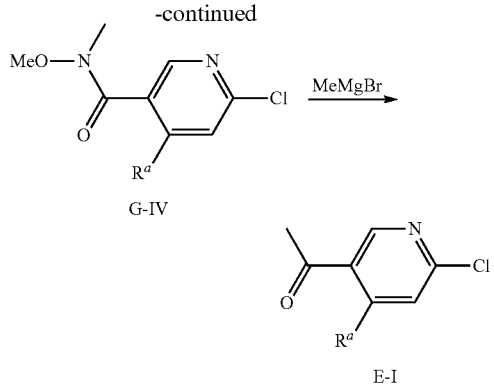

G-IV

MeMgBr

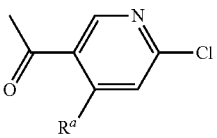

E-I

Halopyridines B-I and C-I can be purchased from commercial suppliers or prepared as described in Scheme 9. Bromination of 2-chloropyridin-4-ol (H-I) using a reagent such as NBS in a solvent such as AcOH can give 3,5-dibromo-2-chloropyridin-4-ol (H-II). Lithiumhalogen exchange reaction between H-II and n-BuLi in a solvent such as THF, followed by protodemetalation using a proton source such as water can give 5-bromo-2-chloropyridin-4-ol (H-III). Difluoromethylation of H-III using a reagent such as sodium chlorodifluoroacetate and a base such as $Cs_2CO_3$ in a solvent such as DMF can give 5-bromo-2-chloro-4-(difluoromethoxy)pyridine (B-I; $R^a$=$OCF_2H$). Lithiation of 5-bromo-2-chloropyridine (B-I; $R^a$=H) using LDA, followed by reaction with iodoethane can give 5-bromo-2-chloro-4-ethylpyridine (B-I; $R^a$=Et). Difluorination of 3-bromoisonicotinaldehyde (H-IV) using a reagent such as Deoxo-Fluor® in a solvent such as DCM can give 3-bromo-4-(difluoromethyl)pyridine (C-I; $U^1$=N, $U^2$=CH, $R^a$=$CF_2H$). Grignard addition reaction between MeMgBr and H-IV in a solvent such as THF, followed by oxidation of the resulting alcohol using $MnO_2$ in a solvent such as toluene can give 1-(3-bromopyridin-4-yl)ethan-1-one (H-V). Difluorination of H-V using a reagent such as DAST in a solvent such as DCM can give 3-bromo-4-(difluoromethyl)pyridine (C-I; $U^1$=N, $U^2$=CH, $R^a$=$CF_2Me$). Sequential treatment of 3-bromopyridine (H-VI) with $BF_3 \cdot Et_2O$, i-PrMgCl·LiCl, and then chloranil in a solvent such as THF can give 3-bromo-4-isopropylpyridine (C-I; $U^1$=N, $U^2$=CH, $R^a$=i-Pr). Difluoromethylation of 3-bromopyridin-4-ol (H-VII) using a reagent such as sodium chlorodifluoroacetate and a base such as $Cs_2CO_3$ in a solvent such as DMF can give 3-bromo-4-(difluoromethoxy)pyridine (C-I; $U^1$=N, $U^2$=CH, $R^a$=$OCF_2H$). Difluoromethylation of 3-bromopyridin-2-ol (H-VIII) using a reagent such as 2,2-difluoro-2-(fluorosulfonyl)acetic acid and a base such as $Na_2CO_3$ in a solvent such as MeCN can give 3-bromo-2-(difluoromethoxy)pyridine (C-I; $U^1$=CH, $U^2$=N, $R^a$=$OCF_2H$).

Scheme 8

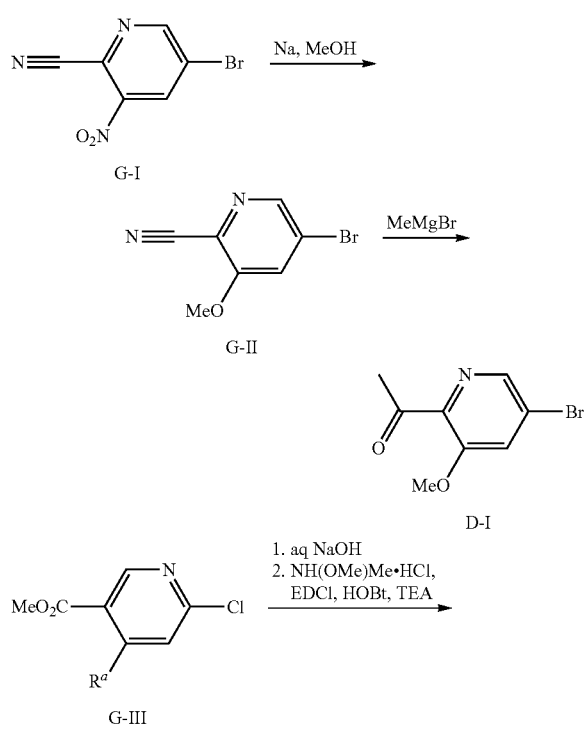

Scheme 9

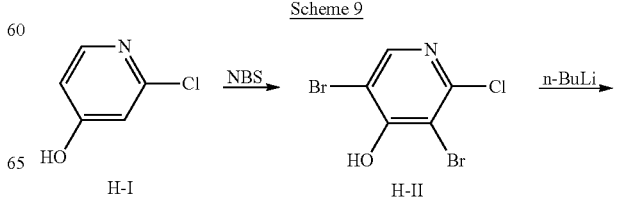

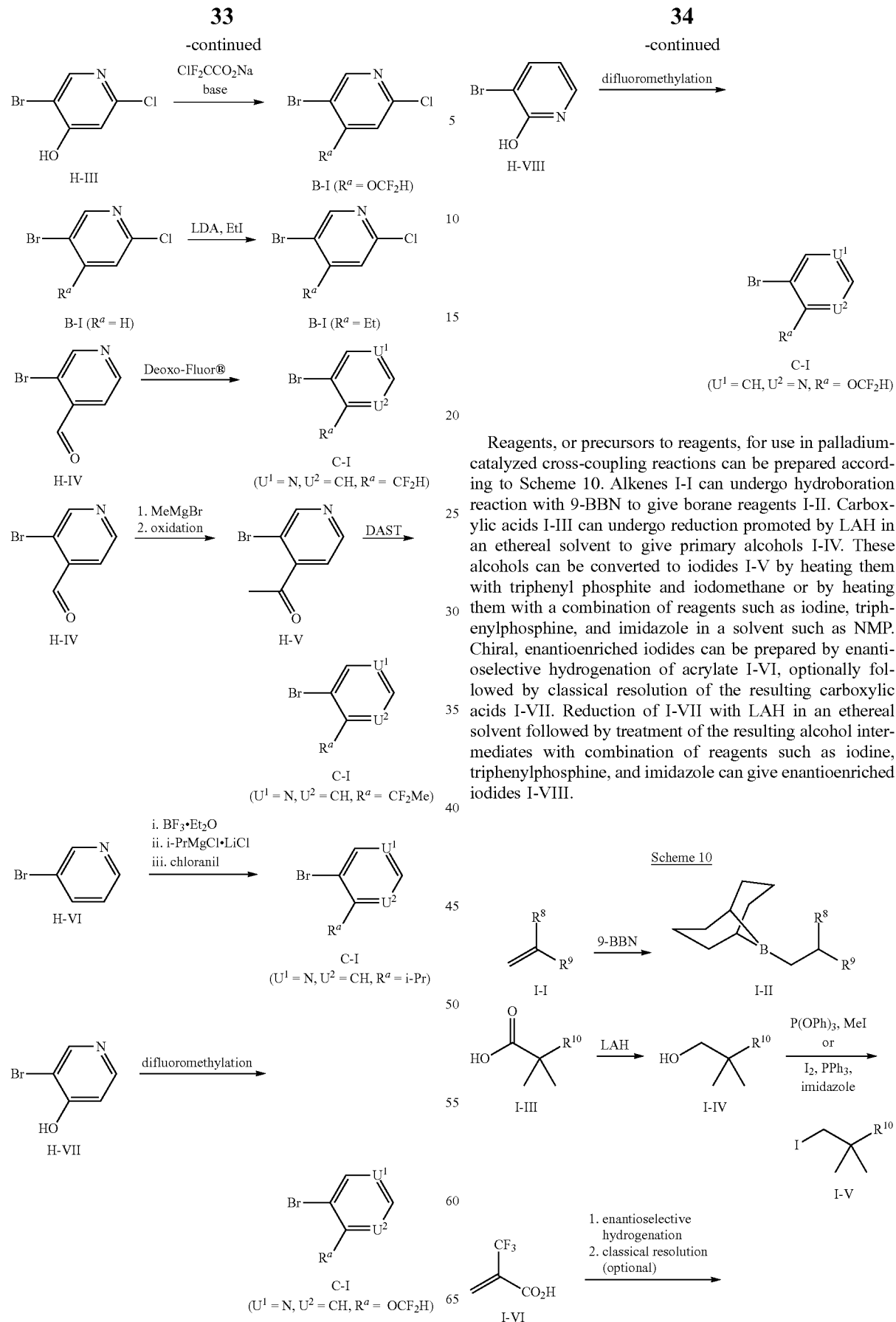

Reagents, or precursors to reagents, for use in palladium-catalyzed cross-coupling reactions can be prepared according to Scheme 10. Alkenes I-I can undergo hydroboration reaction with 9-BBN to give borane reagents I-II. Carboxylic acids I-III can undergo reduction promoted by LAH in an ethereal solvent to give primary alcohols I-IV. These alcohols can be converted to iodides I-V by heating them with triphenyl phosphite and iodomethane or by heating them with a combination of reagents such as iodine, triphenylphosphine, and imidazole in a solvent such as NMP. Chiral, enantioenriched iodides can be prepared by enantioselective hydrogenation of acrylate I-VI, optionally followed by classical resolution of the resulting carboxylic acids I-VII. Reduction of I-VII with LAH in an ethereal solvent followed by treatment of the resulting alcohol intermediates with combination of reagents such as iodine, triphenylphosphine, and imidazole can give enantioenriched iodides I-VIII.

-continued

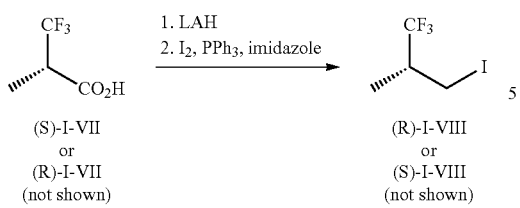

(S)-I-VII
or
(R)-I-VII
(not shown)

1. LAH
2. I₂, PPh₃, imidazole →

(R)-I-VIII
or
(S)-I-VIII
(not shown)

(1s,4s)-1-(Aminomethyl)-4-(methylsulfonyl)cyclohexan-1-ol hydrochloride ((s,s)-J-VI) can be prepared according to Scheme 11. Reduction of 1,4-dioxaspiro[4.5]decan-8-one (J-I) with a reagent such as NaBH₄, followed by mesylation of the resulting secondary alcohol can give cyclohexane mesylate J-II. Reaction of J-II with sodium thiomethoxide in a polar aprotic solvent, followed by hydrolytic cleavage of the 1,3-dioxolane group promoted by an aqueous acid such as HCl can give cyclohexanone sulfide J-III. Oxidation of the sulfide of with a reagent such as mCPBA can give cyclohexanone sulfone J-IV. Cyanosilylation of J-IV using TMSCN and TEA can give nitrile J-V. Reduction of J-V with borane followed by quenching with HCl can give a diastereomeric mixture of amino alcohol HCl salts, J-VI. Equilibration of the isomeric mixture can be promoted by heating with an alkoxide base, such as t-BuONa, in THF/t-BuOH to enrich the mixture in the s,s isomer. Once the thermodynamic ratio is reached, the mixture can undergo reaction with Boc₂O, and the resulting product can be triturated with EtOAc/n-heptane to provide the stereochemically pure hydroxy carbamate (s,s)-J-VII. Removal of the Boc group under acidic conditions, such as ethanolic HCl, can give amine salt (s,s)-J-VI.

Scheme 11

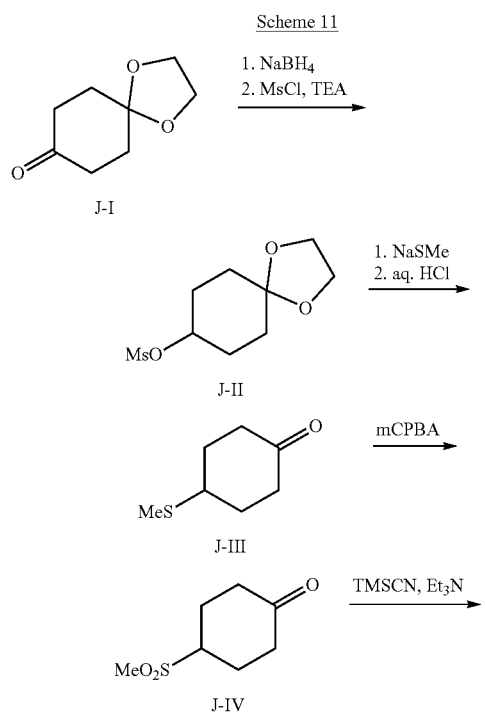

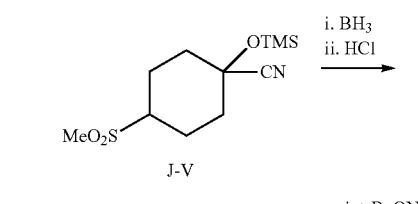

((1r,4r)-4-(Methyl sulfonyl)cyclohexyl)methanamine hydrochloride (trans-K-III.HCl) can be prepared according to Scheme 12. Reductive cyanation of cyclohexanone sulfide J-III using TosMIC with an alkoxide base, such as t-BuONa, in an ethereal solvent can give cyanocyclohexane sulfide K-I. Oxidation of K-I with a reagent system such as Oxone® in acetone/water can give cyanocyclohexane sulfone K-II. Reduction of K-II with LAH in an ethereal solvent can give amine K-III as a mixture of cis and trans isomers. The corresponding Boc carbamate intermediate, K-IV, can be prepared if K-III is not isolated, but instead Boc₂O is added to the solution generated after quenching and filtering the LAH reduction reaction mixture. Isolation of K-IV followed by sequential triturations using IPA/n-heptanes and then EtOAc/n-heptanes can provide stereochemically pure trans-K-IV. Removal of the Boc group under acidic conditions, such as ethanolic HCl, can give amine salt trans-K-III.HCl.

Scheme 12

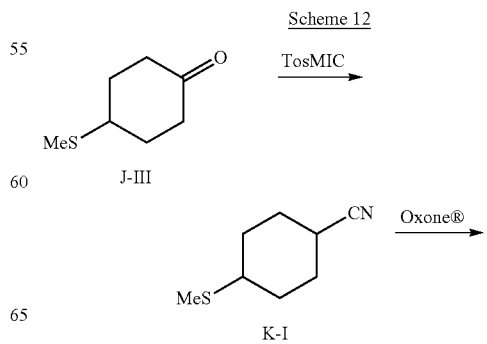

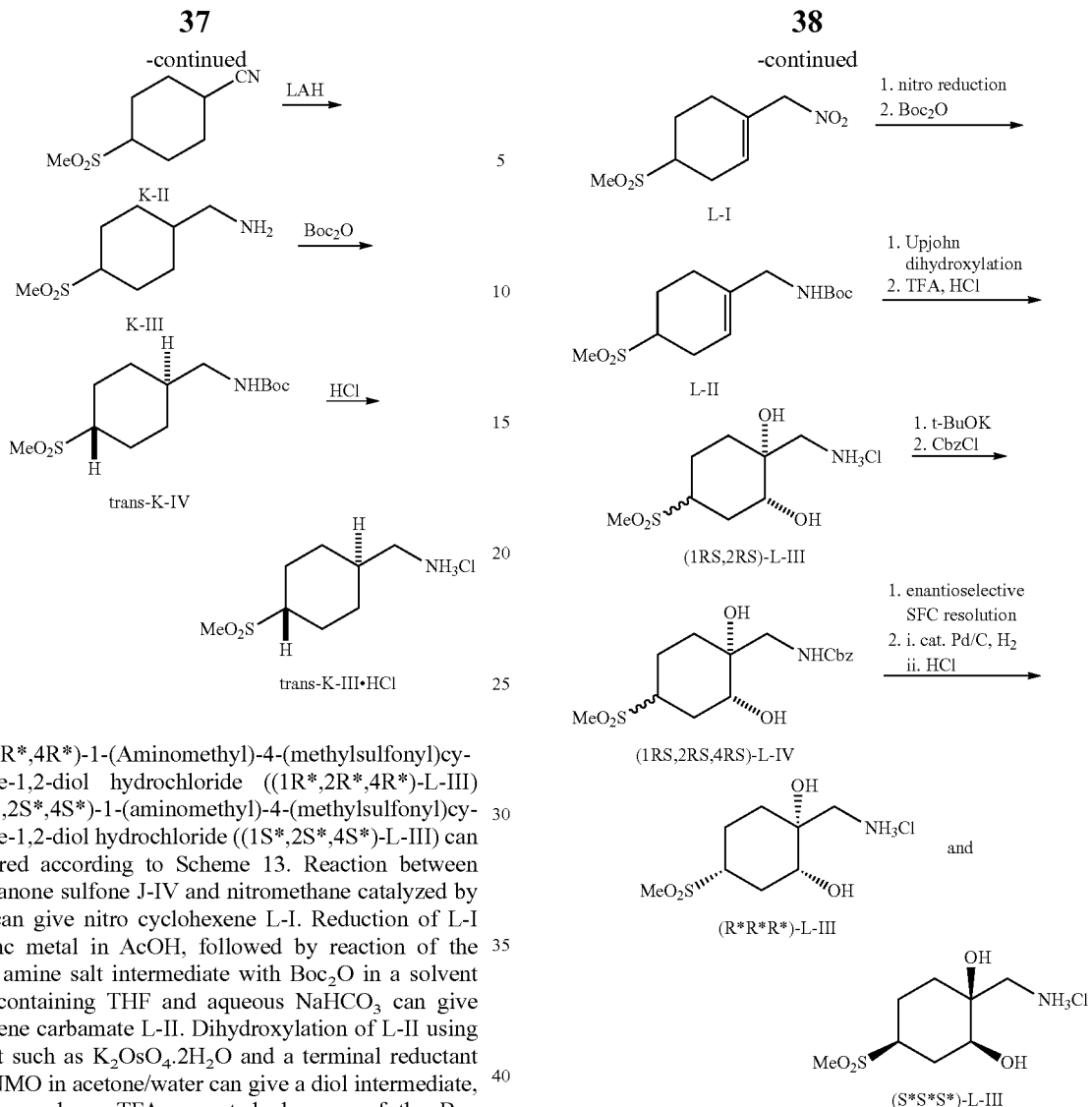

(1R*,2R*,4R*)-1-(Aminomethyl)-4-(methylsulfonyl)cyclohexane-1,2-diol hydrochloride ((1R*,2R*,4R*)-L-III) and (1S*,2S*,4S*)-1-(aminomethyl)-4-(methylsulfonyl)cyclohexane-1,2-diol hydrochloride ((1S*,2S*,4S*)-L-III) can be prepared according to Scheme 13. Reaction between cyclohexanone sulfone J-IV and nitromethane catalyzed by DMEN can give nitro cyclohexene L-I. Reduction of L-I using zinc metal in AcOH, followed by reaction of the resulting amine salt intermediate with Boc$_2$O in a solvent mixture containing THF and aqueous NaHCO$_3$ can give cyclohexene carbamate L-II. Dihydroxylation of L-II using a catalyst such as K$_2$OsO$_4$.2H$_2$O and a terminal reductant such as NMO in acetone/water can give a diol intermediate, which can undergo TFA-promoted cleavage of the Boc group, followed by treatment with HCl to give amino diol HCl salt (1RS,2RS)-L-III as a mixture of C4 epimers. Equilibration of the isomeric mixture can be promoted by heating with an alkoxide base, such as t-BuOK, in t-BuOH to enrich the mixture in the 1RS,2RS,4RS isomer. Reaction of this equilibrated mixture with CbzCl in aqueous NaHCO$_3$ solution, followed by trituration of the product with EtOAc/hexanes can give (1RS,2RS,4RS)-L-IV as a single diastereomer. Resolution of (1RS,2RS,4RS)-L-IV by SFC using a chiral stationary phase can give (1R*,2R*,4R*)-L-IV and (1S*,2S*,4S*)-L-IV in stereochemically pure form. Hydrogenolysis of the Cbz carbamates with hydrogen gas using a catalyst such as Pd/C, followed by treatment of the resulting amines with HCl can give amino diol salts (1R*, 2R*,4R*)-L-III and (1S*,2S*,4S*)-L-III.

Scheme 13

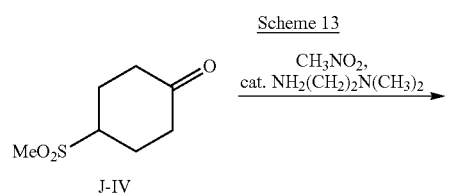

(1s,4s)-4-(Aminomethyl)-4-hydroxycyclohexane-1-sulfonamide hydrochloride ((s,s)-M-VIII) can be prepared according to Scheme 14. Treatment of cyclohexanol M-I with iodine, PPh$_3$, and imidazole can give iodocyclohexane M-II. Treatment of M-II with Rieke® zinc followed, by reaction of the resulting organozinc intermediate with DABSO can give zinc sulfinate M-III. Treatment of a DCM suspension of M-III with NCS, followed by addition of tert-butylamine can give t-butylsulfonamide M-IV. Hydrolytic cleavage of the 1,3-dioxolane group of M-IV under weakly acidic conditions, such as those of a AcOH/water/1,4-dioxane solvent mixture, and heating can give cyclohexanone sulfonamide M-V. Cyanosilylation of M-V using TMSCN and a catalytic amount of ZnI$_2$ can give nitrile M-VI. Reduction of M-VI using an ethereal solution of LAH, followed by treatment of the ensuing amine intermediate with TFA can give a primary sulfonamide amine salt intermediate. This salt can be converted to the corresponding free base, which can then undergo reaction with Boc$_2$O to give hydroxy carbamate M-VII. After chromatographic separation of the diastereomers, the s,s isomer can be treated with TFA and then HCl to afford amino alcohol sulfonamide (s,s)-M-VIII.

Scheme 14

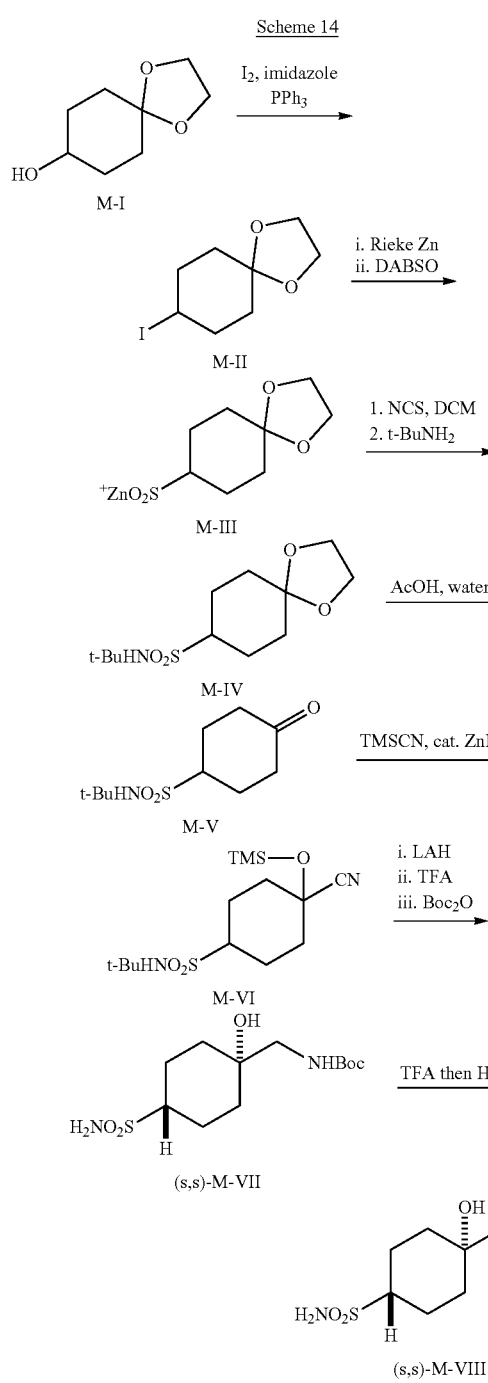

such as pyridine in a solvent such as CHCl$_3$, followed by reaction of the resulting tosylate with potassium ethanethioate can give cyclohexyl ethanethioate N-V. Oxidation of N-V with aqueous hydrogen peroxide in formic acid, followed by treatment of the resulting sulfonic acid with thionyl chloride can give the corresponding sulfonyl chloride N-VI. Reaction of N-VI with THF solutions of amines gives diastereomeric mixtures of sulfonamides N-VII, which can be purified by HPLC to provide the stereochemically pure sulfonamides, trans-N-VII. These sulfonamides can undergo phthalimide cleavage promote by hydrazine hydrate in EtOH, followed by treatment of the resulting amine with HCl to give sulfonamide amine salts trans-N-VIII. If trans-N-VII is a t-butyl sulfonamide ($R^{11}$=H, $R^{12}$=t-Bu), treatment with TFA can provide the primary sulfonamide, trans-N-VII ($R^{11}$=H, $R^{12}$=H), which can undergo the same phthalimide cleavage and subsequent treatment with HCl described above to provide the corresponding primary sulfonamide amine salt trans-N-VIII ($R^{11}$=H, $R^{12}$=H).

Scheme 15

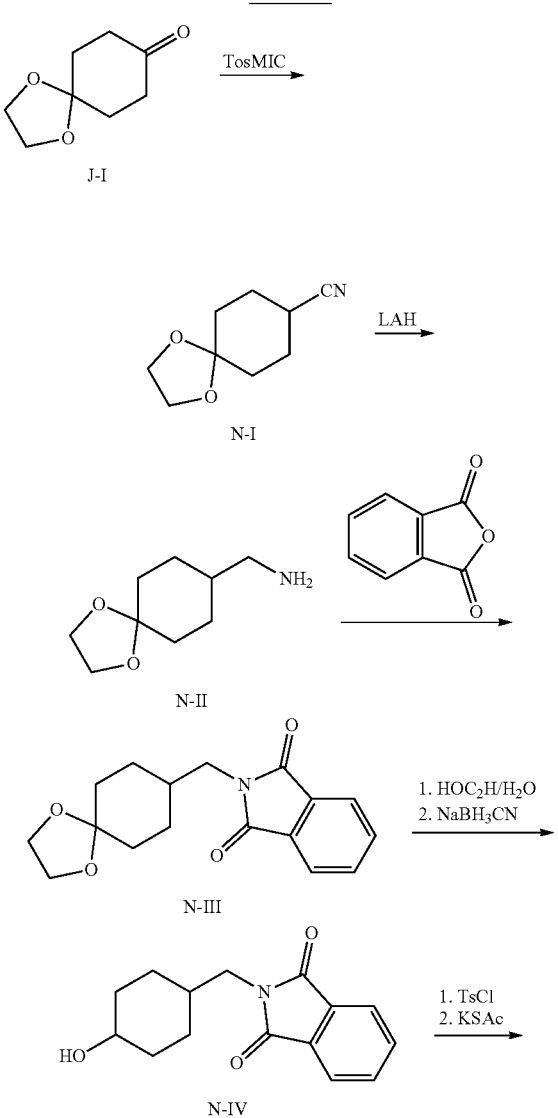

Sulfonamide amine salts trans-N-VIII can be prepared according to Scheme 15. Reductive cyanation of 1,4-dioxaspiro[4.5]decan-8-one (J-I) using TosMIC with an alkoxide base, such as t-BuOK, in a solvent mixture such as DME/t-BuOH can give cyanocyclohexane N-I. Reduction of N-I with LAH in an ethereal solvent can give amine N-II. Reaction of N-II with isobenzofuran-1,3-dione in the presence of an amine base such as TEA and a desiccant such as molecular sieves can give phthalimide N-III. Hydrolytic cleavage of the 1,3-dioxolane group using aqueous acid, such as aqueous formic acid, followed by reduction of the resulting ketone with NaBH$_3$CN in AcOH can give cyclohexanol N-IV. Sulfonylation of N-IV using TsCl with a base -continued

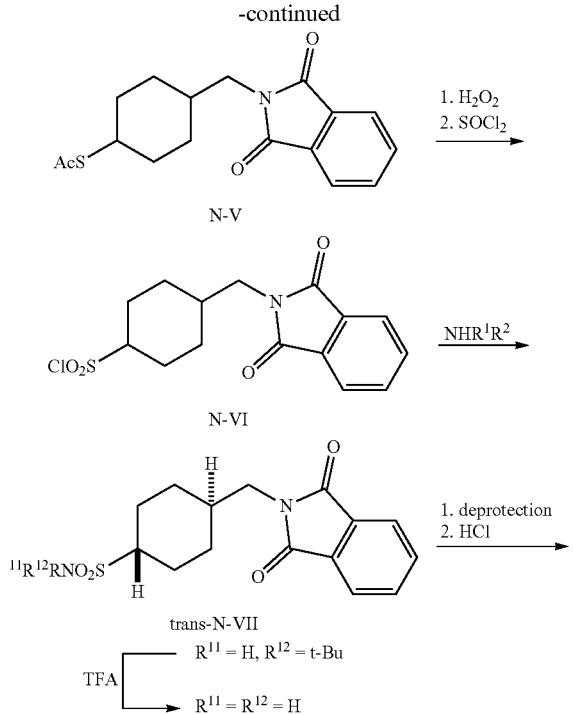

R[11] = H, R[12] = t-Bu
TFA
R[11] = R[12] = H

Intermediate 1

1,4-Dioxaspiro[4.5]decan-8-ol

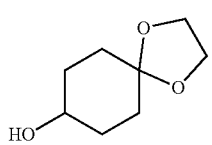

Sodium borohydride (83.4 g, 2.21 mol) was added in portions over 2 h to a stirring 0-5° C. solution of 1,4-dioxaspiro[4.5]decan-8-one (1150 g, 7.372 mol) and MeOH (7.0 L) at a rate that maintained the internal temperature below 5° C. After the reaction went to completion, water was added, and the mixture was concentrated. The residue was then diluted with DCM and water, the layers were separated, and the aqueous layer was extracted twice with DCM. The organic layers were combined, washed with brine, dried with anhydrous $Na_2SO_4$, filtered, and then concentrated to afford the title compound as a colorless liquid (65.9% w/w).

Intermediate 2

1,4-Dioxaspiro[4.5]decan-8-yl methanesulfonate

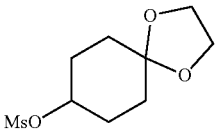 [SMILES: CS(=O)(=O)OC1CCC2(CC1)OCCO2]

Methanesulfonyl chloride (1000 g, 8.790 mol) was added dropwise to a stirring solution of 1,4-dioxaspiro[4.5]decan-8-ol (1722 g, 65.9% w/w, 7.17 mol, Intermediate 1) and TEA (2178 g, 21.52 mol) in DCM (10 L) at a rate that maintained the internal temperature between 10 and 20° C. After the reaction went to completion, it was combined with another mixture prepared in a similar way. The combined mixture was washed with water and then concentrated. The residue was slurried in n-heptane and EtOH (10:1 v/v) at rt, and the suspension was filtered. The filter cake was dried under vacuum to afford the title compound as a yellow solid.

Intermediate 3

8-(Methylthio)-1,4-dioxaspiro[4.5]decane

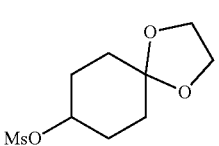 [SMILES: CS(=O)(=O)OC1CCC2(CC1)OCCO2]

Sodium thiomethoxide (249 g, 3.56 mol) was added in five portions to a stirring 0-5° C. solution of 1,4-dioxaspiro[4.5]decan-8-yl methanesulfonate (800 g, 3.39 mol, Intermediate 2) in DMF (4.8 L), and the reaction mixture was allowed to warm to 15-20° C. over 24 h. An additional portion of NaSMe (23.7 g, 0.339 mol) was then added, and stirring was continued until the reaction went to completion. Water and MTBE were then added, and the layers were separated. The organic layer was washed three times with water, concentrated, and then dried under vacuum to afford the title compound as a yellow oil.

Intermediate 4

4-(Methylthio)cyclohexan-1-one

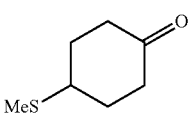

A mixture of 8-(methylthio)-1,4-dioxaspiro[4.5]decane (680 g, 3.61 mol, Intermediate 3), i-PrOAc (6.8 L), and 3 N aqueous HCl (680 mL) was stirred at 20-25° C. for 30 min. After this time, the layers were separated. The organic layer was treated with a 3 N aqueous HCl (680 mL) as described in the process above eight additional times. During the final

Intermediate 5

4-(Methylsulfonyl)cyclohexan-1-one

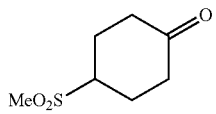

m-Chloroperbenzoic acid (1151 g, 85% w/w, 5.668 mol) was added in portions to a stirring −5 to 5° C. solution of 4-(methylthio)cyclohexan-1-one (545 g, 3.78 mol, Intermediate 4) in DCM (11 L) at a rate that maintained the internal temperature below 5° C. After the addition was complete, stirring was continued for 45 min before an additional portion of mCPBA (231 g, 85% w/w, 1.13 mol) was added, and stirring was continued for 30 min. A third portion of mCPBA (76.9 g, 85% w/w, 0.378 mol) was added, and stirring was continued at −5 to 5° C. for 30 min. The reaction mixture was then filtered. The filter cake was rinsed with DCM, and the filtrate and rinse were combined and then concentrated. The residual DCM was then removed by three cycles of sequential dilution with MTBE and concentration. The concentrate was then diluted with MTBE and stirred at 50° C. for 1 h before it was allowed to cool to rt and stir for 16 h. The slurry was then filtered, and the filter cake was rinsed with MTBE and dried under vacuum to afford the title compound as a colorless solid.

Intermediate 6

4-(Methylsulfonyl)-1-((trimethylsilyl)oxy)cyclo-hexane-1-carbonitrile

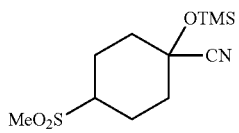

Trimethylsilyl cyanide (410 g, 4.13 mol) was added dropwise to a stirring solution of 4-(methylsulfonyl)cyclo-hexan-1-one (560 g, 3.18 mol, Intermediate 5) and TEA (113 g, 1.11 mol) in DCM (5.6 L) at a rate that maintained an internal temperature of 25-30° C., and the resulting mixture was stirred for 30 min. After this time, a saturated aqueous NaHCO₃ solution was added, and the layers were separated. The organic layer was washed with brine and then concentrated. The residual DCM was then removed by two cycles of sequential dilution with n-heptane and concentration. The concentrate was then stirred as a slurry in n-heptane at rt for 16 h before it was filtered. The filter cake was rinsed with n-heptane and then dried under vacuum to afford the title compound as a colorless solid.

Intermediate 7

1-(Aminomethyl)-4-(methylsulfonyl)cyclohexan-1-ol hydrochloride

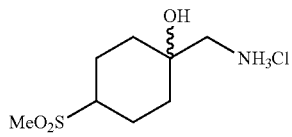

Borane (1.74 L, 1.0 M in THF, 1.74 mol) was added dropwise to a stirring 60° C. solution of 4-(methyl sulfonyl)-1-((trimethyl silyl)oxy)cyclohexane-1-carbonitrile (400 g, 1.45 mol, Intermediate 6) in THF (1.6 L), and the solution was stirred until the reaction went to completion. The solution was then cooled in an ice-water bath and quenched by carefully adding MeOH. After the quench was completed, the mixture was acidified with 33% ethanolic HCl solution (200 mL) and stirred for 30 min. The mixture was then filtered, and the filter cake was rinsed with MTBE and then dried under vacuum to afford the title compound as a colorless solid.

Intermediate 8 tert-Butyl (((1s,4s)-1-hydroxy-4-(methylsulfonyl) cyclohexyl)methyl)carbamate

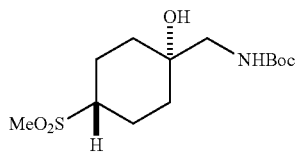

Sodium tert-butoxide (118 g, 1.05 mol) was added in portions to a stirring solution of 1-(aminomethyl)-4-(methyl sulfonyl)cyclohexan-1-ol hydrochloride (170 g, 0.70 mol, Intermediate 7) in t-BuOH (850 mL) and THF (850 mL) at rt. The resulting mixture was then heated to 60° C. and stirred until the cis and trans isomers reached equilibrium as judged by HPLC analysis. The reaction mixture was then allowed to cool to rt before 3 N aqueous HCl (70 mL, 0.21 mol) was added. A solution of Boc₂O (159 g, 0.728 mol) in THF (510 mL) was then added dropwise at rt, and the mixture was stirred until the reaction went to completion. The resulting mixture was combined with another mixture prepared in a similar way on a similar scale. The combined mixture was filtered, and the filter cake was rinsed with DCM. The filtrate and wash were combined and then concentrated to afford an off-white solid, which was stirred as a slurry in EtOAc/n-heptane (0.8 L, 1:1 v/v) at 60° C. for 1 h. The suspension was allowed to cool and then filtered. The filter cake was rinsed with EtOAc/n-heptane (1:1 v/v) and then dried under vacuum to afford the title compound as a colorless solid.

Intermediate 9

(1s,4s)-1-(Aminomethyl)-4-(methylsulfonyl)cyclohexan-1-ol Hydrochloride

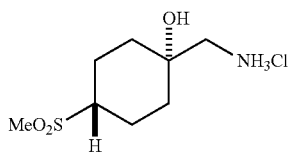

Ethanolic HCl (0.9 L, 33 wt %) was added dropwise to a solution of tert-butyl (((1s,4s)-1-hydroxy-4-(methylsulfonyl)cyclohexyl)methyl)carbamate (290 g, 0.94 mol, Intermediate 8) in EtOH (0.9 L), and the mixture was stirred at rt. After the reaction went to completion, the suspension was filtered, and the filter cake was rinsed with EtOH. The filter cake was then stirred as a slurry in EtOH at reflux temperature for 2 h before it was allowed to cool to rt. The suspension was then filtered, and the filter cake was washed three times with EtOH. The filter cake was then dried at under vacuum at 50° C. the title compound as a colorless solid.

Intermediate 10

4-(Methylthio)cyclohexane-1-carbonitrile

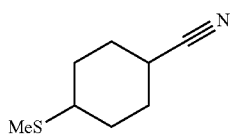

Sodium tert-butoxide (655 g, 5.82 mol) was added in portions to a stirring −38° C. mixture of 4-(methylthio)cyclohexan-1-one (350 g, 2.43 mol, Intermediate 4), Tos-MIC (616 g, 3.15 mol) and EtOH (263 mL, 4.50 mol) in MTBE (7.0 L) at a rate that maintained the internal temperature between 40 and 35° C., and the resulting mixture was stirred for 1 h. After this time, the mixture was allowed to warm to 3° C., and then it was filtered. The filter cake was washed with water, and the layers of the combined filtrate and wash were separated. The filter cake was then suspended in the aqueous layer, and the resulting mixture was filtered. The filter cake was washed with MTBE. Then the layers of the combined filtrate and wash were separated, and the aqueous layer was extracted with MTBE. The organic layers were combined, washed with water, washed with brine, and then concentrated. The concentrate was purified by vacuum distillation to afford the title compound as a light-yellow oil.

Intermediate 11

4-(Methylsulfonyl)cyclohexane-1-carbonitrile

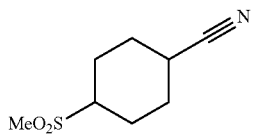

Oxone (2238 g, 3.640 mol) was added to a stirring −10° C. mixture of 4-(methylthio)cyclohexane-1-carbonitrile (255 g, 1.64 mol, Intermediate 10), acetone (2.5 L), and water (2.5 L) over 45 min at a rate that maintained the internal temperature below 2° C., and the resulting mixture was stirred for 40 min. The reaction mixture was then filtered, and the filter cake was washed with acetone. The filtrate was concentrated to remove most of acetone, and the residue was extracted with five times with EtOAc. The organic layers were combined, dried over anhydrous $Na_2SO_4$, filtered, and concentrated to afford a colorless solid. This solid was stirred as a slurry in n-heptane at rt overnight, and then the suspension was filtered. The filter cake was dried under vacuum to afford the title compound as a colorless solid.

Intermediate 12 tert-Butyl (((1r,4r)-4-(methylsulfonyl)cyclohexyl)methyl)carbamate

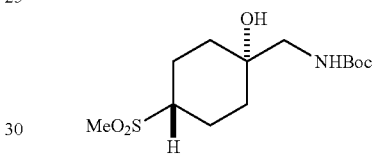

A solution of 4-(methylsulfonyl)cyclohexane-1-carbonitrile (200 g, 1.07 mol, Intermediate 11) in THF (3.0 L) was added dropwise to a stirring −10 to −5° C. suspension of LAH (123 g, 3.24 mol) in THF (1.0 L) over 3 h at a rate that maintained an internal temperature of 10 to 10° C., and the resulting mixture stirred for 2 h. After the reaction went to completion, a solution of THF and water (246 g, 1:1 w/w), 15% aqueous NaOH (123 g), and water (369 g) were sequentially added. The mixture was then filtered, and the filter cake was rinsed with THF. Di-tert-butyl dicarbonate (245 g, 3.40 mol) was then added to the combined filtrate and rinse, and the mixture was stirred at rt overnight. The mixture was then concentrated. The residue was diluted with water, and the mixture was extracted three times with EtOAc. The organic layers were combined, washed with brine, dried with anhydrous $Na_2SO_4$, filtered, and then concentrated. This concentrate was combined with an additional concentrate prepared in a similar way on a similar scale, diluted with i-PrOH (0.6 L), and stirred at 85° C. for 30 min. n-Heptane (1.2 L) was added dropwise, and the resulting mixture was stirred for 30 min. The mixture was allowed to cool to 25° C., and stirring was continued for 2 h. The mixture was then filtered, and the filter cake was washed with n-heptane and dried under vacuum at 45° C. to give a colorless solid. This solid was combined with another batch prepared in a similar way but on one-fourth scale, dissolved in EtOAc (0.6 L), and stirred at 60° C. for about 2 h. n-Heptane (2.4 L) was then added dropwise over 2 h, and stirring was continued at 60° C. for 1 h. The resulting mixture was then allowed to cool to 25° C. and was stirred for 2 h. The mixture was then filtered, and the filter cake was washed with n-heptane and dried under vacuum at 40° C. to afford the title compound as a colorless solid.

Intermediate 13

((1r,4r)-4-(Methylsulfonyl)cyclohexyl)methanamine Hydrochloride

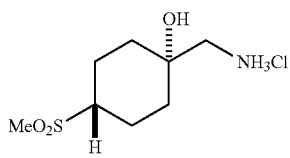

Ethanolic HCl (684 g, 33 wt %, 6.27 mol) was added dropwise to a solution of tert-butyl (((1r,4r)-4-(methylsulfonyl)cyclohexyl)methyl)carbamate (180 g, 0.62 mol, Intermediate 12) in EtOH (0.6 L), and the resulting mixture was stirred at rt. After the reaction went to completion, MTBE (2.5 L) was added, and the suspension was filtered. The filter cake was rinsed with MTBE and then dried under vacuum at 50° C. to afford the title compound as a colorless solid.

Intermediate 14

8-Iodo-1,4-dioxaspiro[4.5]decane

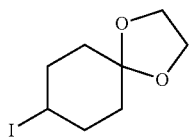

A solution of iodine (31.6 g, 125 mmol) in THF (75 mL) was added dropwise over 1 h to a stirring 0-5° C. solution of 1,4-dioxaspiro[4.5]decan-8-ol (16.4 g, 104 mmol, Intermediate 1), imidazole (8.5 g, 130 mmol), and triphenylphosphine (32.7 g, 125 mmol) in THF (115 mL), and the resulting mixture was allowed to warm to rt over 16 h. After this time, the reaction mixture was filtered, concentrated, and then diluted with DCM. The resulting solution was washed with water, dried with anhydrous MgSO$_4$, filtered, and concentrated. Hexane was added, and the resulting mixture agitated for 30 min at 32° C. The mixture was then filtered, and the filtrate was concentrated. The concentrate was purified by silica gel chromatography (5→15% EtOAc/hexanes) to afford the title compound as a pale yellow oil.

Intermediate 15

N-(tert-Butyl)-1,4-dioxaspiro[4.5]decane-8-sulfonamide

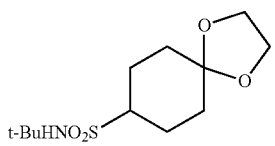

8-Iodo-1,4-dioxaspiro[4.5]decane (21.5 g, 98% w/w, 78.6 mmol, Intermediate 14) was added to a suspension of Rieke® zinc in THF (113 mL, 0.05 g/mL, 86.5 mmol) over 5 min, and 10 mL of THF was used to wash the residue in the transfer vessel into the reaction mixture. The mixture was stirred at 65° C. for 3 h. After this time, the suspension was allowed to cool and then DABSO (11.3 g, 47.2 mmol) was added, and the mixture was stirred at rt for 16 h. After this time, the mixture was filtered through Celite®, and the filter cake was washed with THF. The filtrate and wash were combined and then concentrated to afford the crude zinc sulfinate as a beige foam.

N-Chlorosuccinimide (7.4 g, 56 mmol) was added to a suspension of the crude zinc sulfinate described above (29.9 g, 74% w/w, 55.7 mmol) in DCM (280 mL), and the resulting mixture was stirred at rt for 1 h. After his time, Celite® was added and the mixture was filtered. The filter cake was washed with DCM, and then the filtrate and wash were combined and concentrated. The concentrate was diluted with THF (115 mL), and the solution was cooled to 0-5° C. tert-Butylamine (23 mL, 220 mmol) was then added in one portion, and the resulting mixture was stirred and allowed to warm to rt over 18 h. After this time, the mixture was diluted with water and EtOAc. The layers were mixed and then separated, and the aqueous layer was extracted three times with EtOAc. The organic layers were combined, washed with brine, dried with anhydrous MgSO$_4$, filtered, and then concentrated. The concentrate was then purified by silica gel chromatography (20→60% EtOAc/hexanes) to afford the title compound as a colorless solid.

Intermediate 16

N-(tert-Butyl)-4-oxocyclohexane-1-sulfonamide

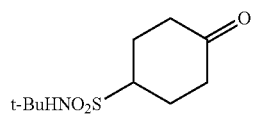

N-(tert-Butyl)-1,4-dioxaspiro[4.5]decane-8-sulfonamide (8.2 g, 30 mmol, Intermediate 15) was dissolved in a mixture of AcOH, 1,4-dioxane, and water (175 mL, 2:2:1 v/v/v), and the solution was maintained at 105° C. for 18 h. After this time, the solution was allowed to cool and then concentrated to afford an off-white solid. This solid was crystallized from a hot toluene/heptane solution to afford the title compound as a colorless solid.

Intermediate 17

N-(tert-Butyl)-4-cyano-4-hydroxycyclohexane-1-sulfonamide

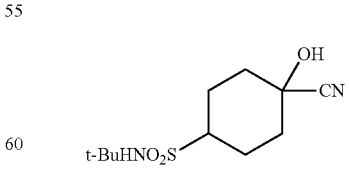

Trimethylsilyl cyanide (0.77 mL, 6.1 mmol) was added to a mixture of N-(tert-butyl)-4-oxocyclohexane-1-sulfonamide (1.1 g, 4.7 mmol, Intermediate 16) and zinc iodide (30 mg, 0.094 mmol) in DCM (9.5 mL), and the mixture was stirred at rt for 72 h. After this time, the reaction mixture was diluted with a saturated aqueous NaHCO₃ solution and filtered. The layers of the filtrate were separated, and the aqueous layer was extracted with DCM. The combined organic layers were dried with MgSO₄, filtered, and then concentrated. The concentrate was dissolved in DCM (9 mL), and then trimethylsilyl cyanide (0.77 mL, 6.1 mmol) and zinc iodide (30 mg, 0.094 mmol) were added, and the mixture was stirred at rt for 20 h. The mixture was then diluted with hexanes, filtered, and concentrated to afford the title compound as a tan solid.

Intermediate 18 tert-Butyl (((1s,4s)-1-hydroxy-4-sulfamoylcyclohexyl)methyl)carbamate

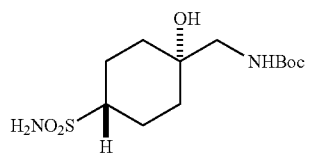 [SMILES: CC(C)(C)OC(=O)NC[C@]1(O)CC[C@@H](S(N)(=O)=O)CC1]

N-(tert-Butyl)-4-cyano-4-hydroxycyclohexane-1-sulfonamide (1.28 g, 3.85 mmol, Intermediate 17) was added portionwise to a 0-5° C. solution of LAH in THF (12.3 mL, 1.0 M, 12.3 mmol), and the resulting solution was allowed to warm to rt over 3 h. The solution was then cooled to 0-5° C. before water (0.50 mL), 15% aqueous NaOH (0.50 mL), and more water (1.5 mL) were sequentially added. The mixture was then allowed to warm to rt over 15 min before anhydrous MgSO₄ was added, and the mixture was filtered through Celite. The filter cake was washed with THF, and the filtrate and wash were combined and concentrated. The concentrate was then diluted with 6 mL of TFA, and the solution was maintained at rt for 15 h. After this time, the solution was concentrated and then diluted with THF (12 mL) and a saturated aqueous NaHCO₃ solution (5 mL). Di-tert-butyl dicarbonate (0.83 mL, 3.9 mmol) was added, and the mixture was stirred at rt for 40 h. After this time, the mixture was diluted with EtOAc and water, the layers were separated, and the aqueous layer was extracted twice with EtOAc. The organic layers were combined, washed with brine, dried with anhydrous MgSO₄, filtered, and then concentrated to give the crude product as a mixture of diastereomers. The concentrate was purified by silica gel chromatography (80→100% EtOAc/hexanes) to afford a fraction enriched in the first-eluting diastereomer as a colorless film. This residue was diluted with CHCl₃, and the resulting solution was stirred overnight at rt. After this time, a suspension had formed. The mixture was filtered, and the filter cake was washed with cold CHCl₃ and then dried by aspiration to afford the title compound as a colorless solid.

Intermediate 19

(1s,4s)-4-(Aminomethyl)-4-hydroxycyclohexane-1-sulfonamide hydrochloride

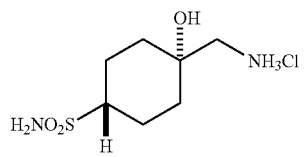

Trifluoracetic acid (0.63 mL, 8.2 mmol) was added to a solution of tert-butyl (((1s,4s)-1-hydroxy-4-sulfamoylcyclohexyl)methyl)carbamate (210 mg, 0.681 mmol, Intermediate 18) in DCM (2.3 mL), and the resulting solution was maintained to rt for 14 h. After this time, the solution was concentrated, and the residue was diluted with MeOH and concentrated again. The residue was dissolved in DCM and MeOH (5 mL, 1:1 v/v), a solution of HCl in 1,4-dioxane (0.18 mL, 4.0 M, 0.73 mmol) was added, and the resulting solution was concentrated to give a solid residue. This residue was triturated with EtOAc, filtered, washed with EtOAc, and then dried by aspiration to afford the title compound as a colorless solid.

Intermediate 20

4-(Methylsulfonyl)-1-(nitromethyl)cyclohex-1-ene

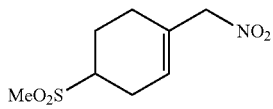 [SMILES: CS(=O)(=O)C1CC=C(C[N+](=O)[O-])CC1]

A solution of 4-(methylsulfonyl)cyclohexanone (15.27 g, 86.65 mmol, Intermediate 5), nitromethane (15 mL, 350 mmol), and DMEN (2.8 mL, 26 mmol) in benzene (220 mL) was stirred at reflux temperature for 16 h in a reactor fitted with a Dean-Stark trap. After this time, the solution was allowed to cool and then diluted with 1 N aqueous HCl (200 mL). The layers of the resulting mixture were mixed then separated, and the aqueous layer was extracted EtOAc. The organic layers were combined, washed with brine, dried with anhydrous MgSO₄, filtered, and then concentrated to afford the title compound as a colorless solid.

Intermediate 21

(4-(Methylsulfonyl)cyclohex-1-en-1-yl)methanamine Hydrochloride

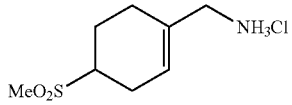

A warm solution of 4-(methylsulfonyl)-1-(nitromethyl)cyclohex-1-ene (15.52 g, 70.78 mmol, Intermediate 20) in AcOH (80 mL) was added dropwise over 1.5 h to a stirring suspension of zinc (50 g, 760 mmol) in AcOH (100 mL), which was submerged in a 70° C. bath. The drip rate was periodically adjusted to maintain the internal reaction temperature below 85° C. After the addition was complete, stirring was continued at 70° C. for 4 h before the reaction mixture was allowed to cool. The mixture was then diluted with an equal volume of EtOAc and filtered through Celite®. The filtrate was concentrated, diluted with IPA (300 mL), and filtered. The filtrate was then concentrated to half its original volume before a 1,4-dioxane solution of HCl (18 mL, 4.0 M, 72 mmol) was added. The resulting mixture was concentrated, diluted with MeOH (200 mL) and stirred until the solids were well-dispersed. The resulting suspension was concentrated to half the original volume, diluted with an Intermediate 22 tert-Butyl ((4-(methylsulfonyl)cyclohex-1-en-1-yl)methyl)carbamate

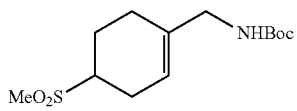

A solution of (4-(methyl sulfonyl)cyclohex-1-en-1-yl)methanamine hydrochloride (22.0 g, 97.5 mmol, Intermediate 21) in THF (100 mL) was diluted with a saturated aqueous NaHCO$_3$ solution, Boc$_2$O (20.9 mL, 97.5 mmol) was added, and then the mixture was stirred at rt for 16 h. After this time, the mixture was diluted with EtOAc and filtered. The layers were separated, and the aqueous layer was extracted with EtOAc. The organic layers were combined, washed with brine, dried with anhydrous MgSO$_4$, filtered, and then concentrated to afford the title compound as a tan solid.

Intermediate 23 tert-Butyl (((1RS,2RS)-1,2-dihydroxy-4-(methylsulfonyl)cyclohexyl)methyl)carbamate

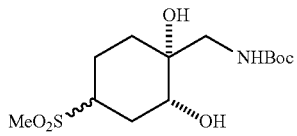

Potassium osmate(VI) dihydrate (470 mg, 1.3 mmol) was added to a solution of tert-butyl ((4-(methylsulfonyl)cyclohex-1-en-1-yl)methyl)carbamate (17.55 g, 57.01 mmol, 94%, Intermediate 22) and NMO (8.7 g, 61 mmol) in acetone/water (250 mL, 4:1 v/v), and the mixture was stirred at rt for 20 h. After this time, a solution of Na$_2$S$_2$O$_4$ (3.1 g, 15 mmol) in water (15 mL) was added, and the mixture was stirred for 30 min. After this time, the mixture was concentrated to one-third its original volume. The concentrate was diluted with EtOAc and enough hexanes to make the mixture biphasic. The pH of the aqueous layer was adjusted to pH <4 with 10 M aqueous H$_2$SO$_4$, and the layers were mixed and then separated. The aqueous layer was extracted four times with EtOAc, and then the organic layers were combined, dried anhydrous MgSO$_4$, filtered, and concentrated to afford the title compound as a pale-purple gum.

Intermediate 24

(1RS,2RS)-1-(Aminomethyl)-4-(methylsulfonyl)cyclohexane-1,2-diol hydrochloride

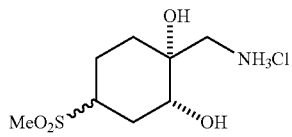

Trifluoroacetic acid (48 mL, 0.63 mol) was added to a solution of tert-butyl (((1RS,2RS)-1,2-dihydroxy-4-(methylsulfonyl)cyclohexyl)methyl)carbamate (17.77 g, 94% w/w, 51.65 mmol, Intermediate 23) in DCM (180 mL), and the resulting solution was maintained at rt for 2 h. After this time, the solution was concentrated, MeOH was added, and the solution was concentrated again. The concentrate was dissolved in MeOH (50 mL), a solution of HCl in 1,4-dioxane (14.2 mL, 4.0 M, 56.8 mmol) was added, and the solution was concentrated to give a brown oil. This oil was dissolved in MeOH (50 mL) and then EtOAc (200 mL) was added over 30 min to induce crystallization. The resulting slurry was filtered, and the solids were washed with EtOAc and then dried by aspiration to afford the title compound as a tan solid (dr=1.6:1.0 according to NMR analysis).

Intermediate 25

(1RS,2RS,4RS)-1-(Aminomethyl)-4-(methylsulfonyl)cyclohexane-1,2-diol hydrochloride

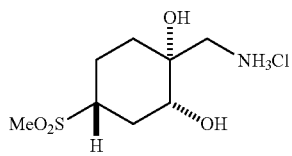

Potassium tert-butoxide (7.7 g, 68 mmol) was added to a suspension of (1RS,2RS)-1-(aminomethyl)-4-(methylsulfonyl)cyclohexane-1,2-diol hydrochloride (11.84 g, 45.58 mmol, Intermediate 24) in t-BuOH (120 mL), and the resulting thick, heterogeneous mixture was stirred at 60° C. for 65 h. After this time, the mixture was allowed to cool, and then a solution of HCl in 1,4-dioxane (18.2 mL, 4.0 M, 72.9 mmol) was added. The mixture was then concentrated to afford the title compound as a tan solid (dr=10:1.0 according to NMR analysis).

Intermediate 26

Benzyl (((1RS,2RS,4RS)-1,2-dihydroxy-4-(methylsulfonyl)cyclohexyl)methyl)carbamate

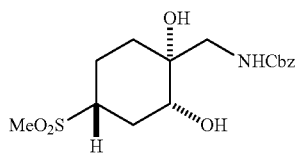 [SMILES: CS(=O)(=O)[C@@H]1CC[C@@](O)(CNC(=O)OCc2ccccc2)[C@H](O)C1]

Benzyl chloroformate (16.6 mL, 112 mmol) was added to a 0-5° C. mixture of (1RS,2RS,4RS)-1-(aminomethyl)-4-(methylsulfonyl)cyclohexane-1,2-diol hydrochloride (19.81 g, 56.05 mmol, Intermediate 25) and NaHCO$_3$ (14.1 g, 168 mmol) in water (160 mL), and the resulting mixture was stirred vigorously and allowed to gradually warm to rt over 24 h. After this time, the resulting suspension was filtered, and the filter cake was washed with water and then dried by aspiration. The solids were diluted with hexanes and EtOAc (100 mL, 3:1 v/v) and stirred for 3 h. The slurry was filtered, and the filter cake was washed with hexanes and then dried by aspiration to afford the title compound as a light-tan solid (dr>100:1 according to NMR analysis).

Intermediate 27

Benzyl (((1S*,2S*,4S*)-1,2-dihydroxy-4-(methylsulfonyl)cyclohexyl)methyl)carbamate

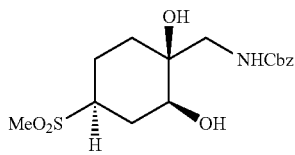 [SMILES: CS(=O)(=O)[C@H]1CC[C@](O)(CNC(=O)OCc2ccccc2)[C@@H](O)C1]

Intermediate 28

Benzyl (((1R*,2R*,4R*)-1,2-dihydroxy-4-(methylsulfonyl)cyclohexyl)methyl)carbamate

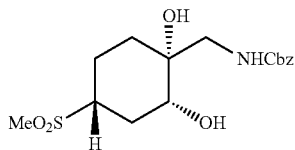 [SMILES: CS(=O)(=O)[C@@H]1CC[C@@](O)(CNC(=O)OCc2ccccc2)[C@H](O)C1]

Intermediate 26 was purified by SFC using a chiral stationary phase (Chiralpak IA, 60% CO$_2$, 40% EtOH/i-PrOH (1:1 v/v)) to give a pair of enantiomers. The first-eluting enantiomer was Intermediate 27, and the second-eluting enantiomer was Intermediate 28.

Intermediate 29

(1R*,2R*,4R*)-1-(Aminomethyl)-4-(methylsulfonyl)cyclohexane-1,2-diol Hydrochloride

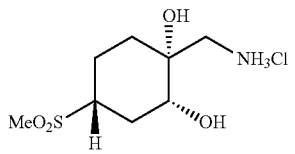

A vessel containing benzyl (((1R*,2R*,4R*)-1,2-dihydroxy-4-(methylsulfonyl)cyclohexyl)methyl)carbamate (4.22 g, 11.8 mmol, Intermediate 28) and Pd/C (10% Pd, 50% water, Degussa E101 NE/W) (2.5 g, 1.2 mmol Pd) was evacuated and backfilled three times with nitrogen before EtOH (130 mL) was added, and the mixture was stirred under an atmosphere of hydrogen at rt for 16 h. After this time, the suspension was diluted with enough water to dissolve the newly-formed precipitate, filtered through Celite®, and then concentrated. This concentrate was dissolved in MeOH and water (30 mL, 1:1 v/v) before a solution of HCl in 1,4-dioxane (3.0 mL, 4.0 M, 12 mmol) was added, and the resulting mixture was concentrated. The oily residue was diluted with EtOH and concentrated again to afford a colorless solid. This solid was suspended in EtOAc and then isolated by filtration. The moist filter cake was dried under vacuum to afford the title compound as a colorless solid. $[\alpha]_{589}^{20}$+1.9, $[\alpha]_{436}^{20}$+5.2, $[\alpha]_{365}^{20}$+10 (c 1.1, MeOH).

Intermediate 30

(1S*,2S*,4S*)-1-(Aminomethyl)-4-(methylsulfonyl)cyclohexane-1,2-diol Hydrochloride

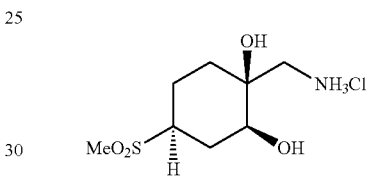

The title compound was prepared as described for the synthesis of Intermediate 29, using benzyl (((1S*,2S*,4S*)-1,2-dihydroxy-4-(methylsulfonyl)cyclohexyl)methyl)carbamate (Intermediate 27) in place of benzyl (((1R*,2R*,4R*)-1,2-dihydroxy-4-(methylsulfonyl)cyclohexyl)methyl)carbamate. $[\alpha]_{589}^{20}$–1.7, $[\alpha]_{436}^{20}$–5.1, $[\alpha]_{365}^{20}$–10 (c 1.7, MeOH).

Intermediate 31

1,4-Dioxaspiro[4.5]decane-8-carbonitrile

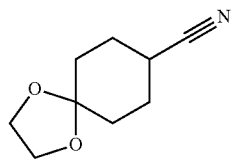 [SMILES: N#CC1CCC2(CC1)OCCO2]

A solution of t-BuOK (147 g, 1.31 mol) in t-BuOH and DME (2.0 L, 1:1 v/v) was added dropwise to a 0-5° C. solution of 1,4-dioxaspiro[4.5]decan-8-one (100 g, 640 mmol) and TosMIC (131 g, 672 mmol) in DME (2.0 L), and the resulting mixture was stirred at 0-5° C. for 1 h before it was allowed to warm to rt over 12 h. After this time, the mixture was poured into water and then extracted three timed with MTBE. The organic layers were combined, washed with brine, dried with anhydrous Na$_2$SO$_4$, filtered, and then concentrated to afford the title compound, which was used in the next step without further purification.

Intermediate 32

(1,4-Dioxaspiro[4.5]decan-8-yl)methanamine

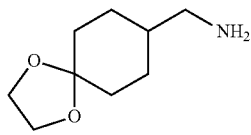 [SMILES: NCC1CCC2(CC1)OCCO2]

A solution of 1,4-dioxaspiro[4.5]decane-8-carbonitrile (130 g, 0.777 mol, Intermediate 31) in THF (500 mL) was added dropwise to a 0-5° C. suspension of LAH (44.3 g, 1.17 mol) in THF (2.0 L), and the resulting mixture was stirred at 65° C. for 12 h. After this time, the mixture was allowed to cool to rt and stirred for another 12 h. The mixture was then cooled to 0-5° C. before water (45 mL) and 15% aqueous NaOH (135 mL) were sequentially added dropwise. The resulting mixture was allowed to warm to rt over 1 h with stirring before anhydrous $MgSO_4$ was added, and the suspension was stirred for another 1 h at rt. The mixture was then filtered through a pad of Celite®, and the pad was washed with EtOAc. The filtrate and wash were combined, concentrated, and then purified by distillation to afford the title compound as a colorless oil.

Intermediate 33

2-(1,4-Dioxaspiro[4.5]decan-8-ylmethyl)isoindoline-1,3-dione

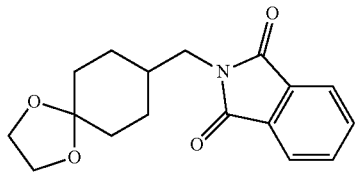 [SMILES: O=C1c2ccccc2C(=O)N1CC1CCC2(CC1)OCCO2]

A mixture of isobenzofuran-1,3-dione (64.2 g, 433 mmol), 1,4-dioxaspiro[4.5]decan-8-ylmethanamine (90.0 g, 433 mmol, Intermediate 32), TEA (52.6 g, 0.519 mol), and 4 Å molecular sieves (90 g) in toluene and DMF (990 mL, 10:1 v/v) was stirred at 110° C. for 12 h. After this time, the suspension was allowed to cool to rt and then filtered through a pad of Celite®. The pad was washed with EtOAc, and the filtrate and wash were combined, concentrated, and then purified by silica gel chromatography (10→50% EtOAc/petroleum ether) to afford the title compound as a colorless solid.

Intermediate 34

2-((4-Oxocyclohexyl)methyl)isoindoline-1,3-dione

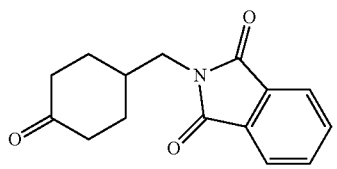 [SMILES: O=C1CCC(CN2C(=O)c3ccccc3C2=O)CC1]

Water (11.0 mL, 611 mmol) was added to a solution of 2-(1,4-dioxaspiro[4.5]decan-8-ylmethyl)isoindoline-1,3-dione (122 g, 405 mmol, Intermediate 33) in formic acid (900 mL), and the resulting solution was maintained at rt for 16 h. After this time, the solution was concentrated and then diluted with EtOAc. The resulting solution washed twice with a saturated aqueous $NaHCO_3$ solution, dried with anhydrous $Na_2SO_4$, filtered, and then concentrated to afford the title compound as a colorless solid.

Intermediate 35

2-((4-Hydroxycyclohexyl)methyl)isoindoline-1,3-dione

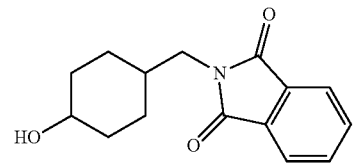 [SMILES: O=C1c2ccccc2C(=O)N1CC1CCC(O)CC1]

Sodium cyanoborohydride (48.5 g, 772 mmol) was added portionwise to a solution of 2-((4-oxocyclohexyl)methyl)isoindoline-1,3-dione (100 g, 389 mmol, Intermediate 34) in AcOH (1.0 L), and the resulting mixture was stirred at rt for 16 h. After this time, the mixture was concentrated, and the concentrate was dissolved in EtOAc. The resulting solution washed twice with a saturated aqueous $NaHCO_3$ solution, dried with anhydrous $Na_2SO_4$, filtered, and concentrated to afford the title compound as a colorless solid, which was used in the next step without further purification.

Intermediate 36

4-((1,3-Dioxoisoindolin-2-yl)methyl)cyclohexyl 4-methylbenzenesulfonate

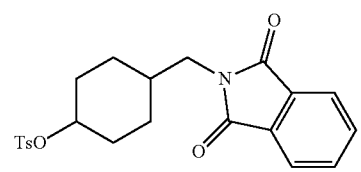 [SMILES: Cc1ccc(S(=O)(=O)OC2CCC(CN3C(=O)c4ccccc4C3=O)CC2)cc1]

4-Methylbenzene-1-sulfonyl chloride (199 g, 1.04 mol) was added to a 0-5° C. solution of 2-((4-hydroxycyclohexyl)-methyl)isoindoline-1,3-dione (135 g, 0.521 mol, Intermediate 35), and pyridine (165 g, 2.08 mol) in $CHCl_3$ (800 mL), and the resulting mixture was allowed to warm to rt over 12 h with stirring. After this time, the mixture was concentrated, and the concentrate was dissolved in EtOAc, washed with 2 N aqueous HCl, dried with anhydrous $Na_2SO_4$, filtered, and then concentrated. The concentrate was purified by silica gel chromatography (5→25% EtOAc/petroleum ether) to afford the title compound as a colorless solid.

Intermediate 37

S-(4-((1,3-dioxoisoindolin-2-yl)methyl)cyclohexyl) ethanethioate

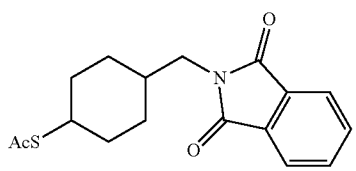

Potassium ethanethioate (27.6 g, 242 mmol) was added to a solution of 4-((1,3-dioxoisoindolin-2-yl)methyl)cyclohexyl 4-methylbenzenesulfonate (40.0 g, 96.7 mmol, Intermediate 36) in DMF (600 mL), and the resulting mixture was stirred at 75° C. for 12 h. After this time, the mixture was allowed to cool to rt and then concentrated. The concentrate was dissolved in EtOAc, washed with brine, dried with anhydrous $Na_2SO_4$, filtered, and then concentrated. The concentrate was purified by silica gel chromatography (5→25% EtOAc/petroleum ether) to afford the title compound as a yellow solid.

Intermediate 38

4-((1,3-Dioxoisoindolin-2-yl)methyl)cyclohexane-1-sulfonic acid

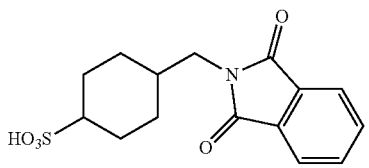 [SMILES: O=C1c2ccccc2C(=O)N1CC1CCC(S(=O)(=O)O)CC1]

A solution of $H_2O_2$ in water (20 mL, 30-34% w/w, 19 mmol) was added to formic acid (200 mL) at 0-5° C., and the solution was maintained at 0-5° C. for 1 h. A solution of S-(4-((1,3-dioxoisoindolin-2-yl)methyl)cyclohexyl) ethanethioate (10.0 g, 31.5 mmol, Intermediate 37) in formic acid and DCM (100 mL, 1:1 v/v) was then added, the mixture was allowed to warm to rt over 12 h with stirring. After this time, the mixture was cooled to 0-5° C. before solid $Na_2SO_3$ was added. The resulting mixture was filtered, concentrated, and then purified by silica gel chromatography (5→25% MeOH/DCM) to afford the title compound as a colorless solid.

Intermediate 39

4-((1,3-Dioxoisoindolin-2-yl)methyl)cyclohexane-1-sulfonyl Chloride

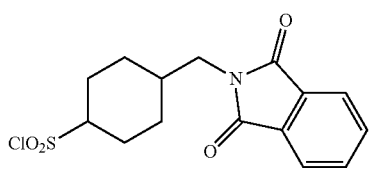 [SMILES: O=C1c2ccccc2C(=O)N1CC1CCC(S(=O)(=O)Cl)CC1]

Thionyl chloride (44.2 g, 371 mmol) and DMF (1.0 mL, 13 mmol) were added to a solution of 4-((1,3-dioxoisoindolin-2-yl)methyl)cyclohexane-1-sulfonic acid (24.0 g, 74.2 mmol, Intermediate 38) in $CHCl_3$ (300 mL), and the resulting mixture was stirred at 75° C. for 12 h. After this time, the mixture was allowed to cool to rt, and then it was concentrated. The concentrate underwent two cycles of sequential dilution with toluene and concentration to afford the title compound as a colorless solid.

Intermediate 40

N-(tert-Butyl)-4-((1,3-dioxoisoindolin-2-yl)methyl)cyclohexane-1-sulfonamide

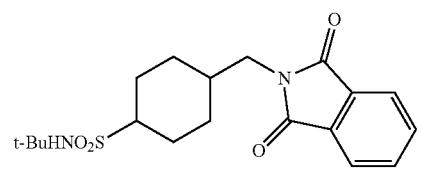

tert-Butylamine (10.7 g, 146 mmol) was added to a 0-5° C. mixture of 4-((1,3-dioxoisoindolin-2-yl)methyl)cyclohexane-1-sulfonyl chloride (5.0 g, 15 mmol, Intermediate 39) and 4 Å molecular sieves (11 g) in THF (60 mL), and the resulting mixture was allowed to warm to rt over 12 h with stirring. After this time, the mixture was filtered through Celite®, concentrated, and then purified by silica gel chromatography (3→25% MeOH/DCM). The product was repurified by preparative HPLC (Agela Durashell C18, 50%→70% $MeCN/H_2O$, 0.2% formic acid) to afford the title compound as a colorless solid.

Intermediate 41

4-((1,3-Dioxoisoindolin-2-yl)methyl)cyclohexane-1-sulfonamide

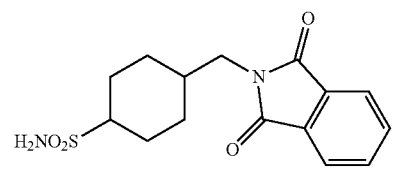 [SMILES: NS(=O)(=O)C1CCC(CN2C(=O)c3ccccc3C2=O)CC1]

Trifluoroacetic acid (10 mL, 130 mmol) was added dropwise to a 0-5° C. solution of N-(tert-butyl)-4-((1,3-dioxoisoindolin-2-yl)methyl)cyclohexane-1-sulfonamide (2.0 g, 5.3 mmol, Intermediate 40) in DCM (10 mL), and the resulting mixture was stirred at 0-5° C. for 12 h before it was concentrated. The concentrate was purified by preparative HPLC (Phenomenex Synergi Max-RP, 12%-52% MeCN/$H_2O$, 10 mM $NH_4HCO_3$) to afford the title compound as a colorless solid.

Intermediate 42

(1r,4r)-4-((1,3-Dioxoisoindolin-2-yl)methyl)cyclohexane-1-sulfonamide

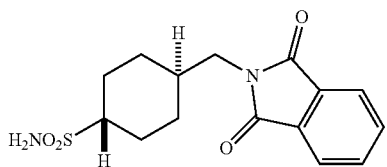 [SMILES: NS(=O)(=O)[C@H]1CC[C@H](CN2C(=O)c3ccccc3C2=O)CC1]

Intermediate 41 was purified by SFC (Chiralcel OJ-H, 80% $CO_2$, 20% MeOH) to give the title compound as a colorless solid.

Intermediate 43

(1r,4r)-4-(Aminomethyl)cyclohexane-1-sulfonamide Hydrochloride

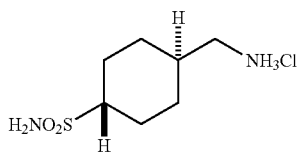

(1r,4r)-4-((1,3-Dioxoisoindolin-2-yl)methyl)cyclohexane-1-sulfonamide (1.1 g, 3.4 mmol, Intermediate 42) was suspended in EtOH (20 mL), hydrazine hydrate (0.51 mL, 65% w/w, 6.9 mmol) was added, and the resulting mixture was stirred at 80° C. for 16 h. After this time, the thick suspension was allowed to cool to rt and then was concentrated to afford a colorless solid. This solid was suspended in THF (20 mL), $Boc_2O$ (3.7 mL, 17 mmol) and enough water to dissolve the solids were added, and the mixture was stirred at rt overnight. The mixture was then concentrated to afford a colorless solid. This solid was diluted with acetone (15 mL), mixed, and then filtered. The filter cake was discarded. The filtrate was diluted with enough hexanes to promote formation of a precipitate, and the resulting suspension was stirred for 10 min and then filtered. The filter cake was washed with hexanes and dried by aspiration to afford tert-butyl (((1r,4r)-4-sulfamoylcyclohexyl)methyl)carbamate as a colorless solid. This solid was diluted with DCM (10 mL), TFA (2.6 mL, 34 mmol) was added, and the resulting solution was maintained at rt for 2 h. After this time, the solution was concentrated to afford a colorless solid. This solid was dissolved in MeOH, a 1,4-dioxane solution of HCl (0.77 mL, 4.0 M, 3.1 mmol) was added, and then the solution was concentrated. The resulting solid residue was suspended in EtOAc, and the solids were collected by filtration, washed with EtOAc, and dried by aspiration to afford the title compound as a colorless solid.

Intermediate 44

3,3,3-Trifluoro-2,2-dimethylpropan-1-ol

A solution of 3,3,3-trifluoro-2,2-dimethylpropanoic acid (340 g, 2.18 mol) in $Et_2O$ (340 mL) was added dropwise to a −15 to −5° C. suspension of LAH (108 g, 2.83 mol) in $Et_2O$ (3.1 L), and the mixture was stirred for 15 min. After this time, water (108 mL), 15% aqueous NaOH (108 mL), and more water (324 mL) were added at a rate that maintained the internal temperature at 0-10° C. Anhydrous $MgSO_4$ was then added, and the mixture was stirred for 30 min. The mixture was then filtered, and the filter cake was washed with $Et_2O$. The filtrate and wash were combined and then concentrated to afford the title compound as a pale-yellow liquid.

Intermediate 45

1,1,1-Trifluoro-3-iodo-2,2-dimethylpropane

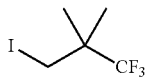

Iodine (536 g, 2.11 mol) was added in five portions to a stirring solution of $PPh_3$ (554 g, 2.11 mol), 3,3,3-trifluoro-2,2-dimethylpropan-1-ol (200 g, 1.41 mol, Intermediate 44), and imidazole (144 g, 2.11 mol) in NMP (1.0 L) at a rate that maintained the internal temperature between 45 and 50° C. The mixture was then warmed to 95-100° C. and stirred until the reaction went to completion. The reaction mixture was then allowed to cool to 50-65° C. and purified by distillation to give the title compound as a solution in NMP (58% w/w, bp 50-65° C. at 1-2 mmHg).

Intermediate 46

3,3-Difluoro-2,2-dimethylpropan-1-ol

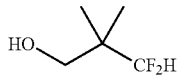

A suspension of LAH was prepared by adding solid LAH (5.67 g, 145 mmol) in portions to $Et_2O$ (170 mL) with stirring at 0° C. A solution of 3,3-difluoro-2,2-dimethylpropanoic acid (10 g, 72 mmol) in $Et_2O$ (50 mL) was then added dropwise over 1 h to the stirring LAH suspension before the mixture was allowed to warm to rt over 4 h. The reaction mixture was then cooled to 0° C., and water (5.6 mL), 10% aqueous NaOH (8.4 mL), and water (14 mL) were sequentially added. The mixture was stirred overnight, then anhydrous $MgSO_4$ was added, and the mixture was filtered. The filtrate was concentrated under atmospheric pressure at 55-70° C. to afford the title compound as a colorless liquid.

Intermediate 47

1,1-Difluoro-3-iodo-2,2-dimethylpropane

3,3-Difluoro-2,2-dimethylpropan-1-ol (11 g, 76% w/w, 67 mmol, Intermediate 46), MeI (8.4 mL, 140 mmol), and triphenyl phosphite (25 g, 81 mmol) were combined in a sealed vessel and the resulting solution was maintained at 80° C. for 25 h. The reaction mixture was allowed to cool, diluted with pentane (200 mL), and washed six times with 1 N aqueous NaOH (200 mL per wash). The organic layer was dried with $MgSO_4$, filtered, and then concentrated under atmospheric pressure. The concentrate was then purified by distillation under reduced pressure to afford the title compound as a colorless liquid.

Intermediate 48

(S*)-3,3,3-Trifluoro-2-methylpropanoic Acid

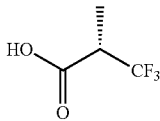

A solution of 2-(trifluoromethyl)acrylic acid (60.0 g, 0.429 mol), dicyclohexylamine (77.6 g, 0.428 mol), and (R)—RuCl[(p-cymene(BINAP)]Cl (3.96 g, 4.26 mmol) in MeOH (1.2 L) was stirred under an atmosphere of hydrogen (4-5 MPa) at 35-40° C. for 48 h. After this time, the mixture was filtered, and then the filtrate was concentrated. The concentrate was diluted with MTBE and EtOAc (600 mL, 1:1 v/v), and the solution was washed with a 10% aqueous $Na_2CO_3$ solution (300 mL×3). The aqueous phases were combined, and the pH was adjusted to pH 2-4 with aqueous HCl. The resulting mixture was filtered, and the filtrate was extracted with three times with MTBE. The organic layers were combined, dried with anhydrous $Na_2SO_4$, filtered, and then concentrated to give a yellow liquid (82.6% ee).

(S)-(+)-1,2,3,4-Tetrahydronaphthalen-1-amine (14.6 g, 99.2 mmol) was added dropwise to a 30° C. solution of (S*)-3,3,3-trifluoro-2-methylpropanoic acid from the previous step (17.6 g, 0.124 mol) in MTBE (210 mL), and then the mixture was cooled to 20° C. and stirred for 16 h. After this time, the suspension was filtered and the filter cake was dried to give (S)-1,2,3,4-tetrahydronaphthalen-1-amine (S*)-3,3,3-trifluoro-2-methylpropanoic acid salt as a colorless solid (dr=97.4:2.6).

A 5% aqueous $KHSO_4$ solution (400 mL) was added to a suspension of (S)-1,2,3,4-tetrahydronaphthalen-1-amine (S*)-3,3,3-trifluoro-2-methylpropanoic acid salt (26.7 g, 0.0924 mol) from the previous step in MTBE (260 mL), and the mixture was stirred until the solids dissolved. The layers were then separated, and the aqueous layer was extracted three times with MTBE. The organic layers were combined, washed twice with a 5% aqueous $KHSO_4$ solution, washed with water, and then concentrated to afford the title compound as yellow liquid (95.0% ee).

Intermediate 49

(P)-3,3,3-Trifluoro-2-methylpropan-1-ol

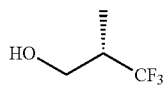

Lithium aluminum hydride (15.0 g, 0.369 mol) was added in portions to a stirring solution of (S*)-3,3,3-trifluoro-2-methylpropanoic acid (34.6 g, 0.244 mol, Intermediate 48) in $Et_2O$ (350 mL), which was cooled in an ice bath, at a rate that maintained the internal temperature below 15° C. The mixture was then allowed to warm to 20° C., and stirring was continued for 2 h. After this time, water (25 mL) was carefully added, and then the mixture was dried with anhydrous $Na_2SO_4$, filtered, and then concentrated under atmospheric pressure to give the title compound as a colorless liquid (95.8% ee).

Intermediate 50

(R*)-1,1,1-Trifluoro-3-iodo-2-methylpropane

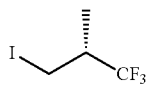

Iodine (44.58 g, 175.6 mmol) was added in five portions to a stirring solution of (S*)-3,3,3-trifluoro-2-methylpropan-1-ol (15.0 g, 117 mmol, Intermediate 49), $PPh_3$ (46.07 g, 175.6 mmol) and imidazole (11.96 g, 175.7 mmol) in NMP (75 mL) at a rate that maintained the internal temperature between 40 and 50° C. The mixture was then warmed to 55-60° C. and stirred until the reaction went to completion. The reaction mixture was then distilled directly to afford the title compound as a solution in NMP (50.5% w/w, bp 50-65° C. at 1-2 mm Hg).

Intermediate 51

(S*)-1,1,1-Trifluoro-3-iodo-2-methylpropane

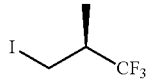

The title compound was prepared as described for the synthesis of Intermediate 50, using (S)—RuCl[(p-cymene (BINAP)]Cl and (S)-(−)-phenylethylamine in place of (R)—RuCl[(p-cymene(BINAP)]Cl and (S)-(+)-1,2,3,4-tetrahydronaphthalen-1-amine.

Intermediate 52

9-(3,3,3-Trifluoro-2-methylpropyl)-9-borabicyclo[3.3.1]nonane (0.5 M in THF)

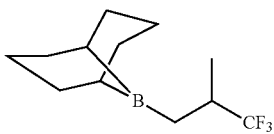

3,3,3-Trifluoro-2-methylprop-1-ene (6.5 g, 59 mmol) was condensed into a pressure vessel at −78° C. before a solution of 9-BBN in THF (100 mL, 0.5 M, 50 mmol) was slowly added. The vessel was then sealed and the suspension was allowed to warm to rt over 2 h. The resulting solution was then maintained at 65° C. for 18 h before it was allowed to cool to rt, sparged with argon, and then transferred to a Schlenk flask for storage.

Intermediate 53

9-(4,4,4-Trifluorobutyl)-9-borabicyclo[3.3.1]nonane (0.5 M in THF)

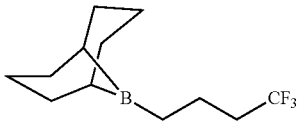

The title compound was prepared as described for Intermediate 52, using 4,4,4-trifluorobut-1-ene in place of 3,3,3-trifluoro-2-methylprop-1-ene.

Intermediate 54

4-Chloro-5-(6-chloro-4-ethylpyridin-3-yl)-1-ethyl-1H-pyrazole-3-carboxylic Acid

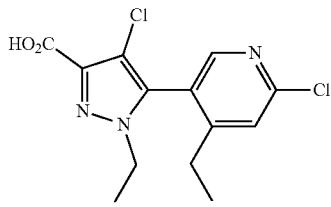 [SMILES: CCc1cc(Cl)ncc1-c1c(Cl)c(C(=O)O)nn1CC]

The title compound was prepared as described for the synthesis of Intermediate 69, using ethyl 4-chloro-5-(6-chloro-4-ethylpyridin-3-yl)-1-ethyl-1H-pyrazole-3-carboxylate (Intermediate 140) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 55

3,5-Dibromo-2-chloropyridin-4-ol

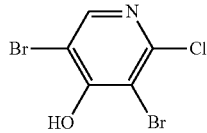

Bromine (3.70 kg, 23.3 mol) was added dropwise to a solution of 2-chloropyridin-4-ol (1.43 kg, 11.1 mol) in AcOH (7.0 L), and the resulting solution was stirred at 25° C. for 2 h. The solution was then poured into water, and the resulting suspension was filtered. The filter cake was stirred as a slurry in water, filtered, and then dried to afford the title compound as light-yellow solid.

Intermediate 56

5-Bromo-2-chloropyridin-4-ol

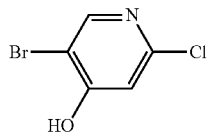

n-Butyl lithium (2.71 L, 2.5 M, 6.8 mol) was added dropwise to a stirring −78° C. solution of 3,5-dibromo-2-chloropyridin-4-ol (1130 g, 3.93 mol, Intermediate 55) in THF (13.6 L), and the resulting mixture was stirred at −78° C. for 10 min. After this time, water (2 L) was added dropwise to the reaction mixture, and then the mixture was allowed to warm to 0-5° C. The mixture was then washed three times with 2 N aqueous HCl, and the combined aqueous washes were back-extracted twice with EtOAc. All the organic layers were then combined and concentrated. The concentrate was stirred as a slurry in heptane at 25-30° C. for 3 h, filtered, and then dried under vacuum to afford the title compound as a light-yellow solid.

Intermediate 57

5-Bromo-2-chloro-4-(difluoromethoxy)pyridine

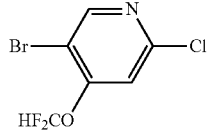

A solution of 5-bromo-2-chloropyridin-4-ol (200 g 0.960 mol, Intermediate 56) and sodium chlorodifluoroacetate (264 g, 1.73 mol) in DMF (1 L) was added dropwise to a 110-115° C. suspension of $Cs_2CO_3$ (469 g, 1.44 mol) in DMF (1 L), and the resulting mixture was stirred at 110-115° C. After the reaction went to completion, mixture was allowed to cool to 50-60° C., and then it was poured into ice water. The resulting mixture was extracted twice with MTBE, and the combined organic layers were washed with water and then concentrated. The concentrate was purified by distillation to afford the title compound as a colorless liquid (bp 75-78° C. at 1-2 mmHg).

Intermediate 58

Ethyl 1-ethyl-5-(4,4,5,5-tetramethyl-1,3,2-dioxaborolan-2-yl)-1H-pyrazole-3-carboxylate

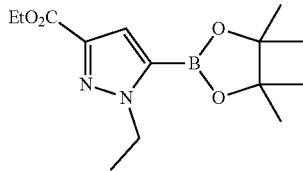 [SMILES: CCOC(=O)c1cc(B2OC(C)(C)C(C)(C)O2)n(CC)n1]

Iodoethane (836 g, 5.36 mol) was added dropwise to a mixture of ethyl 1H-pyrazole-3-carboxylate (500 g, 3.57 mol) and $K_2CO_3$ (987 g, 7.14 mol) in THF (15 L), and the resulting mixture was stirred at reflux temperature for 24 h. The mixture was then allowed to cool to rt before it was filtered, and the filter cake was washed with THF. The filtrate and wash were combined and then concentrated. The concentrate was purified by silica gel chromatography (9→33% EtOAc/petroleum ether) to afford ethyl 1-ethyl-1H-pyrazole-3-carboxylate as a light-yellow oil.

A mixture of (1,5-cyclooctadiene)(methoxy)iridium(I) dimer (1.18 g, 1.78 mmol), 1,10-phenanthroline (840 mg, 3.6 mmol), pinacolborane (37.2 g, 291 mmol) and pentane (180 mL) was stirred for 20 min at 10° C. before ethyl 1-ethyl-1H-pyrazole-3-carboxylate (30 g, 178 mmol) in pentane/THF (2:1 v/v) was added, and the resulting mixture was stirred at rt for 16 h. The mixture was then concentrated, and the concentrate was purified by silica gel chromatography (9→11%, EtOAc/petroleum ether) to afford the title compound as a colorless solid.

Intermediate 59

Ethyl 5-(6-chloro-4-(difluoromethoxy)pyridin-3-yl)-1-ethyl-1H-pyrazole-3-carboxylate

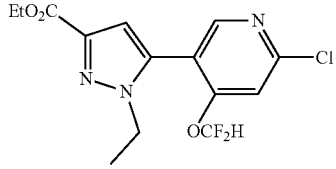

5-Bromo-2-chloro-4-(difluoromethoxy)pyridine (243 g, 0.938 mol, Intermediate 57), ethyl 1-ethyl-5-(4,4,5,5-tetramethyl-1,3,2-dioxaborolan-2-yl)-1H-pyrazole-3-carboxylate (230 g, 0.780 mol, Intermediate 58), $K_2CO_3$ (216 g, 1.56 mol), $Pd_2(dba)_3$ (35.8 g, 39.1 mmol), and $P(t-Bu)_3 \cdot HBF_4$ (22.7 g, 78.2 mmol) were diluted with toluene (3.5 L) and $H_2O$ (69 mL), and the resulting mixture was stirred at 25-30° C. for 7 h. Then the reaction mixture was then allowed to cool to 15-20° C. before it was filtered. The layers of the filtrate were separated, and the organic layer was washed twice with water. The organic layer was then concentrated, and the concentrate underwent two cycles of successive dilution with heptane and concentration. The concentrate was stirred as a slurry in heptane and then filtered. The filter cake was next stirred as a slurry in DME and heptane (1:2 v/v) and then filtered. The filter cake was dried to afford the title compound as an off-white solid.

Intermediate 60

Ethyl 5-(4-(difluoromethoxy)-6-(3,3,3-trifluoro-2,2-dimethylpropyl)pyridin-3-yl)-1-ethyl-1H-pyrazole-3-carboxylate

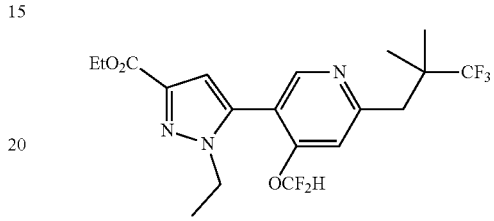

Trimethylsilyl chloride (7.54 g, 69.5 mmol), 1,2-dibromoethane (13 g, 0.070 mmol), and then 1,1,1-trifluoro-3-iodo-2,2-dimethylpropane (301 g, 58% w/w in NMP, 0.694 mol, Intermediate 45) were added dropwise to a stirring 45-50° C. suspension of Zn dust (63.6 g, 0.972 mol) in DMA (800 mL) at a rate that maintained the internal temperature at 45-50° C. The resulting mixture was then stirred at 60-65° C. for 40 min. After allowing the mixture to cool to 25-30° C., LiBr (129 g, 1.48 mol) was added in four portions at a rate that maintained the internal temperature at 30-45° C. The mixture was allowed to cool to 25-30° C. before PEPPSI-IPr (6.30 g, 9.24 mmol) and ethyl 5-(6-chloro-4-(difluoromethoxy)pyridin-3-yl)-1-ethyl-1H-pyrazole-3-carboxylate (160 g, 0.463 mol, Intermediate 59) were added, and the resulting mixture was stirred at 30-35° C. for 3 h. After this time, the reaction mixture was allowed to cool to rt and then poured into 5% aqueous citric acid solution. The mixture was diluted with MTBE, filtered, and the filter cake was washed with MTBE. The layers of the combined filtrate and wash were separated, and the aqueous layer was back-extracted with MTBE. The organic layers were all combined, washed with water, and then concentrated. The concentrate was stirred as a slurry in heptane, stirred, and then filtered. The filter cake was dried to give the title compound as a light-yellow solid.

Intermediate 61

Ethyl 4-chloro-5-(4-(difluoromethoxy)-6-(3,3,3-trifluoro-2,2-dimethylpropyl)pyridin-3-yl)-1-ethyl-1H-pyrazole-3-carboxylate

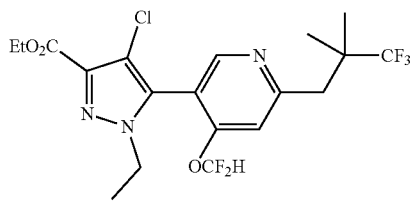

Sulfuryl chloride (515 g, 3.82 mol) was added dropwise to a solution of ethyl 5-(4-(difluoromethoxy)-6-(3,3,3-trifluoro-2,2-dimethylpropyl)pyridin-3-yl)-1-ethyl-1H-pyrazole-3-carboxylate (560 g, 1.29 mol, Intermediate 60) in DCM (1.7 L), and the resulting mixture was stirred at 25-30° C. for 16 h. After this time, heptane (2.5 L) was added dropwise to the reaction mixture, the resulting suspension was filtered, and the filter cake was washed with heptane. The filter cake was dissolved in EtOAc, washed with a saturated aqueous NaHCO$_3$ solution and then washed with brine. The organic layer was then concentrated, and the resulting residue was stirred as a slurry in heptane and then filtered. The filter cake was purified by silica gel chromatography (EtOAc/petroleum ether, 1:5 v/v) to afford the title compound as colorless solid.

Intermediate 62

5-(4-(Difluoromethoxy)-6-(3,3,3-trifluoro-2,2-dimethylpropyl)pyridin-3-yl)-1-ethyl-4-methyl-1H-pyrazole-3-carboxylic Acid

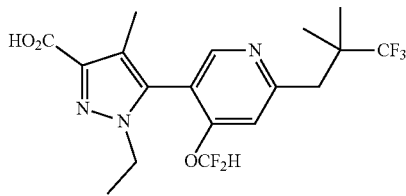

Ethyl 4-chloro-5-(4-(difluoromethoxy)-6-(3,3,3-trifluoro-2,2-dimethylpropyl)pyridin-3-yl)-1-ethyl-1H-pyrazole-3-carboxylate (32.0 g, 68.1 mmol, Intermediate 61), K$_2$CO$_3$ (37.6 g, 272 mmol), RuPhos (1.33 g, 2.85 mmol), and RuPhos Pd G2 (2.38, 3.06 mmol) were combined in a vessel, and the vessel was evacuated and backfilled with nitrogen three times. 1,4-Dioxane (320 mL) and trimethylboroxine (160 g, 50 wt % in THF, 200 mmol) were added and the reaction mixture was heated at 85-90° C. for 30 min. After this time, the mixture was allowed to cool to rt, combined with another three batches prepared in the same way (from a total of 80.9 mmol of Intermediate 61), and the resulting mixture was filtered. The filter cake was then rinsed with 1,4-dioxane (250 mL). The combined filtrate and rinse was used directly in the next step without further purification.

A solution of aqueous NaOH (600 mL, 1.0 N, 600 mmol) was added dropwise to a 1,4-dioxane solution of the crude ethyl 5-(4-(difluoromethoxy)-6-(3,3,3-trifluoro-2,2-dimethylpropyl)pyridin-3-yl)-1-ethyl-4-methyl-1H-pyrazole-3-carboxylate from the previous step (~150 mmol in 800 mL), and the mixture was stirred at rt overnight. After this time, the mixture was concentrated to removed most of 1,4-dioxane, and the concentrate was washed twice with MTBE. The combined organic washes were extracted with water, and then the all aqueous layers were combined. The pH of this solution was adjusted to pH 1-2 with 2 N aqueous HCl, and the resulting mixture was extracted twice with EtOAc. The organic layers were combined, washed with brine, dried with anhydrous Na$_2$SO$_4$, filtered, and concentrated. The concentrate was crystallized from n-heptane and MTBE (8:1 v/v) to afford the title compound as a yellow solid.

Intermediate 63

4-Chloro-5-(4-(difluoromethoxy)-6-(3,3,3-trifluoro-2,2-dimethylpropyl)pyridin-3-yl)-1-ethyl-1H-pyrazole-3-carboxylic Acid

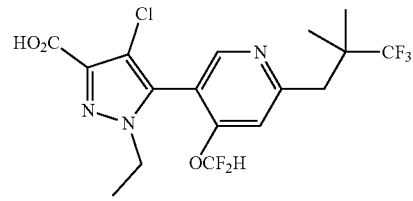

A solution of aqueous NaOH (366 mL, 1.0 N, 0.37 mmol) was added dropwise to a solution of ethyl 4-chloro-5-(4-(difluoromethoxy)-6-(3,3,3-trifluoro-2,2-dimethylpropyl)pyridin-3-yl)-1-ethyl-1H-pyrazole-3-carboxylate (43.0 g, 91.5 mmol, Intermediate 61) in 1,4-dioxane (300 mL), and the mixture was stirred at rt for 1 h. After this time, the resulting solution was concentrated to remove most of 1,4-dioxane and then diluted with water (400 mL). The pH of the solution was adjusted to pH 1-2 with 2 N aqueous HCl, and the resulting suspension was filtered and then dried under vacuum at 60° C. to give a sticky solid. The filtrate was extracted twice with EtOAc, and then the sticky solid was dissolved in the combined organic layers. The resulting solution was washed with brine, dried with anhydrous Na$_2$SO$_4$, filtered, and then concentrated. The concentrate underwent two cycles of successive dilution with heptane and concentration. The residue was then slurried with n-heptane and MTBE (20:3 v/v), stirred overnight, and filtered. The filter cake was rinsed with n-heptane and then dried under vacuum at 50° C. to the title compound as a colorless solid.

Intermediate 64

Ethyl 4-chloro-5-(6-chloro-4-(difluoromethoxy)pyridin-3-yl)-1-ethyl-1H-pyrazole-3-carboxylate

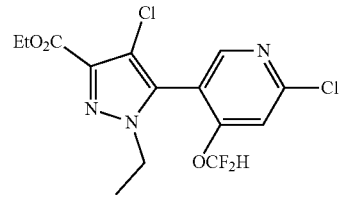

Sulfuryl chloride (35.1 g, 260 mmol) was added dropwise to solution of ethyl 5-(6-chloro-4-(difluoromethoxy)pyridin-3-yl)-1-ethyl-1H-pyrazole-3-carboxylate (45.0 g, 118 mmol, Intermediate 59) in DCM (450 mL) and the resulting mixture was stirred at rt until the reaction went to completion. The mixture was then cooled in an ice bath, and a saturated aqueous NaHCO$_3$ solution was added at a rate that maintained the internal temperature at 5-15° C. The pH of the aqueous layer was then adjusted to pH 7 and the layers were separated. The organic layer was washed with a saturated aqueous NaHCO$_3$ solution, the layers were separated, and the aqueous layer was back-extracted with DCM. The organic layers were combined, washed with water, and then concentrated. The concentrate was then slurried with heptane, filtered, and the filter cake was dried by aspiration to afford the title compound as an off-white solid.

Intermediate 65

1-(3-Bromopyridin-4-yl)ethan-1-ol

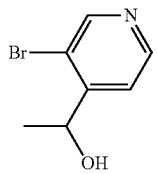

A solution of MeMgBr in Et$_2$O (54 mL, 3.0 M, 162 mmol) was added dropwise to a 65° C. solution of 3-bromoisonicotinaldehyde (10 g, 54 mmol) in THF (100 mL), and the resulting mixture was stirred and allowed to warm to 0° C. over 3 h. After this time, a saturated aqueous NH$_4$Cl solution was added, and the resulting mixture was extracted three times with EtOAc. The organic extracts were combined, washed with brine, dried with anhydrous Na$_2$SO$_4$, filtered, and then concentrated to afford the title compound as a colorless solid.

Intermediate 66

1-(3-Bromopyridin-4-yl)ethan-1-one

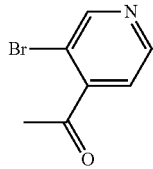

A mixture of the crude 1-(3-bromopyridin-4-yl)ethanol (9.5 g, 47 mmol, Intermediate 65) from the previous step and MnO$_2$ (33.0 g, 380 mmol) in toluene (100 mL) was stirred at 120° C. for 3 h. After this time, the mixture was allowed to cool to rt and then filtered through a pad of Celite®. The pad was washed with EtOAc, and the filtrate and wash were combined and then concentrated to afford the title compound as a yellow oil.

Intermediate 67

3-Bromo-4-(1,1-difluoroethyl)pyridine

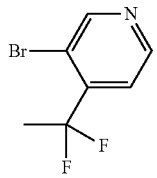

Diethylamino sulfurtrifluoride (14.5 g, 90.0 mmol) was added to a 0-5° C. solution of 1-(3-bromopyridin-4-yl)ethan-1-one (6.0 g, 30 mmol, Intermediate 66) in DCM (80 mL) and the resulting mixture was stirred at 0-5° C. for 2 h before it was allowed to warm to rt over 16 h. After this time, a saturated aqueous NaHCO$_3$ solution was added and the resulting mixture was extracted three times with DCM. The organic extracts were combined, dried with anhydrous Na$_2$SO$_4$, filtered, and then concentrated. The residue was purified by silica gel chromatography (2→10% EtOAc/petroleum ether) afford the title compound as a yellow oil.

Intermediate 68

Ethyl (S*)-4-chloro-5-(4-(difluoromethoxy)-6-(3,3,3-trifluoro-2-methylpropyl)pyridin-3-yl)-1-ethyl-1H-pyrazole-3-carboxylate

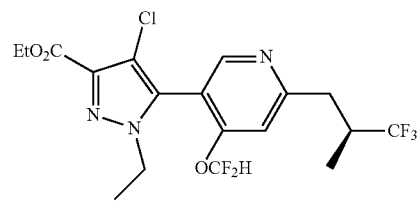

(R*)-1,1,1-Trifluoro-3-iodo-2-methylpropane (0.3 mL, 2.3 mmol, Intermediate 50) was added to a suspension of Rieke® zinc in THF (2.7 mL, 0.05 g/mL, 2.1 mmol), and the resulting mixture was stirred at 60-65° C. for 1 h. Ethyl 4-chloro-5-(6-chloro-4-(difluoromethoxy)pyridin-3-yl)-1-ethyl-1H-pyrazole-3-carboxylate (607 mg, 1.60 mmol, Intermediate 64) and Pd(t-Bu$_3$P)$_2$ (86 mg, 0.17 mmol) were combined in a separate vessel, and the vessel was evacuated and backfilled with nitrogen three times. The organozinc suspension was then added by cannula transfer to the vessel containing the aryl bromide, and the resulting suspension was stirred at 65° C. for 2 h. After this time, the mixture was allowed to cool to rt and then diluted with a saturated aqueous NH$_4$Cl solution and EtOAc. The layers were mixed and then separated, and the aqueous layer was extracted with EtOAc. The organic layers were combined, dried with anhydrous MgSO$_4$, filtered, and then concentrated. The residue was purified by silica gel chromatography (20→60% EtOAc/hexanes) to afford the title compound as a colorless oil.

Intermediate 69

(S*)-4-Chloro-5-(4-(difluoromethoxy)-6-(3,3,3-trifluoro-2-methylpropyl)pyridin-3-yl)-1-ethyl-1H-pyrazole-3-carboxylic Acid

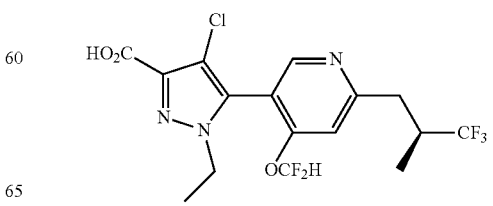

A solution of aqueous NaOH (1.45 mL, 1.0 N, 1.45 mmol) was added to a solution of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate (145 mg, 0.318 mmol, Intermediate 68) in 1,4-dioxane (1.5 mL), and the mixture was stirred at rt for 18 h. The pH of the resulting solution was adjusted to pH 1-2 with 1 N aqueous HCl, and the resulting mixture was extracted twice with EtOAc. The organic layers were combined, washed with brine, dried with anhydrous MgSO$_4$, filtered, and concentrated.

Intermediate 70

Ethyl (S*)-5-(4-(difluoromethoxy)-6-(3,3,3-trifluoro-2-methylpropyl)pyridin-3-yl)-1-ethyl-4-methyl-1H-pyrazole-3-carboxylate

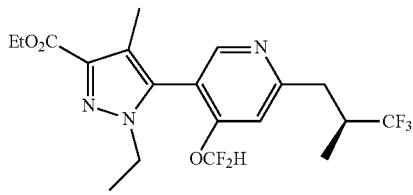

Ethyl (S*)-4-chloro-5-(4-(difluoromethoxy)-6-(3,3,3-trifluoro-2-methylpropyl)pyridin-3-yl)-1-ethyl-1H-pyrazole-3-carboxylate (95 mg, 0.21 mmol, Intermediate 68), RuPhos G1 precatalyst (16 mg, 0.019 mmol), RuPhos (8 mg, 0.020 mmol), and K$_2$CO$_3$ (116 mg, 0.839 mmol) were combined in a vessel, and the vessel was evacuated and backfilled with nitrogen three times. 1,4-Dioxane (0.71 mL) and then trimethylboroxine (0.088 mL, 0.63 mmol) were added and the mixture was stirred at 90° C. for 5 h. After this time, the mixture was allowed to cool and then diluted with EtOAc and water. The layers were separated, and the aqueous layer was extracted with EtOAc. The organic layers were combined, dried with anhydrous MgSO$_4$, filtered, and then concentrated. The residue was purified by silica gel chromatography (20→50% EtOAc/hexanes) to afford the title compound as a colorless oil.

Intermediate 71

(S*)-5-(4-(Difluoromethoxy)-6-(3,3,3-trifluoro-2-methylpropyl)pyridin-3-yl)-1-ethyl-4-methyl-1H-pyrazole-3-carboxylic Acid

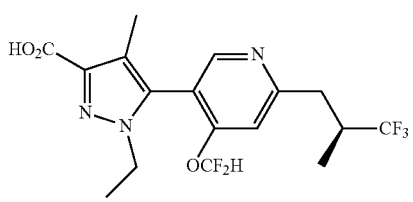

The title compound was prepared as described for the synthesis of Intermediate 69 using ethyl (S*)-5-(4-(difluoromethoxy)-6-(3,3,3-trifluoro-2-methylpropyl)pyridin-3-yl)-1-ethyl-4-methyl-1H-pyrazole-3-carboxylate (Intermediate 70) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 72

Ethyl (R*)-4-chloro-5-(4-(difluoromethoxy)-6-(3,3,3-trifluoro-2-methylpropyl)pyridin-3-yl)-1-ethyl-1H-pyrazole-3-carboxylate

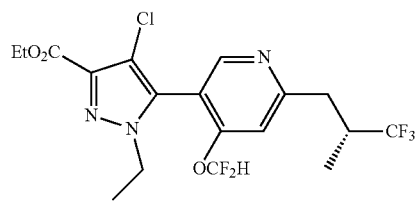

The title compound was prepared as described for the synthesis of Intermediate 68, using (S*)-1,1,1-trifluoro-3-iodo-2-methylpropane (Intermediate 51) in place of (R*)-1,1,1-trifluoro-3-iodo-2-methylpropane.

Intermediate 73

(R*)-4-Chloro-5-(4-(difluoromethoxy)-6-(3,3,3-trifluoro-2-methylpropyl)pyridin-3-yl)-1-ethyl-1H-pyrazole-3-carboxylic acid

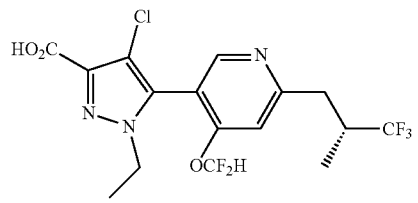

The title compound was prepared as described for the synthesis of Intermediate 69 using ethyl (R*)-4-chloro-5-(4-(difluoromethoxy)-6-(3,3,3-trifluoro-2-methylpropyl)pyridin-3-yl)-1-ethyl-1H-pyrazole-3-carboxylate (Intermediate 72) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 74

Ethyl (R*)-5-(4-(difluoromethoxy)-6-(3,3,3-trifluoro-2-methylpropyl)pyridin-3-yl)-1-ethyl-4-methyl-1H-pyrazole-3-carboxylate

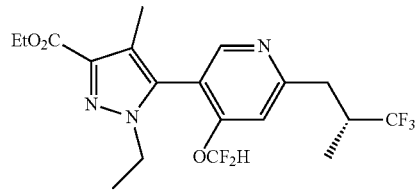

The title compound was prepared as described for the synthesis of Intermediate 70, using ethyl (R*)-4-chloro-5-(4-(difluoromethoxy)-6-(3,3,3-trifluoro-2-methylpropyl)pyridin-3-yl)-1-ethyl-1H-pyrazole-3-carboxylate (Intermediate 72) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 75

(R*)-5-(4-(Difluoromethoxy)-6-(3,3,3-trifluoro-2-methylpropyl)pyridin-3-yl)-1-ethyl-4-methyl-1H-pyrazole-3-carboxylic Acid

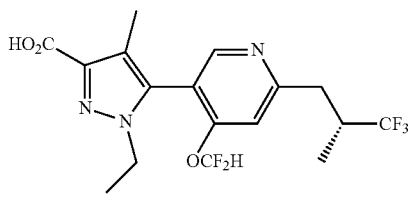

The title compound was prepared as described for the synthesis of Intermediate 69 using ethyl (R*)-5-(4-(difluoromethoxy)-6-(3,3,3-trifluoro-2-methylpropyl)pyridin-3-yl)-1-ethyl-4-methyl-1H-pyrazole-3-carboxylate (Intermediate 74) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 76

4-Chloro-5-(6-chloro-4-(difluoromethoxy)pyridin-3-yl)-1-ethyl-1H-pyrazole-3-carboxylic Acid

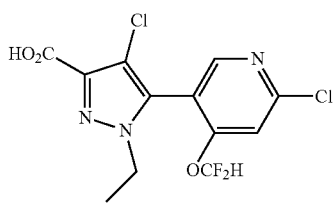

The title compound was prepared as described for the synthesis of Intermediate 69 using ethyl 4-chloro-5-(6-chloro-4-(difluoromethoxy)pyridin-3-yl)-1-ethyl-1H-pyrazole-3-carboxylate (Intermediate 64) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 77

4-Chloro-5-(6-chloro-4-(difluoromethoxy)pyridin-3-yl)-1-ethyl-N-(((1r,4r)-4-(methylsulfonyl)cyclohexyl)methyl)-1H-pyrazole-3-carboxamide

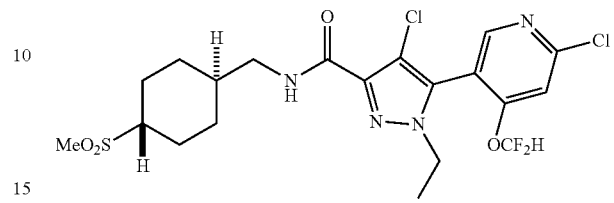

The title compound was prepared as described for the synthesis of Example 11 using 4-chloro-5-(6-chloro-4-(difluoromethoxy)pyridin-3-yl)-1-ethyl-1H-pyrazole-3-carboxylic acid (Intermediate 76) and ((1r,4r)-4-(methyl sulfonyl)cyclohexyl)methanamine hydrochloride (Intermediate 13) in place of 4-chloro-5-(4-(difluoromethoxy)-6-(3,3,3-trifluoro-2,2-di methylpropyl)pyridin-3-yl)-1-ethyl-1H-pyrazole-3-carboxylic acid and (1r,4r)-4-(aminomethyl)cyclohexane-1-sulfonamide hydrochloride.

Intermediate 78

4-Chloro-5-(6-chloro-4-(difluoromethoxy)pyridin-3-yl)-1-ethyl-N-(((1s,4s)-1-hydroxy-4-(methylsulfonyl)cyclohexyl)methyl)-1H-pyrazole-3-carboxamide

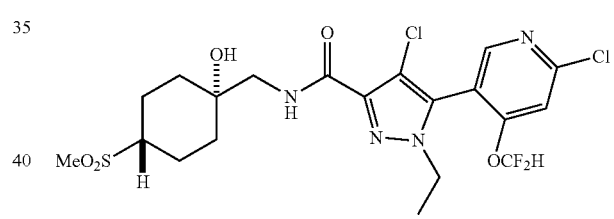

The title compound was prepared as described for the synthesis of Example 11 using 4-chloro-5-(6-chloro-4-(difluoromethoxy)pyridin-3-yl)-1-ethyl-1H-pyrazole-3-carboxylic acid (Intermediate 76) and (1s,4s)-1-(aminomethyl)-4-(methyl sulfonyl)cyclohexan-1-ol hydrochloride (Intermediate 9) in place of 4-chloro-5-(4-(difluoromethoxy)-6-(3,3,3-trifluoro-2,2-dim ethyl propyl)pyridin-3-yl)-1-ethyl-1H-pyrazole-3-carboxylic acid and (1r,4r)-4-(aminomethyl)cyclohexane-1-sulfonamide hydrochloride.

Intermediate 79

3-Bromo-4-isopropylpyridine

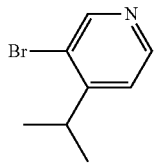

Neat BF$_3$.Et$_2$ (8.9 g, 63 mmol) was added dropwise to a 0° C. solution of 3-bromopyridine (9.0 g, 57 mmol) in THF (100 mL), and the resulting mixture was stirred at 0° C. for 15 min. The solution was then cooled to 50° C., and a solution of i-PrMgCl.LiCl (53 mL, 1.3 M in THF, 69 mol) was added. The resulting mixture was stirred at −50° C. for 30 min, chloranil (28.0 g, 114 mmol) was then added, and the resulting mixture was allowed to warm to 0° C. and stirred for 2 h. After this time, the mixture was allowed to warm to rt and a 25% aqueous ammonia solution was added. The mixture was extracted three times with EtOAc. The organic extracts were combined, washed with brine, dried with anhydrous Na$_2$SO$_4$, filtered, and concentrated. The concentrate was purified by silica gel chromatography (0→20% EtOAc/petroleum ether) to afford the title compound as a red oil.

Intermediate 80

Ethyl 1-ethyl-5-(4-isopropylpyridin-3-yl)-1H-pyrazole-3-carboxylate

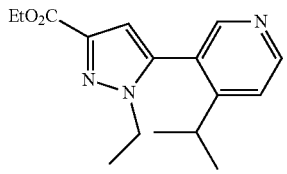 [SMILES: CCOC(=O)c1cc(-c2cnccc2C(C)C)n(CC)n1]

A mixture of 3-bromo-4-isopropylpyridine (3.5 g, 17 mmol, Intermediate 79), ethyl 1-ethyl-5-(4,4,5,5-tetramethyl-1,3,2-dioxaborolan-2-yl)-1H-pyrazole-3-carboxylate (5.66 g, 19.2 mmol, Intermediate 58), K$_2$CO$_3$ (7.25 g, 52.5 mmol), 1,4-dioxane (25 mL), and H$_2$O (5 mL) was sparged with argon for 5 min before Pd(t-Bu$_3$P)$_2$ (894 mg, 1.75 mmol) was added, and the resulting mixture was sparged with argon for another 5 min. The mixture was then stirred at 100° C. for 16 h. After this time, the mixture was allowed to cool to rt, diluted with water, and extracted three times with EtOAc. The organic extracts were combined, dried with anhydrous Na$_2$SO$_4$, filtered, and concentrated. The residue was purified by silica gel chromatography (5→50% EtOAc/petroleum ether) to afford the title compound as a yellow oil.

Intermediate 81

Ethyl 4-chloro-1-ethyl-5-(4-isopropylpyridin-3-yl)-1H-pyrazole-3-carboxylate

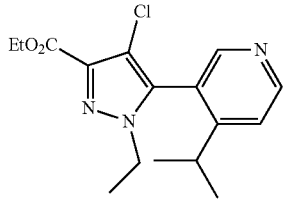 [SMILES: CCOC(=O)c1nn(CC)c(-c2cnccc2C(C)C)c1Cl]

The title compound was prepared as described for the synthesis of Intermediate 61, using ethyl 1-ethyl-5-(4-isopropylpyridin-3-yl)-1H-pyrazole-3-carboxylate (Intermediate 80) in place of ethyl 5-(4-(difluoromethoxy)-6-(3,3,3-trifluoro-2,2-dimethylpropyl)pyridin-3-yl)-1-ethyl-1H-pyrazole-3-carboxylate.

Intermediate 82

3-(4-Chloro-3-(ethoxycarbonyl)-1-ethyl-1H-pyrazol-5-yl)-4-isopropylpyridine 1-oxide

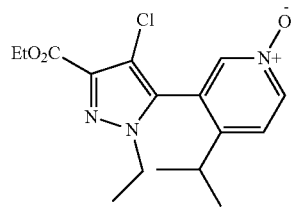 [SMILES: CCOC(=O)c1nn(CC)c(-c2c[n+](O)ccc2C(C)C)c1Cl]

Solid mCPBA (3.8 g, 80% w/w, 18 mol) was added to a 0° C. solution of ethyl 4-chloro-1-ethyl-5-(4-isopropylpyridin-3-yl)-1H-pyrazole-3-carboxylate (2.8 g, 8.7 mmol, Intermediate 81) in DCM (30 mL), and the resulting mixture was gradually allowed to warm to rt stirred over 16 h. After this time, the reaction was poured it into a saturated aqueous NaHCO$_3$ solution, and the resulting mixture was extracted twice with DCM. The organic extracts were combined, washed with an aqueous Na$_2$S$_2$O$_3$ solution, dried with anhydrous Na$_2$SO$_4$, filtered, and concentrated to give the crude product, which purified by silica gel chromatography (0→10% MeOH/DCM) to afford the title compound as a gray solid.

Intermediate 83

Ethyl 4-chloro-5-(6-chloro-4-isopropylpyridin-3-yl)-1-ethyl-1H-pyrazole-3-carboxylate

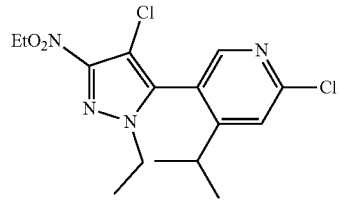

3-(4-Chloro-3-(ethoxycarbonyl)-1-ethyl-1H-pyrazol-5-yl)-4-isopropylpyridine 1-oxide (1.0 g, 3.0 mmol, Intermediate 82) and POCl$_3$ (30 g, 196 mmol) were stirred at 110° C. for 19 h. After this time, the reaction mixture was cooled to 0° C. and quenched by dropwise addition of 1 M aqueous NaOH (200 mL). The resulting mixture was extracted with DCM. The combined organic extracts were washed with brine, dried with anhydrous Na$_2$SO$_4$, filtered, and concentrated. The crude product was purified by silica gel chromatography (5→20% EtOAc/petroleum ether). The product was then repurified by silica gel chromatography (2→25% EtOAc/petroleum ether) to afford the title compound as a yellow oil.

Intermediate 84

Ethyl 4-chloro-1-ethyl-5-(4-isopropyl-6-(3,3,3-trifluoro-2,2-dimethylpropyl)pyridin-3-yl)-1H-pyrazole-3-carboxylate

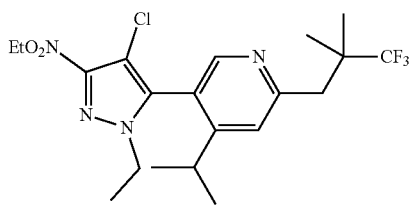

Lithium bromide (69 mg, 0.80 mmol) was heated under vacuum at 140° C. for 14 h. The dried salt was allowed to cool before DMI (0.4 mL) and THF (0.3 mL) were added, and the mixture was stirred at rt until it became homogeneous. In a separate vessel, 1,1,1-trifluoro-3-iodo-2,2-dimethylpropane (0.048 mL, 0.33 mmol, Intermediate 45) was added to a suspension of Rieke® zinc in THF (0.43 mL, 0.05 g/mL, 0.33 mmol) and the mixture was stirred at 65° C. for 30 min. After this time, the LiBr solution and then the organozinc suspension were sequentially added by cannula transfers to a vessel containing ethyl 4-chloro-5-(6-chloro-4-isopropylpyridin-3-yl)-1-ethyl-1H-pyrazole-3-carboxylate (89 mg, 0.25 mmol, Intermediate 83) and PEPPSI-IPr (5 mg, 0.007 mmol), and the resulting mixture was stirred at 65° C. for 18 h. The reaction mixture was then allowed to cool before it was diluted with EtOAc and a saturated aqueous solution of NH$_4$Cl. Water was added to dissolve salts in the aqueous layer, and the mixture was filtered. The layers of the filtrate were mixed and then separated. The organic layer was washed sequentially with water, washed with a saturated aqueous solution of NH$_4$Cl, dried with anhydrous MgSO$_4$, filtered, and then concentrated. The residue was purified by silica gel chromatography (10→40% EtOAc/hexanes) to afford the title compound.

Intermediate 85

4-Chloro-1-ethyl-5-(4-isopropyl-6-(3,3,3-trifluoro-2,2-dimethylpropyl)pyridin-3-yl)-1H-pyrazole-3-carboxylic acid

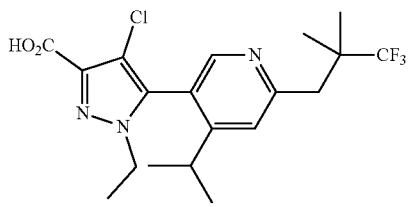

The title compound was prepared as described for the synthesis of Intermediate 69, using ethyl 4-chloro-1-ethyl-5-(4-isopropyl-6-(3,3,3-trifluoro-2,2-dimethylpropyl)pyridin-3-yl)-1H-pyrazole-3-carboxylate (Intermediate 84) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 86

3-Bromo-4-(difluoromethyl)pyridine

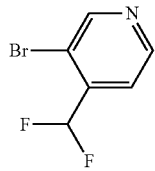

Deoxo-Fluor® (24.0 g, 108 mmol) was added to a 0° C. solution of 3-bromoisonicotinaldehyde (5.0 g, 27 mmol) in DCM (50 mL), and the reaction mixture was stirred at 0° C. for 2 h. After this time, a saturated aqueous NaHCO$_3$ solution was added, and the resulting mixture was extracted twice with DCM. The organic extracts were combined, washed with brine, dried with anhydrous Na$_2$SO$_4$, filtered, and concentrated. The residue was purified by silica gel chromatography (5→20% petroleum ether/EtOAc) to afford the title compound as a yellow oil.

Intermediate 87

Ethyl 5-(4-(difluoromethyl)pyridin-3-yl)-1-ethyl-1H-pyrazole-3-carboxylate

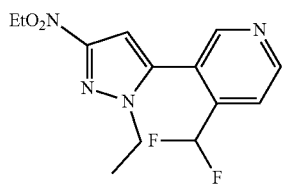

The title compound was prepared as described for the synthesis of Intermediate 80, using 3-bromo-4-(difluoromethyl)pyridine (Intermediate 86) in place of 3-bromo-4-isopropylpyridine.

Intermediate 88

Ethyl 4-chloro-5-(4-(difluoromethyl)pyridin-3-yl)-1-ethyl-1H-pyrazole-3-carboxylate

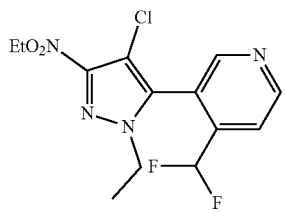

The title compound was prepared as described for the synthesis of Intermediate 61, using ethyl 5-(4-(difluoromethyl)pyridin-3-yl)-1-ethyl-1H-pyrazole-3-carboxylate (Intermediate 87) in place of ethyl 5-(4-(difluoromethoxy)-6-(3,3,3-trifluoro-2,2-dim ethyl propyl)pyridin-3-yl)-1-ethyl-1H-pyrazole-3-carboxylate.

Intermediate 89

3-(4-Chloro-3-(ethoxycarbonyl)-1-ethyl-1H-pyrazol-5-yl)-4-(difluoromethyl)pyridine 1-oxide

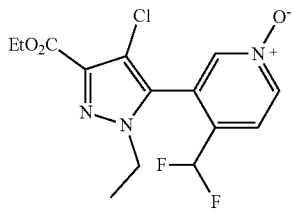

The title compound was prepared as described for the synthesis of Intermediate 82, using ethyl 4-chloro-5-(4-(difluoromethyl)pyridin-3-yl)-1-ethyl-1H-pyrazole-3-carboxylate (Intermediate 88) in place ethyl 4-chloro-1-ethyl-5-(4-isopropylpyridin-3-yl)-1H-pyrazole-3-carboxylate.

Intermediate 90

Ethyl 4-chloro-5-(6-chloro-4-(difluoromethyl)pyridin-3-yl)-1-ethyl-1H-pyrazole-3-carboxylate

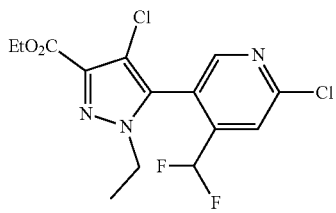 [SMILES: CCOC(=O)c1nn(CC)c(-c2cnc(Cl)cc2C(F)F)c1Cl]

The title compound was prepared as described for the synthesis of Intermediate 83, using 3-(4-chloro-3-(ethoxycarbonyl)-1-ethyl-1H-pyrazol-5-yl)-4-(difluoromethyl)pyridine 1-oxide (Intermediate 89) in place of 3-(4-chloro-3-(ethoxycarbonyl)-1-ethyl-1H-pyrazol-5-yl)-4-isopropylpyridine 1-oxide.

Intermediate 91

Ethyl 4-chloro-5-(4-(difluoromethyl)-6-(3,3,3-trifluoro-2,2-dimethylpropyl)pyridin-3-yl)-1-ethyl-1H-pyrazole-3-carboxylate

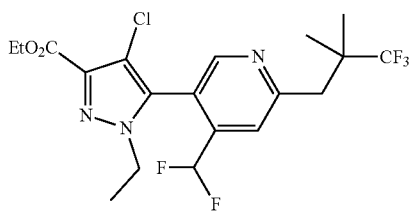

The title compound was prepared as described for the synthesis of Intermediate 84, using ethyl 4-chloro-5-(6-chloro-4-(difluoromethyl)pyridin-3-yl)-1-ethyl-1H-pyrazole-3-carboxylate (Intermediate 90) in place of ethyl 4-chloro-5-(6-chloro-4-isopropylpyridin-3-yl)-1-ethyl-1H-pyrazole-3-carboxylate.

Intermediate 92

4-Chloro-5-(4-(difluoromethyl)-6-(3,3,3-trifluoro-2,2-dimethylpropyl)pyridin-3-yl)-1-ethyl-1H-pyrazole-3-carboxylic Acid

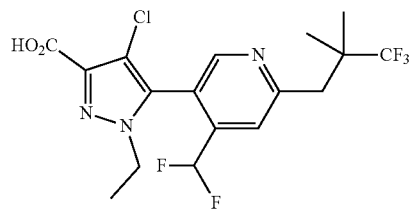

The title compound was prepared as described for the synthesis of Intermediate 69, using ethyl 4-chloro-5-(4-(difluoromethyl)-6-(3,3,3-trifluoro-2,2-di methylpropyl)pyridin-3-yl)-1-ethyl-1H-pyrazole-3-carboxylate (Intermediate 91) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 93

Ethyl 5-(4-(difluoromethyl)-6-(3,3,3-trifluoro-2,2-dimethylpropyl)pyridin-3-yl)-1-ethyl-4-methyl-1H-pyrazole-3-carboxylate

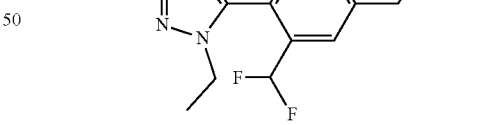

The title compound was prepared as described for the synthesis of Intermediate 70, using ethyl 4-chloro-5-(4-(difluoromethyl)-6-(3,3,3-trifluoro-2,2-di methylpropyl)pyridin-3-yl)-1-ethyl-1H-pyrazole-3-carboxylate (Intermediate 91) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 94

5-(4-(Difluoromethyl)-6-(3,3,3-trifluoro-2,2-dimethylpropyl)pyridin-3-yl)-1-ethyl-4-methyl-1H-pyrazole-3-carboxylic Acid

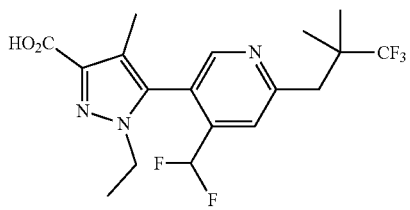 [SMILES: CCn1nc(C(=O)O)c(C)c1-c1cnc(CC(C)(C)C(F)(F)F)cc1C(F)F]

The title compound was prepared as described for the synthesis of Intermediate 69, using ethyl 5-(4-(difluoromethyl)-6-(3,3,3-trifluoro-2,2-dimethylpropyl)pyridin-3-yl)-1-ethyl-4-methyl-1H-pyrazole-3-carboxylate (Intermediate 93) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 95

3-Bromo-4-(difluoromethoxy)pyridine

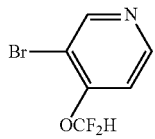

3-Bromopyridin-4-ol (10 g, 57 mmol), sodium chlorodifluoroacetate (9.64 g, 63.2 mmol), and $Cs_2CO_3$ (28.1 g, 86.2 mmol) were diluted with DMF (120 mL) and $H_2O$ (1.0 mL), and the resulting mixture was stirred at 100° C. for 1 h. The mixture was then allowed to cool to rt and was concentrated. The concentrate was dissolved in water and extracted twice with petroleum ether. The organic extracts were combined, washed with brine, dried over anhydrous $MgSO_4$, filtered and concentrated to afford the title product as a colorless oil.

Intermediate 96

Ethyl 1-methyl-5-(4,4,5,5-tetramethyl-1,3,2-dioxaborolan-2-yl)-1H-pyrazole-3-carboxylate

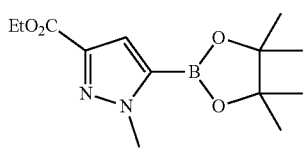 [SMILES: CCOC(=O)c1cc(B2OC(C)(C)C(C)(C)O2)n(C)n1]

The title compound was prepared as described for the synthesis of Intermediate 58, using iodomethane in place of iodoethane.

Intermediate 97

Ethyl 5-(4-(difluoromethoxy)pyridin-3-yl)-1-methyl-1H-pyrazole-3-carboxylate

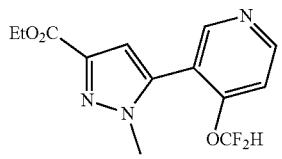

The title compound was prepared as described for the synthesis of Intermediate 80, using 3-bromo-4-(difluoromethoxy)pyridine (Intermediate 95) and ethyl 1-methyl-5-(4,4,5,5-tetramethyl-1,3,2-dioxaborolan-2-yl)-1H-pyrazole-3-carboxylate (Intermediate 96) in place of 5-bromo-2-chloro-4-(difluoromethoxy)pyridine and ethyl 1-ethyl-5-(4,4,5,5-tetramethyl-1,3,2-dioxaborolan-2-yl)-1H-pyrazole-3-carboxylate.

Intermediate 98

Ethyl 4-chloro-5-(4-(difluoromethoxy)pyridin-3-yl)-1-methyl-1H-pyrazole-3-carboxylate

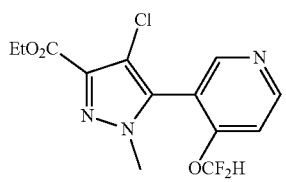

The title compound was prepared as described for the synthesis of Intermediate 61, using ethyl 5-(4-(difluoromethoxy)pyridin-3-yl)-1-methyl-1H-pyrazole-3-carboxylate (Intermediate 97) in place of ethyl 5-(4-(difluoromethoxy)-6-(3,3,3-trifluoro-2,2-dimethylpropyl)pyridin-3-yl)-1-ethyl-1H-pyrazole-3-carboxylate.

Intermediate 99

3-(4-Chloro-3-(ethoxycarbonyl)-1-methyl-1H-pyrazol-5-yl)-4-(difluoromethoxy)pyridine 1-oxide

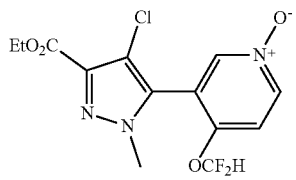

The title compound was prepared as described for the synthesis of Intermediate 82, using ethyl 4-chloro-5-(4-(difluoromethoxy)pyridin-3-yl)-1-methyl-1H-pyrazole-3-carboxylate (Intermediate 98) in place of ethyl 4-chloro-1-ethyl-5-(4-isopropylpyridin-3-yl)-1H-pyrazole-3-carboxylate.

Intermediate 100

Ethyl 4-chloro-5-(6-chloro-4-(difluoromethoxy)pyridin-3-yl)-1-methyl-1H-pyrazole-3-carboxylate

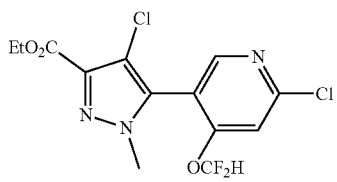

The title compound was prepared as described for the synthesis of Intermediate 83, using 3-(4-chloro-3-(ethoxycarbonyl)-1-methyl-1H-pyrazol-5-yl)-4-(difluoromethoxy)pyridine 1-oxide (Intermediate 99) in place of 3-(4-chloro-3-(ethoxycarbonyl)-1-ethyl-1H-pyrazol-5-yl)-4-isopropylpyridine 1-oxide.

Intermediate 101

Ethyl 4-chloro-5-(4-(difluoromethoxy)-6-(3,3,3-trifluoro-2,2-dimethylpropyl)pyridin-3-yl)-1-methyl-1H-pyrazole-3-carboxylate

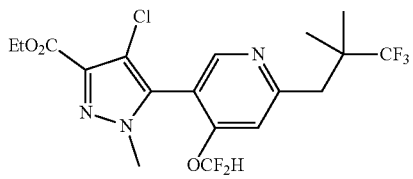

The title compound was prepared as described for the synthesis of Intermediate 68, using ethyl 4-chloro-5-(6-chloro-4-(difluoromethoxy)pyridin-3-yl)-1-methyl-1H-pyrazole-3-carboxylate (Intermediate 100) and 1,1,1-trifluoro-3-iodo-2,2-dimethylpropane (Intermediate 45) in place of ethyl 4-chloro-5-(6-chloro-4-(difluoromethoxy)pyridin-3-yl)-1-ethyl-1H-pyrazole-3-carboxylate and (R*)-1,1,1-trifluoro-3-iodo-2-methylpropane.

Intermediate 102

4-Chloro-5-(4-(difluoromethoxy)-6-(3,3,3-trifluoro-2,2-dimethylpropyl)pyridin-3-yl)-1-methyl-1H-pyrazole-3-carboxylic Acid

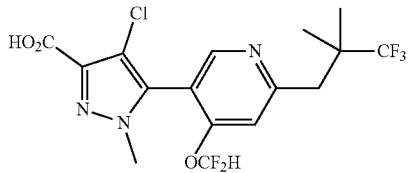

The title compound was prepared as described for the synthesis of Intermediate 69, using ethyl 4-chloro-5-(4-(difluoromethoxy)-6-(3,3,3-trifluoro-2,2-dimethylpropyl)pyridin-3-yl)-1-methyl-1H-pyrazole-3-carboxylate (Intermediate 101) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 103

Ethyl 5-(4-(difluoromethoxy)-6-(3,3,3-trifluoro-2,2-dimethylpropyl)pyridin-3-yl)-1,4-dimethyl-1H-pyrazole-3-carboxylate

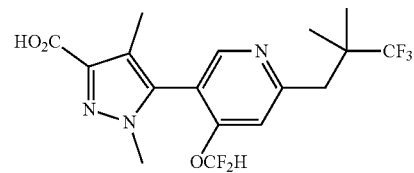

The title compound was prepared as described for the synthesis of Intermediate 70, using ethyl 4-chloro-5-(4-(difluoromethoxy)-6-(3,3,3-trifluoro-2,2-di methylpropyl)pyridin-3-yl)-1-methyl-1H-pyrazole-3-carboxylate (Intermediate 101) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 104

5-(4-(Difluoromethoxy)-6-(3,3,3-trifluoro-2,2-dimethylpropyl)pyridin-3-yl)-1,4-dimethyl-1H-pyrazole-3-carboxylic Acid

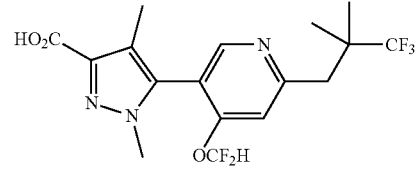

The title compound was prepared as described for the synthesis of Intermediate 69, using ethyl 5-(4-(difluoromethoxy)-6-(3,3,3-trifluoro-2,2-di methylpropyl)pyridin-3-yl)-1,4-di methyl-1H-pyrazole-3-carboxylate (Intermediate 103) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate (Intermediate 68).

Intermediate 105

Ethyl 4-chloro-5-(4-(difluoromethoxy)-6-(4,4,4-trifluorobutyl)pyridin-3-yl)-1-ethyl-1H-pyrazole-3-carboxylate

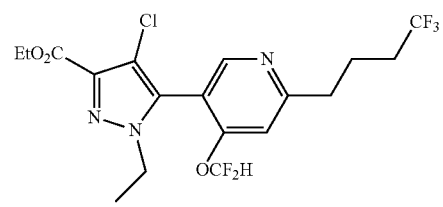

Ethyl 4-chloro-5-(6-chloro-4-(difluoromethoxy)pyridin-3-yl)-1-ethyl-1H-pyrazole-3-carboxylate (979 mg, 2.58 mmol, Intermediate 64), K$_2$CO$_3$ (783 mg, 5.67 mmol), and Pd(dppf)Cl$_2$.DCM (168 mg, 0.206 mmol) were combined in a vessel, and the vessel was evacuated and backfilled with nitrogen three times. A solution of 9-(4,4,4-trifluorobutyl)-9-borabicyclo[3.3.1]nonane (10.3 mL, 0.5 M in THF, 5.2 mmol, Intermediate 53) and DMF (3 mL) were then added, and the resulting mixture was stirred at 65° C. for 18 h. After this time, the mixture was allowed to cool and then it was diluted with EtOAc and water. The layers were separated, and the organic layer was washed with water, washed with brine, dried with anhydrous MgSO$_4$, filtered, and then concentrated. The residue was purified by silica gel chromatography (20→40% EtOAc/hexanes) to afford the title compound.

Intermediate 106

4-Chloro-5-(4-(difluoromethoxy)-6-(4,4,4-trifluorobutyl)pyridin-3-yl)-1-ethyl-1H-pyrazole-3-carboxylic Acid

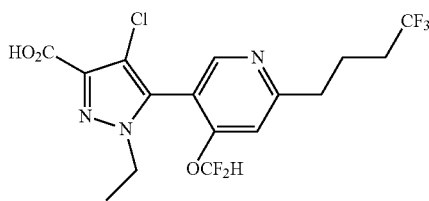

The title compound was prepared as described for the synthesis of Intermediate 69 using ethyl 4-chloro-5-(4-(difluoromethoxy)-6-(4,4,4-trifluorobutyl)pyridin-3-yl)-1-ethyl-1H-pyrazole-3-carboxylate (Intermediate 105) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 107

Ethyl 5-(4-(difluoromethoxy)-6-(4,4,4-trifluorobutyl)pyridin-3-yl)-1-ethyl-4-methyl-1H-pyrazole-3-carboxylate

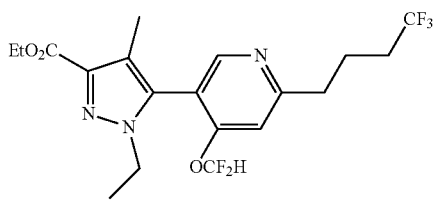

The title compound was prepared as described for the synthesis of Intermediate 70, using ethyl 4-chloro-5-(4-(difluoromethoxy)-6-(4,4,4-trifluorobutyl)pyridin-3-yl)-1-ethyl-1H-pyrazole-3-carboxylate (Intermediate 105) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 108

5-(4-(Difluoromethoxy)-6-(4,4,4-trifluorobutyl)pyridin-3-yl)-1-ethyl-4-methyl-1H-pyrazole-3-carboxylic Acid

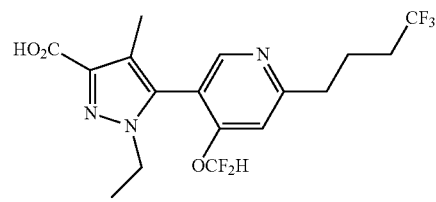

The title compound was prepared as described for the synthesis of Intermediate 69, using ethyl 5-(4-(difluoromethoxy)-6-(4,4,4-trifluorobutyl)pyridin-3-yl)-1-ethyl-4-methyl-1H-pyrazole-3-carboxylate (Intermediate 107) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 109

4-Chloro-1-ethyl-5-(4-methoxy-6-(3,3,3-trifluoro-2,2-dimethylpropoxy)pyridin-3-yl)-1H-pyrazole-3-carboxylic Acid

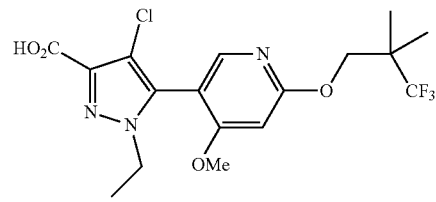 [SMILES: CCn1nc(C(=O)O)c(Cl)c1-c1cnc(OCC(C)(C)C(F)(F)F)cc1OC]

To 3,3,3-trifluoro-2,2-dimethylpropan-1-ol (93 mg, 0.58 mmol, Intermediate 44) in DMA (1.0 mL) was added NaH (22 mg, 60% dispersion in mineral oil, 0.55 mmol) and the reaction mixture was stirred at rt for 30 min. Ethyl 4-chloro-5-(6-chloro-4-methoxypyridin-3-yl)-1-ethyl-1H-pyrazole-3-carboxylate (100 mg, 0.291 mmol, Intermediate 137) in DMA (1.0 mL) was then added and the reaction was stirred 30 min. The reaction was then heated to 40° C. for 72 h. After this time, the reaction was partitioned between EtOAc and saturated aqueous NH$_4$Cl solution. The organic layer was concentrated, and the residue purified by silica gel chromatography (0→10%, MeOH/DCM) to afford the title compound.

Intermediate 110

Ethyl 4-chloro-5-(6-(3,3-difluoro-2,2-dimethylpropyl)-4-(difluoromethoxy)pyridin-3-yl)-1-ethyl-1H-pyrazole-3-carboxylate

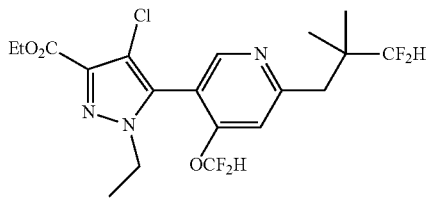

The title compound was prepared as described for the synthesis of Intermediate 84, using ethyl 4-chloro-5-(6-chloro-4-(difluoromethoxy)pyridin-3-yl)-1-ethyl-1H-pyrazole-3-carboxylate (Intermediate 64) and 1,1-difluoro-3-iodo-2,2-dimethylpropane (Intermediate 47) in place of ethyl 4-chloro-5-(6-chloro-4-isopropylpyridin-3-yl)-1-ethyl-1H-pyrazole-3-carboxylate and 1,1,1-trifluoro-3-iodo-2,2-dimethylpropane.

Intermediate 111

4-Chloro-5-(6-(3,3-difluoro-2,2-dimethylpropyl)-4-(difluoromethoxy)pyridin-3-yl)-1-ethyl-1H-pyrazole-3-carboxylic Acid

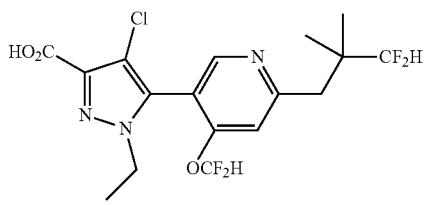

The title compound was prepared as described for the synthesis of Intermediate 69 using ethyl 4-chloro-5-(6-(3,3-difluoro-2,2-dimethylpropyl)-4-(difluoromethoxy)pyridin-3-yl)-1-ethyl-1H-pyrazole-3-carboxylate (Intermediate 110) in place of ethyl (S)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 112

Ethyl 5-(6-(3,3-difluoro-2,2-dimethylpropyl)-4-(difluoromethoxy)pyridin-3-yl)-1-ethyl-4-methyl-1H-pyrazole-3-carboxylate

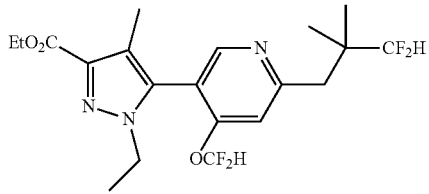

The title compound was prepared as described for the synthesis of Intermediate 70, using ethyl 4-chloro-5-(6-(3,3-difluoro-2,2-dimethylpropyl)-4-(difluoromethoxy)pyridin-3-yl)-1-ethyl-1H-pyrazole-3-carboxylate (Intermediate 110) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 113

5-(6-(3,3-Difluoro-2,2-dimethylpropyl)-4-(difluoromethoxy)pyridin-3-yl)-1-ethyl-4-methyl-1H-pyrazole-3-carboxylic Acid

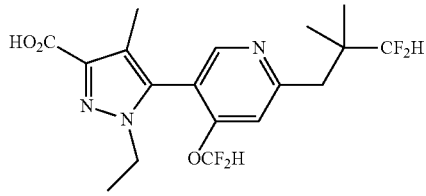

The title compound was prepared as described for the synthesis of Intermediate 69, using ethyl 5-(6-(3,3-difluoro-2,2-dimethyl propyl)-4-(difluoromethoxy)pyridin-3-yl)-1-ethyl-4-methyl-1H-pyrazole-3-carboxylate (Intermediate 112) in place of ethyl (S)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 114

3-Bromo-2-(difluoromethoxy)pyridine

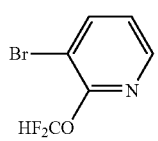

To 3-bromopyridin-2-ol (30.0 g, 172 mmol) and $Na_2CO_3$ (36.6 g, 345 mmol) in MeCN (180 mL) at 0° C. was added 2,2-difluoro-2-(fluorosulfonyl)acetic acid (18.0 mL, 174 mmol) drop-wise. The resulting mixture was stirred for 15 h with gradual warming to rt before pouring into brine (50 mL) and extracting with DCM (100 mL×3). The combined organic extracts were dried over anhydrous $Na_2SO_4$, filtered, and concentrated to give the crude product, which was purified by silica gel chromatography (0→10% EtOAc/petroleum ether) to afford the title compound as a colorless oil.

Intermediate 115

Ethyl 5-(2-(difluoromethoxy)pyridin-3-yl)-1-ethyl-1H-pyrazole-3-carboxylate

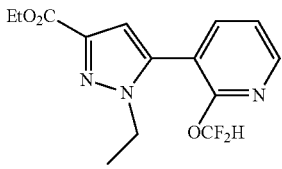

The title compound was prepared as described for the synthesis of Intermediate 80, using 3-bromo-2-(difluoromethoxy)pyridine (Intermediate 114) in place of 3-bromo-4-isopropylpyridine.

Intermediate 116

Ethyl 4-chloro-5-(2-(difluoromethoxy)pyridin-3-yl)-1-ethyl-1H-pyrazole-3-carboxylate

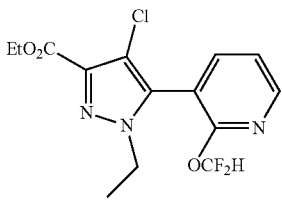

The title compound was prepared as described for the synthesis of Intermediate 61, using ethyl 5-(2-(difluoromethoxy)pyridin-3-yl)-1-ethyl-1H-pyrazole-3-carboxylate (Intermediate 115) in place of ethyl 5-(4-(difluoromethoxy)-6-(3,3,3-trifluoro-2,2-dimethylpropyl)pyridin-3-yl)-1-ethyl-1H-pyrazole-3-carboxylate.

Intermediate 117

3-(4-Chloro-3-(ethoxycarbonyl)-1-ethyl-1H-pyrazol-5-yl)-2-(difluoromethoxy)pyridine 1-oxide

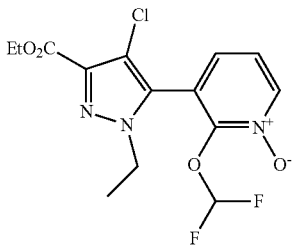 [SMILES: CCOC(=O)c1nn(CC)c(-c2ccc[n+]([O-])c2OC(F)F)c1Cl]

Hydrogen peroxide (17.4 mL, 30% w/w, 173 mmol) was added dropwise to trifluoroacetic anhydride (65.2 mL, 463 mmol) at 0° C., and the resulting mixture stirred and allowed to warm to rt gradually over 4 h. The resulting mixture was added dropwise to a solution of ethyl 4-chloro-5-(2-(difluoromethoxy)pyridin-3-yl)-1-ethyl-1H-pyrazole-3-carboxylate (10 g, 29 mmol, Intermediate 116) in DCE (85 mL). The resulting mixture was stirred at rt for 1 h and then heated to 80° C. for 15 h before it was poured into a 1.0 M aqueous $Na_2SO_3$ solution (300 mL). The resulting mixture was stirred at rt for 15 min before its pH was adjusted to pH 9 using $K_2CO_3$. The mixture was extracted with three times with DCM, and the organic extracts were combined, washed with brine, dried with anhydrous $Na_2SO_4$, filtered, and concentrated. The residue was purified by preparative HPLC (Phenomenex Synergi Max-RP, 20→55% $CH_3CN/H_2O$, 0.2% formic acid) to afford the title compound.

Intermediate 118

Ethyl 4-chloro-5-(6-chloro-2-(difluoromethoxy)pyridin-3-yl)-1-ethyl-1H-pyrazole-3-carboxylate

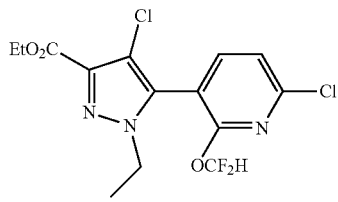

The title compound was prepared as described for the synthesis of Intermediate 83, using 3-(4-chloro-3-(ethoxycarbonyl)-1-ethyl-1H-pyrazol-5-yl)-2-(difluoromethoxy)pyridine 1-oxide (Intermediate 117) in place of 3-(4-chloro-3-(ethoxycarbonyl)-1-ethyl-1H-pyrazol-5-yl)-4-isopropylpyridine 1-oxide.

Intermediate 119

Ethyl 4-chloro-5-(2-(difluoromethoxy)-6-(3,3,3-trifluoro-2,2-dimethylpropyl)pyridin-3-yl)-1-ethyl-1H-pyrazole-3-carboxylate

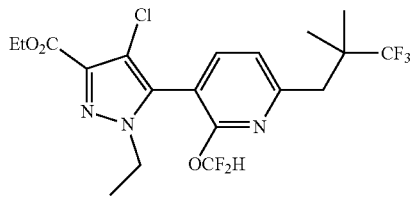

The title compound was prepared as described for the synthesis of Intermediate 84, using ethyl 4-chloro-5-(6-chloro-2-(difluoromethoxy)pyridin-3-yl)-1-ethyl-1H-pyrazole-3-carboxylate (Intermediate 118) in place of ethyl 4-chloro-5-(6-chloro-4-isopropyl pyridin-3-yl)-1-ethyl-1H-pyrazole-3-carboxylate.

Intermediate 120

4-Chloro-5-(2-(difluoromethoxy)-6-(3,3,3-trifluoro-2,2-dimethylpropyl)pyridin-3-yl)-1-ethyl-1H-pyrazole-3-carboxylic Acid

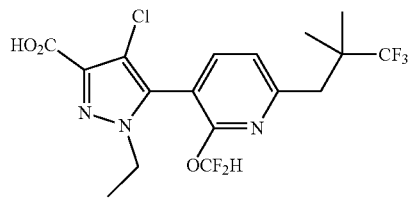

The title compound was prepared as described for the synthesis of Intermediate 69, using ethyl 4-chloro-5-(2-(difluoromethoxy)-6-(3,3,3-trifluoro-2,2-di methylpropyl) pyridin-3-yl)-1-ethyl-1H-pyrazole-3-carboxylate (Intermediate 119) in place of ethyl (S*)-4-chloro-5-(4-(difluoromethoxy)-6-(3,3,3-trifluoro-2-methylpropyl) pyridin-3-yl)-1-ethyl-1H-pyrazole-3-carboxylate.

Intermediate 121

Ethyl 5-(2-(difluoromethoxy)-6-(3,3,3-trifluoro-2,2-dimethylpropyl)pyridin-3-yl)-1-ethyl-4-methyl-1H-pyrazole-3-carboxylate

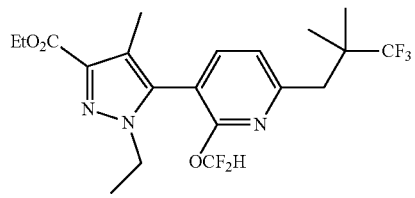

The title compound was prepared as described for the synthesis of Intermediate 70, using ethyl 4-chloro-5-(2-(difluoromethoxy)-6-(3,3,3-trifluoro-2,2-di methylpropyl) pyridin-3-yl)-1-ethyl-1H-pyrazole-3-carboxylate (Intermediate 119) in place of ethyl (S*)-4-chloro-5-(4-(difluoromethoxy)-6-(3,3,3-trifluoro-2-methylpropyl) pyridin-3-yl)-1-ethyl-1H-pyrazole-3-carboxylate.

Intermediate 122

5-(2-(Difluoromethoxy)-6-(3,3,3-trifluoro-2,2-dimethylpropyl)pyridin-3-yl)-1-ethyl-4-methyl-1H-pyrazole-3-carboxylic Acid

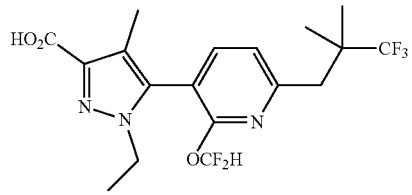

The title compound was prepared as described for the synthesis of Intermediate 69 using ethyl 5-(2-(difluoromethoxy)-6-(3,3,3-trifluoro-2,2-dim ethyl propyl)pyridin-3-yl)-1-ethyl-4-methyl-1H-pyrazole-3-carboxylate (Intermediate 121) in place of ethyl (S*)-4-chloro-5-(4-(difluoromethoxy)-6-(3,3,3-trifluoro-2-methylpropyl) pyridin-3-yl)-1-ethyl-1H-pyrazole-3-carboxylate.

Intermediate 123

5-Bromo-3-methoxypicolinonitrile

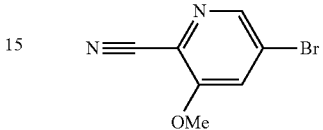

Sodium (5.80 g, 252 mmol) was added to 0° C. MeOH (500 mL) in portions. The resulting solution (0.5 M NaOMe in MeOH) was added to a rt solution of 5-bromo-3-nitropicolinonitrile (50.0 g, 219 mmol) in MeOH (500 mL), and the resulting mixture was heated at reflux temperature for 1.5 h. After this time, the mixture was allowed to cool to rt, and then it was concentrated. The residue was purified by silica gel chromatography (10→25% EtOAc/petroleum ether) to afford the title compound as a light yellow solid.

Intermediate 124

1-(5-Bromo-3-methoxypyridin-2-yl)ethan-1-one

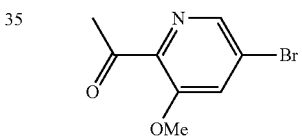

A solution of MeMgBr (40.0 mL, 3.0 M in Et₂O, 120 mmol) was added to a 0° C. solution of 5-bromo-3-methoxypicolinonitrile (23.5 g, 110 mmol, Intermediate 123) in THF (500 mL), and the mixture was stirred at 0° C. for 30 min and then at rt for 1 h. The mixture was then added to saturated aqueous citric acid solution (150 mL) and extracted five times with EtOAc. The extracts were combined, dried with anhydrous Na₂SO₄, filtered, and concentrated. The concentrate was purified by silica gel chromatography (6% EtOAc/petroleum ether) to afford the title compound as a yellow solid.

Intermediate 125

Ethyl 4-(5-bromo-3-methoxypyridin-2-yl)-2,4-dioxobutanoate

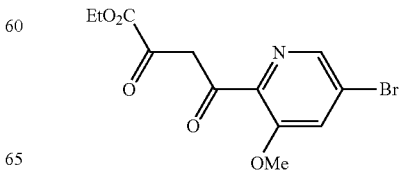

A solution of LiHMDS (60 mL, 1 M in THF, 60 mmol) was added dropwise to a rt solution of 1-(5-bromo-3-methoxypyridin-2-yl)ethan-1-one (10.0 g, 43.5 mmol Intermediate 124) in THF (120 mL), and the resulting mixture was stirred for 30 min. After this time, solution of diethyl oxalate (7.7 g, 53 mmol) in THF was added, and the reaction mixture was stirred for 2 h. The mixture was then diluted with water and extracted three times with EtOAc. The extracts were combined, dried with anhydrous Na₂SO₄, filtered and concentrated to give the title compound.

Intermediate 126

Ethyl 5-(5-bromo-3-methoxypyridin-2-yl)-1-ethyl-1H-pyrazole-3-carboxylate

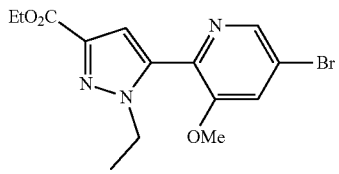 [SMILES: CCOC(=O)c1cc(-c2ncc(Br)cc2OC)n(CC)n1]

A mixture of ethyl 4-(5-bromo-3-methoxypyridin-2-yl)-2,4-dioxobutanoate (10 g, 30 mmol Intermediate 125), ethyl hydrazine oxalate (6.9 g, 46 mmol), and EtOH (500 mL) was stirred at 80° C. for 4 h. The mixture was poured into a saturated aqueous NaHCO₃ solution and extracted three times with EtOAc. The organic extracts were combined, dried with anhydrous Na₂SO₄, filtered and concentrated. The crude product was purified by silica gel chromatography (10→30% EtOAc/petroleum ether) to afford the title compound.

Intermediate 127

Ethyl 5-(5-bromo-3-hydroxypyridin-2-yl)-1-ethyl-1H-pyrazole-3-carboxylate

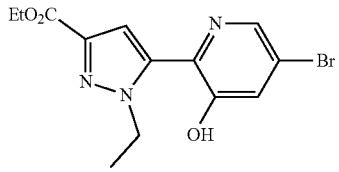 [SMILES: CCOC(=O)c1cc(-c2ncc(Br)cc2O)n(CC)n1]

Trimethylsilyl iodide (1.4 mL, 9.9 mmol) was added to a solution of ethyl 5-(5-bromo-3-methoxypyridin-2-yl)-1-ethyl-1H-pyrazole-3-carboxylate (1.2 g, 3.4 mmol, Intermediate 126) in MeCN (15 mL), and the solution was heated to 100° C. by microwave irradiation for 1 h. After this time, the mixture was allowed to cool to rt, additional TMSI (1.2 mL, 8.4 mmol) was added, and then the mixture was heated at 100° C. for an additional 1 h. After this time, the mixture was allowed to cool to rt, additional TMSI (1.2 mL, 8.4 mmol) was added, and then the mixture was heated at 100° C. for an additional 2 h. The mixture was then allowed to cool and combined with additional reaction mixtures prepared in the same way (6.0 g, 77 mmol of Intermediate 126 used in total).

Methanol (150 mL) and 37% aqueous HCl (6 mL) were added, and the resulting mixture was heated at 70° C. for 20 h. The mixture was then allowed to cool, and then it was concentrated to give the crude product, which was purified by preparative HPLC (Phenomenex Synergi Max-RP, 40→90% MeCN/H₂O, 0.05% NH₄OH) to afford the title compound.

Intermediate 128

Ethyl 5-(5-bromo-3-(difluoromethoxy)pyridin-2-yl)-1-ethyl-1H-pyrazole-3-carboxylate

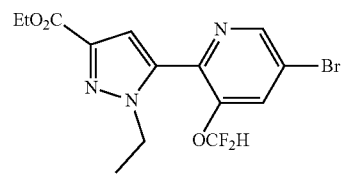

A solution of ethyl 5-(5-bromo-3-hydroxypyridin-2-yl)-1-ethyl-1H-pyrazole-3-carboxylate (1.0 g, 2.9 mmol, Intermediate 127), sodium 2-chloro-2,2-difluoroacetate (896 mg, 5.88 mmol) and K₂CO₃ (4.06 g, 29.4 mmol) in DMF (15 mL) was heated to 100° C. for 3 h. The reaction mixture was then allowed to cool, concentrated, triturated with EtOAc (50 mL), and filtered. The filtrate concentrated, and this concentrate was purified by silica gel chromatography (10→100% EtOAc/petroleum ether) to afford the title compound as a colorless solid.

Intermediate 129

Ethyl 5-(5-bromo-3-(difluoromethoxy)pyridin-2-yl)-4-chloro-1-ethyl-1H-pyrazole-3-carboxylate

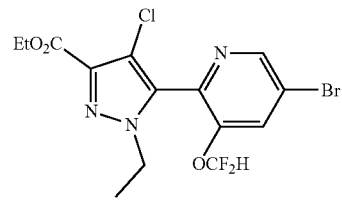

Sulfuryl dichloride (899 mg, 6.66 mmol) was added dropwise to a 0° C. solution of ethyl 5-(5-bromo-3-(difluoromethoxy)pyridin-2-yl)-1-ethyl-1H-pyrazole-3-carboxylate (1.3 g, 3.3 mmol, Intermediate 128) in DCM (10 mL), and the resulting mixture was stirred at rt for 1 h. The mixture was then diluted with DCM (50 mL), washed with a saturated aqueous NaHCO₃ solution, washed with brine, dried with anhydrous Na₂SO₄, filtered and concentrated. The residue was purified by silica gel chromatography (10→50% EtOAc/petroleum ether) to afford the title compound as a colorless solid.

Intermediate 130

Ethyl 4-chloro-5-(3-(difluoromethoxy)-5-(3,3,3-trifluoro-2,2-dimethylpropyl)pyridin-2-yl)-1-ethyl-1H-pyrazole-3-carboxylate

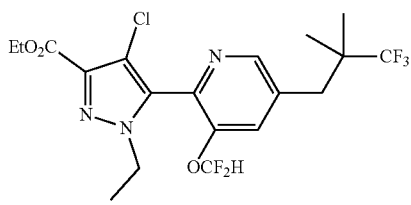

1,2-Dibromoethane (23 uL, 0.31 mmol) was added to a suspension of zinc (160 mg, 2.45 mmol) in THF (20 mL), and the resulting mixture was stirred at 80° C. for 10 min before it was allowed to cool to rt. Solutions TMSCl (0.036 mL, 0.28 mmol) in THF (5 mL) and 1,1,1-trifluoro-3-iodo-2,2-dimethylpropane (522 mg, 2.07 mmol, Intermediate 45) in THF (5 mL) were then added in sequence over a period of 30 min, and the resulting mixture was stirred at rt for 2 h. After this time, Pd(t-Bu$_3$P)$_2$ (136 mg, 0.266 mmol) and a solution of ethyl 5-(5-bromo-3-(difluoromethoxy)pyridin-2-yl)-4-chloro-1-ethyl-1H-pyrazole-3-carboxylate (800 mg, 1.88 mmol (Intermediate 129) in THF (20 mL) were added, and the resulting mixture was stirred at 65° C. for 16 h. After this time, the mixture was allowed to cool to rt, passed through a pad of silica gel, and then concentrated. The residue was purified by preparative HPLC (Phenomenex Gemini, 60→90% MeCN/H$_2$O, 0.05% NH$_4$OH) to afford the title compound.

Intermediate 131

4-Chloro-5-(3-(difluoromethoxy)-5-(3,3,3-trifluoro-2,2-dimethylpropyl)pyridin-2-yl)-1-ethyl-1H-pyrazole-3-carboxylic Acid

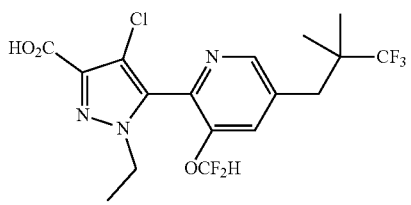

The title compound was prepared as described for the synthesis of Intermediate 69 using ethyl 4-chloro-5-(3-(difluoromethoxy)-5-(3,3,3-trifluoro-2,2-dimethylpropyl)pyridin-2-yl)-1-ethyl-1H-pyrazole-3-carboxylate (Intermediate 130) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 132

6-Chloro-4-methoxynicotinic Acid

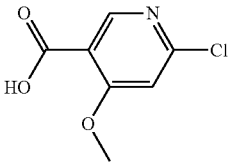

Aqueous NaOH (200 mL, 1.0 N, 200 mmol) was added to a solution of methyl 6-chloro-4-methoxynicotinate (20 g, 99 mmol) in 1,4-dioxane (250 mL). The mixture was stirred at rt for 2 h. After this time, the mixture concentrated and then diluted with water. The pH of the mixture was adjusted to pH 2 with 1 N aqueous HCl solution, and then the mixture was the then extracted twice with EtOAc. The organic layers were combined, dried with anhydrous MgSO$_4$, filtered, and concentrated to provide the title compound.

Intermediate 133

6-Chloro-N,4-dimethoxy-N-methylnicotinamide

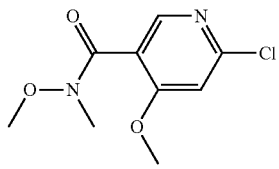

Triethylamine (7.0 mL, 51 mmol) was added to a suspension of 6-chloro-4-methoxynicotinic acid (2.615 g, 13.94 mmol, Intermediate 132) in MeCN (93 mL). N-(3-Dimethylaminopropyl)-N'-ethylcarbodiimide hydrochloride (3.74 g, 19.5 mmol), HOBt (2.64 g, 19.5 mmol), and N,O-dimethylhydroxylamine hydrochloride (2.05 g, 21.0 mmol) were added, and the resulting mixture was stirred at rt for 3 days. After this time, the mixture was concentrated, and the residue was dissolved in EtOAc and water. The layers were mixed and separated, and the aqueous layer was extracted five times with EtOAc. The organic layers were combined, dried with anhydrous MgSO$_4$, filtered, and concentrated. The residue was purified by silica gel chromatography (0→20% EtOAc/hexanes) to provide the title compound.

Intermediate 134

1-(6-Chloro-4-methoxypyridin-3-yl)ethan-1-one

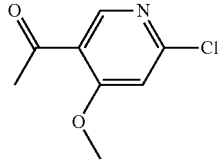

Methylmagnesium chloride (17 mL, 3.0 M in THF, 51 mmol) was added to a 0° C. solution of 6-chloro-N,4-dimethoxy-N-methylnicotinamide (8.88 g, 38.5 mmol, Intermediate 133) in THF (150 mL) and the resulting mixture was stirred at 0° C. for 3 h before it was allowed to gradually warm to rt. Upon reaching rt, the reaction was submerged in an ice bath and quenched with saturated aqueous NH₄Cl solution. The mixture was then diluted with water and EtOAc. The layers were separated, and the aqueous layer was extracted five times with EtOAc. The organic layers were combined, dried with anhydrous MgSO₄, filtered, and concentrated to provide the title compound.

Intermediate 135

Ethyl 4-(6-chloro-4-methoxypyridin-3-yl)-2,4-dioxobutanoate

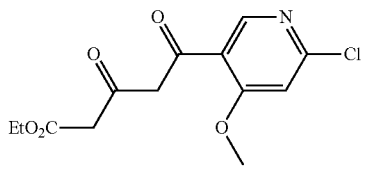 [SMILES: CCOC(=O)CC(=O)CC(=O)c1cnc(Cl)cc1OC]

A solution of 1-(6-chloro-4-m ethoxypyridin-3-yl)ethan-1-one (6.84 g, 36.8 mmol, Intermediate 134) in THF (37 mL) was added to a 78° C. solution of LiHMDS (46 mL, 1.0 M in THF, 46 mmol) in THF (145 mL), and the resulting solution was stirred for 30 min. Diethyl oxalate (6.2 mL, 46 mmol) was then slowly added, and after 10 min of stirring at −78° C., the reaction mixture was allowed to warm to rt over 3 h. The mixture was then quenched with a saturated aqueous NH₄Cl solution. The layers were separated, and the aqueous layer was extracted with EtOAc. The organic layers were combined, washed with brine, dried with anhydrous MgSO₄, filtered, and concentrated. The residue was triturated with ether, filtered, and dried by aspiration to provide the title compound.

Intermediate 136

Ethyl 5-(6-chloro-4-methoxypyridin-3-yl)-1-ethyl-1H-pyrazole-3-carboxylate

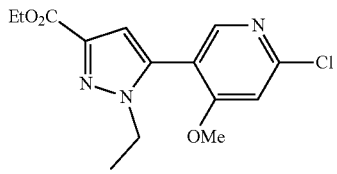 [SMILES: CCOC(=O)c1cc(-c2cnc(Cl)cc2OC)n(CC)n1]

Ethyl 4-(6-chloro-4-methoxypyridin-3-yl)-2,4-di oxobutanoate (8.81 g, 30.8 mmol, Intermediate 135), ethylhydrazine oxalate (5.26 g, 35.0 mmol), and AcOH (100 mL) were combined and stirred at 100° C. for 2 h. After this time, the mixture was allowed to cool to rt and then concentrated. The residue was diluted with water and the mixture was cooled in an ice bath. A 6 M aqueous NaOH solution was added to neutralize the pH of the mixture, and then EtOAc was added. The layers were mixed and separated, and the aqueous layer was extracted with EtOAc. The organic layers were combined, washed with brine, dried with anhydrous MgSO₄, filtered, and concentrated. The residue was purified by silica gel chromatography (0→50% EtOAc/hexanes) to provide the title compound.

Intermediate 137

Ethyl 4-chloro-5-(6-chloro-4-methoxypyridin-3-yl)-1-ethyl-1H-pyrazole-3-carboxylate

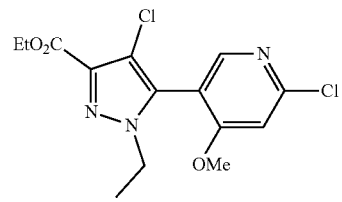 [SMILES: CCOC(=O)c1nn(CC)c(-c2cnc(Cl)cc2OC)c1Cl]

Sulfuryl dichloride (0.8 mL, 10 mmol) was added to a solution of ethyl 5-(6-chloro-4-m ethoxypyridin-3-yl)-1-ethyl-1H-pyrazole-3-carboxylate (2.0 g, 6.5 mmol, Intermediate 136) in DCM (30 mL), and the resulting mixture was stirred at rt overnight. After this time, the reaction was quenched with a saturated aqueous NaHCO₃ solution. The layers were separated and the aqueous layer was extracted with EtOAc. The organic layers were combined, dried with anhydrous MgSO₄, filtered, and concentrated. The residue was purified by silica gel chromatography (0→40% EtOAc/hexanes) to provide the title compound.

Intermediate 138

5-Bromo-2-chloro-4-ethylpyridine

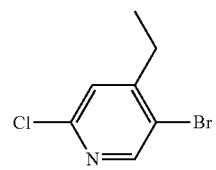

A solution of 5-bromo-2-chloropyridine (50 g, 260 mmol) and anhydrous THF (500 mL) was added dropwise to a 70° C. solution of LDA (137 mL, 2.0 M in hexanes, 274 mmol) and THF (100 mL), and the resulting mixture was stirred at −70° C. for 5 h. Then iodoethane (23 mL, 286 mmol) was added, and the reaction mixture was allowed to gradually warm to rt over 2 h. The reaction was quenched with a saturated aqueous NH₄Cl solution and extracted three times with EtOAc. The organic layers were combined, washed with brine, dried with anhydrous Na₂SO₄, filtered, and concentrated. The residue was purified by preparative HPLC (Phenomenex Synergi Max-RP, 50→100% MeCN/water, 0.1% TFA). Product fractions were combined and concentrated. The residue was dissolved in water (50 mL) and the pH of the resulting solution was adjusted to pH 8 with solid sodium bicarbonate. The mixture was extracted with three times with DCM, and the organic layers were combined, dried with anhydrous Na₂SO₄, filtered, and concentrated to provide the title compound.

Intermediate 139

Ethyl 5-(6-chloro-4-ethylpyridin-3-yl)-1-ethyl-1H-pyrazole-3-carboxylate

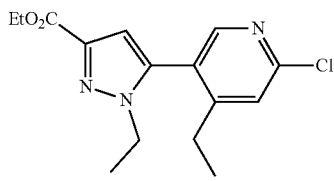 [SMILES: CCOC(=O)c1cc(-c2cnc(Cl)cc2CC)n(CC)n1]

The title compound was prepared as described for the synthesis of Intermediate 59, using 5-bromo-2-chloro-4-ethyl pyridine (Intermediate 138) in place of 5-bromo-2-chloro-4-(difluoromethoxy)pyridine and Pd(dtbpf)Cl$_2$ in place of Pd$_2$(dba)$_3$/P(t-Bu)$_3$.HBF$_4$.

Intermediate 140

Ethyl 4-chloro-5-(6-chloro-4-ethylpyridin-3-yl)-1-ethyl-1H-pyrazole-3-carboxylate

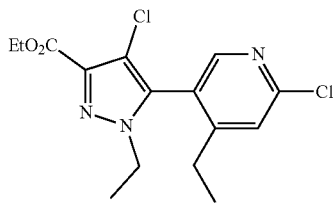 [SMILES: CCOC(=O)c1nn(CC)c(-c2cnc(Cl)cc2CC)c1Cl]

The title compound was prepared as described for the synthesis of Intermediate 61, using ethyl 5-(6-chloro-4-ethylpyridin-3-yl)-1-ethyl-1H-pyrazole-3-carboxylate (Intermediate 139) in place of ethyl 5-(4-(difluoromethoxy)-6-(3,3,3-trifluoro-2,2-dim ethyl propyl)pyridin-3-yl)-1-ethyl-1H-pyrazole-3-carboxylate.

Intermediate 141

Ethyl 4-chloro-1-ethyl-5-(4-methoxy-6-(3,3,3-trifluoro-2-methylpropyl)pyridin-3-yl)-1H-pyrazole-3-carboxylate

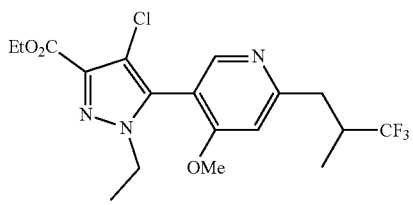 [SMILES: CCn1nc(C(=O)O)c(Cl)c1-c1cnc(CC(C)C(F)(F)F)cc1OC]

The title compound was prepared as described for the synthesis of Intermediate 105, using ethyl 4-chloro-5-(6-chloro-4-methoxypyridin-3-yl)-1-ethyl-1H-pyrazole-3-carboxylate (Intermediate 137) and 9-(3,3,3-trifluoro-2-methylpropyl)-9-borabicyclo[3.3.1]nonane (Intermediate 52) in place of ethyl 4-chloro-5-(6-chloro-4-(difluoromethoxy)pyridin-3-yl)-1-ethyl-1H-pyrazole-3-carboxylate and (4,4,4-trifluorobutyl)-9-borabicyclo[3.3.1]nonane.

Intermediate 142

4-Chloro-1-ethyl-5-(4-methoxy-6-(3,3,3-trifluoro-2-methylpropyl)pyridin-3-yl)-1H-pyrazole-3-carboxylic Acid

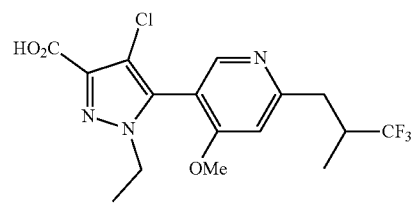

The title compound was prepared as described for the synthesis of Intermediate 69, using ethyl 4-chloro-1-ethyl-5-(4-methoxy-6-(3,3,3-trifluoro-2-methylpropyl)pyridin-3-yl)-1H-pyrazole-3-carboxylate (Intermediate 141) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 143

Ethyl (R)-4-chloro-1-ethyl-5-(4-methoxy-6-((1,1,1-trifluoropropan-2-yl)oxy)pyridin-3-yl)-1H-pyrazole-3-carboxylate

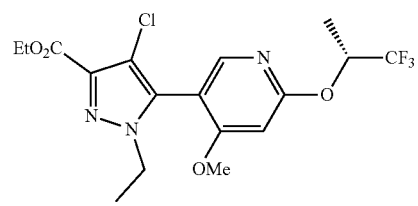 [SMILES: CCn1nc(C(=O)O)c(Cl)c1-c1cnc(O[C@H](C)C(F)(F)F)cc1OC]

(R)-1,1,1-Trifluoropropan-2-ol (300 mg, 2.63 mmol) was added to a suspension of NaH (88 mg, 60% in mineral oil, 2.2 mmol) in DMA (20 mL), and the resulting mixture was stirred for 10 min. A solution of ethyl 4-chloro-5-(6-chloro-4-methoxypyridin-3-yl)-1-ethyl-1H-pyrazole-3-carboxylate (503 mg, 1.46 mmol, Intermediate 137) in DMA was then added, and the resulting mixture was stirred at 60° C. for 5 h. After this time, the mixture was cooled to 0° C. and then diluted with water and 1 N aqueous HCl (5 mL). The mixture was extracted five times with EtOAc, and the organic layers were combined, washed with brine, dried with anhydrous MgSO$_4$, filtered and concentrated. The residue was purified by silica gel chromatography (0→5% EtOAc/DCM then 10% MeOH/DCM) afforded the title compound.

101

Intermediate 144

(R)-4-Chloro-1-ethyl-5-(4-methoxy-6-((1,1,1-trifluoropropan-2-yl)oxy)pyridin-3-yl)-1H-pyrazole-3-carboxylic Acid

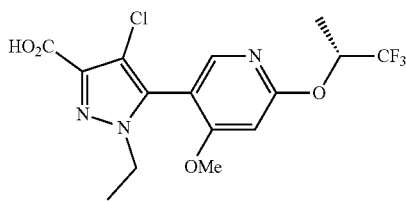

The title compound was prepared as described for the synthesis of Intermediate 69, using ethyl (R)-4-chloro-1-ethyl-5-(4-methoxy-6-((1,1,1-trifluoropropan-2-yl)oxy)pyridin-3-yl)-1H-pyrazole-3-carboxylate (Intermediate 143) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 145

(S)-4-Chloro-1-ethyl-5-(4-methoxy-6-((1,1,1-trifluoropropan-2-yl)oxy)pyridin-3-yl)-1H-pyrazole-3-carboxylic Acid

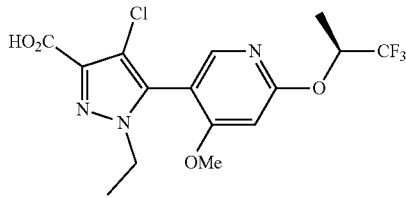 [SMILES: CCn1nc(C(=O)O)c(Cl)c1-c1cnc(O[C@@H](C)C(F)(F)F)cc1OC]

The title compound was prepared as described for the synthesis of Intermediate 144, using (S)-1,1,1-trifluoropropan-2-ol in place of (R)-1,1,1-trifluoropropan-2-ol.

Intermediate 146

4-Chloro-5-(4-(1,1-difluoroethyl)-6-(3,3,3-trifluoro-2,2-dimethylpropyl)pyridin-3-yl)-1-ethyl-1H-pyrazole-3-carboxylic Acid

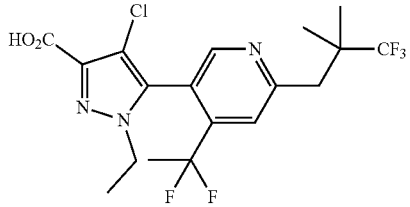 [SMILES: CCn1nc(C(=O)O)c(Cl)c1-c1cnc(CC(C)(C)C(F)(F)F)cc1C(C)(F)F]

The title compound was prepared as described for the synthesis of Intermediate 85, using 3-bromo-4-(1,1-difluoroethyl)pyridine (Intermediate 67) in place of in place of 3-bromo-4-isopropylpyridine.

102

Intermediate 147

4-Chloro-5-(6-chloro-4-ethylpyridin-3-yl)-1-ethyl-N-(((1s,4s)-1-hydroxy-4-(methylsulfonyl)cyclohexyl)methyl)-1H-pyrazole-3-carboxamide

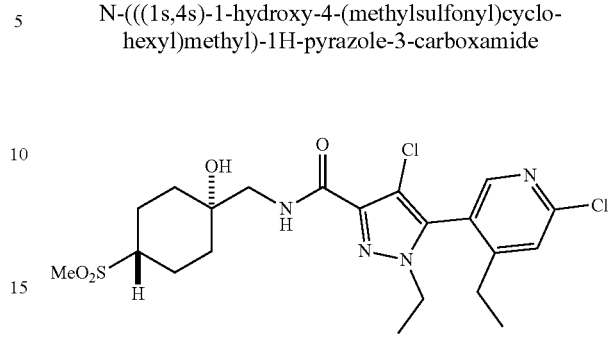

HATU (0.737 g, 1.94 mmol) was added to a solution of 4-chloro-5-(6-chloro-4-ethylpyridin-3-yl)-1-ethyl-1H-pyrazole-3-carboxylic acid (0.505 g, 1.61 mmol, Intermediate 54) in DMF (8.0 mL). (1s,4s)-1-(Aminomethyl)-4-(methylsulfonyl)cyclohexan-1-ol hydrochloride (0.679 g, 2.42 mmol, Intermediate 9) and DIPEA (0.84 mL, 4.9 mmol) were added, and the resulting mixture was stirred at rt for 3 h. After this time, the reaction mixture was diluted with water and EtOAc. The layers were separated and the aqueous layer was extracted with EtOAc. The combined organic layers were dried with anhydrous MgSO$_4$, filtered, and concentrated. The residue was purified by silica gel chromatography (20→100% EtOAc/hexanes) to provide the title compound.

Intermediate 148

Ethyl (R*)-4-chloro-1-ethyl-5-(4-ethyl-6-(3,3,3-trifluoro-2-methylpropyl)pyridin-3-yl)-1H-pyrazole-3-carboxylate

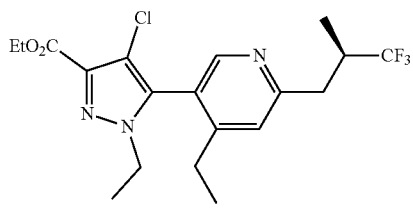 [SMILES: CCc1cc(C[C@@H](C)C(F)(F)F)ncc1-c1c(Cl)c(C(=O)O)nn1CC]

The title compound was prepared as described for the synthesis of Example 55 using (S*)-1,1,1-trifluoro-3-iodo-2-methylpropane (Intermediate 51) and ethyl 4-chloro-5-(6-chloro-4-ethyl pyridin-3-yl)-1-ethyl-1H-pyrazole-3-carboxylate (Intermediate 140) in place of 1,1,1-trifluoro-3-iodo-2,2-dimethylpropane and 4-chloro-5-(6-chloro-4-ethyl pyridin-3-yl)-1-ethyl-N-(((1s,4s)-1-hydroxy-4-(methylsulfonyl)cyclohexyl)methyl)-1H-pyrazole-3-carboxamide.

Intermediate 149

(R*)-4-Chloro-1-ethyl-5-(4-ethyl-6-(3,3,3-trifluoro-2-methylpropyl)pyridin-3-yl)-1H-pyrazole-3-carboxylic Acid

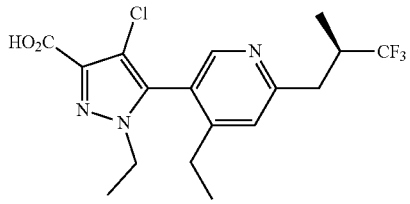

The title compound was prepared as described for the synthesis of Intermediate 69 using ethyl (R*)-4-chloro-1-ethyl-5-(4-ethyl-6-(3,3,3-trifluoro-2-methylpropyl)pyridin-3-yl)-1H-pyrazole-3-carboxylate (Intermediate 148) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 150

Ethyl (R*)-1-ethyl-5-(4-ethyl-6-(3,3,3-trifluoro-2-methylpropyl)pyridin-3-yl)-4-methyl-1H-pyrazole-3-carboxylate

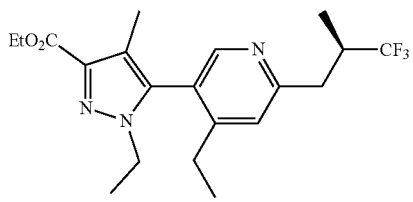 [SMILES: CCc1cc(C[C@@H](C)C(F)(F)F)ncc1-c1c(C)c(C(=O)O)nn1CC]

The title compound was prepared as described for the synthesis of Intermediate 70, using ethyl (R*)-4-chloro-1-ethyl-5-(4-ethyl-6-(3,3,3-trifluoro-2-methylpropyl)pyridin-3-yl)-1H-pyrazole-3-carboxylate (Intermediate 148) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 151

(R*)-1-Ethyl-5-(4-ethyl-6-(3,3,3-trifluoro-2-methylpropyl)pyridin-3-yl)-4-methyl-1H-pyrazole-3-carboxylic Acid

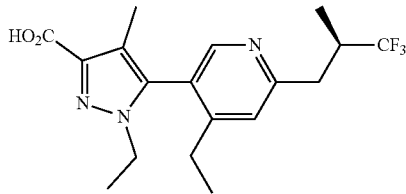

The title compound was prepared as described for the synthesis of Intermediate 69, using ethyl (R*)-1-ethyl-5-(4-ethyl-6-(3,3,3-trifluoro-2-methylpropyl)pyridin-3-yl)-4-methyl-1H-pyrazole-3-carboxylate (Intermediate 150) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate.

Intermediate 152

Ethyl 4-chloro-5-(6-(3,3-dimethylbutyl)-4-ethylpyridin-3-yl)-1-ethyl-1H-pyrazole-3-carboxylate

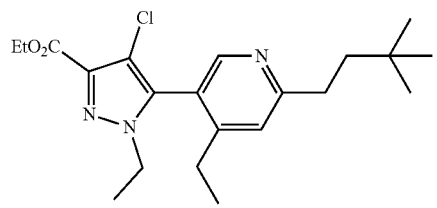 [SMILES: CCOC(=O)c1nn(CC)c(-c2cnc(CCC(C)(C)C)cc2CC)c1Cl]

The title compound was prepared as described for the synthesis of Example 55 using 1-bromo-3,3-dimethylbutane and ethyl 4-chloro-5-(6-chloro-4-ethylpyridin-3-yl)-1-ethyl-1H-pyrazole-3-carboxylate (Intermediate 140) in place of 1,1,1-trifluoro-3-iodo-2,2-dimethylpropane and 4-chloro-5-(6-chloro-4-ethylpyridin-3-yl)-1-ethyl-N-(((1s,4s)-1-hydroxy-4-(methylsulfonyl)cyclohexyl)methyl)-1H-pyrazole-3-carboxamide.

Intermediate 153

4-Chloro-5-(6-(3,3-dimethylbutyl)-4-ethylpyridin-3-yl)-1-ethyl-1H-pyrazole-3-carboxylic Acid

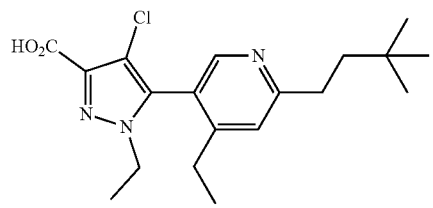 [SMILES: CCc1cc(CCC(C)(C)C)ncc1-c1c(Cl)c(C(=O)O)nn1CC]

The title compound was prepared as described for the synthesis of Intermediate 69 using ethyl ethyl 4-chloro-5-(6-(3,3-di m ethylbutyl)-4-ethyl pyridin-3-yl)-1-ethyl-1H-pyrazole-3-carboxylate (Intermediate 152) in place of ethyl (S)-4-chloro-5-(4-(difluoromethoxy)-6-(3,3,3-trifluoro-2-methylpropyl)pyridin-3-yl)-1-ethyl-1H-pyrazole-3-carboxylate.

Example 1

4-Chloro-5-(4-(difluoromethoxy)-6-(3,3,3-trifluoro-2,2-dimethylpropyl)pyridin-3-yl)-1-ethyl-N-(((1s,4s)-1-hydroxy-4-sulfamoylcyclohexyl)methyl)-1H-pyrazole-3-carboxamide

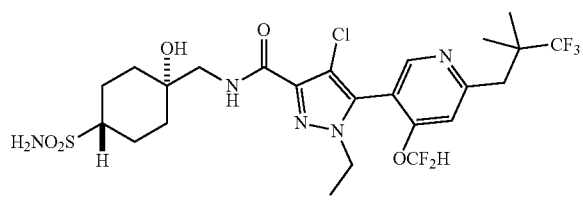

HATU (43 mg, 0.11 mmol) was added to a suspension of 4-chloro-5-(4-(difluoromethoxy)-6-(3,3,3-trifluoro-2,2-dimethylpropyl)pyridin-3-yl)-1-ethyl-1H-pyrazole-3-carboxylic acid (50 mg, 0.11 mmol, Intermediate 63), (1s,4s)-4-(aminomethyl)-4-hydroxycyclohexane-1-sulfonamide hydrochloride (28 mg, 0.11 mmol, Intermediate 19), and DIPEA (0.043 mL, 0.25 mmol) in DMF (0.4 mL), and the mixture was stirred at rt for 2 h. The resulting solution was diluted with MeOH, filtered, and then purified by preparative HPLC (XBridge C18, 30100% MeCN/water, 0.05% TFA) to afford the title compound as a colorless solid. $^1$H NMR (500 MHz, CDCl$_3$) δ 8.57 (s, 1H), 7.29 (t, J=6.3 Hz, 1H), 7.21 (s, 1H), 6.65 (dd, J=72.2, 69.7 Hz, 1H), 4.55 (s, 2H), 4.07-3.93 (m, 2H), 3.53-3.43 (m, 2H), 3.10 (s, 2H), 2.96 (tt, J=11.5, 3.3 Hz, 1H), 2.92 (br s, 1H), 2.19-2.11 (m, 2H), 2.03-1.91 (m, 4H), 1.46 (td, J=14.0, 4.1 Hz, 2H), 1.40 (t, J=7.2 Hz, 3H), 1.23 (d, J=5.3 Hz, 6H). MS (ESI) m/z: [M+H]$^+$ Found 632.2.

Example 2

5-(4-(Difluoromethoxy)-6-(3,3,3-trifluoro-2,2-dimethylpropyl)pyridin-3-yl)-1-ethyl-N-(((1s,4s)-1-hydroxy-4-sulfamoylcyclohexyl)methyl)-4-methyl-1H-pyrazole-3-carboxamide

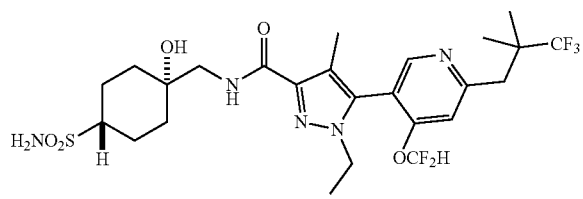

The title compound was prepared as described for the synthesis of Example 1, using ethyl 5-(4-(difluoromethoxy)-6-(3,3,3-trifluoro-2,2-dimethylpropyl)pyridin-3-yl)-1-ethyl-4-methyl-1H-pyrazole-3-carboxylic acid (Intermediate 62) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid. $^1$H NMR (400 MHz, CDCl$_3$) δ 8.52 (s, 1H), 7.37 (t, J=6.3 Hz, 1H), 7.22 (s, 1H), 6.63 (dd, J=71.4, 70.5 Hz, 1H), 4.59 (s, 2H), 4.02-3.85 (m, 2H), 3.52-3.39 (m, 2H), 3.12 (s, 2H), 2.99-2.91 (m, 1H), 2.91 (br s, 1H), 2.18-2.10 (m, 2H), 2.15 (s, 3H), 2.05-1.91 (m, 4H), 1.43 (td, J=14.4, 4.6 Hz, 2H), 1.36 (t, J=7.2 Hz, 3H), 1.23 (s, 6H of one rotamer), 1.22 (s, 6H of one rotamer). MS (ESI) m/z: [M+H]$^+$ Found 612.3.

Example 3

4-Chloro-5-(4-(difluoromethoxy)-6-(3,3,3-trifluoro-2,2-dimethylpropyl)pyridin-3-yl)-N-(((1R*,2R*,4R*)-1,2-dihydroxy-4-(methylsulfonyl)cyclohexyl)methyl)-1-ethyl-1H-pyrazole-3-carboxamide

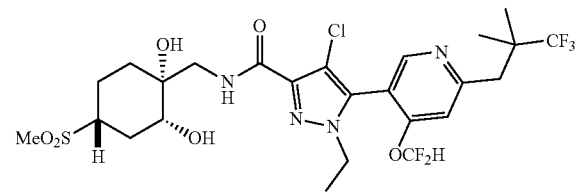

The title compound was prepared as described for the synthesis of Example 1, using (1R*,2R*,4R*)-1-(aminomethyl)-4-(methylsulfonyl)cyclohexane-1,2-diol hydrochloride (Intermediate 29) in place of (1s,4s)-4-(aminomethyl)-4-hydroxycyclohexane-1-sulfonamide hydrochloride. $^1$H NMR (500 MHz, CDCl$_3$) δ 8.59 (s, 1H of one rotamer), 8.58 (s, 1H of one rotamer), 7.29-7.26 (m, 1H), 7.21 (s, 1H), 6.66 (appar ddd, J=72.2, 69.6, 9.0 Hz, 1H), 4.08-3.93 (m, 2H), 3.89 (dt, J=14.2, 8.6 Hz, 1H), 3.61 (dt, J=11.5, 4.5 Hz, 1H), 3.15-3.08 (m, 1H), 3.13 (br s, 2H), 3.11 (s, 2H), 2.89-2.81 (m, 1H), 2.84 (s, 3H of one rotamer), 2.83 (s, 3H of one rotamer), 2.31-2.25 (m, 1H), 2.10-2.04 (m, 1H), 2.02-1.88 (m, 3H), 1.58-1.49 (m, 1H), 1.42 (t, J=7.2 Hz, 3H), 1.24 (s, 6H of one rotamer), 1.23 (s, 6H of one rotamer). MS (ESI) m/z: [M+H]$^+$ Found 647.2.

Example 4

4-Chloro-5-(4-(difluoromethoxy)-6-(3,3,3-trifluoro-2,2-dimethylpropyl)pyridin-3-yl)-N-(((1S*,2S*,4S*)-1,2-dihydroxy-4-(methylsulfonyl)cyclohexyl)methyl)-1-ethyl-1H-pyrazole-3-carboxamide

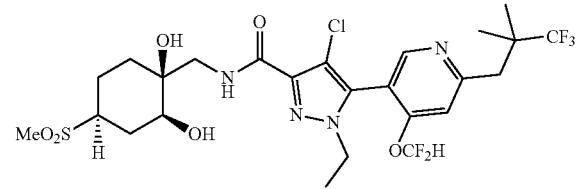

The title compound was prepared as described for the synthesis of Example 1, using (1S*,2S*,4S*)-1-(aminomethyl)-4-(methylsulfonyl)cyclohexane-1,2-diol hydrochloride (Intermediate 30) in place of (1s,4s)-4-(aminomethyl)-4-hydroxycyclohexane-1-sulfonamide hydrochloride. $^1$H NMR (500 MHz, CDCl$_3$) δ 8.59 (s, 1H of one rotamer), 8.58 (s, 1H of one rotamer), 7.29-7.26 (m, 1H), 7.21 (s, 1H), 6.66 (appar ddd, J=72.2, 69.6, 9.0 Hz, 1H), 4.08-3.93 (m, 2H), 3.89 (dt, J=14.2, 8.6 Hz, 1H), 3.61 (dt, J=11.5, 4.5 Hz, 1H), 3.15-3.08 (m, 1H), 3.11 (s, 2H), 2.91 (br s, 2H), 2.89-2.81 (m, 1H), 2.84 (s, 3H of one rotamer), 2.83 (s, 3H of one rotamer), 2.31-2.25 (m, 1H), 2.10-2.04 (m, 1H), 2.02-1.88

(m, 3H), 1.58-1.49 (m, 1H), 1.42 (t, J=7.2 Hz, 3H), 1.24 (s, 6H of one rotamer), 1.23 (s, 6H of one rotamer). MS (ESI) m/z: [M+H]$^+$ Found 647.2.

Example 5

N-(((1r,4r)-4-(N-acetylsulfamoyl)cyclohexyl)methyl)-4-chloro-5-(4-(difluoromethoxy)-6-(3,3,3-trifluoro-2,2-dimethylpropyl)pyridin-3-yl)-1-ethyl-1H-pyrazole-3-carboxamide

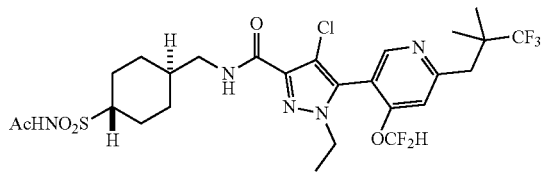

Zinc chloride (1 mg, 0.005 mmol) was added to a solution of (4-chloro-5-(4-(difluoromethoxy)-6-(3,3,3-trifluoro-2,2-dimethylpropyl)pyridin-3-yl)-1-ethyl-N-(((1r,4r)-4-sulfamoylcyclohexyl)methyl)-1H-pyrazole-3-carboxamide (35 mg, 0.057 mmol, Example 11) in Ac$_2$O (0.10 mL), and the mixture was stirred at 80° C. for 1.5 h. After this time, the resulting solution was allowed to cool, diluted with MeOH, filtered, and then purified by preparative HPLC (XBridge C18, 30100% MeCN/water, 0.05% TFA) to afford the title compound as a colorless solid. $^1$H NMR (500 MHz, CDCl$_3$) δ 8.65 (s, 1H), 8.61 (br s, 1H), 7.30 (s, 1H), 7.09 (t, J=6.4 Hz, 1H), 6.70 (dd, J=71.5, 69.5 Hz, 1H), 4.07-3.93 (m, 2H), 3.50 (tt, J=12.4, 3.4 Hz, 1H), 3.40-3.28 (m, 2H), 3.16 (s, 2H), 2.28-2.20 (m, 2H), 2.18 (s, 3H), 2.07-2.00 (m, 2H), 1.74-1.58 (m, 3H), 1.41 (t, J=7.3 Hz, 3H), 1.24 (s, 6H of one rotamer), 1.23 (s, 6H of one rotamer), 1.14 (qd, J=12.7, 3.2 Hz, 2H). MS (ESI) m/z: [M+H]$^+$ Found 657.8.

Example 6

4-Chloro-5-(4-(difluoromethoxy)-6-(3,3,3-trifluoro-2,2-dimethylpropyl)pyridin-3-yl)-1-ethyl-N-(((1r,4r)-4-(N-(methylcarbamoyl)sulfamoyl)cyclohexyl)methyl)-1H-pyrazole-3-carboxamide

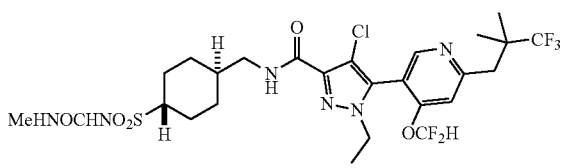

Isocyanatomethane (0.006 mL, 0.1 mmol) was added to a mixture of 4-chloro-5-(4-(difluoromethoxy)-6-(3,3,3-trifluoro-2,2-dimethylpropyl)pyridin-3-yl)-1-ethyl-N-(((1r,4r)-4-sulfamoylcyclohexyl)methyl)-1H-pyrazole-3-carboxamide (30 mg, 0.049 mmol, Example 11) and K$_2$CO$_3$ (14 mg, 0.097 mmol) in acetone (0.25 mL), and the mixture was stirred at 65° C. for 2 h. After this time, the reaction mixture was allowed to cool, diluted with MeOH, filtered, and then purified by preparative HPLC (XBridge C18, 30100% MeCN/water, 0.05% TFA) to afford the title compound as a colorless solid. $^1$H NMR (500 MHz, CDCl$_3$) δ 8.55 (s, 1H), 7.19 (s, 1H), 7.03 (br s, 1H), 6.99 (t, J=6.5 Hz, 1H), 6.63 (dd, J=72.4, 69.8 Hz, 1H), 6.62-6.57 (m, 1H), 4.08-3.90 (m, 2H), 3.41-3.28 (m, 2H), 3.13 (tt, J=12.5, 3.5 Hz, 1H), 3.09 (s, 2H), 2.86 (s, 3H of one rotamer), 2.85 (s, 3H of one rotamer), 2.32-2.25 (m, 2H), 2.09-2.02 (m, 2H), 1.76-1.55 (m, 3H), 1.40 (t, J=7.2 Hz, 3H), 1.23 (s, 6H of one rotamer), 1.22 (s, 6H of one rotamer), 1.14 (qd, J=13.2, 3.5 Hz, 2H). MS (ESI) m/z: [M+H]$^+$ Found 672.8.

Example 7

N-(((1r,4r)-4-(N-carbamoylsulfamoyl)cyclohexyl)methyl)-4-chloro-5-(4-(difluoromethoxy)-6-(3,3,3-trifluoro-2,2-dimethylpropyl)pyridin-3-yl)-1-ethyl-1H-pyrazole-3-carboxamide

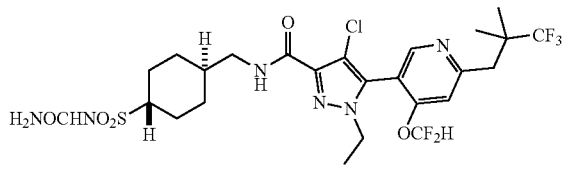

4-Methoxybenzyl isocyanate (0.024 mL, 0.16 mmol) was added to a mixture of 4-chloro-5-(4-(difluoromethoxy)-6-(3,3,3-trifluoro-2,2-dim ethyl propyl)pyridin-3-yl)-1-ethyl-N-(((1r,4r)-4-sulfamoylcyclohexyl)methyl)-1H-pyrazole-3-carboxamide (50 mg, 0.081 mmol, Example 11) and K$_2$CO$_3$ (23 mg, 0.16 mmol) in acetone (0.42 mL), and the mixture was stirred at 65° C. for 18 h. After this time, the reaction mixture was allowed to cool and then concentrated. The residue was diluted with TFA (0.50 mL, 6.5 mmol), and resulting solution was stirred at 45° C. for 5 h. After this time, the solution was concentrated, diluted with MeOH, filtered, and then purified by preparative HPLC (XBridge C18, 30100% MeCN/water, 0.05% TFA) to afford the title compound as a colorless solid. $^1$H NMR (500 MHz, CD$_3$COCD$_3$) δ 8.98 (s, 1H), 8.60 (s, 1H), 7.69 (t, J=6.3 Hz, 1H), 7.49 (s, 1H), 7.47 (t, J=72.6 Hz, 1H), 6.21 (s, 2H), 4.11-3.99 (m, 2H), 3.45 (tt, J=12.3, 3.4 Hz, 1H), 3.30 (t, J=6.5 Hz, 2H), 3.11 (s, 2H), 2.29-2.20 (m, 2H), 2.05-1.98 (m, 2H), 1.74-1.64 (m, 1H), 1.60 (qd, J=13.0, 3.4 Hz, 2H), 1.35 (t, J=7.2 Hz, 3H), 1.21 (s, 2H), 1.21 (s, 6H). MS (ESI) m/z: [M+H]$^+$ Found 658.9.

Example 8

5-(4-(Difluoromethoxy)-6-(3,3,3-trifluoro-2,2-dimethylpropyl)pyridin-3-yl)-1-ethyl-N-(((1s,4s)-1-hydroxy-4-(methylsulfonyl)cyclohexyl)methyl)-4-methyl-1H-pyrazole-3-carboxamide

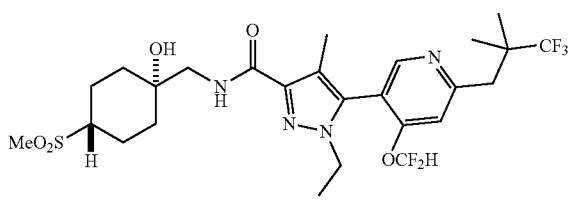

N,N-Diisopropylethylamine (40 mL, 240 mmol) and then T3P (45.5 g, 50% w/w EtOAc solution, 71 mmol) were added dropwise to a solution of 5-(4-(difluoromethoxy)-6-

(3,3,3-trifluoro-2,2-dimethylpropyl)pyridin-3-yl)-1-ethyl-4-methyl-1H-pyrazole-3-carboxylic acid (20.0 g, 47.5 mmol, Intermediate 62) and (1s,4s)-1-(aminomethyl)-4-(methylsulfonyl)cyclohexan-1-ol hydrochloride (13.6 g, 57.0 mmol, Intermediate 9) in MeCN (200 mL). After the reaction went to completion, the mixture was diluted with water (20 mL) and then concentrated to remove most of the MeCN. The concentrate then underwent two cycles of successive dilution with EtOAc and concentration. The concentrate was then diluted with water and EtOAc, and the mixture was made acidic with 1 N aqueous HCl. The layers were mixed then separated, and the aqueous layer was extracted with EtOAc. The combined organic layers were washed twice with a saturated aqueous NaHCO₃ solution, washed with water, dried with anhydrous Na₂SO₄, and then concentrated. The residue was purified by silica gel chromatography (EtOAc/petroleum ether, 1:10 v/v), treated with mercapto-modified silica gel, crystallized from n-heptane/MTBE, and then dried under vacuum to afford the title compound as a colorless solid. $^1$H NMR (500 MHz, CDCl₃) δ 8.55 (s, 1H), 7.19 (s, 1H), 7.03 (br s, 1H), 6.99 (t, J=6.5 Hz, 1H), 6.63 (dd, J=72.4, 69.8 Hz, 1H), 6.62-6.57 (m, 1H), 4.08-3.90 (m, 2H), 3.41-3.28 (m, 2H), 3.13 (tt, J=12.5, 3.5 Hz, 1H), 3.09 (s, 2H), 2.86 (s, 3H of one rotamer), 2.85 (s, 3H of one rotamer), 2.32-2.25 (m, 2H), 2.09-2.02 (m, 2H), 1.76-1.55 (m, 3H), 1.40 (t, J=7.2 Hz, 3H), 1.23 (s, 6H of one rotamer), 1.22 (s, 6H of one rotamer), 1.14 (qd, J=13.2, 3.5 Hz, 2H). MS (ESI) m/z: [M+H]⁺ Found 611.2.

Example 9

4-Chloro-5-(4-(difluoromethoxy)-6-(3,3,3-trifluoro-2,2-dimethylpropyl)pyridin-3-yl)-1-ethyl-N-(((1r,4r)-4-(methylsulfonyl)cyclohexyl)methyl)-1H-pyrazole-3-carboxamide

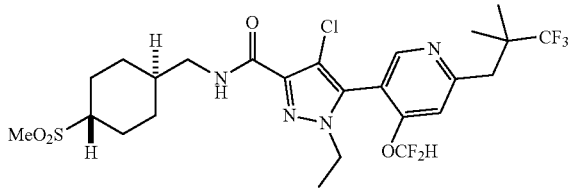

N,N-Diisopropylethylamine (32.0 mL, 183 mmol) and then T3P (34.9 g, 50% w/w EtOAc solution, 54.9 mmol) were added dropwise to a mixture of 4-chloro-5-(4-(difluoromethoxy)-6-(3,3,3-trifluoro-2,2-dimethylpropyl)pyridin-3-yl)-1-ethyl-1H-pyrazole-3-carboxylic acid (16.2 g, 36.6 mmol, Intermediate 63) and ((1r,4r)-4-(methylsulfonyl)cyclohexyl)methanamine hydrochloride (10.0 g, 43.9 mmol, Intermediate 13) in MeCN (160 mL). After the reaction went to completion, the mixture was diluted with water (20 mL) and then concentrated to remove most of the MeCN. The concentrate then underwent two cycles of successive dilution with EtOAc and concentration. The concentrate was then diluted with water (200 mL), and the pH was adjusted to pH 3-4 with 1 N aqueous HCl. The solution was then extracted twice with EtOAc. The combined organic layers were washed with water, washed with a saturated aqueous NaHCO₃ solution, washed with more water, dried over anhydrous Na₂SO₄, and then filtered. The filter cake was rinsed with EtOAc, and the filtrate and wash were combined and then concentrated. The concentrate was crystallized from MTBE, filtered, and the filter cake was rinsed with MTBE. The filter cake was then dried under vacuum at 50° C. to afford the title compound as a colorless solid. $^1$H NMR (400 MHz, CDCl₃) δ 8.52-8.45 (s, 1H), 7.14-7.09 (s, 1H), 6.97-6.90 (t, J=6.4 Hz, 1H), 6.80-6.39 (dd, J=73.0, 70.0 Hz, 1H), 4.07-3.89 (tq, J=13.8, 7.0 Hz, 2H), 3.40-3.31 (t, J=6.6 Hz, 2H), 3.08-3.02 (s, 2H), 2.90-2.77 (m, 4H), 2.34-2.24 (d, J=12.7 Hz, 2H), 2.13-2.03 (m, 2H), 1.78-1.57 (m, 3H), 1.44-1.34 (t, J=7.3 Hz, 3H), 1.27-1.07 (m, 8H). MS (ESI) m/z: [M+H]⁺ Found 615.2.

Example 10

4-Chloro-5-(4-(difluoromethoxy)-6-(3,3,3-trifluoro-2,2-dimethylpropyl)pyridin-3-yl)-1-ethyl-N-(((1s,4s)-1-hydroxy-4-(methylsulfonyl)cyclohexyl)methyl)-1H-pyrazole-3-carboxamide

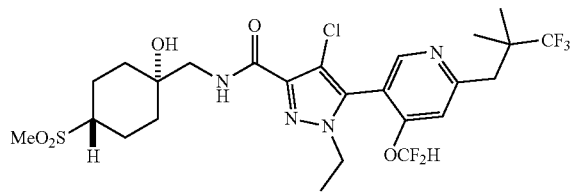

4-Chloro-5-(4-(difluoromethoxy)-6-(3,3,3-trifluoro-2,2-dimethylpropyl)pyridin-3-yl)-1-ethyl-1H-pyrazole-3-carboxylic acid (50.0 mg, 0.11 mmol, Intermediate 63), (1s,4s)-1-(aminomethyl)-4-(methylsulfonyl)cyclohexan-1-ol hydrochloride (33 mg, 0.14 mmol, Intermediate 9), and HOBt (20 mg, 0.15 mmol) were diluted with MeCN (0.63 mL) before DIPEA (0.07 mL, 0.38 mmol) and then EDCI (36 mg, 0.19 mmol) were added, and the mixture was stirred at rt for 72 h. The resulting suspension was diluted with EtOAc and water, the layers were separated, and the aqueous layer was extracted with EtOAc. The organic layers were combined, washed with brine, dried with anhydrous MgSO₄, filtered, and then concentrated. The residue was purified by silica gel chromatography (30→100% acetone/hexanes) to afford the title compound as a colorless film. 41 NMR (400 MHz, CDCl₃) δ 8.48 (s, 1H), 7.24-7.20 (m, 1H), 7.13-7.09 (m, 1H), 6.60 (dd, J=72.9, 70.0 Hz, 1H), 4.08-3.90 (m, 2H), 3.54-3.41 (m, 2H), 3.05 (s, 2H), 2.91 (s, 1H), 2.88-2.75 (m, 4H), 2.19-2.09 (m, 2H), 2.04-1.91 (m, 4H), 1.51-1.35 (m, 5H), 1.24-1.18 (m, 6H). MS (ESI) m/z: [M+H]⁺ Found 631.2.

Example 11

4-Chloro-5-(4-(difluoromethoxy)-6-(3,3,3-trifluoro-2,2-dimethylpropyl)pyridin-3-yl)-1-ethyl-N-(((1r,4r)-4-sulfamoylcyclohexyl)methyl)-1H-pyrazole-3-carboxamide

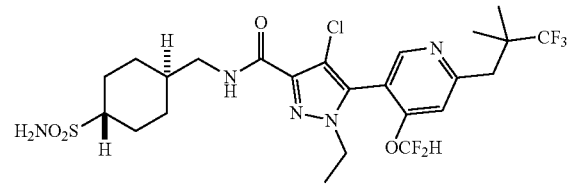

4-Chloro-5-(4-(difluoromethoxy)-6-(3,3,3-trifluoro-2,2-dimethylpropyl)pyridin-3-yl)-1-ethyl-1H-pyrazole-3-carboxylic acid (70 mg, 0.16 mmol, Intermediate 63) and (1r,4r)-4-(aminomethyl)cyclohexane-1-sulfonamide hydrochloride (40 mg, 0.17 mmol, Intermediate 43) were diluted with DMF (0.6 mL), and then DIPEA (0.05 mL, 0.28 mmol) and HATU (48 mg, 0.13 mmol) were added, and the mixture was stirred at rt for 3.5 h. After this time, the resulting solution was diluted with MeOH, filtered, and then purified by preparative HPLC (Inersil ODS-3, 5→95% MeCN/water, 0.05% TFA) to afford the title compound as a colorless solid. $^1$H NMR (400 MHz, CDCl$_3$) δ 8.57 (s, 1H), 7.20 (s, 1H), 6.99 (t, J=6.4 Hz, 1H), 6.63 (dd, J=72.3, 69.7 Hz, 1H), 4.41 (s, 2H), 4.09-3.90 (m, 2H), 3.35 (t, J=6.6 Hz, 2H), 3.10 (br s, 2H plus water), 2.97-2.89 (m, 1H), 2.33 (d, J=12.6 Hz, 2H), 2.04 (d, J=12.6 Hz, 2H), 1.77-1.53 (m, 3H), 1.40 (t, J=7.3 Hz, 3H), 1.27-1.20 (m, 6H), 1.20-1.07 (m, 2H). MS (ESI) m/z: [M+H]$^+$ Found 616.2.

Example 12

5-(4-(Difluoromethoxy)-6-(3,3,3-trifluoro-2,2-dimethylpropyl)pyridin-3-yl)-1-ethyl-4-methyl-N-(((1r,4r)-4-sulfamoylcyclohexyl)methyl)-1H-pyrazole-3-carboxamide

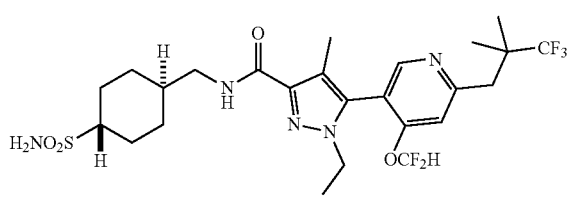

The title compound was prepared as described for the synthesis of Example 11, using 5-(4-(difluoromethoxy)-6-(3,3,3-trifluoro-2,2-dimethylpropyl)pyridin-3-yl)-1-ethyl-4-methyl-1H-pyrazole-3-carboxylic acid (Intermediate 62) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid. $^1$H NMR (400 MHz, CDCl$_3$) δ 8.41 (s, 1H), 7.10 (s, 1H), 7.05 (t, J=6.5 Hz, 1H), 6.56 (dd, J=72.4, 70.7 Hz, 1H), 4.35 (s, 2H), 4.02-3.83 (m, 2H), 3.32 (t, J=6.6 Hz, 2H), 3.04 (s, 2H), 2.93 (tt, J=12.3, 3.5 Hz, 1H), 2.33 (d, J=12.7 Hz, 2H), 2.17 (s, 3H), 2.06 (d, J=12.4 Hz, 2H), 1.74-1.57 (m, 3H), 1.35 (t, J=7.2 Hz, 3H), 1.28-1.07 (m, 8H). MS (ESI) m/z: [M+H]$^+$ Found 596.3.

Example 13

5-(4-(Difluoromethoxy)-6-(3,3,3-trifluoro-2,2-dimethylpropyl)pyridin-3-yl)-1-ethyl-4-methyl-N-(((1r,4r)-4-(methylsulfonyl)cyclohexyl)methyl)-1H-pyrazole-3-carboxamide

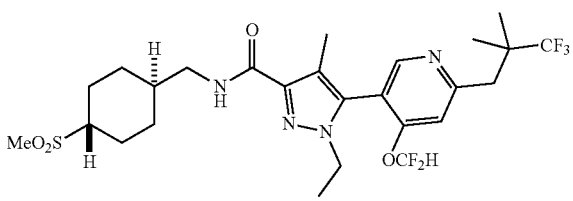

The title compound was prepared as described for the synthesis of Example 11, using 5-(4-(difluoromethoxy)-6-(3,3,3-trifluoro-2,2-dimethylpropyl)pyridin-3-yl)-1-ethyl-4-methyl-1H-pyrazole-3-carboxylic acid (Intermediate 62) and ((1r,4r)-4-(methylsulfonyl)cyclohexyl)methanamine hydrochloride (Intermediate 13) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. $^1$H NMR (400 MHz, CDCl$_3$) δ 8.52 (s, 1H), 7.22 (s, 1H), 7.11 (t, J=6.4 Hz, 1H), 6.61 (dd, J=J=71.6, 70.3 Hz, 1H), 4.03-3.85 (m, 2H), 3.33 (t, J=J=6.6 Hz, 2H), 3.12 (s, 2H), 2.90-2.78 (m, 4H), 2.29 (d, J=J=12.1 Hz, 2H), 2.16 (s, 3H), 2.08 (d, J=J=11.8 Hz, 2H), 1.75-1.65 (m, 1H), 1.66-1.54 (m, 2H), 1.36 (t, J=J=7.3 Hz, 3H), 1.23 (d, J=J=3.5 Hz, 6H), 1.21-1.08 (m, 2H). MS (ESI) m/z: [M+H]$^+$ Found 595.3.

Example 14

4-Chloro-5-(4-(difluoromethoxy)-6-((S*)-3,3,3-trifluoro-2-methylpropyl)pyridin-3-yl)-1-ethyl-N-(((1r,4S)-4-(methylsulfonyl)cyclohexyl)methyl)-1H-pyrazole-3-carboxamide

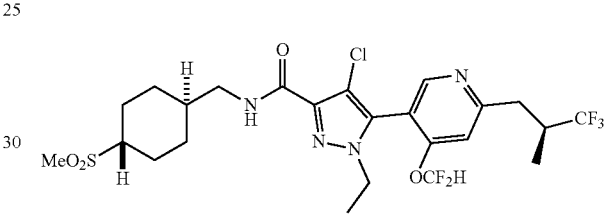

The title compound was prepared as described for the synthesis of Example 11, using (S*)-4-chloro-5-(4-(difluoromethoxy)-6-(3,3,3-trifluoro-2-methylpropyl)pyridin-3-yl)-1-ethyl-1H-pyrazole-3-carboxylic acid (Intermediate 69) and ((1r,4r)-4-(methylsulfonyl)cyclohexyl)methanamine hydrochloride (Intermediate 13) in place of 4-chloro-5-(4-(difluoromethoxy)-6-(3,3,3-trifluoro-2,2-dim ethyl propyl)pyridin-3-yl)-1-ethyl-1H-pyrazole-3-carboxylic acid and (1r,4r)-4-(aminomethyl)cyclohexane-1-sulfonamide hydrochloride. $^1$H NMR (500 MHz, CDCl$_3$) δ 8.55 (s, 1H), 7.19 (s, 1H), 7.03-6.97 (m, 1H), 6.64 (dd, J=72.4, 69.6 Hz, 1H), 4.08-3.91 (m, 2H), 3.42-3.33 (m, 2H), 3.33-3.25 (m, 1H), 3.00-2.79 (m, 6H), 2.29 (d, J=12.8 Hz, 2H), 2.08 (d, J=13.4 Hz, 2H), 1.76-1.66 (m, 1H), 1.66-1.55 (m, 2H), 1.45-1.36 (m, 3H), 1.23-1.09 (m, 5H). MS (ESI) m/z: [M+H]$^+$ Found 601.2.

Example 15

4-Chloro-5-(4-(difluoromethoxy)-6-((S*)-3,3,3-trifluoro-2-methylpropyl)pyridin-3-yl)-1-ethyl-N-(((1s,4R)-1-hydroxy-4-(methylsulfonyl)cyclohexyl)methyl)-1H-pyrazole-3-carboxamide

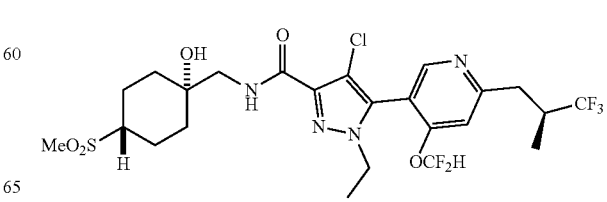

The title compound was prepared as described for the synthesis of Example 11, using (S*)-4-chloro-5-(4-(difluoromethoxy)-6-(3,3,3-trifluoro-2-methylpropyl)pyridin-3-yl)-1-ethyl-1H-pyrazole-3-carboxylic acid (Intermediate 69) and (1s,4s)-1-(aminomethyl)-4-(methylsulfonyl)cyclohexan-1-ol hydrochloride (Intermediate 9) in place of 4-chloro-5-(4-(difluoromethoxy)-6-(3,3,3-trifluoro-2,2-dimethyl propyl)pyridin-3-yl)-1-ethyl-1H-pyrazole-3-carboxylic acid and (1r,4r)-4-(aminomethyl)cyclohexane-1-sulfonamide hydrochloride. $^1$H NMR (500 MHz, CDCl$_3$) δ 8.54 (s, 1H), 7.31-7.27 (m, 1H), 7.18 (s, 1H), 6.81-6.49 (m, 1H), 4.08-3.93 (m, 2H), 3.54-3.44 (m, 2H), 3.32-3.26 (m, 2H), 3.01-2.78 (m, 6H), 2.18-2.10 (m, 2H), 2.05-1.92 (m, 4H), 1.51-1.37 (m, 5H), 1.19 (d, J=6.2 Hz, 3H). MS (ESI) m/z: [M+H]$^+$ Found 617.1.

Example 16

5-(4-(Difluoromethoxy)-6-((S*)-3,3,3-trifluoro-2-methylpropyl)pyridin-3-yl)-1-ethyl-4-methyl-N-(((1r,4S)-4-(methylsulfonyl)cyclohexyl)methyl)-1H-pyrazole-3-carboxamide

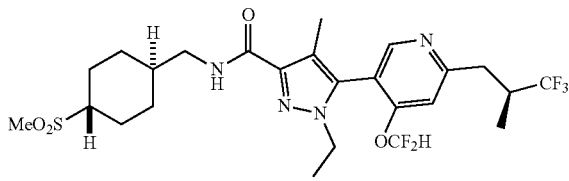

The title compound was prepared as described for the synthesis of Example 11, using (S*)-5-(4-(difluoromethoxy)-6-(3,3,3-trifluoro-2-methylpropyl)pyridin-3-yl)-1-ethyl-4-methyl-1H-pyrazole-3-carboxylic acid (Intermediate 71) and ((1r,4r)-4-(methylsulfonyl)cyclohexyl) methanamine hydrochloride (Intermediate 13) in place of 4-chloro-5-(4-(difluoromethoxy)-6-(3,3,3-trifluoro-2,2-dimethyl propyl)pyridin-3-yl)-1-ethyl-1H-pyrazole-3-carboxylic acid and (1r,4r)-4-(aminomethyl)cyclohexane-1-sulfonamide hydrochloride. $^1$H NMR (500 MHz, CDCl$_3$) δ 8.47 (s, 1H), 7.16 (s, 1H), 7.13-7.07 (m, 1H), 6.79-6.46 (m, 1H), 4.03-3.86 (m, 2H), 3.39-3.26 (m, 3H), 3.05-2.93 (m, 1H), 2.92-2.82 (m, 5H), 2.30 (d, J=12.7 Hz, 2H), 2.18 (d, J=2.5 Hz, 3H), 2.10 (d, J=13.3 Hz, 2H), 1.78-1.56 (m, 3H), 1.42-1.34 (m, 3H), 1.24-1.10 (m, 5H). MS (ESI) m/z: [M+H]$^+$ Found 581.2.

Example 17

4-Chloro-5-(4-(difluoromethoxy)-6-((R*)-3,3,3-trifluoro-2-methylpropyl)pyridin-3-yl)-1-ethyl-N-(((1r,4R)-4-(methylsulfonyl)cyclohexyl)methyl)-1H-pyrazole-3-carboxamide

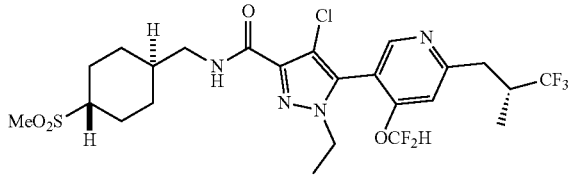

The title compound was prepared as described for the synthesis of Example 11, using (R*)-4-chloro-5-(4-(difluoromethoxy)-6-(3,3,3-trifluoro-2-methylpropyl)pyridin-3-yl)-1-ethyl-1H-pyrazole-3-carboxylic acid (Intermediate 73) and ((1r,4r)-4-(methylsulfonyl)cyclohexyl)methanamine hydrochloride (Intermediate 13) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. $^1$H NMR (400 MHz, CDCl$_3$) δ 8.48 (s, 1H), 7.10 (s, 1H), 6.97-6.90 (m, 1H), 6.60 (dd, J=72.9, 69.9 Hz, 1H), 4.06-3.90 (m, 2H), 3.35 (t, J=6.6 Hz, 2H), 3.33-3.22 (m, 1H), 3.09-2.90 (m, 1H), 2.89-2.76 (m, 5H), 2.29 (d, J=12.7 Hz, 2H), 2.08 (d, J=13.4 Hz, 2H), 1.76-1.66 (m, 1H), 1.66-1.55 (m, 2H), 1.44-1.35 (m, 3H), 1.21-1.08 (m, 5H). MS (ESI) m/z: [M+H]$^+$ Found 601.2.

Example 18

4-Chloro-5-(4-(difluoromethoxy)-6-((R*)-3,3,3-trifluoro-2-methylpropyl)pyridin-3-yl)-1-ethyl-N-(((1s,4S)-1-hydroxy-4-(methylsulfonyl)cyclohexyl) methyl)-1H-pyrazole-3-carboxamide

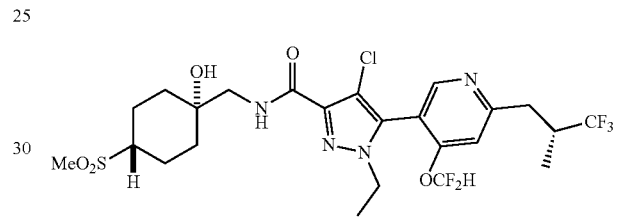

The title compound was prepared as described for the synthesis of Example 11, using (R*)-4-chloro-5-(4-(difluoromethoxy)-6-(3,3,3-trifluoro-2-methylpropyl)pyridin-3-yl)-1-ethyl-1H-pyrazole-3-carboxylic acid (Intermediate 73) and (1s,4s)-1-(aminomethyl)-4-(methylsulfonyl)cyclohexan-1-ol hydrochloride (Intermediate 9) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. $^1$H NMR (400 MHz, CDCl$_3$) δ 8.48 (s, 1H), 7.24-7.19 (m, 1H), 7.10 (s, 1H), 6.82-6.41 (m, 1H), 4.10-3.90 (m, 2H), 3.54-3.41 (m, 2H), 3.33-3.22 (m, 1H), 3.09-2.93 (m, 1H), 2.92-2.88 (m, 1H), 2.86-2.74 (m, 5H), 2.19-2.09 (m, 2H), 2.03-1.91 (m, 4H), 1.50-1.35 (m, 5H), 1.17 (d, J=6.9 Hz, 3H). MS (ESI) m/z: [M+H]$^+$ Found 617.2.

Example 19

5-(4-(Difluoromethoxy)-6-((R*)-3,3,3-trifluoro-2-methylpropyl)pyridin-3-yl)-1-ethyl-4-methyl-N-(((1r,4R)-4-(methylsulfonyl)cyclohexyl)methyl)-1H-pyrazole-3-carboxamide

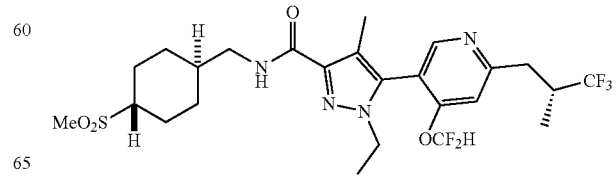

The title compound was prepared as described for the synthesis of Example 11, using (R*)-5-(4-(difluoromethoxy)-6-(3,3,3-trifluoro-2-methylpropyl)pyridin-3-yl)-1-ethyl-4-methyl-1H-pyrazole-3-carboxylic acid (Intermediate 75) and ((1r,4r)-4-(methylsulfonyl)cyclohexyl)methanamine hydrochloride (Intermediate 13) in place of 4-chloro-5-(4-(difluoromethoxy)-6-(3,3,3-trifluoro-2,2-dimethyl propyl)pyridin-3-yl)-1-ethyl-1H-pyrazole-3-carboxylic acid and (1r,4r)-4-(aminomethyl)cyclohexane-1-sulfonamide hydrochloride. $^1$H NMR (400 MHz, CDCl$_3$) δ 8.47 (s, 1H), 7.16 (s, 1H), 7.10 (t, J=6.3 Hz, 1H), 6.80-6.41 (m, 1H), 4.02-3.84 (m, 2H), 3.33 (t, J=6.6 Hz, 2H), 3.31-3.23 (m, 1H), 2.94-2.79 (m, 6H), 2.29 (d, J=12.6 Hz, 2H), 2.16 (d, J=1.8 Hz, 3H), 2.08 (d, J=12.8 Hz, 2H), 1.76-1.54 (m, 3H), 1.40-1.32 (m, 3H), 1.21-1.08 (m, 5H). MS (ESI) m/z: [M+H]$^+$ Found 581.3.

Example 20

5-(4-(Difluoromethoxy)-6-((R*)-3,3,3-trifluoro-2-methylpropyl)pyridin-3-yl)-1-ethyl-N-(((1s,4S)-1-hydroxy-4-(methylsulfonyl)cyclohexyl)methyl)-4-methyl-1H-pyrazole-3-carboxamide

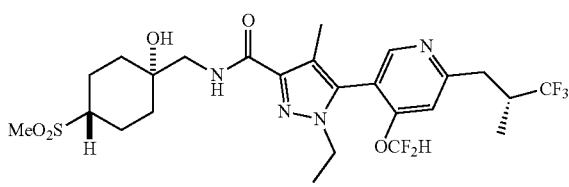

The title compound was prepared as described for the synthesis of Example 11, using (R*)-5-(4-(difluoromethoxy)-6-(3,3,3-trifluoro-2-methylpropyl)pyridin-3-yl)-1-ethyl-4-methyl-1H-pyrazole-3-carboxylic acid (Intermediate 75) and (1s,4S)-1-(aminomethyl)-4-(methylsulfonyl)cyclohexan-1-ol hydrochloride (Intermediate 9) in place of 4-chloro-5-(4-(difluoromethoxy)-6-(3,3,3-trifluoro-2,2-dim ethyl propyl)pyridin-3-yl)-1-ethyl-1H-pyrazole-3-carboxylic acid and (1r,4r)-4-(aminomethyl)cyclohexane-1-sulfonamide hydrochloride. $^1$H NMR (400 MHz, CDCl$_3$) δ 8.51 (s, 1H), 7.39 (t, J=6.2 Hz, 1H), 7.21 (s, 1H), 6.64 (dd, J=71.6, 70.1 Hz, 1H), 4.32-4.16 (m, OH), 4.03-3.84 (m, 2H), 3.54-3.40 (m, 2H), 3.34-3.24 (m, 1H), 2.99-2.77 (m, 6H), 2.20-2.09 (m, 5H), 2.06-1.92 (m, 4H), 1.50-1.33 (m, 5H), 1.20 (dd, J=6.6, 2.2 Hz, 3H). MS (ESI) m/z: [M+H]$^+$ Found 597.2.

Example 21

4-Chloro-5-(4-(difluoromethoxy)-6-(3,3,3-trifluoro-2-(trifluoromethyl)propyl)pyridin-3-yl)-1-ethyl-N-(((1r,4r)-4-(methylsulfonyl)cyclohexyl)methyl)-1H-pyrazole-3-carboxamide

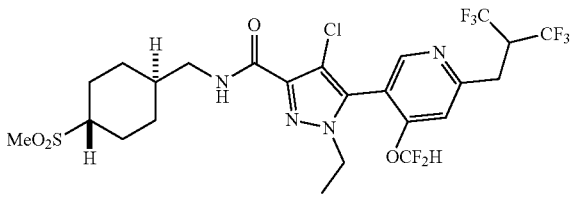

The title compound was prepared as described for the synthesis of Intermediate 68, using 2-(bromomethyl)-1,1,1,3,3,3-hexafluoropropane and 4-chloro-5-(6-chloro-4-(difluoromethoxy)pyridin-3-yl)-1-ethyl-N-(((1r,4r)-4-(methylsulfonyl)cyclohexyl)methyl)-1H-pyrazole-3-carboxamide (Intermediate 77) in place of (R*)-1,1,1-trifluoro-3-iodo-2-methylpropane and ethyl 4-chloro-5-(6-chloro-4-(difluoromethoxy)pyridin-3-yl)-1-ethyl-1H-pyrazole-3-carboxylate. $^1$H NMR (400 MHz, CDCl$_3$) δ 8.49 (s, 1H), 7.16 (s, 1H), 6.93 (t, J=6.4 Hz, 1H), 6.80-6.42 (m, 1H), 4.30-4.16 (m, 1H), 4.08-3.89 (m, 2H), 3.35 (td, J=6.4, 3.3 Hz, 4H), 2.88-2.78 (m, 4H), 2.33-2.23 (m, 2H), 2.13-2.02 (m, 2H), 1.77-1.65 (m, 1H), 1.66-1.52 (m, 2H), 1.39 (t, J=7.3 Hz, 3H), 1.21-1.08 (m, 2H). MS (ESI) m/z: [M+H]$^+$ Found 655.2.

Example 22

4-Chloro-5-(4-(difluoromethoxy)-6-(3,3,3-trifluoro-2-(trifluoromethyl)propyl)pyridin-3-yl)-1-ethyl-N-(((1s,4s)-1-hydroxy-4-(methylsulfonyl)cyclohexyl)methyl)-1H-pyrazole-3-carboxamide

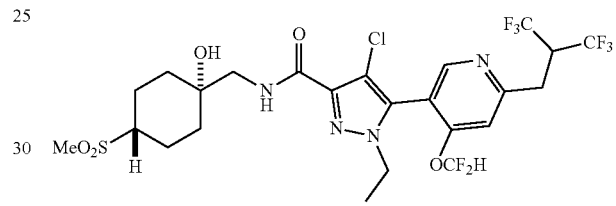

The title compound was prepared as described for the synthesis of Intermediate 68, using 2-(bromomethyl)-1,1,1,3,3,3-hexafluoropropane and 4-chloro-5-(6-chloro-4-(difluoromethoxy)pyridin-3-yl)-1-ethyl-N-(((1s,4s)-1-hydroxy-4-(methylsulfonyl)cyclohexyl)methyl)-1H-pyrazole-3-carboxamide (Intermediate 78) in place of (R*)-1,1,1-trifluoro-3-iodo-2-methylpropane and ethyl 4-chloro-5-(6-chloro-4-(difluoromethoxy)pyridin-3-yl)-1-ethyl-1H-pyrazole-3-carboxylate (Intermediate 64). $^1$H NMR (400 MHz, CDCl$_3$) δ 8.49 (s, 1H), 7.23 (t, J=6.3 Hz, 1H), 7.16 (s, 1H), 6.62 (dd, J=72.7, 69.7 Hz, 1H), 4.30-4.16 (m, 1H), 4.08-3.90 (m, 2H), 3.54-3.42 (m, 2H), 3.41-3.28 (m, 2H), 2.90 (s, 1H), 2.86-2.75 (m, 4H), 2.18-2.09 (m, 2H), 2.04-1.91 (m, 4H), 1.50-1.35 (m, 5H). MS (ESI) m/z: [M+H]$^+$ Found 671.1.

Example 23

5-(4-(Difluoromethoxy)-6-(3,3,3-trifluoro-2-(trifluoromethyl)propyl)pyridin-3-yl)-1-ethyl-4-methyl-N-(((1r,4r)-4-(methylsulfonyl)cyclohexyl)methyl)-1H-pyrazole-3-carboxamide

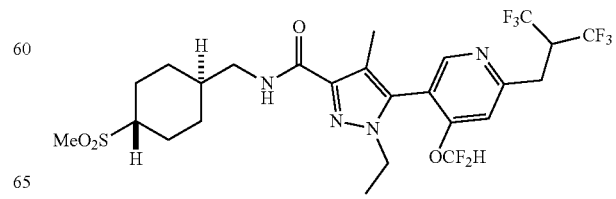

The title compound was prepared as described for the synthesis of Intermediate 70, using 4-chloro-5-(4-(difluoromethoxy)-6-(3,3,3-trifluoro-2-(trifluoromethyl)propyl)pyridin-3-yl)-1-ethyl-N-(((1r,4r)-4-(methyl sulfonyl)cyclohexyl)methyl)-1H-pyrazole-3-carb oxamide (Example 21) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate. $^1$H NMR (500 MHz, CDCl$_3$) δ 8.41 (s, 1H), 7.15 (s, 1H), 7.10-7.02 (m, 1H), 6.58 (dd, J=72.3, 70.5 Hz, 1H), 4.28-4.16 (m, 1H), 4.01-3.84 (m, 2H), 3.40-3.29 (m, 4H), 2.89-2.79 (m, 4H), 2.29 (d, J=12.6 Hz, 2H), 2.16 (s, 3H), 2.09 (d, J=13.2 Hz, 2H), 1.68-1.54 (m, 3H), 1.35 (t, J=7.2 Hz, 3H), 1.21-1.08 (m, 2H). MS (ESI) m/z: [M+H]$^+$ Found 635.2.

Example 24

5-(4-(Difluoromethoxy)-6-(3,3,3-trifluoro-2-(trifluoromethyl)propyl)pyridin-3-yl)-1-ethyl-N-(((1s,4s)-1-hydroxy-4-(methylsulfonyl)cyclohexyl)methyl)-4-methyl-1H-pyrazole-3-carboxamide

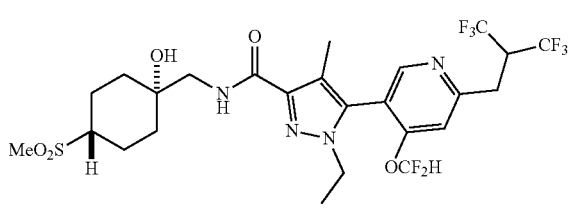

The title compound was prepared as described for the synthesis of Intermediate 70, using 4-chloro-5-(4-(difluoromethoxy)-6-(3,3,3-trifluoro-2-(trifluoromethyl)propyl)pyridin-3-yl)-1-ethyl-N-(((1s,4s)-1-hydroxy-4-(methylsulfonyl)cyclohexyl)methyl)-1H-pyrazole-3-carboxamide (Example 22) in place of ethyl (S*)-4-chloro-5-(4-(difluoromethoxy)-6-(3,3,3-trifluoro-2-methylpropyl)pyridin-3-yl)-1-ethyl-1H-pyrazole-3-carboxylate. $^1$H NMR (500 MHz, CDCl$_3$) δ 8.41 (s, 1H), 7.32 (t, J=6.3 Hz, 1H), 7.15 (s, 1H), 6.59 (dd, J=72.1, 70.5 Hz, 1H), 4.22 (ddd, J=14.3, 8.1, 6.2 Hz, 1H), 4.01-3.84 (m, 2H), 3.50-3.40 (m, 3H), 3.38-3.28 (m, 2H), 2.83 (s, 3H), 2.82-2.76 (m, 1H), 2.18-2.10 (m, 5H), 2.05-1.93 (m, 4H), 1.47-1.38 (m, 2H), 1.35 (t, J=7.3 Hz, 3H). MS (ESI) m/z: [M+H]$^+$ Found 651.1.

Example 25

4-Chloro-1-ethyl-5-(4-isopropyl-6-(3,3,3-trifluoro-2,2-dimethylpropyl)pyridin-3-yl)-N-((1r,4r)-4-(methylsulfonyl)cyclohexyl)methyl)-1H-pyrazole-3-carboxamide

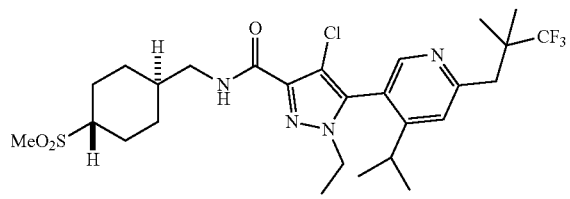 [SMILES: CCn1nc(C(=O)NC[C@H]2CC[C@H](S(C)(=O)=O)CC2)c(Cl)c1-c1cnc(CC(C)(C)C(F)(F)F)cc1C(C)C]

The title compound was prepared as described for the synthesis of Example 11, using 4-chloro-1-ethyl-5-(4-isopropyl-6-(3,3,3-trifluoro-2,2-dimethylpropyl)pyridin-3-yl)-1H-pyrazole-3-carboxylic acid (Intermediate 85) and ((1r,4r)-4-(methylsulfonyl)cyclohexyl)methanamine hydrochloride (Intermediate 13) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. $^1$H NMR (400 MHz, CDCl$_3$) δ 8.60 (s, 1H), 7.52 (s, 1H), 6.98 (t, J=6.1 Hz, 1H), 4.02-3.85 (m, 2H), 3.37 (td, J=6.6, 2.4 Hz, 2H), 3.24 (s, 2H), 2.90-2.79 (m, 5H), 2.29 (d, J=12.1 Hz, 2H), 2.08 (d, J=12.0 Hz, 2H), 1.76-1.67 (m, 1H), 1.61 (qd, J=12.8, 3.5 Hz, 2H), 1.40 (t, J=7.2 Hz, 3H), 1.29 (d, J=6.7 Hz, 3H), 1.27-1.22 (m, 6H), 1.22-1.08 (m, 5H). MS (ESI) m/z: [M+H]$^+$ Found 591.0.

Example 26

4-Chloro-5-(4-(difluoromethyl)-6-(3,3,3-trifluoro-2,2-dimethylpropyl)pyridin-3-yl)-1-ethyl-N-(((1r,4r)-4-(methylsulfonyl)cyclohexyl)methyl)-1H-pyrazole-3-carboxamide

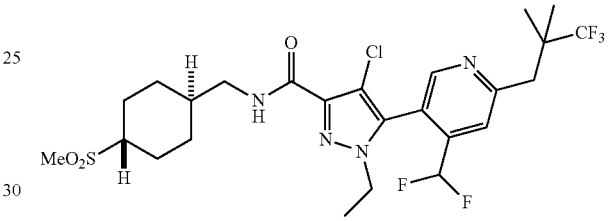

The title compound was prepared as described for the synthesis of Example 11, using 4-chloro-5-(4-(difluoromethyl)-6-(3,3,3-trifluoro-2,2-dimethylpropyl)pyridin-3-yl)-1-ethyl-1H-pyrazole-3-carboxylic acid (Intermediate 92) and ((1r,4r)-4-(methylsulfonyl)cyclohexyl)methanamine hydrochloride (Intermediate 13) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. $^1$H NMR (500 MHz, CDCl$_3$) δ 8.45 (s, 1H), 7.50 (s, 1H), 6.88 (t, J=6.5 Hz, 1H), 6.58-6.32 (m, 1H), 3.88 (ddt, J=22.8, 14.0, 7.0 Hz, 2H), 3.29 (t, J=6.6 Hz, 2H), 3.05 (s, 2H), 2.81-2.72 (m, 4H), 2.26-2.18 (m, 2H), 2.05-1.97 (m, 2H), 1.69-1.59 (m, 1H), 1.59-1.46 (m, 2H), 1.33-1.26 (m, 3H), 1.20-1.02 (m, 8H). MS (ESI) m/z: [M+H]$^+$ Found 599.2.

Example 27

4-Chloro-5-(4-(difluoromethyl)-6-(3,3,3-trifluoro-2,2-dimethylpropyl)pyridin-3-yl)-1-ethyl-N-(((1s,4s)-1-hydroxy-4-(methylsulfonyl)cyclohexyl)methyl)-1H-pyrazole-3-carboxamide

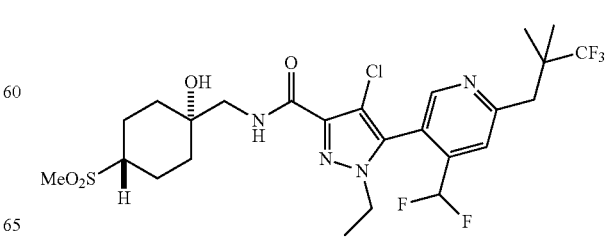

The title compound was prepared as described for the synthesis of Example 11, using 4-chloro-5-(4-(difluoromethyl)-6-(3,3,3-trifluoro-2,2-dimethylpropyl)pyridin-3-yl)-1-ethyl-1H-pyrazole-3-carboxylic acid (Intermediate 92) and (1s,4s)-1-(aminomethyl)-4-(methylsulfonyl)cyclohexan-1-ol hydrochloride (Intermediate 9) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. $^1$H NMR (400 MHz, CDCl$_3$) δ 8.63 (s, 1H), 7.71-7.66 (m, 1H), 7.36 (t, J=6.3 Hz, 1H), 6.74-6.44 (m, 1H), 4.09-3.92 (m, 2H), 3.81 (br s, 1H), 3.60-3.49 (m, 2H), 3.20 (s, 2H), 2.94-2.83 (m, 4H), 2.23-2.14 (m, 2H), 2.08-1.96 (m, 4H), 1.57-1.46 (m, 2H), 1.42 (t, J=7.3 Hz, 3H), 1.27 (d, J=7.3 Hz, 6H). MS (ESI) m/z: [M+H]$^+$ Found 615.3.

Example 28

5-(4-(Difluoromethyl)-6-(3,3,3-trifluoro-2,2-dimethylpropyl)pyridin-3-yl)-1-ethyl-N-(((1s,4s)-1-hydroxy-4-(methylsulfonyl)cyclohexyl)methyl)-4-methyl-1H-pyrazole-3-carboxamide

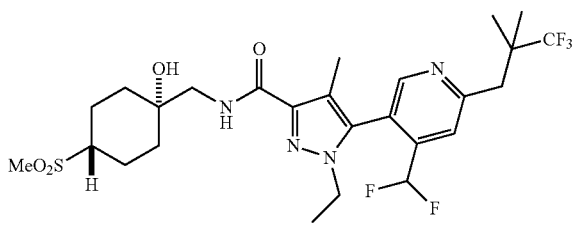 [SMILES: CCn1nc(C(=O)NC[C@]2(O)CC[C@@H](S(C)(=O)=O)CC2)c(C)c1-c1cnc(CC(C)(C)C(F)(F)F)cc1C(F)F]

The title compound was prepared as described for the synthesis of Example 11, using 5-(4-(difluoromethyl)-6-(3,3,3-trifluoro-2,2-dimethylpropyl)pyridin-3-yl)-1-ethyl-4-methyl-1H-pyrazole-3-carboxylic acid (Intermediate 94) and (1s,4s)-1-(aminomethyl)-4-(methylsulfonyl)cyclohexan-1-ol hydrochloride (Intermediate 9) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. $^1$H NMR (400 MHz, CDCl$_3$) δ 8.63 (s, 1H), 7.70 (s, 1H), 7.47 (t, J=6.3 Hz, 1H), 6.40 (t, J=54.3 Hz, 1H), 4.49 (br s, 1H), 3.93 (ddt, J=23.4, 13.9, 7.0 Hz, 2H), 3.59-3.46 (m, 2H), 3.22 (s, 2H), 2.94-2.82 (m, 4H), 2.23-2.13 (m, 5H), 2.09-1.96 (m, 4H), 1.56-1.44 (m, 2H), 1.38 (t, J=7.3 Hz, 3H), 1.31-1.23 (m, 6H). MS (ESI) m/z: [M+H]$^+$ Found 595.2.

Example 29

5-(4-(Difluoromethyl)-6-(3,3,3-trifluoro-2,2-dimethylpropyl)pyridin-3-yl)-1-ethyl-4-methyl-N-(((1r,4r)-4-(methylsulfonyl)cyclohexyl)methyl)-1H-pyrazole-3-carboxamide

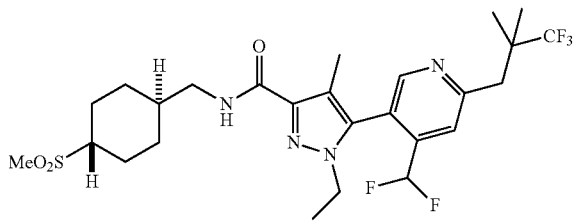 [SMILES: CCn1nc(C(=O)NC[C@H]2CC[C@H](S(C)(=O)=O)CC2)c(C)c1-c1cnc(CC(C)(C)C(F)(F)F)cc1C(F)F]

The title compound was prepared as described for the synthesis of Example 11, using 5-(4-(difluoromethyl)-6-(3,3,3-trifluoro-2,2-dimethylpropyl)pyridin-3-yl)-1-ethyl-4-methyl-1H-pyrazole-3-carboxylic acid (Intermediate 94) and ((1r,4r)-4-(methylsulfonyl)cyclohexyl)methanamine hydrochloride (Intermediate 13) in place of 4-chloro-5-(4-(difluoromethoxy)-6-(3,3,3-trifluoro-2,2-dim ethyl propyl) pyridin-3-yl)-1-ethyl-1H-pyrazole-3-carboxylic acid and (1r,4r)-4-(aminomethyl)cyclohexane-1-sulfonamide hydrochloride. $^1$H NMR (400 MHz, CDCl$_3$) δ 8.51 (s, 1H), 7.58 (s, 1H), 7.10 (t, J=6.4 Hz, 1H), 6.44-6.11 (m, 1H), 3.80 (ddt, J=23.2, 13.8, 7.0 Hz, 2H), 3.27 (t, J=6.6 Hz, 2H), 3.09 (s, 2H), 2.82-2.72 (m, 4H), 2.22 (d, J=11.4 Hz, 2H), 2.06-1.96 (m, 5H), 1.68-1.46 (m, 3H), 1.26 (t, J=7.3 Hz, 3H), 1.14 (d, J=5.2 Hz, 6H), 1.13-1.00 (m, 2H). MS (ESI) m/z: [M+H]$^+$ Found 579.3.

Example 30

4-Chloro-5-(4-(difluoromethoxy)-6-(3,3,3-trifluoro-2,2-dimethylpropyl)pyridin-3-yl)-1-methyl-N-(((1r,4r)-4-(methylsulfonyl)cyclohexyl)methyl)-1H-pyrazole-3-carboxamide

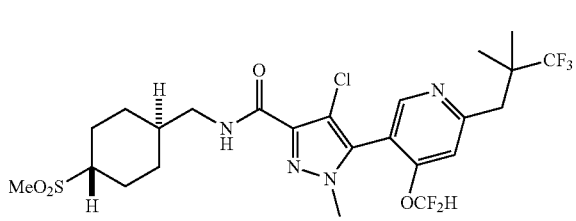

The title compound was prepared as described for the synthesis of Example 11, using 4-chloro-5-(4-(difluoromethoxy)-6-(3,3,3-trifluoro-2,2-dim ethyl propyl)pyridin-3-yl)-1-methyl-1H-pyrazole-3-carboxylic acid (Intermediate 102) and ((1r,4r)-4-(methylsulfonyl)cyclohexyl)methanamine hydrochloride (Intermediate 13) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. $^1$H NMR (500 MHz, CDCl$_3$) δ 8.57 (s, 1H), 7.20-7.15 (m, 1H), 6.95 (t, J=6.3 Hz, 1H), 6.82-6.47 (m, 1H), 3.77 (s, 3H), 3.35 (td, J 6.6, 3.0 Hz, 2H), 3.09 (s, 2H), 2.89-2.79 (m, 4H), 2.29 (d, J=11.4 Hz, 2H), 2.07 (d, J=12.1 Hz, 2H), 1.75-1.66 (m, 1H), 1.60 (qd, J=13.0, 3.7 Hz, 2H), 1.26-1.20 (m, 6H), 1.14 (qd, J=13.1, 3.6 Hz, 2H). MS (ESI) m/z: [M+H]+ Found 601.2.

Example 31

5-(4-(Difluoromethoxy)-6-(3,3,3-trifluoro-2,2-dimethylpropyl)pyridin-3-yl)-1,4-dimethyl-N-((1r,4r)-4-(methylsulfonyl)cyclohexyl)methyl)-1H-pyrazole-3-carboxamide

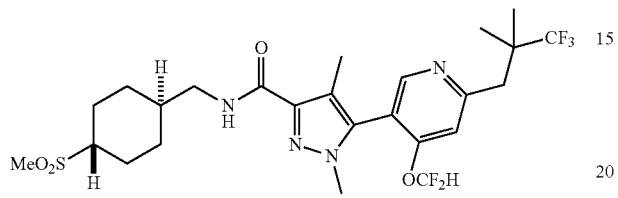

The title compound was prepared as described for the synthesis of Example 11, using 5-(4-(difluoromethoxy)-6-(3,3,3-trifluoro-2,2-dim ethyl propyl)pyridin-3-yl)-1,4-dim ethyl-1H-pyrazole-3-carboxylic acid (Intermediate 104) and ((1r,4r)-4-(methylsulfonyl)cyclohexyl)methanamine hydrochloride (Intermediate 13) in place of 4-chloro-5-(4-(difluoromethoxy)-6-(3,3,3-trifluoro-2,2-dim ethyl propyl)pyridin-3-yl)-1-ethyl-1H-pyrazole-3-carboxylic acid and (1r,4r)-4-(aminomethyl)cyclohexane-1-sulfonamide hydrochloride. 1H NMR (500 MHz, CDCl3) δ 8.54 (s, 1H), 7.22 (s, 1H), 7.08 (t, J=6.4 Hz, 1H), 6.78-6.47 (m, 1H), 3.71 (s, 3H), 3.36-3.30 (m, 2H), 3.12 (s, 2H), 2.88-2.79 (m, 4H), 2.29 (d, J=12.6 Hz, 2H), 2.19 (s, 3H), 2.08 (d, J=14.3 Hz, 2H), 1.74-1.65 (m, 1H), 1.60 (qd, J=13.1, 3.7 Hz, 2H), 1.23 (s, 6H), 1.14 (qd, J=13.1, 3.5 Hz, 2H). MS (ESI) m/z: [M+H]+ Found 581.2.

Example 32

4-Chloro-5-(4-(difluoromethoxy)-6-(4,4,4-trifluorobutyl)pyridin-3-yl)-1-ethyl-N-(((1r,4r)-4-(methylsulfonyl)cyclohexyl)methyl)-1H-pyrazole-3-carboxamide

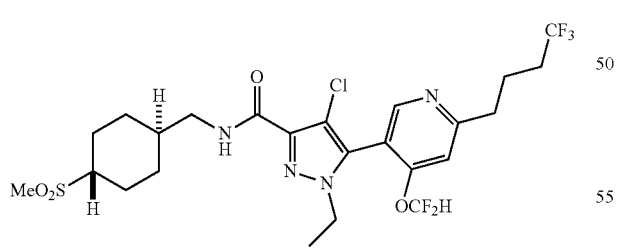

The title compound was prepared as described for the synthesis of Example 11, using 4-chloro-5-(4-(difluoromethoxy)-6-(4,4,4-trifluorobutyl)pyridin-3-yl)-1-ethyl-1H-pyrazole-3-carboxylic acid (Intermediate 106) and ((1r,4r)-4-(methyl sulfonyl)cyclohexyl)methanamine hydrochloride (Intermediate 13) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. 1H NMR (400 MHz, CDCl3) δ 8.58 (s, 1H), 7.23 (s, 1H), 6.99 (t, J=6.4 Hz, 1H), 6.67 (dd, J=72.1, 69.5 Hz, 1H), 4.12-3.90 (m, 2H), 3.43-3.30 (m, 2H), 3.11-2.98 (m, 2H), 2.92-2.77 (m, 4H), 2.34-2.18 (m, 4H), 2.18-2.01 (m, 4H), 1.80-1.51 (m, 3H), 1.41 (t, J=7.3 Hz, 3H), 1.25-1.07 (m, 2H). MS (ESI) m/z: [M+H]+ Found 601.2.

Example 33

4-Chloro-5-(4-(difluoromethoxy)-6-(4,4,4-trifluorobutyl)pyridin-3-yl)-1-ethyl-N-(((1s,4s)-1-hydroxy-4-(methylsulfonyl)cyclohexyl)methyl)-1H-pyrazole-3-carboxamide

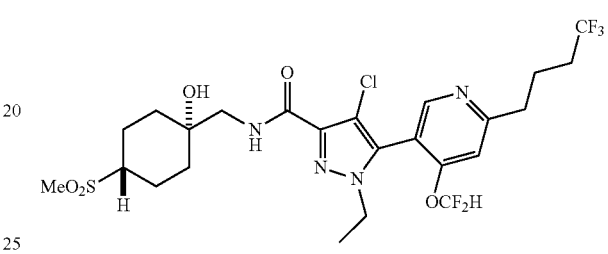

The title compound was prepared as described for the synthesis of Example 11, using 4-chloro-5-(4-(difluoromethoxy)-6-(4,4,4-trifluorobutyl)pyridin-3-yl)-1-ethyl-1H-pyrazole-3-carboxylic acid (Intermediate 106) and (1s,4s)-1-(aminomethyl)-4-(methyl sulfonyl)cyclohexan-1-ol hydrochloride (Intermediate 9) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. 1H NMR (500 MHz, CDCl3) δ 8.56 (s, 1H), 7.30-7.26 (m, 1H), 7.21 (s, 1H), 6.67 (dd, J=72.2, 69.6 Hz, 1H), 4.00 (ddt, J=23.9, 13.7, 6.9 Hz, 2H), 3.70 (br s, 1H), 3.49 (qd, J=14.1, 6.3 Hz, 2H), 3.06-3.00 (m, 2H), 2.87-2.77 (m, 4H), 2.31-2.19 (m, 2H), 2.17-2.06 (m, 4H), 2.03-1.92 (m, 4H), 1.50-1.42 (m, 2H), 1.40 (t, J 7.2 Hz, 3H). MS (ESI) m/z: [M+H]+ Found 617.2.

Example 34

5-(4-(Difluoromethoxy)-6-(4,4,4-trifluorobutyl)pyridin-3-yl)-1-ethyl-4-methyl-N-(((1r,4r)-4-(methylsulfonyl)cyclohexyl)methyl)-1H-pyrazole-3-carboxamide

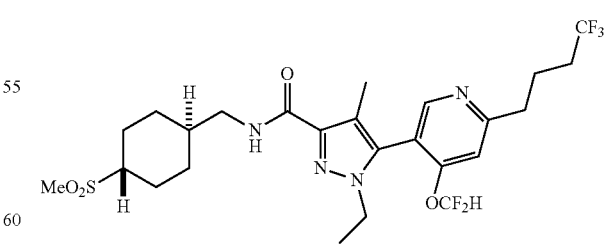

The title compound was prepared as described for the synthesis of Example 11, using 5-(4-(difluoromethoxy)-6-(4,4,4-trifluorobutyl)pyridin-3-yl)-1-ethyl-4-methyl-1H-pyrazole-3-carboxylic acid (Intermediate 108) and ((1r,4r)-4-(methylsulfonyl)cyclohexyl)methanamine hydrochloride (Intermediate 13) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. ¹H NMR (400 MHz, CDCl₃) δ 8.54 (s, 1H), 7.26-7.24 (m, 1H), 7.12 (t, J=6.4 Hz, 1H), 6.66 (dd, J=71.4, 70.1 Hz, 1H), 4.03-3.85 (m, 2H), 3.39-3.28 (m, 2H), 3.11-3.03 (m, 2H), 2.90-2.78 (m, 4H), 2.34-2.19 (m, 4H), 2.16 (s, 3H), 2.14-2.03 (m, 4H), 1.76-1.66 (m, 1H), 1.66-1.54 (m, 2H), 1.37 (t, J=7.2 Hz, 3H), 1.21-1.07 (m, 2H). MS (ESI) m/z: [M+H]⁺ Found 581.2.

Example 35

5-(4-(Difluoromethoxy)-6-(4,4,4-trifluorobutyl)pyridin-3-yl)-1-ethyl-N-(((1s,4s)-1-hydroxy-4-(methylsulfonyl)cyclohexyl)methyl)-4-methyl-1H-pyrazole-3-carboxamide

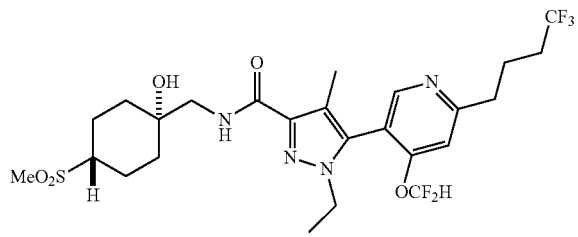

The title compound was prepared as described for the synthesis of Example 11, using 5-(4-(difluoromethoxy)-6-(4,4,4-trifluorobutyl)pyridin-3-yl)-1-ethyl-4-methyl-1H-pyrazole-3-carboxylic acid (Intermediate 108) and (1s,4s)-1-(aminomethyl)-4-(methylsulfonyl)cyclohexan-1-ol hydrochloride (Intermediate 9) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(Aminomethyl)cyclohexane-1-sulfonamide hydrochloride. ¹H NMR (400 MHz, CDCl₃) δ 8.56 (s, 1H), 7.38 (t, J=6.4 Hz, 1H), 7.29-7.27 (m, 1H), 6.67 (dd, J=71.2, 70.0 Hz, 1H), 4.03-3.85 (m, 2H), 3.46 (qd, J=14.2, 6.4 Hz, 2H), 3.13-3.04 (m, 2H), 2.87-2.76 (m, 4H), 2.34-2.19 (m, 2H), 2.19-2.05 (m, 7H), 2.05-1.90 (m, 4H), 1.49-1.34 (m, 5H). MS (ESI) m/z: [M+H]⁺ Found 597.3.

Example 36

4-Chloro-1-ethyl-N-(((1s,4s)-1-hydroxy-4-(methylsulfonyl)cyclohexyl)methyl)-5-(4-methoxy-6-(3,3,3-trifluoro-2,2-dimethylpropoxy)pyridin-3-yl)-1H-pyrazole-3-carboxamide

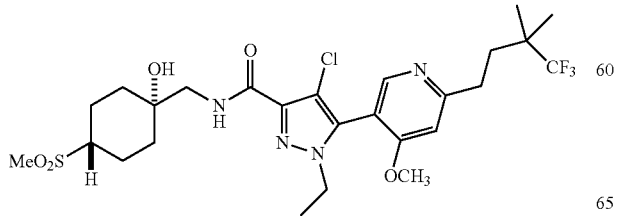

The title compound was prepared as described for the synthesis of Example 10, using 4-chloro-1-ethyl-5-(4-methoxy-6-(3,3,3-trifluoro-2,2-dimethylprop oxy)pyridin-3-yl)-1H-pyrazole-3-carboxylic acid (Intermediate 109) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid. 4¹ NMR (400 MHz, CDCl₃) δ 7.91 (s, 1H), 7.25-7.19 (m, 1H), 6.38 (s, 1H), 4.39-4.30 (m, 2H), 4.03-3.89 (m, 2H), 3.85 (s, 3H), 3.54-3.39 (m, 2H), 3.07 (s, 1H), 2.86-2.74 (m, 4H), 2.18-2.08 (m, 2H), 2.04-1.91 (m, 4H), 1.48-1.32 (m, 5H), 1.31-1.24 (m, 6H). MS (ESI) m/z: [M+H]⁺ Found 611.1.

Example 37

4-Chloro-5-(6-(3,3-difluoro-2,2-dimethylpropyl)-4-(difluoromethoxy)pyridin-3-yl)-1-ethyl-N-(((1r,4r)-4-(methylsulfonyl)cyclohexyl)methyl)-1H-pyrazole-3-carboxamide

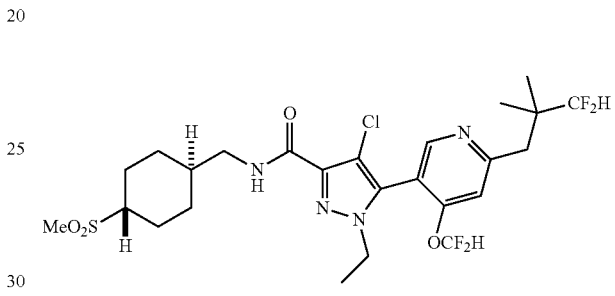

The title compound was prepared as described for the synthesis of Example 11, using 4-chloro-5-(6-(3,3-difluoro-2,2-dimethylpropyl)-4-(difluoromethoxy)pyridin-3-yl)-1-ethyl-1H-pyrazole-3-carboxylic acid (Intermediate 111) and ((1r,4r)-4-(methylsulfonyl)cyclohexyl)methanamine hydrochloride (Intermediate 13) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. ¹H NMR (400 MHz, CDCl₃) δ 8.61 (s, 1H), 7.26-7.24 (m, 1H), 6.99 (t, J=6.4 Hz, 1H), 6.66 (dd, J=71.9, 69.6 Hz, 1H), 5.63 (t, J=56.5 Hz, 1H), 4.08-3.92 (m, 2H), 3.42-3.31 (m, 2H), 3.04 (s, 2H), 2.89-2.80 (m, 4H), 2.33-2.24 (m, 2H), 2.11-2.03 (m, 2H), 1.76-1.66 (m, 1H), 1.66-1.54 (m, 2H), 1.40 (t, J=7.3 Hz, 3H), 1.21-1.07 (m, 8H). MS (ESI) m/z: [M+H]⁺ Found 597.0.

Example 38

4-Chloro-5-(6-(3,3-difluoro-2,2-dimethylpropyl)-4-(difluoromethoxy)pyridin-3-yl)-1-ethyl-N-(((1s,4s)-1-hydroxy-4-(methylsulfonyl)cyclohexyl)methyl)-1H-pyrazole-3-carboxamide

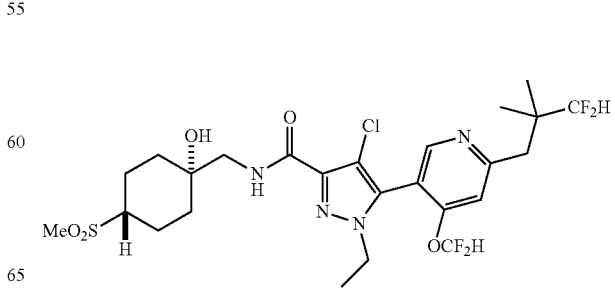

The title compound was prepared as described for the synthesis of Example 11, using 4-chloro-5-(6-(3,3-difluoro-2,2-dimethylpropyl)-4-(difluoromethoxy)pyridin-3-yl)-1-ethyl-1H-pyrazole-3-carboxylic acid (Intermediate 111) and (1s,4s)-1-(aminomethyl)-4-(methylsulfonyl)cyclohexan-1-ol hydrochloride (Intermediate 9) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. $^1$H NMR (400 MHz, CDCl$_3$) δ 8.56 (s, 1H), 7.29-7.23 (m, 1H), 7.21-7.17 (m, 1H), 6.64 (dd, J=72.4, 69.7 Hz, 1H), 5.65 (t, J=56.6 Hz, 1H), 4.00 (qd, J=13.8, 6.9 Hz, 2H), 3.55-3.42 (m, 2H), 3.04 (br s, 1H), 3.00 (s, 2H), 2.86-2.77 (m, 4H), 2.17-2.09 (m, 2H), 2.04-1.91 (m, 4H), 1.51-1.36 (m, 5H), 1.13-1.07 (m, 6H). MS (ESI) m/z: [M+H]$^+$ Found 612.9.

Example 39

4-Chloro-5-(6-(3,3-difluoro-2,2-dimethylpropyl)-4-(difluoromethoxy)pyridin-3-yl)-N-(((1S*,2S*,4S*)-1,2-dihydroxy-4-(methylsulfonyl)cyclohexyl)methyl)-1-ethyl-1H-pyrazole-3-carboxamide

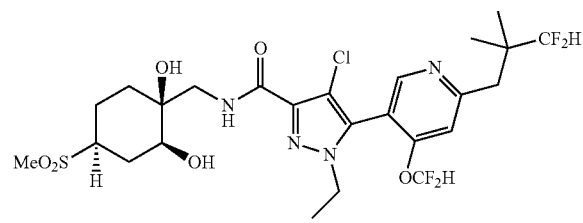

The title compound was prepared as described for the synthesis of Example 11, using 4-chloro-5-(6-(3,3-difluoro-2,2-dimethylpropyl)-4-(difluoromethoxy)pyridin-3-yl)-1-ethyl-1H-pyrazole-3-carboxylic acid (Intermediate 111) and (1S*,2S*,4S*)-1-(aminomethyl)-4-(methylsulfonyl)cyclohexane-1,2-diol hydrochloride (Intermediate 30) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. $^1$H NMR (400 MHz, CDCl$_3$) δ 8.57 (d, J=1.9 Hz, 1H), 7.28-7.23 (m, 1H), 7.20 (s, 1H), 6.66 (ddd, J 72.3, 69.7, 7.3 Hz, 1H), 5.65 (t, J=56.6 Hz, 1H), 4.08-3.84 (m, 3H), 3.64-3.56 (m, 1H), 3.16-3.06 (m, 1H), 3.01 (s, 2H), 2.89-2.79 (m, 4H), 2.32-2.23 (m, 1H), 2.10-2.03 (m, 1H), 2.03-1.87 (m, 3H), 1.60-1.48 (m, 1H), 1.41 (t, J 7.2 Hz, 3H), 1.10 (d, J 1.5 Hz, 6H). MS (ESI) m/z: [M+H]$^+$ Found 628.9.

Example 40

4-Chloro-5-(6-(3,3-difluoro-2,2-dimethylpropyl)-4-(difluoromethoxy)pyridin-3-yl)-N-(((1R*,2R*,4R*)-1,2-dihydroxy-4-(methylsulfonyl)cyclohexyl)methyl)-1-ethyl-1H-pyrazole-3-carboxamide

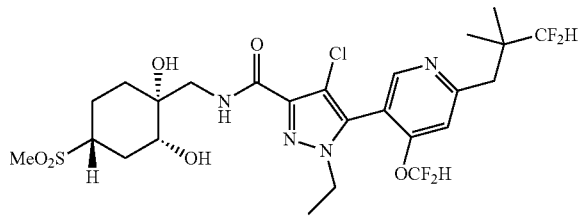

The title compound was prepared as described for the synthesis of Example 11, using 4-chloro-5-(6-(3,3-difluoro-2,2-dimethylpropyl)-4-(difluoromethoxy)pyridin-3-yl)-1-ethyl-1H-pyrazole-3-carboxylic acid (Intermediate 111) and (1R*,2R*,4R*)-1-(aminomethyl)-4-(methylsulfonyl)cyclohexane-1,2-diol hydrochloride (Intermediate 29) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. $^1$H NMR (400 MHz, CDCl$_3$) δ 8.57 (d, J=1.8 Hz, 1H), 7.29-7.23 (m, 1H), 7.20 (d, J=1.7 Hz, 1H), 6.66 (ddd, J=72.3, 69.7, 7.3 Hz, 1H), 5.65 (t, J=56.5 Hz, 1H), 4.10-3.98 (m, 2H), 3.98-3.89 (m, 1H), 3.60 (dt, J=11.4, 4.3 Hz, 1H), 3.11 (dt, J=14.2, 5.8 Hz, 1H), 3.01 (s, 2H), 2.90-2.78 (m, 4H), 2.31-2.23 (m, 1H), 2.09-1.92 (m, 1H), 2.02-1.86 (m, 3H), 1.60-1.47 (m, 1H), 1.41 (t, J 7.2 Hz, 3H), 1.10 (s, 6H). MS (ESI) m/z: [M+H]$^+$ Found 628.9.

Example 41

5-(6-(3,3-Difluoro-2,2-dimethylpropyl)-4-(difluoromethoxy)pyridin-3-yl)-1-ethyl-4-methyl-N-(((1r,4r)-4-(methylsulfonyl)cyclohexyl)methyl)-1H-pyrazole-3-carboxamide

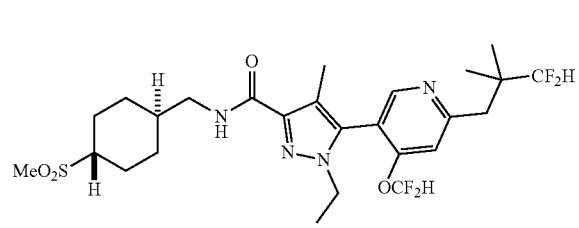

The title compound was prepared as described for the synthesis of Example 11, using 5-(6-(3,3-difluoro-2,2-dimethylpropyl)-4-(difluoromethoxy)pyridin-3-yl)-1-ethyl-4-methyl-1H-pyrazole-3-carboxylic acid (Intermediate 113) and ((1r,4r)-4-(methylsulfonyl)cyclohexyl)methanamine hydrochloride (Intermediate 13) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. $^1$H NMR (400 MHz, CDCl$_3$) δ 8.52 (s, 1H), 7.23-7.20 (m, 1H), 7.13-7.06 (m, 1H), 6.62 (dd, J=71.7, 70.3 Hz, 1H), 5.64 (t, J=56.5 Hz, 1H), 3.93 (dd, J=12.5, 7.2 Hz, 2H), 3.36-3.29 (m, 2H), 3.02 (s, 2H), 2.88-2.79 (m, 4H), 2.29 (d, J=11.4 Hz, 2H), 2.16 (s, 3H), 2.12-2.04 (m, 2H), 1.74-1.53 (m, 3H), 1.36 (t, J=7.2 Hz, 3H), 1.20-1.06 (m, 8H). MS (ESI) m/z: [M+H]⁺ Found 577.0.

Example 42

5-(6-(3,3-Difluoro-2,2-dimethylpropyl)-4-(difluoromethoxy)pyridin-3-yl)-1-ethyl-N-(((1s,4s)-1-hydroxy-4-(methylsulfonyl)cyclohexyl)methyl)-4-methyl-1H-pyrazole-3-carboxamide

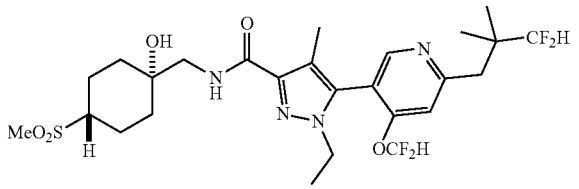

The title compound was prepared as described for the synthesis of Example 11, using 5-(6-(3,3-difluoro-2,2-dimethylpropyl)-4-(difluoromethoxy)pyridin-3-yl)-1-ethyl-4-methyl-1H-pyrazole-3-carboxylic acid (Intermediate 113) and (1s,4s)-1-(aminomethyl)-4-(methylsulfonyl)cyclohexan-1-ol hydrochloride (Intermediate 9) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. ¹H NMR (400 MHz, CDCl₃) δ 8.51 (s, 1H), 7.38-7.32 (m, 1H), 7.20 (s, 1H), 6.62 (dd, J=71.7, 70.4 Hz, 1H), 5.65 (t, J=56.6 Hz, 1H), 4.03-3.85 (m, 2H), 3.52-3.39 (m, 2H), 3.01 (s, 2H), 2.86-2.76 (m, 4H), 2.18-2.09 (m, 5H), 2.05-1.91 (m, 4H), 1.48-1.33 (m, 5H), 1.12-1.07 (m, 6H). MS (ESI) m/z: [M+H]⁺ Found 592.9.

Example 43

5-(6-(3,3-Difluoro-2,2-dimethylpropyl)-4-(difluoromethoxy)pyridin-3-yl)-N-(41S*,2S*,4S*)-1,2-dihydroxy-4-(methylsulfonyl)cyclohexyl)methyl)-1-ethyl-4-methyl-1H-pyrazole-3-carboxamide

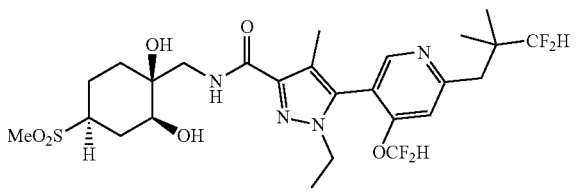

The title compound was prepared as described for the synthesis of Example 11, using 5-(6-(3,3-difluoro-2,2-dimethylpropyl)-4-(difluoromethoxy)pyridin-3-yl)-1-ethyl-4-methyl-1H-pyrazole-3-carboxylic acid (Intermediate 113) and (1S*,2S*,4S*)-1-(aminomethyl)-4-(methylsulfonyl)cyclohexane-1,2-diol hydrochloride (Intermediate 30) in place of 4-chloro-5-(4-(difluoromethoxy)-6-(3,3,3-trifluoro-2,2-dim ethyl propyl)pyridin-3-yl)-1-ethyl-1H-pyrazole-3-carboxylic acid and (1r,4r)-4-(aminomethyl)cyclohexane-1-sulfonamide hydrochloride. ¹H NMR (400 MHz, CDCl₃) δ 8.60-8.54 (m, 1H), 7.37-7.30 (m, 1H), 7.28-7.26 (m, 1H), 6.86-6.46 (m, 1H), 5.80-5.48 (t, J=56.4 Hz, 1H), 4.02-3.80 (m, 3H), 3.63-3.55 (m, 1H), 3.13-3.03 (m, 3H), 2.89-2.78 (m, 4H), 2.32-2.23 (m, 1H), 2.18-2.13 (s, 3H), 2.10-2.02 (m, 1H), 2.02-1.87 (m, 3H), 1.60-1.49 (m, 1H), 1.37 (t, J=7.2 Hz, 3H), 1.11 (s, 6H). MS (ESI) m/z: [M+H]⁺ Found 609.0.

Example 44

5-(6-(3,3-Difluoro-2,2-dimethylpropyl)-4-(difluoromethoxy)pyridin-3-yl)-N-(((1R*,2R*,4R*)-1,2-dihydroxy-4-(methylsulfonyl)cyclohexyl)methyl)-1-ethyl-4-methyl-1H-pyrazole-3-carboxamide

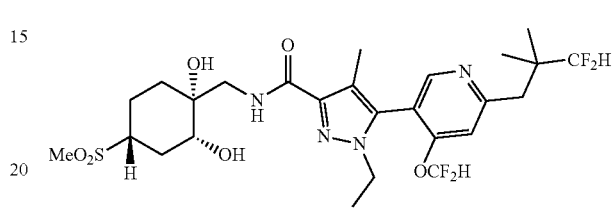

The title compound was prepared as described for the synthesis of Example 11, using 5-(6-(3,3-difluoro-2,2-dimethylpropyl)-4-(difluoromethoxy)pyridin-3-yl)-1-ethyl-4-methyl-1H-pyrazole-3-carboxylic acid (Intermediate 113) and (1R*,2R*,4R*)-1-(aminomethyl)-4-(methylsulfonyl)cyclohexane-1,2-diol hydrochloride (Intermediate 29) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. ¹H NMR (400 MHz, CDCl₃) δ 8.56-8.51 (m, 1H), 7.35-7.30 (m, 1H), 7.25-7.20 (m, 1H), 6.84-6.45 (m, 1H), 5.64 (t, J=56.5 Hz, 1H), 4.03-3.81 (m, 3H), 3.62-3.55 (m, 1H), 3.40-3.15 (br s, 2H), 3.13-3.01 (m, 3H), 2.89-2.78 (m, 4H), 2.32-2.23 (m, 1H), 2.16 (s, 3H), 2.11-2.04 (m, 1H), 2.03-1.86 (m, 3H), 1.60-1.49 (m, 1H), 1.37 (t, J=7.2 Hz, 3H), 1.11 (s, 6H). MS (ESI) m/z: [M+H]⁺ Found 609.0.

Example 45

4-Chloro-5-(2-(difluoromethoxy)-6-(3,3,3-trifluoro-2,2-dimethylpropyl)pyridin-3-yl)-1-ethyl-N-(((1r,4r)-4-(methylsulfonyl)cyclohexyl)methyl)-1H-pyrazole-3-carboxamide

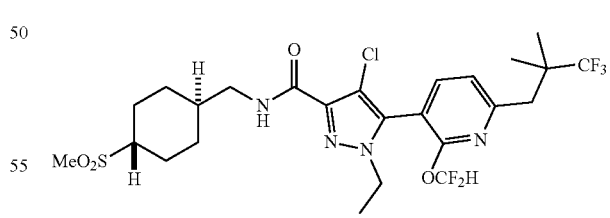

The title compound was prepared as described for the synthesis of Example 11, using 4-chloro-5-(2-(difluoromethoxy)-6-(3,3,3-trifluoro-2,2-dimethylpropyl)pyridin-3-yl)-1-ethyl-1H-pyrazole-3-carboxylic acid (Intermediate 120) and (((1r,4r)-4-(methylsulfonyl)cyclohexyl)methanamine hydrochloride (Intermediate 13) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. ¹H NMR (400 MHz, CDCl₃) δ 7.64-7.25 (m, 2H), 7.07 (d, J=7.7 Hz, 1H), 6.95 (t, J=6.4 Hz, 1H), 4.02-3.82 (m, 2H), 3.35-3.21 (m, 2H), 2.89-2.85 (m, 2H), 2.85-2.71 (m, 4H), 2.26-2.15 (m, 2H), 2.04-1.95 (m, 2H), 1.67-1.58 (m, 1H), 1.57-1.45 (m, 2H), 1.33 (t, J=7.2 Hz, 3H), 1.15-1.00 (m, 8H). MS (ESI) m/z: [M+H]⁺ Found 615.0.

Example 46

4-Chloro-5-(2-(difluoromethoxy)-6-(3,3,3-trifluoro-2,2-dimethylpropyl)pyridin-3-yl)-1-ethyl-N-(((1s,4s)-1-hydroxy-4-(methylsulfonyl)cyclohexyl)methyl)-1H-pyrazole-3-carboxamide

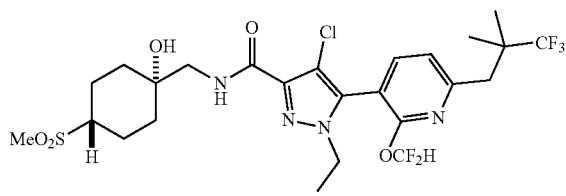

The title compound was prepared as described for the synthesis of Example 11, using 4-chloro-5-(2-(difluoromethoxy)-6-(3,3,3-trifluoro-2,2-dim ethyl propyl)pyridin-3-yl)-1-ethyl-1H-pyrazole-3-carboxylic acid (Intermediate 120) and (1s,4s)-1-(aminomethyl)-4-(methylsulfonyl)cyclohexan-1-01 hydrochloride (Intermediate 9) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. ¹H NMR (400 MHz, CDCl₃) δ 7.77-7.34 (m, 3H), 7.20 (d, J=7.7 Hz, 1H), 4.15-3.97 (m, 2H), 3.63 (s, 1H), 3.56-3.51 (m, 2H), 3.04-2.94 (m, 2H), 2.92-2.82 (m, 4H), 2.23-2.14 (m, 2H), 2.08-1.95 (m, 4H), 1.56-1.42 (m, 5H), 1.27-1.22 (m, 6H). MS (ESI) m/z: [M+H]⁺ Found 630.9.

Example 47

4-Chloro-5-(2-(difluoromethoxy)-6-(3,3,3-trifluoro-2,2-dimethylpropyl)pyridin-3-yl)-N-(((1R*,2R*,4R*)-1,2-dihydroxy-4-(methylsulfonyl)cyclohexyl)methyl)-1-ethyl-1H-pyrazole-3-carboxamide

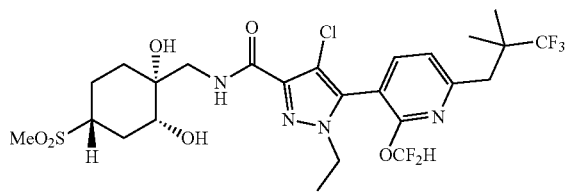

The title compound was prepared as described for the synthesis of Example 11, using 4-chloro-5-(2-(difluoromethoxy)-6-(3,3,3-trifluoro-2,2-dimethylpropyl)pyridin-3-yl)-1-ethyl-1H-pyrazole-3-carboxylic acid (Intermediate 120) and (1R*,2R*,4R*)-1-(aminomethyl)-4-(methylsulfonyl)cyclohexane-1,2-diol hydrochloride (Intermediate 29) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. ¹H NMR (400 MHz, CDCl₃) δ 7.77-7.32 (m, 3H), 7.20 (d, J=7.7 Hz, 1H), 4.15-3.89 (m, 3H), 3.71-3.60 (m, 1H), 3.20-3.08 (m, 1H), 3.02-2.98 (m, 2H), 2.97-2.84 (m, 4H), 2.32 (d, J=11.9 Hz, 1H), 2.15-2.08 (m, 1H), 2.07-1.90 (m, 3H), 1.66-1.52 (m, 1H), 1.46 (t, J=7.4 Hz, 3H), 1.25 (s, 6H). MS (ESI) m/z: [M+H]⁺ Found 646.9.

Example 48

4-Chloro-5-(2-(difluoromethoxy)-6-(3,3,3-trifluoro-2,2-dimethylpropyl)pyridin-3-yl)-N-(((1S*,2S*,4S*)-1,2-dihydroxy-4-(methylsulfonyl)cyclohexyl)methyl)-1-ethyl-1H-pyrazole-3-carboxamide

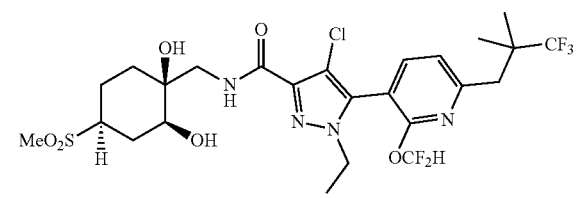

The title compound was prepared as described for the synthesis of Example 11, using 4-chloro-5-(2-(difluoromethoxy)-6-(3,3,3-trifluoro-2,2-dimethylpropyl)pyridin-3-yl)-1-ethyl-1H-pyrazole-3-carboxylic acid (Intermediate 120) and (1S*,2S*,4S*)-1-(aminomethyl)-4-(methylsulfonyl)cyclohexane-1,2-diol hydrochloride (Intermediate 30) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. ¹H NMR (500 MHz, CDCl₃) δ 7.73-7.39 (m, 2H), 7.32-7.29 (m, 1H), 7.18 (dd, J=7.7, 1.5 Hz, 1H), 4.12-3.87 (m, 3H), 3.69-3.59 (m, 1H), 3.18-3.08 (m, 1H), 3.01-2.81 (m, 8H), 2.34-2.26 (m, 1H), 2.14-2.05 (m, 1H), 2.05-1.90 (m, 3H), 1.63-1.51 (m, 1H), 1.47-1.40 (m, 3H), 1.25-1.19 (m, 6H). MS (ESI) m/z: [M+H]⁺ Found 646.9.

Example 49

5-(2-(Difluoromethoxy)-6-(3,3,3-trifluoro-2,2-dimethylpropyl)pyridin-3-yl)-1-ethyl-4-methyl-N-(((1r,4r)-4-(methylsulfonyl)cyclohexyl)methyl)-1H-pyrazole-3-carboxamide

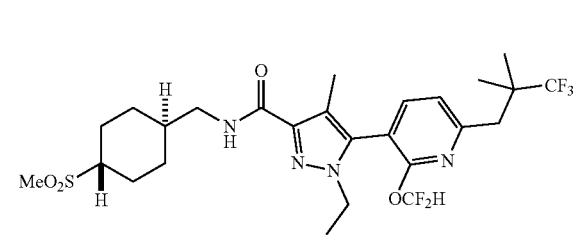

The title compound was prepared as described for the synthesis of Example 11, using 5-(2-(difluoromethoxy)-6-(3,3,3-trifluoro-2,2-dim ethyl propyl)pyridin-3-yl)-1-ethyl-4-methyl-1H-pyrazole-3-carboxylic acid (Intermediate 122) and ((1r,4r)-4-(methylsulfonyl)cyclohexyl)methanamine hydrochloride (Intermediate 13) in place of 4-chloro-5-(4-(difluoromethoxy)-6-(3,3,3-trifluoro-2,2-dim ethyl propyl)

pyridin-3-yl)-1-ethyl-1H-pyrazole-3-carboxylic acid and (1r,4r)-4-(aminomethyl)cyclohexane-1-sulfonamide hydrochloride. ¹H NMR (400 MHz, CDCl₃) δ 7.61 (d, J=7.6 Hz, 1H), 7.76-7.37 (m, 1H), 7.23 (t, J=6.5 Hz, 1H), 7.16 (d, J 7.6 Hz, 1H), 4.09-3.89 (m, 2H), 3.44-3.31 (m, 2H), 3.00-2.96 (m, 2H), 2.92-2.84 (m, 4H), 2.33 (d, J=12.2 Hz, 2H), 2.20 (s, 3H), 2.13 (d, J=13.8 Hz, 2H), 1.79-1.58 (m, 3H), 1.41 (t, J 7.2 Hz, 3H), 1.28-1.11 (m, 8H). MS (ESI) m/z: [M+H]⁺ Found 595.0.

Example 50

5-(2-(Difluoromethoxy)-6-(3,3,3-trifluoro-2,2-dimethylpropyl)pyridin-3-yl)-1-ethyl-N-(((1s,4s)-1-hydroxy-4-(methylsulfonyl)cyclohexyl)methyl)-4-methyl-1H-pyrazole-3-carboxamide

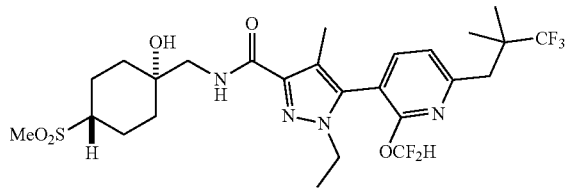

The title compound was prepared as described for the synthesis of Example 11, using 5-(2-(difluoromethoxy)-6-(3,3,3-trifluoro-2,2-dimethylpropyl)pyridin-3-yl)-1-ethyl-4-methyl-1H-pyrazole-3-carboxylic acid (Intermediate 122) and (1s,4s)-1-(aminomethyl)-4-(methylsulfonyl)cyclohexan-1-ol hydrochloride (Intermediate 9) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. ¹H NMR (400 MHz, CDCl₃) δ 7.48 (d, J=7.5 Hz, 1H), 7.63-7.25 (m, 1H), 7.36 (t, J=6.3 Hz, 1H), 7.04 (d, J=7.6 Hz, 1H), 3.96-3.79 (m, 3H), 3.39 (d, J=6.4 Hz, 2H), 2.91-2.82 (m, 2H), 2.79-2.69 (m, 4H), 2.11-2.02 (m, 5H), 1.97-1.83 (m, 4H), 1.41-1.26 (m, 5H), 1.12 (s, 6H). MS (ESI) m/z: [M+H]⁺ Found 610.9.

Example 51

5-(2-(Difluoromethoxy)-6-(3,3,3-trifluoro-2,2-dimethylpropyl)pyridin-3-yl)-N-(((1S*,2S*,4S*)-1,2-dihydroxy-4-(methylsulfonyl)cyclohexyl)methyl)-1-ethyl-4-methyl-1H-pyrazole-3-carboxamide

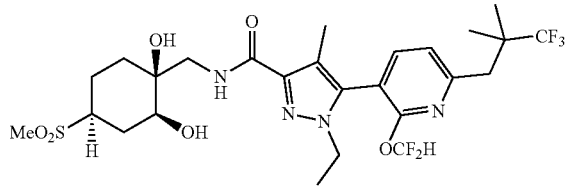

The title compound was prepared as described for the synthesis of Example 11, using 5-(2-(difluoromethoxy)-6-(3,3,3-trifluoro-2,2-dimethylpropyl)pyridin-3-yl)-1-ethyl-4-methyl-1H-pyrazole-3-carboxylic acid (Intermediate 122) and (1S*,2S*,4S*)-1-(aminomethyl)-4-(methylsulfonyl)cyclohexane-1,2-diol hydrochloride (Intermediate 30) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. ¹H NMR (400 MHz, CDCl₃) δ 7.62-7.22 (m, 3H), 7.02 (d, J=7.6 Hz, 1H), 3.93-3.70 (m, 3H), 3.56-3.45 (m, 1H), 3.04-2.92 (m, 1H), 2.88-2.66 (m, 6H), 2.21-2.13 (m, 1H), 2.04 (s, 3H), 2.01-1.76 (m, 4H), 1.52-1.38 (m, 1H), 1.30-1.22 (m, 3H), 1.09 (s, 6H). MS (ESI) m/z: [M+H]⁺ Found 627.0.

Example 52

4-Chloro-5-(3-(difluoromethoxy)-5-(3,3,3-trifluoro-2,2-dimethylpropyl)pyridin-2-yl)-1-ethyl-N-(((1r,4r)-4-(methylsulfonyl)cyclohexyl)methyl)-1H-pyrazole-3-carboxamide

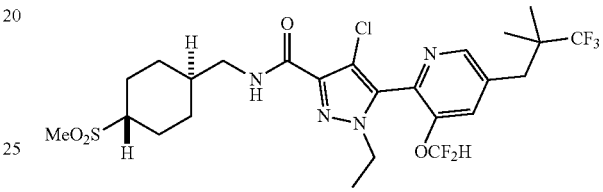

The title compound was prepared as described for the synthesis of Example 11, using 4-chloro-5-(3-(difluoromethoxy)-5-(3,3,3-trifluoro-2,2-dimethylpropyl)pyridin-2-yl)-1-ethyl-1H-pyrazole-3-carboxylic acid (Intermediate 131) and ((1r,4r)-4-(methylsulfonyl)cyclohexyl)methanamine hydrochloride (Intermediate 13) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. 41 NMR (400 MHz, CDCl₃) δ 8.49-8.44 (m, 1H), 7.61-7.56 (m, 1H), 7.04 (t, J=6.4 Hz, 1H), 6.50 (t, J=71.6 Hz, 1H), 4.12 (q, J=7.3 Hz, 2H), 3.53 (s, 3H), 3.36 (t, J=6.6 Hz, 2H), 2.92 (s, 2H), 2.88-2.79 (m, 4H), 2.33-2.23 (m, 2H), 2.12-2.02 (m, 2H), 1.75-1.53 (m, 3H), 1.36 (t, J=7.3 Hz, 3H), 1.22-1.08 (m, 8H). MS (ESI) m/z: [M+H]⁺ Found 615.2.

Example 53

4-Chloro-5-(3-(difluoromethoxy)-5-(3,3,3-trifluoro-2,2-dimethylpropyl)pyridin-2-yl)-1-ethyl-N-(((1s,4s)-1-hydroxy-4-(methylsulfonyl)cyclohexyl)methyl)-1H-pyrazole-3-carboxamide

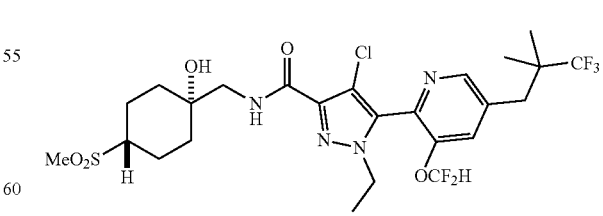

The title compound was prepared as described for the synthesis of Example 11, using 4-chloro-5-(3-(difluoromethoxy)-5-(3,3,3-trifluoro-2,2-dimethylpropyl)pyridin-2-yl)-1-ethyl-1H-pyrazole-3-carboxylic acid (Intermediate 131) and (1s,4s)-1-(aminomethyl)-4-(methylsulfonyl)cyclohexan-1-ol hydrochloride (Intermediate 9) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. $^1$H NMR (400 MHz, CDCl$_3$) δ 8.51-8.45 (m, 1H), 7.63-7.57 (s, 1H), 7.39-7.30 (t, J=6.1 Hz, 1H), 6.72-6.30 (m, 1H), 4.22-4.03 (m, 2H plus OH plus excess water), 3.53-3.45 (m, 2H), 2.92 (s, 2H), 2.88-2.78 (m, 4H), 2.19-2.09 (m, 2H), 2.05-1.90 (m, 4H), 1.53-1.41 (m, 2H), 1.37 (t, J=7.2 Hz, 3H), 1.17 (s, 6H). MS (ESI) m/z: [M+H]$^+$ Found 631.2.

Example 54

4-Chloro-5-(4-(1,1-difluoroethyl)-6-(3,3,3-trifluoro-2,2-dimethylpropyl)pyridin-3-yl)-1-ethyl-N-(((1r,4r)-4-(methylsulfonyl)cyclohexyl)methyl)-1H-pyrazole-3-carboxamide

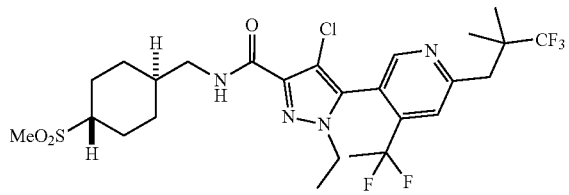 [SMILES: CCn1nc(C(=O)NC[C@H]2CC[C@H](S(C)(=O)=O)CC2)c(Cl)c1-c1cnc(CC(C)(C)C(F)(F)F)cc1C(C)(F)F]

The title compound was prepared as described for the synthesis of Example 11, using 4-chloro-5-(4-(1,1-difluoroethyl)-6-(3,3,3-trifluoro-2,2-dimethylpropyl)pyridin-3-yl)-1-ethyl-1H-pyrazole-3-carboxylic acid (Intermediate 146) and ((1r,4r)-4-(methylsulfonyl)cyclohexyl)methanamine hydrochloride (Intermediate 13) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. $^1$H NMR (400 MHz, CDCl$_3$) δ 8.48 (s, 1H), 7.54 (s, 1H), 7.05 (t, J=6.4 Hz, 1H), 3.99-3.75 (m, 2H), 3.37 (t, J=6.6 Hz, 2H), 3.21-3.09 (m, 2H), 2.90-2.78 (m, 4H), 2.35-2.24 (d, J=11.7 Hz, 2H), 2.14-2.04 (m, 2H), 1.79 (t, J=18.8 Hz, 3H), 1.74-1.67 (m, 1H), 1.67-1.55 (m, 2H), 1.37 (t, J=7.3 Hz, 3H), 1.25-1.08 (m, 8H). MS (ESI) m/z: [M+H]$^+$ Found 613.0.

Example 55

4-Chloro-1-ethyl-5-(4-ethyl-6-(3,3,3-trifluoro-2,2-dimethylpropyl)pyridin-3-yl)-N-(((1s,4s)-1-hydroxy-4-(methylsulfonyl)cyclohexyl)methyl)-1H-pyrazole-3-carboxamide

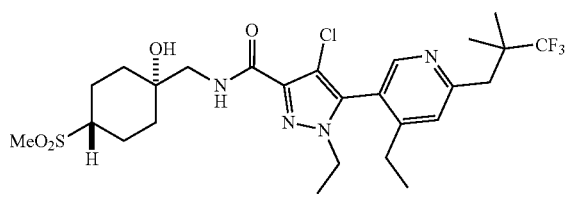 [SMILES: CCc1cc(CC(C)(C)C(F)(F)F)ncc1-c1c(Cl)c(C(=O)NC[C@]2(O)CC[C@@H](S(C)(=O)=O)CC2)nn1CC]

1,1,1-Trifluoro-3-iodo-2,2-dimethylpropane (0.25 mL, 1.68 mmol, Intermediate 45) was added to a suspension of Rieke® zinc in THF (2 mL, 0.05 g/mL, 1.53 mmol), and the resulting suspension was stirred at 65° C. for 1 h. 4-Chloro-5-(6-chloro-4-ethylpyridin-3-yl)-1-ethyl-N-(((1s,4s)-1-hydroxy-4-(methyl sulfonyl)cyclohexyl)methyl)-1H-pyrazole-3-carboxamide (0.062 g, 0.123 mmol, Intermediate 147) and Pd(t-Bu$_3$P)$_2$ (0.0063 g, 0.012 mmol) were combined in a separate vessel, and the vessel was evacuated and backfilled with nitrogen three times. A portion of the prepared organozinc suspension (0.614 mL, 0.491 mmol) was then added to the vessel containing the aryl bromide and the resulting suspension was stirred at 65° C. for 2 h. The mixture was then diluted with a saturated aqueous NH$_4$Cl solution and EtOAc. The aqueous layer was extracted with EtOAc, and the combined organic layers were washed with brine, dried with anhydrous MgSO$_4$, filtered, and then concentrated. The residue was purified by silica gel chromatography (20→100% EtOAc/hexanes) to afford the title compound. $^1$H NMR (500 MHz, CDCl$_3$) δ 8.33-8.30 (m, 1H), 7.25-7.21 (m, 1H), 7.22-7.20 (m, 1H), 4.03-3.82 (m, 2H), 3.55-3.42 (m, 2H), 3.02 (s, 2H), 2.93 (s, 1H), 2.87-2.76 (m, 4H), 2.47 (q, J=7.6 Hz, 2H), 2.18-2.09 (m, 2H), 2.04-1.92 (m, 4H), 1.50-1.40 (m, 2H), 1.36 (t, J=7.3 Hz, 3H), 1.20 (d, J=13.3 Hz, 6H), 1.14 (t, J=7.6 Hz, 3H). MS (ESI) m/z: [M+H]$^+$ Found 593.3.

Example 56

4-Chloro-1-ethyl-5-(4-ethyl-6-((R*)-3,3,3-trifluoro-2-methylpropyl)pyridin-3-yl)-N-(((1s,4S)-1-hydroxy-4-(methylsulfonyl)cyclohexyl)methyl)-1H-pyrazole-3-carboxamide

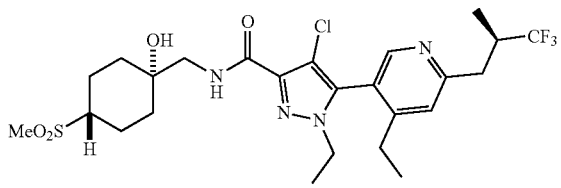 [SMILES: CCc1cc(C[C@@H](C)C(F)(F)F)ncc1-c1c(Cl)c(C(=O)NC[C@]2(O)CC[C@@H](S(C)(=O)=O)CC2)nn1CC]

The title compound was prepared as described for the synthesis of Example 55, using (S*)-1,1,1-trifluoro-3-iodo-2-methylpropane (Intermediate 51) in place of 1,1,1-trifluoro-3-iodo-2,2-dimethylpropane. $^1$H NMR (400 MHz, CDCl$_3$) δ 8.31 (s, 1H), 7.25-7.18 (m, 2H), 4.02-3.82 (m, 2H), 3.55-3.42 (m, 2H), 3.31-3.20 (m, 1H), 2.97-2.90 (m, 1H), 2.87-2.72 (m, 5H), 2.47 (q, J 7.6 Hz, 2H), 2.20-2.08 (m, 2H), 2.06-1.90 (m, 4H), 1.51-1.41 (m, 2H), 1.39-1.32 (m, 3H), 1.17-1.11 (m, 6H). MS (ESI) m/z: [M+H]$^+$ Found 579.2.

Example 57

4-Chloro-1-ethyl-5-(4-ethyl-6-((R*)-3,3,3-trifluoro-2-methylpropyl)pyridin-3-yl)-N-((1r,4R)-4-(methylsulfonyl)cyclohexyl)methyl)-1H-pyrazole-3-carboxamide

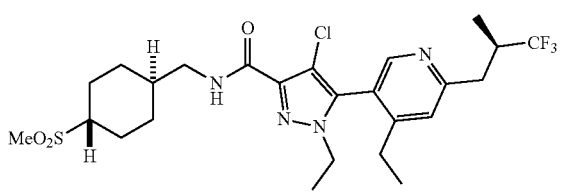 [SMILES: CCc1cc(C[C@@H](C)C(F)(F)F)ncc1-c1c(Cl)c(C(=O)NC[C@H]2CC[C@H](S(C)(=O)=O)CC2)nn1CC]

The title compound was prepared as described for the synthesis of Example 11, using (R*)-4-chloro-1-ethyl-5-(4-ethyl-6-(3,3,3-trifluoro-2-methylpropyl)pyridin-3-yl)-1H-pyrazole-3-carboxylic acid (Intermediate 149) and ((1r,4r)-4-(methylsulfonyl)cyclohexyl)methanamine hydrochloride (Intermediate 13) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. $^1$H NMR (400 MHz, CDCl$_3$) δ 8.54 (s, 1H), 7.48-7.42 (m, 1H), 7.04-6.93 (m, 1H), 4.03-3.84 (m, 2H), 3.43-3.26 (m, 3H), 3.10-3.01 (m, 1H), 2.95-2.78 (m, 5H), 2.70-2.53 (m, 2H), 2.35-2.24 (m, 2H), 2.13-2.03 (m, 2H), 1.77-1.54 (m, 3H), 1.42-1.33 (m, 3H), 1.26-1.08 (m, 8H). MS (ESI) m/z: [M+H]$^+$ Found 563.2.

Example 58

1-Ethyl-5-(4-ethyl-6-((R*)-3,3,3-trifluoro-2-methylpropyl)pyridin-3-yl)-4-methyl-N-((1r,4R)-4-(methylsulfonyl)cyclohexyl)methyl)-1H-pyrazole-3-carboxamide

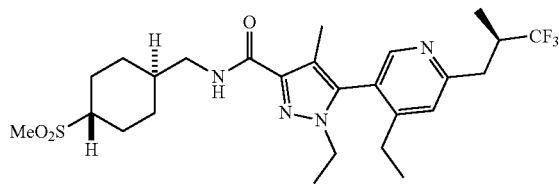 [SMILES: CCc1cc(C[C@@H](C)C(F)(F)F)ncc1-c1c(C)c(C(=O)NC[C@H]2CC[C@H](S(C)(=O)=O)CC2)nn1CC]

The title compound was prepared as described for the synthesis of Example 11, using (R*)-1-ethyl-5-(4-ethyl-6-(3,3,3-trifluoro-2-methylpropyl)pyridin-3-yl)-4-methyl-1H-pyrazole-3-carboxylic acid (Intermediate 151) and ((1r,4r)-4-(methyl sulfonyl)cyclohexyl)methanamine hydrochloride (Intermediate 13) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. $^1$H NMR (400 MHz, CDCl$_3$) δ 8.52 (s, 1H), 7.49-7.44 (m, 1H), 7.09 (t, J=6.4 Hz, 1H), 3.96-3.75 (m, 2H), 3.37-3.26 (m, 3H), 3.16-3.07 (m, 1H), 2.96-2.79 (m, 5H), 2.56 (q, J=7.6 Hz, 2H), 2.35-2.24 (m, 2H), 2.15-2.04 (m, 5H), 1.76-1.53 (m, 3H), 1.38-1.30 (m, 3H), 1.26-1.21 (m, 3H), 1.21-1.08 (m, 5H). MS (ESI) m/z: [M+H]$^+$ Found 543.3.

Example 59

4-Chloro-5-(6-(3,3-dimethylbutyl)-4-ethylpyridin-3-yl)-1-ethyl-N-(((1s,4s)-1-hydroxy-4-(methylsulfonyl)cyclohexyl)methyl)-1H-pyrazole-3-carboxamide

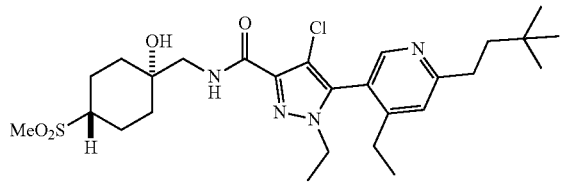 [SMILES: CCc1cc(CCC(C)(C)C)ncc1-c1c(Cl)c(C(=O)NC[C@]2(O)CC[C@@H](S(C)(=O)=O)CC2)nn1CC]

The title compound was prepared as described for the synthesis of Example 11, using 4-chloro-5-(6-(3,3-dim ethylbutyl)-4-ethylpyridin-3-yl)-1-ethyl-1H-pyrazole-3-carboxylic acid (Intermediate 153) and (1s,4s)-1-(aminomethyl)-4-(methyl sulfonyl)cyclohexan-1-ol hydrochloride (Intermediate 9) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1r,4r)-4-(aminomethyl)cyclohexane-1-sulfonamide hydrochloride. $^1$H NMR (400 MHz, CDCl$_3$) δ 8.58 (s, 1H), 7.53 (s, 1H), 7.30-7.23 (m, 1H), 6.25-5.33 (br s, OH plus excess water), 4.05-3.85 (m, 2H), 3.59-3.38 (m, 2H), 3.12-2.95 (m, 2H), 2.92-2.75 (m, 4H), 2.73-2.54 (m, 2H), 2.18-2.08 (m, 2H), 2.06-1.90 (m, 4H), 1.74-1.65 (m, 2H), 1.52-1.41 (m, 2H), 1.38 (t, J=7.2 Hz, 3H), 1.23 (t, J 7.6 Hz, 3H), 1.02 (s, 9H). MS (ESI) m/z: [M+H]$^+$ Found 553.3.

Example 60

4-Chloro-1-ethyl-5-(4-methoxy-6-(3,3,3-trifluoro-2-methylpropyl)pyridin-3-yl)-N-(((1r,4r)-4-(methylsulfonyl)cyclohexyl)methyl)-1H-pyrazole-3-carboxamide

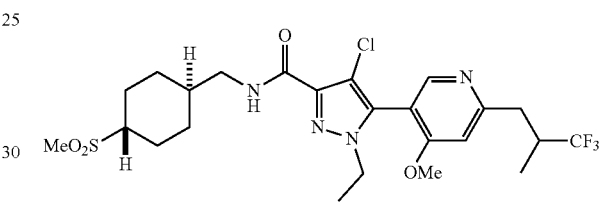

The title compound was prepared as described for the synthesis of Example 1, using 4-chloro-1-ethyl-5-(4-methoxy-6-(3,3,3-trifluoro-2-methylpropyl)pyridin-3-yl)-1H-pyrazole-3-carboxylic acid (Intermediate 142) and ((1r,4r)-4-(methyl sulfonyl)cyclohexyl)methanamine hydrochloride (Intermediate 13) in place of 4-chloro-5-(4-(difluoromethoxy)-6-(3,3,3-trifluoro-2,2-dimethylpropyl) pyridin-3-yl)-1-ethyl-1H-pyrazole-3-carboxylic acid and (1s,4s)-4-(aminomethyl)-4-hydroxycyclohexane-1-sulfonamide hydrochloride. $^1$H NMR (400 MHz, CDCl$_3$) δ 8.29 (s, 1H), 6.94 (t, J=6.1 Hz, 1H), 6.81 (d, J=1.3 Hz, 1H), 4.02-3.91 (m, 2H), 3.88 (s, 3H), 3.38-3.30 (m, 2H), 3.30-3.16 (m, 1H), 3.06-2.89 (m, 1H), 2.89-2.67 (m, 5H), 2.33-2.21 (m, 2H), 2.13-2.00 (m, 2H), 1.70-1.65 (m, 1H), 1.64-1.52 (m, 2H), 1.43-1.29 (m, 3H), 1.22-1.02 (m, 5H). MS (ESI) m/z: [M+H]$^+$ Found 565.0.

Example 61

4-Chloro-1-ethyl-5-(4-methoxy-6-((R*)-3,3,3-trifluoro-2-methylpropyl)pyridin-3-yl)-N-((1r,4r)-4-(methylsulfonyl)cyclohexyl)methyl)-1H-pyrazole-3-carboxamide

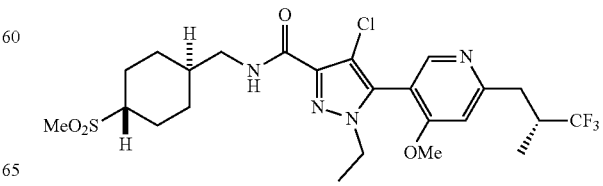

Example 62

4-Chloro-1-ethyl-5-(4-methoxy-6-((S*)-3,3,3-trifluoro-2-methylpropyl)pyridin-3-yl)-N-((1r,4r)-4-(methylsulfonyl)cyclohexyl)methyl)-1H-pyrazole-3-carboxamide

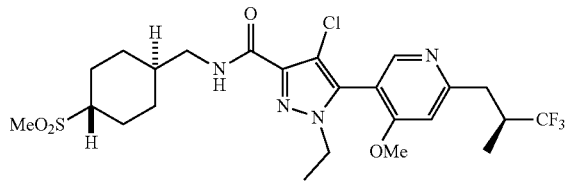 [SMILES: CCn1nc(C(=O)NC[C@H]2CC[C@H](S(C)(=O)=O)CC2)c(Cl)c1-c1cnc(C[C@H](C)C(F)(F)F)cc1OC]

Example 60 was purified by SFC using a chiral stationary phase (CHIRALCEL OJ-H, 92% CO₂, 8% MeOH) to give a pair of enantiomers. The first-eluting enantiomer was Example 61 and the second-eluting was Example 62. Example 61: ¹H NMR (500 MHz, CDCl₃) δ 8.30 (s, 1H), 7.02-6.88 (m, 1H), 6.81 (s, 1H), 4.04-3.89 (m, 2H), 3.88 (s, 3H), 3.39-3.29 (m, 2H), 3.29-3.18 (m, 1H), 3.05-2.88 (m, 1H), 2.88-2.68 (m, 5H), 2.34-2.20 (m, 2H), 2.11-1.98 (m, 2H), 1.71-1.53 (m, 3H), 1.39-1.30 (m, 3H), 1.20-1.05 (m, 5H). MS (ESI) m/z: [M+H]⁺ Found 565.2. Example 62: ¹H NMR (500 MHz, CDCl₃) δ 8.30 (s, 1H), 7.02-6.88 (m, 1H), 6.81 (s, 1H), 4.04-3.89 (m, 2H), 3.88 (s, 3H), 3.39-3.29 (m, 2H), 3.29-3.18 (m, 1H), 3.05-2.88 (m, 1H), 2.88-2.68 (m, 5H), 2.34-2.20 (m, 2H), 2.11-1.98 (m, 2H), 1.71-1.53 (m, 3H), 1.39-1.30 (m, 3H), 1.20-1.05 (m, 5H). MS (ESI) m/z: [M+H]⁺ Found 565.2.

Example 63

4-Chloro-1-ethyl-N-(((1r,4R)-1-hydroxy-4-(methylsulfonyl)cyclohexyl)methyl)-5-(4-methoxy-6-(((R)-1,1,1-trifluoropropan-2-yl)oxy)pyridin-3-yl)-1H-pyrazole-3-carboxamide

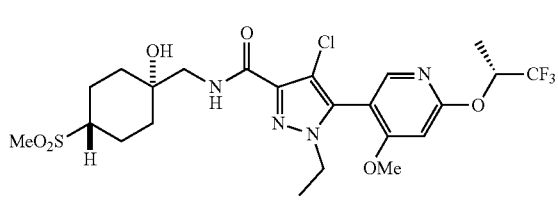 [SMILES: CCn1nc(C(=O)NC[C@]2(O)CC[C@@H](S(C)(=O)=O)CC2)c(Cl)c1-c1cnc(O[C@H](C)C(F)(F)F)cc1OC]

The title compound was prepared as described for the synthesis of Example 1, using (R)-4-chloro-1-ethyl-5-(4-methoxy-6-((1,1,1-trifluoropropan-2-yl)oxy)pyridin-3-yl)-1H-pyrazole-3-carboxylic acid (Intermediate 144) and (1s,4s)-1-(aminomethyl)-4-(methylsulfonyl)cyclohexan-1-ol hydrochloride (Intermediate 9) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1s,4s)-4-(aminomethyl)-4-hydroxycyclohexane-1-sulfonamide hydrochloride. ¹H NMR (500 MHz, CD₃OD) δ 7.95 (s, 1H), 6.64 (s, 1H), 5.98-5.81 (m, 1H), 4.16-3.93 (m, 2H), 3.89 (s, 3H), 3.48-3.34 (m, 2H), 3.11-2.96 (m, 2H), 2.90 (s, 3H), 2.81 (s, 2H), 2.09-1.79 (m, 4H), 1.60-1.46 (m, 4H), 1.35 (t, J=7.2 Hz, 3H). MS (ESI) m/z: [M+H]⁺ Found 584.2.

Example 64

4-Chloro-1-ethyl-5-(4-methoxy-6-(((S)-1,1,1-trifluoropropan-2-yl)oxy)pyridin-3-yl)-N-((1r,4S)-4-(methylsulfonyl)cyclohexyl)methyl)-1H-pyrazole-3-carboxamide

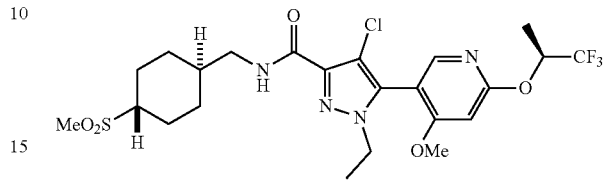

The title compound was prepared as described for the synthesis of Example 1, using (S)-4-chloro-1-ethyl-5-(4-methoxy-6-((1,1,1-trifluoropropan-2-yl)oxy)pyridin-3-yl)-1H-pyrazole-3-carboxylic acid (Intermediate 145) and ((1r,4r)-4-(methylsulfonyl)cyclohexyl)methanamine hydrochloride (Intermediate 13) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1s,4s)-4-(aminomethyl)-4-hydroxycyclohexane-1-sulfonamide hydrochloride. ¹H NMR (500 MHz, CD₃OD) δ 7.95 (s, 1H), 6.64 (s, 1H), 5.96-5.86 (m, 1H), 3.99 (m, 2H), 3.89 (s, 3H), 3.26 (m, 1H), 3.01 (m, 1H), 2.89 (s, 3H), 2.24 (m, 2H), 2.02 (m, 2H), 1.69-1.62 (m, 2H), 1.61-1.48 (m, 6H), 1.35 (t, J=7.2 Hz, 3H), 1.15 (m, 3H). MS (ESI) m/z: [M+H]ᴾ Found 568.2.

Example 65

4-Chloro-1-ethyl-5-(4-methoxy-6-(((R)-1,1,1-trifluoropropan-2-yl)oxy)pyridin-3-yl)-N-((1r,4R)-4-(methylsulfonyl)cyclohexyl)methyl)-1H-pyrazole-3-carboxamide

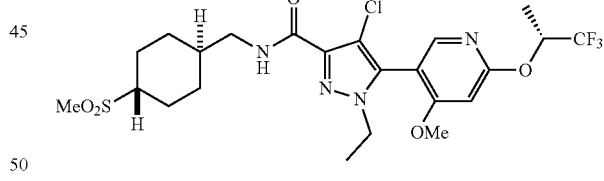

The title compound was prepared as described for the synthesis of Example 1, using (R)-4-chloro-1-ethyl-5-(4-methoxy-6-((1,1,1-trifluoropropan-2-yl)oxy)pyridin-3-yl)-1H-pyrazole-3-carboxylic acid (Intermediate 144) and ((1r,4r)-4-(methyl sulfonyl)cyclohexyl)methanamine hydrochloride (Intermediate 13) in place of 4-chloro-5-(4-(difluoromethoxy)-6-(3,3,3-trifluoro-2,2-dimethylpropyl)pyridin-3-yl)-1-ethyl-1H-pyrazole-3-carboxylic acid and (1s,4s)-4-(aminomethyl)-4-hydroxycyclohexane-1-sulfonamide hydrochloride. 41 NMR (500 MHz, CD₃OD) δ 7.95 (s, 1H), 6.64 (s, 1H), 5.94-5.86 (m, 1H), 4.07-3.91 (m, 2H), 3.89 (s, 3H), 3.26 (dd, J=6.8, 2.0 Hz, 2H), 3.06-2.97 (m, 1H), 2.89 (s, 3H), 2.24 (d, J=11.3 Hz, 2H), 2.02 (d, J=10.7 Hz, 2H), 1.69-1.64 (m, 1H), 1.61-1.48 (m, 5H), 1.34 (t, J=7.2 Hz, 3H), 1.21-1.09 (m, 2H). MS (ESI) m/z: [M+H]⁺ Found 568.2.

In Vitro Biological Data
ThermoFluor® Assay

ThermoFluor® is a fluorescence based assay that estimates ligand binding affinities by measuring the effect of a ligand on protein thermal stability (Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovery. *J Biomol Screen* 6, 429-40, and Matulis, D., Kranz, J. K., Salemme, F. R., and Todd, M. J. (2005) Thermodynamic stability of carbonic anhydrase: measurements of binding affinity and stoichiometry using ThermoFluor. *Biochemistry* 44, 5258-66). This approach is applicable to a wide variety of systems, and rigorous in theoretical interpretation through quantitation of equilibrium binding constants ($K_D$).

In a ThermoFluor® experiment where protein stability is monitored as the temperature is steadily increased, an equilibrium binding ligand causes the midpoint of an unfolding transition ($T_m$) to occur at a higher temperature. The shift in the melting point described as a $\Delta T_m$ is proportional to the concentration and affinity of the ligand. The compound potency may be compared as a rank order of either values at a single compound concentration or in terms of $K_D$ values, estimated from concentration response curves.

RORγt ThermoFluor® Assay Construct

For the RORγt construct used in the ThermoFluor® assay, numbering for the nucleotide sequences was based on the reference sequence for human RORγt, transcript variant 2, NCBI Accession: NM 001001523.1 (SEQ ID NO:1). Nucleotides 850-1635 (SEQ ID NO:2) coding for the wild type human RORγt ligand binding domain (RORγt LBD) were cloned into the pHIS1 vector, a modified pET *E. coli* expression vector (Accelagen, San Diego), containing an in-frame N-terminal His-tag and a TurboTEV protease cleavage site (ENLYFQG, SEQ ID NO:3) upstream of the cloned insert sequence. The amino acid sequence for the RORγt construct used in the Thermofluor® assay is shown as SEQ ID NO:4.

ThermoFluor® experiments were carried out using instruments owned by Janssen Research and Development, L.L.C. through its acquisition of 3-Dimensional Pharmaceuticals, Inc. 1,8-ANS (Invitrogen) was used as a fluorescent dye. Protein and compound solutions are dispensed into black 384-well polypropylene PCR microplates (Abgene) and overlayed with silicone oil (1 μL, Fluka, type DC 200) to prevent evaporation.

Bar-coded assay plates are robotically loaded onto a thermostatically controlled PCR-type thermal block and then heated at a typical ramp-rate of 1° C./min for all experiments. Fluorescence was measured by continuous illumination with UV light (Hamamatsu LC6) supplied via fiber optic and filtered through a band-pass filter (380-400 nm; >6 OD cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. Images were collected at each temperature, and the sum of the pixel intensity in a given area of the assay plate was recorded versus temperature. Reference wells contained RORγt without compounds, and the assay conditions were as follows:

0.065 mg/mL RORγt
60 μM 1,8-ANS
100 mM Hepes, pH 7.0
10 mM NaCl
2.5 mM GSH
0.002% Tween-20

Project compounds were arranged in a pre-dosed mother plate (Greiner Bio-one) wherein compounds are serially diluted in 100% DMSO by 1:2 from a high concentration of 10 mM over 12 columns within a series (column 12 is a reference well containing DMSO, no compound). The compounds were robotically dispensed directly into assay plates (1×=46 nL) using a Hummingbird capillary liquid handling instrument (Digilab). Following compound dispense, protein and dye in buffer was added to achieve the final assay volume of 3 μL, followed by 1 μL of silicone oil.

The binding affinity was estimated as described previously (Matulis, D., Kranz, J. K., Salemme, F. R., and Todd, M. J. (2005) Thermodynamic stability of carbonic anhydrase: measurements of binding affinity and stoichiometry using ThermoFluor®. *Biochemistry* 44, 5258-66) using the following thermodynamic parameters of protein unfolding:

Reference RORγt $T_m$: 47.8° C.

$\Delta H_{(Tm)}$=115 kcal/mol $\Delta C_{p(Tm)}$=3 kcal/mol

Cell Based Biological Data

RORγt (Full-Length Human) Reporter Assay:

Two similar reporter assay protocols, shown below, have been used to test the functional activity of RORγt modulatory compounds on transcriptional activation driven by full-length human RORγt. Both provide similar data and can be used interchangeably.

Conditions A

Cells used in this assay were transiently co-transfected with three different plasmids, one expressing the GAL4-DNA binding domain (DBD)-RORγt fusion protein under control of a CMV promoter ($NH_2$-Gal4-DBD:RORC—COOH in pCMV-BD, Stratagene #211342), and two reporter plasmids—the firefly luciferase reporter under control of a GAL4 promoter (pFR-Luc 2×GAL4) and Renilla luciferase reporter under control of CMV promoter (pRL-CMV, Promega #E2261). The full-length coding sequence was used for human RORγt, i.e., nucleotides 142-1635 of human RORγt, transcript variant 2, NCBI Accession: NM 001001523.1 (SEQ ID NO:1). HEK293T cells were plated at 35,000 per well in 96-well plate in medium of DMEM with 10% FBS. After 18-22 hours incubation, the transfection was carried out by using a PEI solution with 170.5 ng total DNA/well (50 ng pCMV-BD-ROR plus 20 ng of pFR-Luc reporter and 0.5 ng of pRL-CMV reporter plus 100 ng Carrier DNA (Clontech #630440) for each well). 4-6 hours after transfection, cells were treated with compounds for overnight in the medium with final concentration of FBS 1.3% and DMSO 0.1%. After overnight (16 to 20 hours) incubation, media were removed and cells were lysed with 50 μL Glo Lysis Buffer (Promega) for 10-15 minutes followed by 10 minute incubation with 50 μL Dual Glo reagent (Promega) at room temperature. Firefly luciferase luminescence was measured using a BMG Pherastar plate reader. To each well, 50 μL Stop and Glo reagent was added and incubated for 10 minutes at room temperature. Renilla luminescence was measured using a BMG Pherastar plate reader. To calculate the effect of compounds on RORγt activity, firefly values were normalized against values of DMSO only and values of reference compound at saturating concentration, then further normalized against Renilla signals. IC50s were generated by plotting final Renilla normalized data against compound concentration and percent inhibition was calculated against DMSO control.

Conditions B

Cells used in this assay were transiently co-transfected with three different plasmids, one expressing the GAL4-

DNA binding domain (DBD)-RORγt fusion protein under control of a CMV promoter (NH$_2$-Gal4-DBD:RORC—COOH in pCMV-BD, Stratagene #211342), and two reporter plasmids the firefly luciferase reporter under control of a GAL4 promoter (pFR-Luc 2×GAL4) and Renilla luciferase reporter under control of CMV promoter (pRL-CMV, Promega #E2261). The full-length coding sequence was used for human RORγt, i.e., nucleotides 142-1635 of human RORγt, transcript variant 2, NCBI Accession: NM 001001523.1 (SEQ ID NO:1). HEK293T cells were plated at 8750 cells per well in 384-well plate in medium of DMEM with 10% FBS. After 18-22 hours incubation, the transfection was carried out by using a PEI solution with 42.6 ng total DNA/well (12.5 ng pCMV-BD-ROR plus 5 ng of pFR-Luc reporter and 0.125 ng of pRL-CMV reporter plus 25 ng Carrier DNA (Clontech #630440) for each well). 4-6 hours after transfection, cells were treated with compounds for overnight in the medium with final concentration of FBS 1.3% and DMSO 0.1%. After overnight (16 to 20 hours) incubation, media were removed and cells were lysed with 20 μL Glo Lysis Buffer (Promega) for 10-15 minutes followed by 10 minute incubation with 20 μL Dual Glo reagent (Promega) at room temperature. Firefly luciferase luminescence was measured using a BMG Pherastar plate reader. To each well, 20 μL Stop and Glo reagent was added and incubated for 10 minutes at room temperature. Renilla luminescence was measured using a BMG Pherastar plate reader. To calculate the effect of compounds on RORγt activity, firefly values were normalized against values of DMSO only and values of reference compound at saturating concentration, then further normalized against Renilla signals. IC50s were generated by plotting final Renilla normalized data against compound concentration and percent inhibition was calculated against DMSO control.

Human Th17 Assay

The human Th17 assay tests the effect of RORγt modulatory compounds on IL-17 production by CD4 T cells under conditions which favor Th17 differentiation. Total CD4$^+$ T cells were isolated from the peripheral blood mononuclear cells (PBMC) of healthy donors using a CD4$^+$ T cell isolation kit II, following the manufacturer's instructions (Miltenyi Biotec). Cells were resuspended in a medium of RPMI-1640 supplemented with 10% fetal bovine serum, penicillin, streptomycin, glutamate, and β-mercaptoethanol and were added to 96-well plates at 1.5×10$^5$ per 100 μL per well. 50 μL of compound at titrated concentrations in DMSO were added into each well at final DMSO concentration at 0.2%. Cells were incubated for 1 hour, then 50 μL of Th17 cell differentiation medium was added to each well. The final concentrations of antibodies and cytokines (R&D Systems) in differentiation medium were: 3×10$^6$/mL anti-CD3/CD28 beads (prepared using human T cell activation/expansion kit, Miltenyi Biotec), 10 μg/mL anti-IL4, 10 μg/mL anti-IFNγ, 10 ng/mL IL1β, 10 ng/mL IL23, 50 ng/mL IL6, 3 ng/mL TGFβ and 20 U/mL IL2. Cells were cultured at 37° C. and 5% CO$_2$ for 3 days. Supernatants were collected and the accumulated IL-17 in culture was measured by using MULTI-SPOT® Cytokine Plate following manufacture's instruction (Meso Scale Discovery). The plate was read using Sector Imager 6000, and IL-17 concentration was extrapolated from the standard curve. The IC50s were determined by GraphPad.

TABLE 1

| Example # | ThermoFluor® Assay, Kd (μM) | RORγt (FL) Reporter Assay A or B, IC$_{50}$ (μM) | RORγt (FL) Reporter Assay A or B, % inhibition @ 6 μM | Human Th17 Assay, IC$_{50}$ (μM) |
|---|---|---|---|---|
| 1 | 0.011 | 0.11 | 116* | ND |
| 2 | 0.029 | 0.93 | 104* | ND |
| 3 | 0.0081 | 0.063 | 105* | ND |
| 4 | 0.0091 | 0.055 | 100* | ND |
| 5 | 0.0087 | 0.43 | 79* | ND |
| 6 | 0.0019 | 0.27 | 87* | ND |
| 7 | 0.0029 | 0.24 | 100* | ND |
| 8 | 0.011 | 0.056 | 100* | 0.051 |
| 9 | 0.00075 | 0.0081 | 117* | 0.011 |
| 10 | 0.0032 | 0.014 | 98* | 0.048 |
| 11 | 0.0014 | 0.023 | 108* | ND |
| 12 | 0.0043 | 0.029 | 110* | ND |
| 13 | 0.0022 | 0.011 | 91* | 0.038 |
| 14 | 0.0036 | 0.036 | 82* | ND |
| 15 | 0.012 | 0.098 | 71* | ND |
| 16 | 0.0052 | 0.016 | 101* | ND |
| 17 | 0.0041 | 0.034 | 125* | ND |
| 18 | 0.018 | 0.14 | 100* | ND |
| 19 | 0.017 | 0.040 | 105* | ND |
| 20 | 0.034 | 0.099 | 123* | ND |
| 21 | 0.0012 | 0.020 | 120*** | ND |
| 22 | 0.0064 | 0.046 | 115*** | ND |
| 23 | 0.0025 | 0.015 | 100* | ND |
| 24 | 0.0089 | 0.063 | 113* | ND |
| 25 | 0.015 | 0.34 | 94* | ND |
| 26 | 0.017 | 0.014 | 88* | ND |
| 27 | 0.047 | 0.13 | 20* | ND |
| 28 | 0.097 | 0.0020 | 76* | ND |
| 29 | 0.024 | 0.36 | 39* | 0.21 |
| 30 | 0.010 | 0.10 | 98* | ND |
| 31 | 0.026 | 0.16 | 100*** | ND |
| 32 | 0.018 | 0.054 | 129* | ND |
| 33 | 0.062 | 1.1 | 66* | ND |
| 34 | 0.034 | 0.058 | 92*** | ND |
| 35 | 0.10 | 0.063 | 76*** | ND |
| 36 | 0.020 | 0.033 | 104* | ND |
| 37 | 0.0035 | 0.021 | 98* | 0.034 |
| 38 | 0.015 | 0.22 | 88* | ND |
| 39 | 0.040 | 0.73 | 72* | ND |
| 40 | 0.040 | 0.57 | 84* | ND |
| 41 | 0.0069 | 0.045 | 102* | ND |
| 42 | 0.035 | 0.43 | 95* | ND |
| 43 | 0.066 | 0.32 | 84*** | ND |
| 44 | 0.069 | 0.89 | 85* | ND |
| 45 | 0.00035 | 0.011 | 86* | ND |
| 46 | 0.00066 | 0.089 | 97* | ND |
| 47 | 0.0017 | 0.044 | 95* | ND |
| 48 | 0.0020 | 0.0057 | 101* | ND |
| 49 | 0.00028 | 0.0064 | 106* | ND |
| 50 | 0.0013 | 0.020 | 100*** | ND |
| 51 | 0.0032 | 0.035 | 97* | ND |
| 52 | 0.0047 | 0.058 | 85* | ND |
| 53 | 0.018 | 0.25 | 83* | ND |
| 54 | 0.013 | 0.24 | 42* | ND |
| 55 | 0.030 | 0.28 | 78* | ND |
| 56 | 0.12 | 2.3 | 30* | 0.37 |
| 57 | 0.020 | 0.34 | 43* | 0.45 |
| 58 | 0.043 | >2.9 | 23* | 0.73 |
| 59 | 0.035 | 0.21 | 82* | ND |
| 60 | 0.011 | 0.24 | 88 | ND |
| 61 | 0.016 | 0.11 | 87** | ND |
| 62 | 0.017 | 0.18 | 89** | 0.081 |
| 63 | 0.012 | 0.14 | 86 | ND |
| 64 | 0.015 | 0.28 | 39** | ND |
| 65 | 0.012 | 0.041 | 75** | ND |

ND: value not determined.
*% inhibition is shown at 3 μM compound concentration,
**% inhibition is shown at 2 μM compound concentration,
***% inhibition is shown at 1 μM compound concentration While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All documents cited herein are incorporated by reference.

We claim:

1. A compound of Formula I

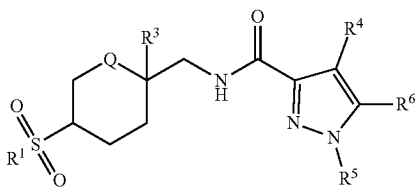

Formula I wherein
R¹ is $C_{(1-4)}$alkyl, —NH₂, —NHC(O)NH₂, —NHC(O)$C_{(1-4)}$alkyl, —NHC(O)NHC$_{(1-4)}$alkyl, —NHC$_{(1-4)}$alkyl, —NHC(O)H, or —NC$_{(1-4)}$alkyl)₂;
Q is CHR², NC(O)CH₃, NCH₂C(O)NH₂, NH, or O;
R² is H, —OH, or —NH₂;
R³ is —H, —OH, —CN, —NH₂, —CONH₂, —CO₂H, —CO₂C$_{(1-4)}$alkyl, —CH₂OH, —CH₂NH₂, —CH₂CN, —NHC$_{(1-4)}$alkyl, or —CONHC$_{(1-4)}$alkyl;
R⁴ is —Cl, —C$_{(1-4)}$alkyl, —F, —CN, —C(O)NH₂,

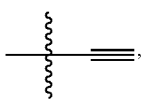

or —H; wherein said —C$_{(1-4)}$alkyl is optionally substituted with up to six fluorine atoms;
R⁵ is —C$_{(1-4)}$alkyl, wherein said —C$_{(1-4)}$alkyl is optionally substituted with —CN, —OH, —OCH₃, —OCF₃, or up to six fluorine atoms;
R⁶ is

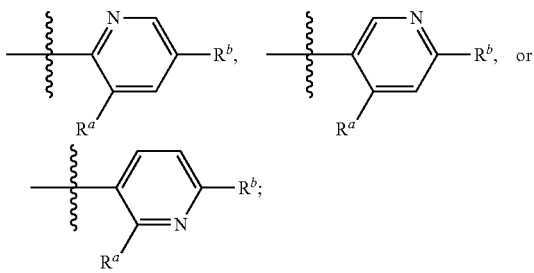

R$^a$ is —H, —F, —Cl, —OCD₃, —CN, —C$_{(1-3)}$alkyl, or —OC$_{(1-3)}$alkyl, wherein said —C$_{(1-3)}$alkyl and said OC$_{(1-3)}$alkyl are optionally substituted with up to three fluorine atoms;
R$^b$ is

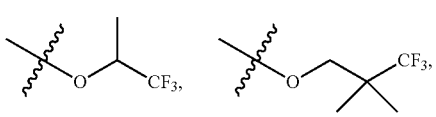

or —C$_{(4-6)}$alkyl, wherein said alkyl is optionally substituted with up to six fluorine atoms;
and pharmaceutically acceptable salts thereof.

2. The compound of claim 1 wherein
R¹ is —C$_{(1-2)}$alkyl, —NH₂, —NHC(O)NH₂, —NHC(O)C$_{(1-2)}$alkyl, —NHC(O)NHCH₃, —NHCH₃, —NHC(O)H, or —N(CH₃)₂;
R³ is —H, —OH, —CN, —NH₂, —CONH₂, —CO₂H, —CO₂CH₂CH₃, or —CH₂OH;
R⁴ is —Cl, —C$_{(1-4)}$alkyl, —F, —CN, —CF₃, —C(O)NH₂,

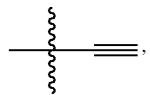

or —H;
R⁵ is —C$_{(1-4)}$alkyl, wherein said —C$_{(1-4)}$alkyl is optionally substituted with —CN, —OH, or —OCH₃;
and pharmaceutically acceptable salts thereof.

3. The compound of claim 2 wherein
R¹ is —C$_{(1-2)}$alkyl, —NH₂, —NHC(O)NH₂, —NHC(O)C$_{(1-2)}$alkyl, —NHC(O)NHCH₃, —NHCH₃, —NHC(O)H, or —N(CH₃)₂;
Q is CHR²;
R² is —H or —OH;
R³ is —H, —OH, —CN, or —NH₂;
R⁴ is —Cl, —C$_{(1-4)}$alkyl, —F, or —CN;
R⁵ is —C$_{(1-4)}$alkyl;
R$^a$ is —H, —F, —C$_{(1-3)}$alkyl, or —OC$_{(1-3)}$alkyl, wherein said —C$_{(1-3)}$alkyl and said OC$_{(1-3)}$alkyl are optionally substituted with up to three fluorine atoms;
and pharmaceutically acceptable salts thereof.

4. The compound of claim 3 wherein
R¹ is —C$_{(1-2)}$alkyl, —NH₂, —NHC(O)NH₂, —NHC(O)C$_{(1-2)}$alkyl, or —NHC(O)NHCH₃;
R³ is —H or —OH;
R⁴ is —Cl or —C$_{(1-4)}$alkyl;
R$^a$ is —C$_{(1-3)}$alkyl, or —OC$_{(1-3)}$alkyl, wherein said —C$_{(1-3)}$alkyl and said OC$_{(1-3)}$alkyl are optionally substituted with up to three fluorine atoms;
and pharmaceutically acceptable salts thereof.

5. The compound of claim 4 wherein
R¹ is —CH₃, —NH₂, —NHC(O)NH₂, —NHC(O)CH₃, or —NHC(O)NHCH₃;
R⁴ is —Cl or —CH₃;
R⁵ is —CH₃ or —CH₂CH₃;
R$_a$ is —OCHF₂, —CF₂CH₃, —CH(CH₃)₂, —CHF₂, —CH₂CH₃, or —OCH₃;
and pharmaceutically acceptable salts thereof.

6. The compound of claim 5 selected from the group consisting of:

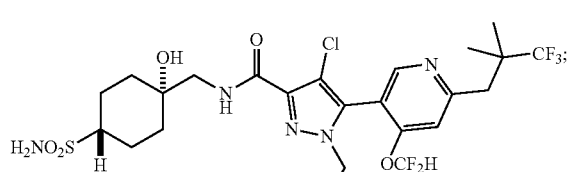

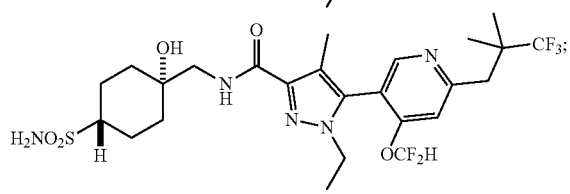

-continued
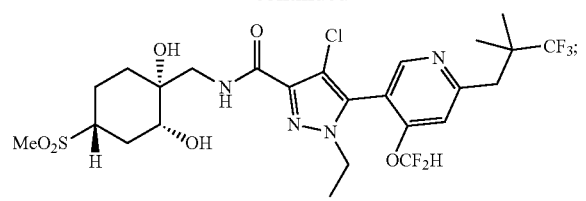
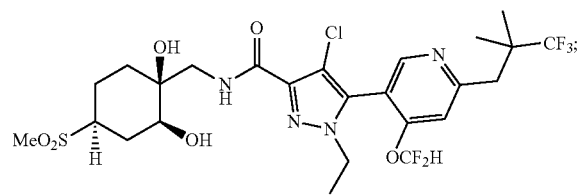
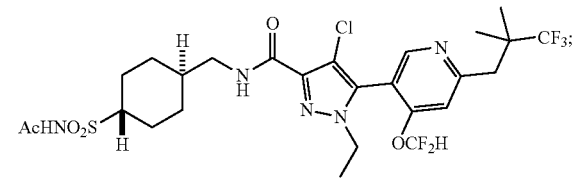
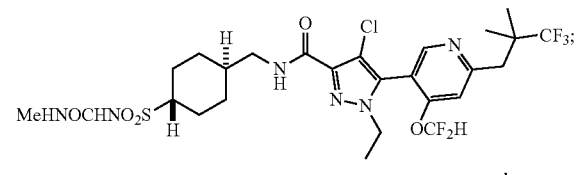
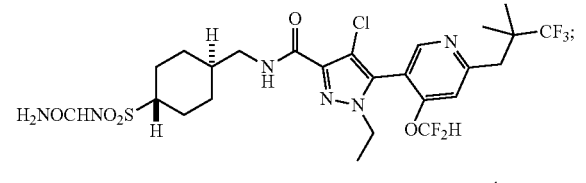
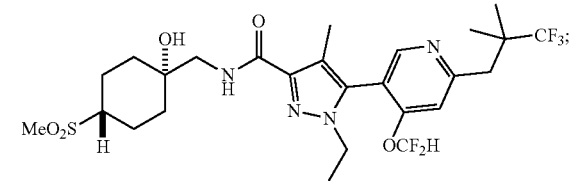
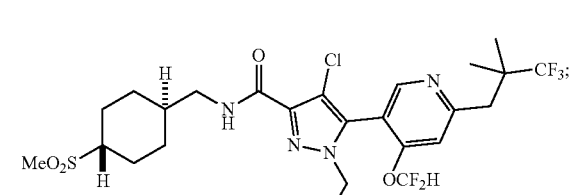
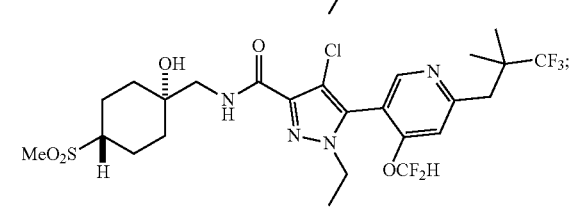
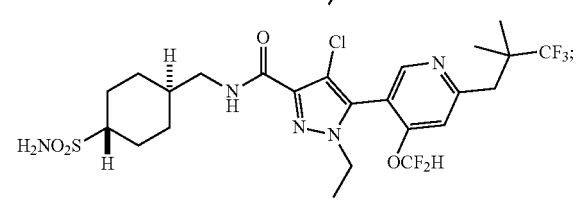
-continued
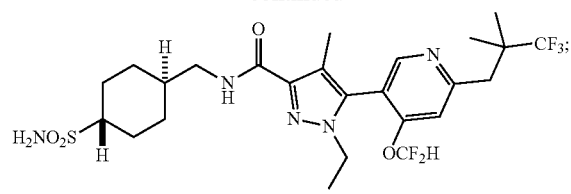
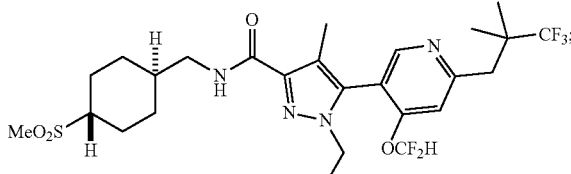
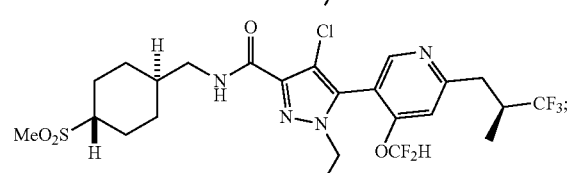
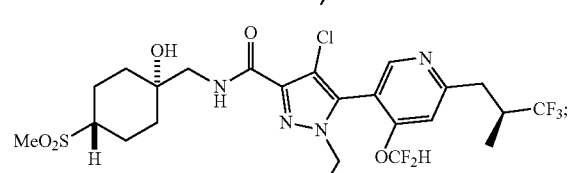
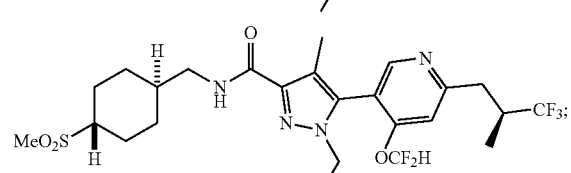
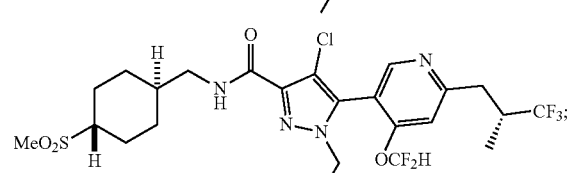
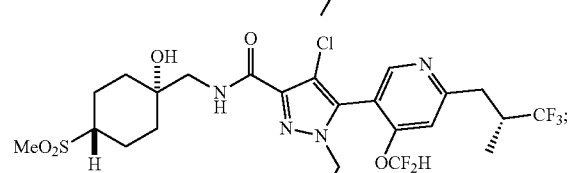
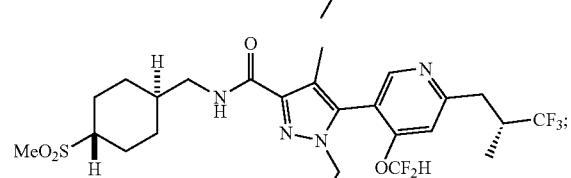
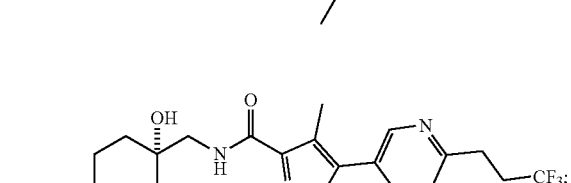
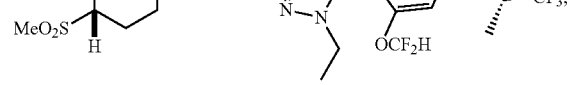

153
-continued
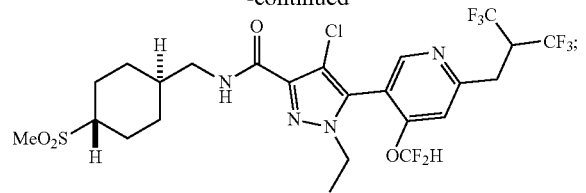
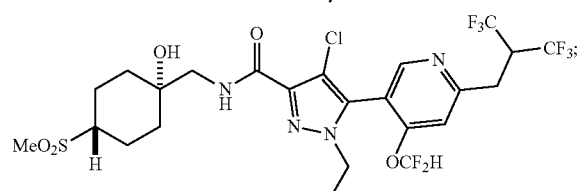
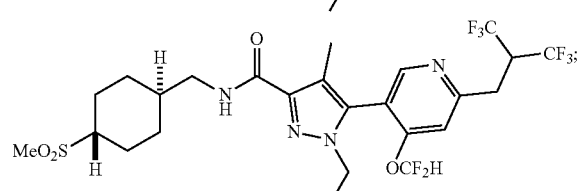
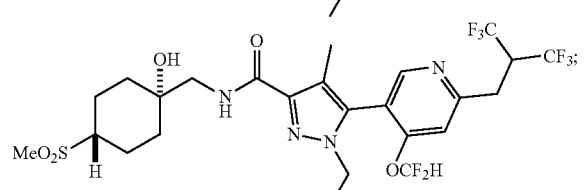
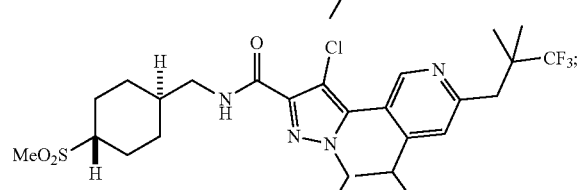
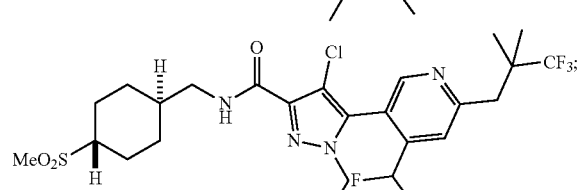
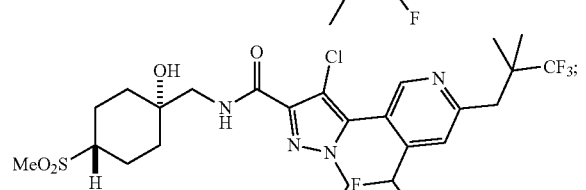
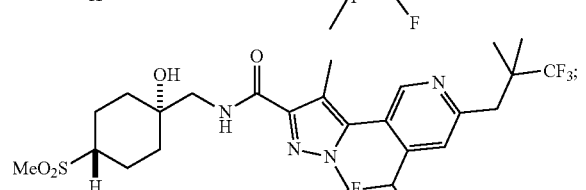
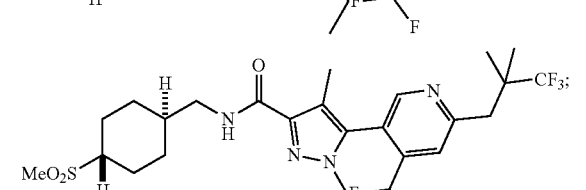
154
-continued
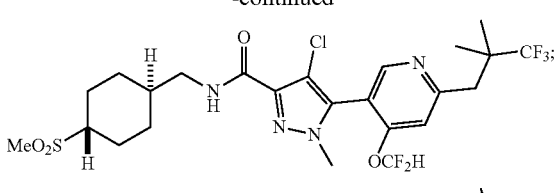
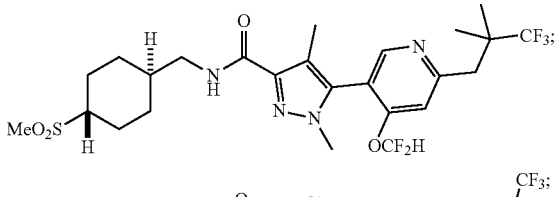
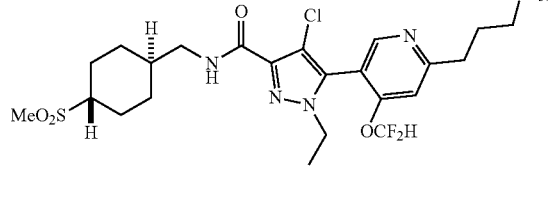
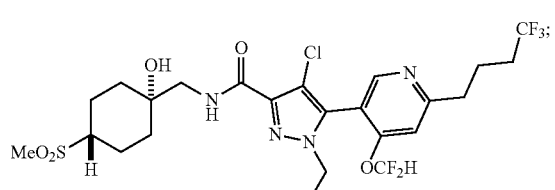
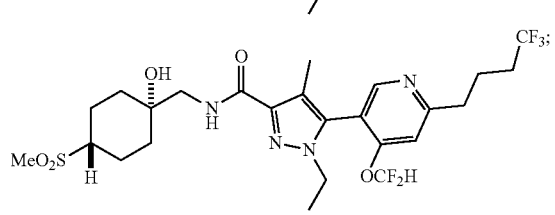
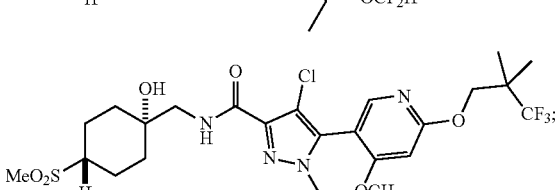
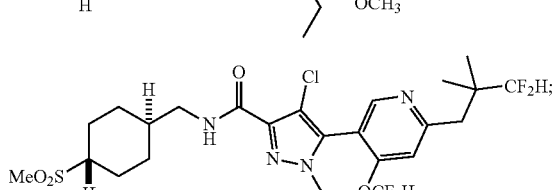
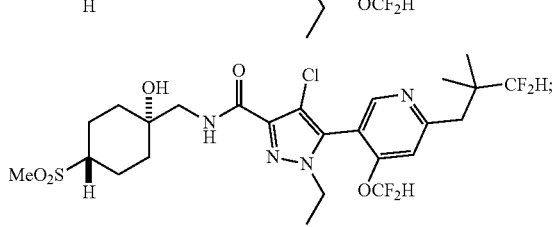

-continued
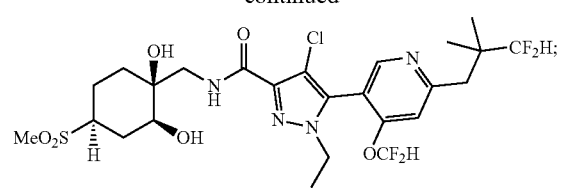
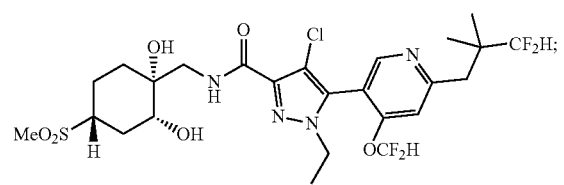
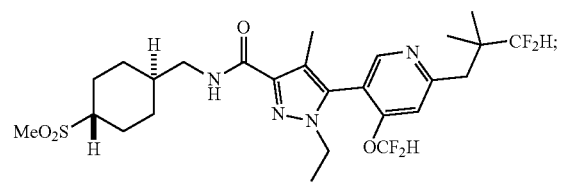
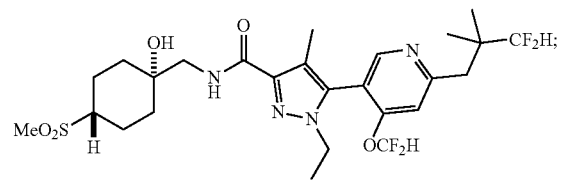
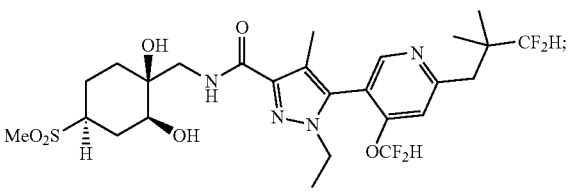
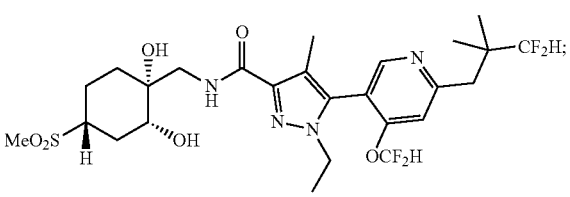
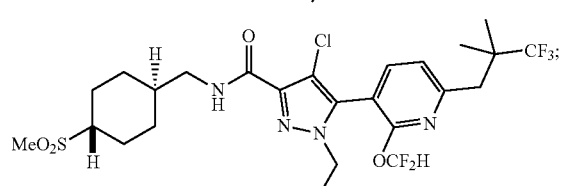
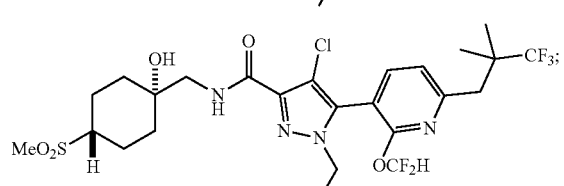
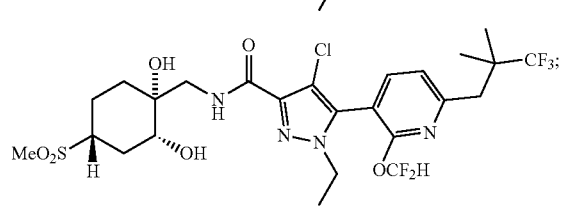
-continued
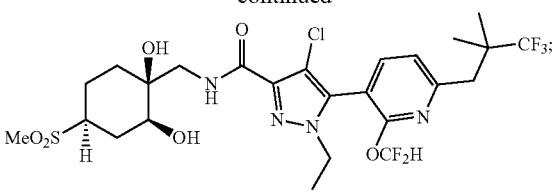
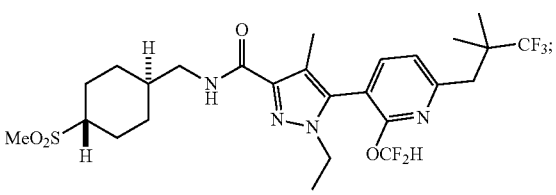
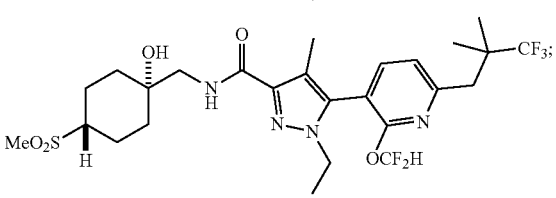
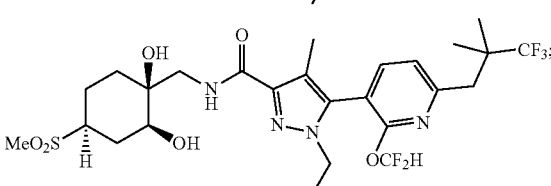
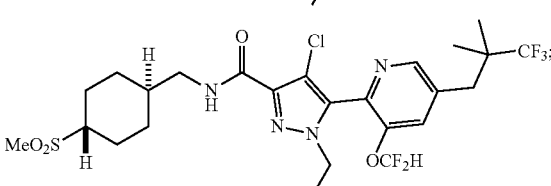
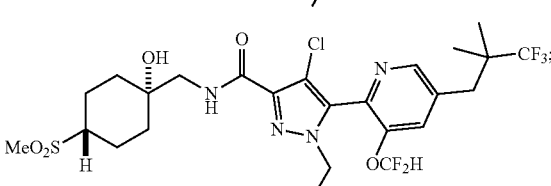
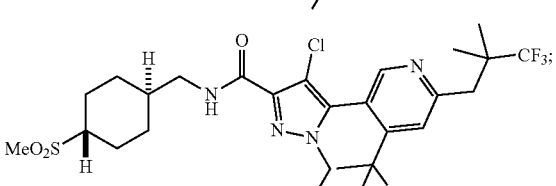
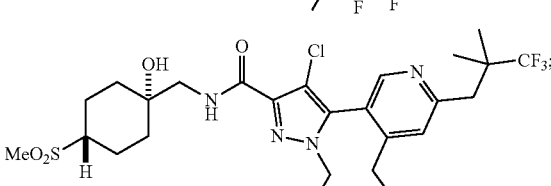
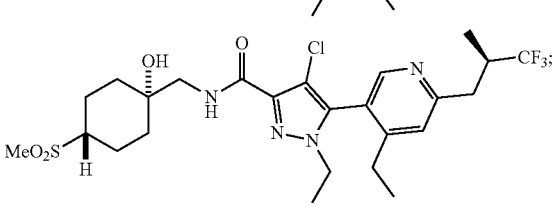

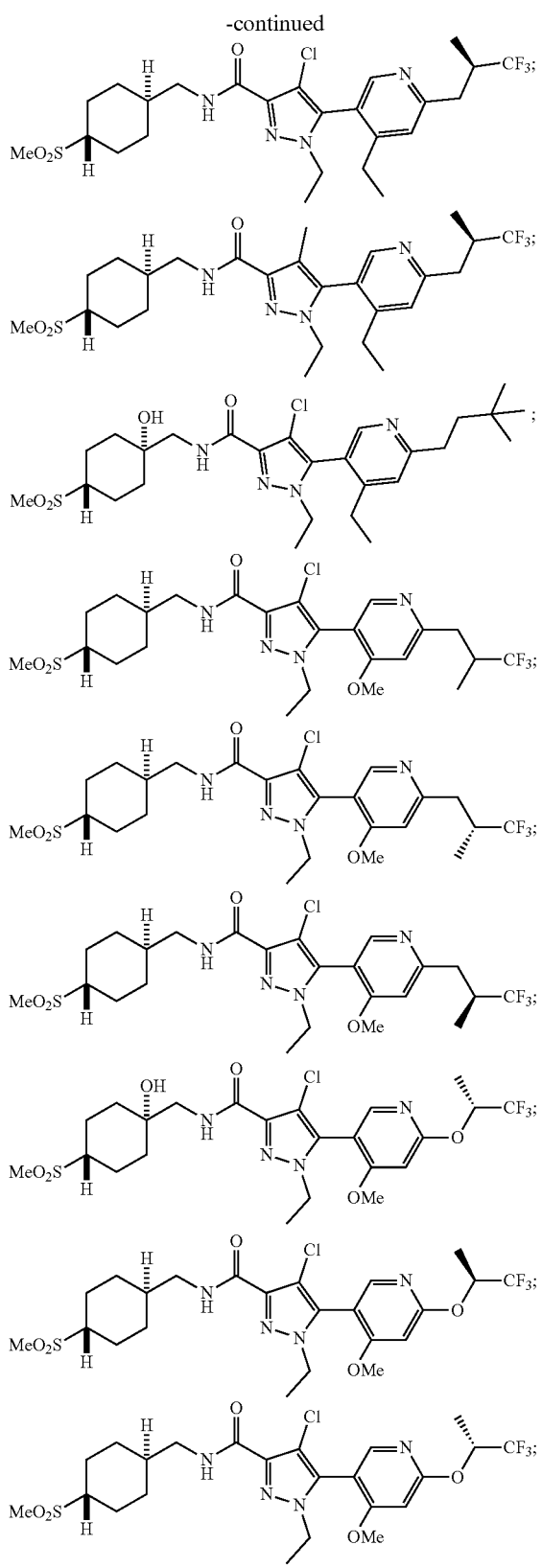

and pharmaceutically acceptable salts thereof.

7. A pharmaceutical composition, comprising a compound of claim 1 and a pharmaceutically acceptable carrier.

8. A pharmaceutical composition made by mixing a compound of claim 1 and a pharmaceutically acceptable carrier.

9. A process for making a pharmaceutical composition comprising mixing a compound of claim 1 and a pharmaceutically acceptable carrier.

10. A method for treating or ameliorating a RORγt mediated inflammatory syndrome, disorder or disease selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, systemic lupus erythematosus, depression and metabolic syndrome, comprising administering to a subject in need thereof an effective amount of a compound of claim 1.

11. The method of claim 10, wherein the disease is selected from the group consisting of: depression and metabolic syndrome.

12. The method of claim 10, wherein the disease is psoriasis.

13. The method of claim 10, wherein the disease is rheumatoid arthritis.

14. The method of claim 10, wherein the inflammatory bowel disease is ulcerative colitis.

15. The method of claim 10, wherein the inflammatory bowel disease is Crohn's disease.

16. The method of claim 10, wherein the disease is multiple sclerosis.

17. The method of claim 10, wherein the disease is neutrophilic asthma.

18. The method of claim 10, wherein the disease is steroid resistant asthma.

19. The method of claim 10, wherein the disease is psoriatic arthritis.

20. The method of claim 10, wherein the disease is ankylosing spondylitis.

21. The method of claim 10, wherein the disease is systemic lupus erythematosus.

22. The method of claim 10, wherein the disease is chronic obstructive pulmonary disorder.

23. The method of claim 11, wherein the disease is depression.

24. The method of claim 11, wherein the disease is metabolic syndrome.

25. A method of treating or ameliorating a syndrome, disorder or disease, in a subject in need thereof comprising administering to the subject an effective amount of a compound of claim 1 or composition or medicament thereof in a combination therapy with one or more anti-inflammatory agents, or immunosuppressive agents, wherein said syndrome, disorder or disease is selected from the group consisting of: rheumatoid arthritis and psoriasis.

26. A method of treating or ameliorating a syndrome, disorder or disease, in a subject in need thereof comprising administering to the subject an effective amount of a compound of claim 1 or composition or medicament thereof in a combination therapy with one or more anti-inflammatory agents, or immunosuppressive agents, wherein said syndrome, disorder or disease is selected from the group consisting of: psoriatic arthritis and psoriasis.

27. A method of inhibiting production of interleukin-17, comprising administering to a subject in need thereof an effective amount of a compound of claim 1.

* * * * *